(12) United States Patent
Tang et al.

(10) Patent No.: US 8,691,822 B2
(45) Date of Patent: Apr. 8, 2014

(54) DIHYDROPTERIDINONE DERIVATIVES, PREPARATION PROCESS AND PHARMACEUTICAL USE THEREOF

(75) Inventors: Peng Cho Tang, Shanghai (CN); Nong Zhang, Shanghai (CN); Baolei Zhang, Shanghai (CN); Weimin Wang, Shanghai (CN); Hao Zheng, Shanghai (CN); Lin Wu, Shanghai (CN)

(73) Assignees: Jiangsu Hengrui Medicine Co., Ltd., Lianyungang, Jiangsu (CN); Shanghai Hengrui Pharmaceutical Co., Ltd., Shanghai (CN)

( * ) Notice: Subject to any disclaimer, the term of this patent is extended or adjusted under 35 U.S.C. 154(b) by 6 days.

(21) Appl. No.: 13/497,067

(22) PCT Filed: Sep. 14, 2010

(86) PCT No.: PCT/CN2010/001405
§ 371 (c)(1),
(2), (4) Date: Mar. 20, 2012

(87) PCT Pub. No.: WO2011/035534
PCT Pub. Date: Mar. 31, 2011

(65) Prior Publication Data
US 2012/0184543 A1 Jul. 19, 2012

(30) Foreign Application Priority Data
Sep. 22, 2009 (CN) .......................... 2009 1 0196399

(51) Int. Cl.
| C07D 475/00 | (2006.01) |
|---|---|
| C07D 519/00 | (2006.01) |
| A61K 31/519 | (2006.01) |
| A61K 31/5377 | (2006.01) |
| A61K 31/5383 | (2006.01) |
| A61P 35/00 | (2006.01) |
| A61P 31/00 | (2006.01) |

(52) U.S. Cl.
USPC .......................................... 514/249; 544/258

(58) Field of Classification Search
USPC .......................................... 544/258; 514/249
See application file for complete search history.

(56) References Cited

U.S. PATENT DOCUMENTS

| 2004/0029885 A1 | 2/2004 | Bauer et al. |
| 2004/0176380 A1 | 9/2004 | Hoffmann et al. |

FOREIGN PATENT DOCUMENTS

| CN | 1551881 A | 12/2004 |
| EP | 1953163 A1 | 8/2008 |
| WO | 01019825 A1 | 3/2001 |
| WO | 2003020722 A1 | 3/2003 |
| WO | 2004014899 A1 | 2/2004 |
| WO | 2004076454 A1 | 9/2004 |
| WO | 2006018182 A1 | 2/2006 |
| WO | 2006018185 A2 | 2/2006 |
| WO | 2006018220 A2 | 2/2006 |
| WO | 2006018222 A1 | 2/2006 |
| WO | 2006058876 A1 | 6/2006 |
| WO | 2007135374 A1 | 11/2007 |

OTHER PUBLICATIONS

Int'l Search Report issued Dec. 23, 2010 in Int'l Application No. PCT/CN2010/001405.
Glover et al, "Polo-like kinases: a team that plays throughout mitosis," Genes & Development, vol. 12, pp. 3777-3787 (1998).
Qian et al, "The Polo-like Kinase Plx1 Is Required for Activation of the Phosphatase Cdc25C and Cyclin B-Cdc2 in Xenopus Oocytes," Molecular Biology of the Cell, vol. 12, pp. 1791-1799 (2001).
Wolf et al, "Prognostic significance of polo-like kinase (PLK) expression in non-small cell lung cancer," Oncogene, vol. 14, pp. 543-549 (1997).
Knecht et al, "Prognostic Significance of Polo-like Kinase (PLK) Expression in Squamous Cell Carcinomas of the Head and Neck," Cancer Research, vol. 59, pp. 2794-2797 (1999).
Wolf et al, "Polo-like Kinase: a Novel Marker of Proliferation: Correlation with Estrogen-receptor Expression in Human Breast Cancer," Pathology Research and Practice, vol. 196, pp. 753-759 (2000).
Weichert et al, "Polo-like kinase isoform expression is a prognostic factor in ovarian carcinoma," British Journal of Cancer, vol. 90, pp. 815-821 (2004).
Ito et al, "Polo-like kinase I overexpression is an early event in the progression of papillary carcinoma," British Journal of Cancer, vol. 90, pp. 414-418 (2004).
Takahashi et al, "Polo-like kinase 1 (PLK1) is overexpressed in primary colorectal cancers," Cancer Science, vol. 94, No. 2, pp. 148-152 (2003).

*Primary Examiner* — Bruck Kifle
(74) *Attorney, Agent, or Firm* — Panitch Schwarze Belisario & Nadel LLP

(57) ABSTRACT

Dihydroperidinone derivatives, preparation process and pharmaceutical use thereof are disclosed. Specially, new dihydroperidinone derivatives represented by general formula (I), wherein each substituent of the general formula (I) is defined as in the description, their preparation process, pharmaceutical compositions comprising said derivatives and their use as therapeutical agents, especially as Plk kinase inhibitors are disclosed.

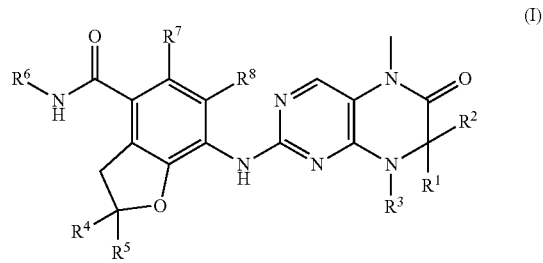

17 Claims, No Drawings

DIHYDROPTERIDINONE DERIVATIVES, PREPARATION PROCESS AND PHARMACEUTICAL USE THEREOF

CROSS-REFERENCE TO RELATED APPLICATION

This application is a Section 371 of International Application No. PCT/CN2010/001405, filed Sep. 14, 2010, which was published in the Chinese language on Mar. 31, 2011, under International Publication No. WO 2011/035534 A1, and the disclosure of which is incorporated herein by reference.

FIELD OF THE INVENTION

The present invention relates to novel dihydroperidinone derivatives, preparation process, pharmaceutical compositions containing said derivatives and therapeutic uses thereof, particularly their pharmaceutical use as a Plk kinase inhibitor.

BACKGROUND OF THE INVENTION

The Cyclin dependent kinase family (Cdks) have long been considered as the master regulators of the cell cycle, but more and more diverse protein kinases are emerging which play important role in cell cycle progression. One of these is the polo-like kinase family (Plks).

Plks are serine/threonine kinases that play important role in regulating cell circle. There are four Plks disclosed in the state of the art, i.e. Plk1, Plk2, Plk3 and Plk4. Plks play important role in the regulation of the eukaryotic cell cycle (e.g. regulation of the mitosis in mammalian cells). Especially, Plk1 play a central role in the regulation of mitosis (Glover et al. 1998, Genes Dev. 12: 3777-87; Qian et al. 2001, Mol Biol Cell. 12: 1791-9). Overexpression of Plk1 seems to be strongly associated with neoplastic cells including cancers (WO2004014899). Overexpression of Plk1 has been proven to be associated with various types tumor such as non-small cell lung cancer, aquamous cell carcinomas, breast, ovary or papillary carcinomas as well was colorectal cancers (Wolf et al. 1997, Oncogene 14: 543-549; Knecht et al. 1999, Cancer Res. 59: 2794-2797; Wolf et al. 2000, Pathol Res Pract. 196: 753-759; Weichert et al. 2004, Br. J. Cancer 90: 815-821; Ito et al. 2004, Br. J. Cancer 90: 414-418; Takahashi et al. 2003, Cancer Sci. 94: 148-152).

It is reported that Plk1 is conserved from yeast to man and has been involved in numerous mitotic process including activation of Cdc25C and Cdk1/Cyclin B at the G2-M transition, centrosome maturation, spindle formation and assembly. In the later stages of mitosis, Plk1 is also involved in separation of sister chromatids, activation of components of the anaphase-promoting complex and septin regulation during cytokinesis.

Lots of pteridinone derivatives as Plk inhibitors were disclosed in the prior art with antiproliferative activity. For example, WO2003020722 and WO2004076454 describes pteridinone derivatives, preparation process and pharmaceutical compositions which were used for the treatment of diseases related to the activity of cyclin kinase, and characterised by overexpression or abnormal cell proliferation. WO01/019825 describes the use of pteridinone derivatives for the treatment of neoplastic and viral diseases. Because of the drug resistance of different type tumor, new drugs are urgently needed to treat tumor. The other patent applications such as WO2004076454, WO2006018220, US20040176380, WO2007135374, WO2006018185, WO2006058876, WO2006018222 and WO2006018182 also disclose the compounds as Plk inhibitors.

However, although several Plk kinase inhibitors were disclosed, safe Plk inhibitors with improved pharmacokinetics are also needed.

The purpose of the present invention is to provide a Plk kinase inhibitor of novel structure with more effective activities, safety and less toxity, which is used to treat cell proliferation disorder such as cancer, infections, inflammatory and autoimmune disease.

SUMMARY OF THE INVENTION

In order to overcome the insufficiency of the prior art, the present invention is directed to dihydroperidinone derivatives of formula (I) and tautomers, enantiomers, diastereomers, racemates, and mixtures thereof, and pharmaceutically acceptable salts, hydrates or solvates, as well as their metabolites, metabolites or prodrugs thereof:

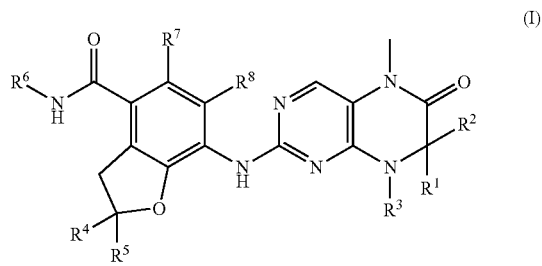

(I)

wherein:

$R^1$ and $R^2$ are each independently selected from the group consisting of hydrogen, alkyl, alkenyl, alkynyl, cycloalkyl, heterocyclyl, aryl, heteroaryl, carboxy or carboxylic ester, wherein the alkyl, alkenyl, alkynyl, cycloalkyl, heterocyclyl, aryl or heteroaryl is each optionally substituted with one or more groups selected from the group consisting of alkyl, halogen, hydroxyl, aryl, sulfuryl, carboxy or carboxylic ester;

or, $R^1$ and $R^2$ are taken together with the attached atom to form a 3 to 6 membered ring, wherein the 3 to 6 membered ring optionally contains 1 to 2 N, O or S(O)n heteroatoms;

$R^3$ is selected from the group consisting of hydrogen, alkyl, alkenyl, alkynyl, cycloalkyl, heterocyclyl, aryl or heteroaryl, wherein the alkyl, alkenyl, alkynyl, cycloalkyl, heterocyclyl, aryl or heteroaryl is each optionally substituted with one or more groups selected from the group consisting of alkyl, alkoxyl, halogen, hydroxyl, aryl, sulfuryl, carboxy or carboxylic ester;

or, $R^1$ and $R^3$ or $R^2$ and $R^3$ are taken together with the attached atom to form a 3 to 6 membered ring, wherein the 3 to 6 membered ring contains 1 to 2 N, O or S(O)n heteroatoms, and the 3 to 6 membered ring is each optionally substituted with one or more groups selected from the group consisting of alkyl, alkoxyl, halogen, carbonyl, aryl, benzyl, —C(O)$R^9$, —C(O)NR$^9$R$^{10}$, —NR$^9$R$^{10}$, carboxy or carboxylic ester;

$R^4$ and $R^5$ are each independently selected from the group consisting of hydrogen, alkyl, alkoxyl, cyano, hydroxyl, halogen, alkenyl, alkynyl, cycloalkyl, heterocyclyl, aryl, heteroaryl, carboxy or carboxylic ester, wherein the alkyl, alkoxyl, alkenyl, alkynyl, cycloalkyl, heterocyclyl, aryl and heteroaryl is each optionally substituted with one or more groups selected from the group consisting of alkyl, alkoxyl, halogen, hydroxyl, aryl, sulfuryl, —NR$^9$R$^{10}$, carboxy or carboxylic ester;

R⁶ is selected from the group consisting of alkyl, cycloalkyl, heterocyclyl, aryl or heteroaryl, wherein the alkyl, cycloalkyl, heterocyclyl, aryl or heteroaryl is each optionally substituted with one or more groups selected from the group consisting of alkyl, alkoxyl, hydroxyl, sulfuryl, carbonyl, cycloalkyl, cycloalkylalkyl, heterocyclyl, aryl, benzyl, —C(O)R⁹, —C(O)NR⁹R¹⁰, —NR⁹R¹⁰, carboxy or carboxylic ester;

R⁷ and R⁸ are each independently selected from the group consisting of hydrogen, alkyl or halogen;

R⁹ and R¹⁰ are each independently selected from the group consisting of hydrogen, alkyl, cycloalkyl, heterocyclyl, aryl, heteroaryl, carboxy or carboxylic ester, wherein the alkyl, cycloalkyl, heterocyclyl, aryl or heteroaryl is each optionally substituted with one or more groups selected from the group consisting of alkyl, halogen, hydroxyl, cyano, alkoxyl, aryloxyl, cycloalkyl, cycloalkylalkyl, heterocyclyl, aryl, heteroaryl, sulfuryl, carboxy or carboxylic ester;

or, R⁹ and R¹⁰ are taken together with the attached N atom to form a 4 to 8 membered heterocycle, wherein the 4 to 8 membered heterocycle contains one or more N, O or S(O)n heteroatoms, and the 4 to 8 membered heterocycle is each optionally substituted with one or more groups selected from the group consisting of alkyl, halogen, hydroxyl, haloalkyl, cyano, alkoxyl, aryloxyl, hydroxyl alkyl, cycloalkyl, cycloalkylalkyl, heterocyclyl, aryl, heteroaryl, sulfuryl, carboxy or carboxylic ester; and n is 0, 1 or 2.

In one preferable embodiment of the invention, the dihydroperidinone derivatives of formula (I), wherein R¹ and R² are each independently selected from the group consisting of hydrogen or alkyl;

R³ is selected from the group consisting of hydrogen, alkyl or cycloalkyl.

Furthermore, one preferable embodiment of the invention, in the dihydroperidinone derivatives of formula (I), wherein R¹ and R² are each independently selected from the group consisting of hydrogen or alkyl;

R³ is selected from the group consisting of alkyl or cycloalkyl;

R⁴ and R⁵ are each independently selected from the group consisting of hydrogen or alkyl, wherein the alkyl is optionally substituted with one or more groups selected from the group consisting of alkoxyl or —NR⁹R¹⁰;

R⁶ is selected from the group consisting of alkyl, cycloalkyl or heterocyclyl, wherein the alkyl, cycloalkyl or heterocyclyl is each optionally substituted with one or more groups selected from the group consisting of alkyl, hydroxyl, cycloalkylalkyl, heterocyclyl, —NR⁹R¹⁰, carboxy or carboxylic ester;

R⁷ and R⁸ are each independently hydrogen;

R⁹ and R¹⁰ are each independently selected from the group consisting of hydrogen, alkyl, cycloalkyl, heterocyclyl, aryl, heteroaryl, carboxy or carboxylic ester, wherein the alkyl, cycloalkyl, heterocyclyl, aryl or heteroaryl is each optionally substituted with one or more groups selected from the group consisting of alkyl, halogen, hydroxyl, cyano, alkoxyl, aryloxyl, heterocyclyl, aryl, heteroaryl, sulfuryl, carboxy or carboxylic ester;

or, R⁹ and R¹⁰ are taken together with the attached N atom to form a 4 to 8 membered heterocycle, wherein the 4 to 8 membered heterocycle contains one or more N, O or S(O)n heteroatoms, and the 4 to 8 membered heterocycle is each optionally substituted with one or more groups selected from the group consisting of alkyl, halogen, hydroxyl, haloalkyl, cyano, alkoxyl, aryloxyl, hydroxyl alkyl, cycloalkyl, cycloalkylalkyl, heterocyclyl, aryl, heteroaryl, sulfuryl, carboxy or carboxylic ester; and n is 0, 1 or 2.

The compounds of the invention include, but not limited to the following:

| Example No. | Structure and Name |
|---|---|
| 1 | 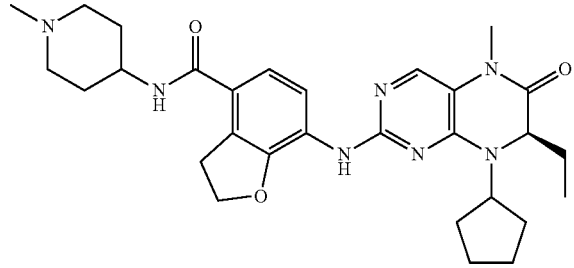 [SMILES: CC[C@@H]1C(=O)N(C)c2cnc(Nc3ccc(C(=O)NC4CCN(C)CC4)c4c3OCC4)nc2N1C1CCCC1]<br>7-[[(7R)-8-Cyclopentyl-7-ethyl-5-methyl-6-oxo-7H-pteridin-2-yl]amino]-N-(1-methyl-piperidyl)-2,3-dihydrobenzofuran-4-carboxamide |
| 2 | 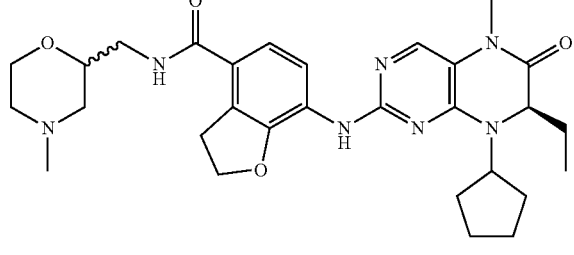<br>7-[[(7R)-8-cyclopentyl-7-ethyl-5-methyl-6-oxo-7H-pteridin-2-yl]amino]-N-[(4-methylmorpholin-2-yl)methyl]-2,3-dihydrobenzofuran-4-carboxamide |

-continued

| Example No. | Structure and Name |
|---|---|
| 3 | 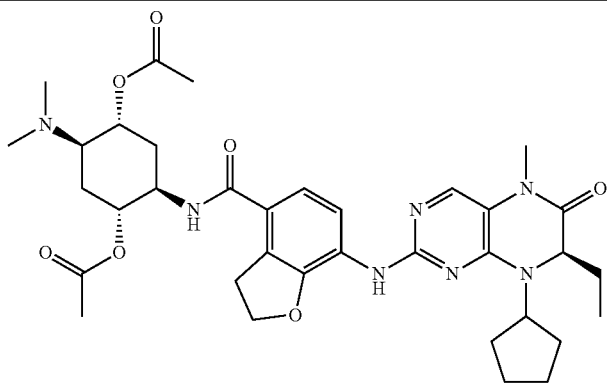<br>[(1R,2R,4R,5R)-4-Acetoxy-5-[[7-[[(7R)-8-cyclopentyl-7-ethyl-5-methyl-6-oxo-7H-pteridin-2-yl]amino]-2,3-dihydrobenzofuran-4-carbonyl]amino]-2-dimethylamino-cyclohexyl]acetate |
| 4 | 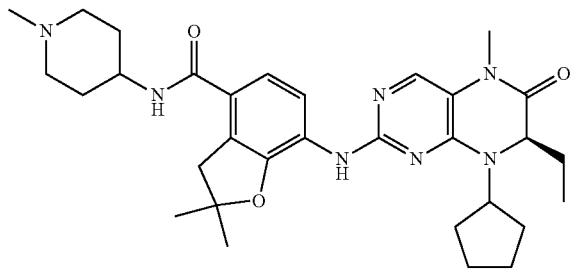 [SMILES: CC[C@@H]1C(=O)N(C)c2cnc(Nc3ccc(C(=O)NC4CCN(C)CC4)c4c3OC(C)(C)C4)nc2N1C1CCCC1]<br>7-[[(7R)-8-Cyclopentyl-7-ethyl-5-methyl-6-oxo-7H-pteridin-2-yl]amino]-2,2-dimethyl-N-(1-methyl-4-piperidyl)-3H-benzofuran-4-carboxamide |
| 5 | 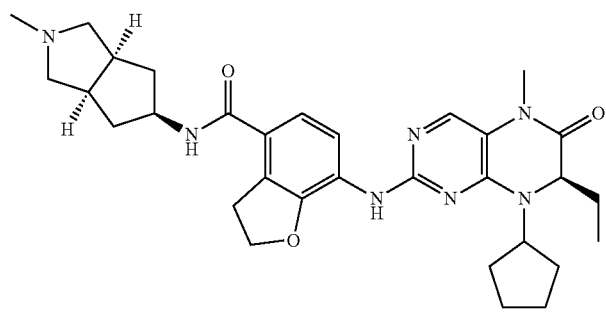 [SMILES: CC[C@@H]1C(=O)N(C)c2cnc(Nc3ccc(C(=O)N[C@@H]4C[C@@H]5CN(C)C[C@@H]5C4)c4c3OCC4)nc2N1C1CCCC1]<br>(cis-exo)-N-2-Methyl-3,3α,4,5,6,6α-hexahydro-1H-cyclopenta[c]pyrrol-5-yl]-7-[[[(7R)-8-cyclopentyl-7-ethyl-5-methyl-6-oxo-7H-pteridin-2-yl]amino]-2,3-dihydrobenzofuran-4-carboxamide |
| 6 | 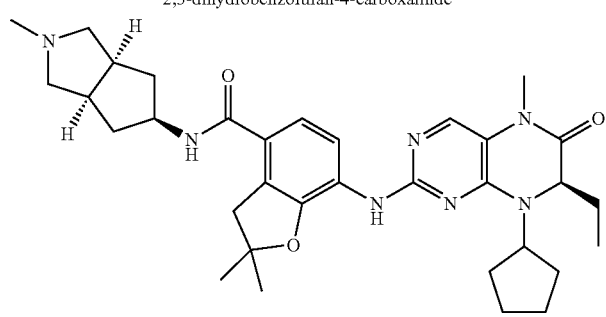<br>(cis-exo)-N-[2-Methyl-3,3α,4,5,6,6α-hexahydro-1H-cyclopenta[c]pyrrol-5-yl]-7-[[(7R)-8-cyclopentyl-7-ethyl-5-methyl-6-oxo-7H-pteridin-2-yl]amino]-2,2-dimethyl-3H-benzofuran-4-carboxamide |

| Example No. | Structure and Name |
|---|---|
| 7 | 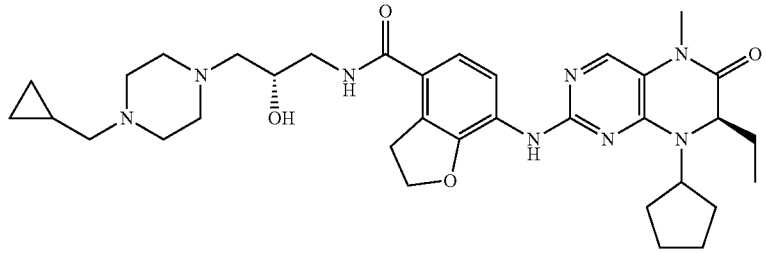 [SMILES: CC[C@@H]1C(=O)N(C)c2cnc(Nc3ccc(C(=O)NC[C@H](O)CN4CCN(CC5CC5)CC4)c4c3OCC4)nc2N1C1CCCC1]<br>7-[[(7R)-8-Cyclopentyl-7-ethyl-5-methyl-6-oxo-7H-pteridin-2-yl]amino]-N-[(2S)-3-[4-(cyclopropylmethyl)piperazin-1-yl]-2-hydroxy-propyl]-2,3-dihydrobenzofuran-4-carboxamide |
| 8 | 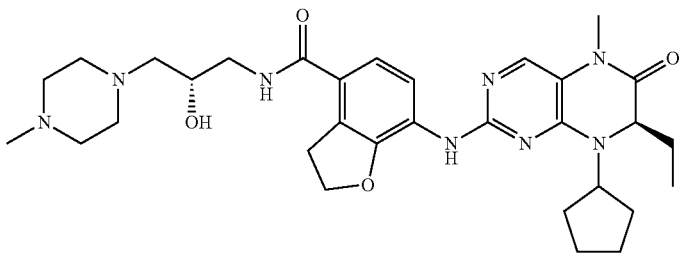 [SMILES: CC[C@@H]1C(=O)N(C)c2cnc(Nc3ccc(C(=O)NC[C@H](O)CN4CCN(C)CC4)c4c3OCC4)nc2N1C1CCCC1]<br>7-[[(7R)-8-Cyclopentyl-7-ethyl-5-methyl-6-oxo-7H-pteridin-2-yl]amino]-N-[(2S)-2-hydroxy-3-(4-methylpiperazin-1-yl)propyl]-2,3-dihydrobenzofuran-4-carboxamide |
| 9 | 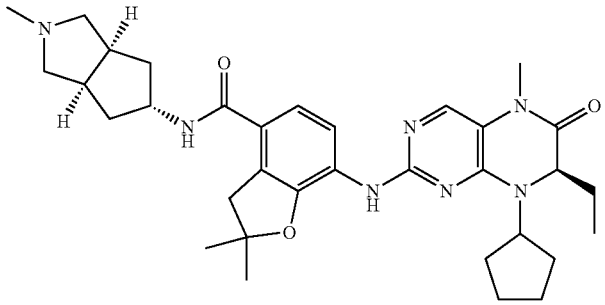 [SMILES: CC[C@@H]1C(=O)N(C)c2cnc(Nc3ccc(C(=O)N[C@H]4C[C@@H]5CN(C)C[C@@H]5C4)c4c3OC(C)(C)C4)nc2N1C1CCCC1]<br>(cis-endo)-N-[2-Methyl-3,3α,4,5,6,6α-hexahydro-1H-cyclopenta[c]pyrrol-5-yl]-7-[[(7R)-8-cyclopentyl-7-ethyl-5-methyl-6-oxo-7H-pteridin-2-yl]amino]-2,2-dimethyl-3H-benzofuran-4-carboxamide |
| 10 | 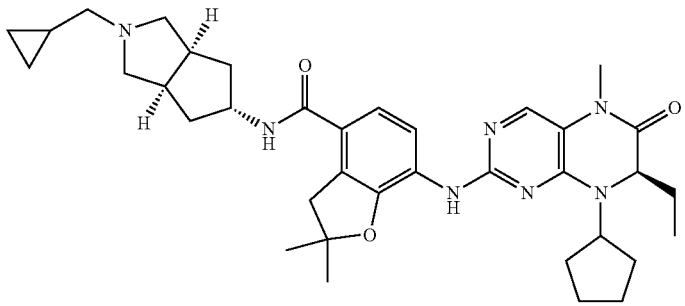 [SMILES: CC[C@@H]1C(=O)N(C)c2cnc(Nc3ccc(C(=O)N[C@H]4C[C@@H]5CN(CC6CC6)C[C@@H]5C4)c4c3OC(C)(C)C4)nc2N1C1CCCC1]<br>N-[(cis-endo)-2-(Cyclopropylmethyl)-3,3α,4,5,6,6α-hexahydro-1H-cyclopenta[c]pyrrol-5-yl]-7-[[(7R)-8-cyclopentyl-7-ethyl-5-methyl-6-oxo-7H-pteridin-2-yl]amino]-2,2-dimethyl-3H-benzofuran-4-carboxamide |

-continued

| Example No. | Structure and Name |
|---|---|
| 11 | 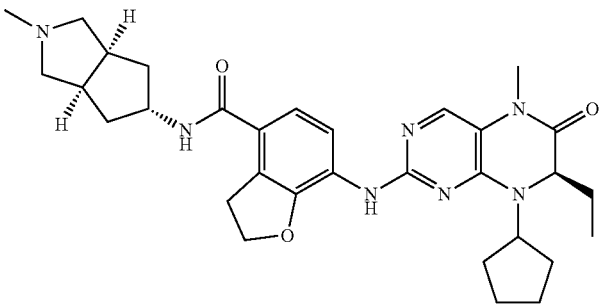 [SMILES: CC[C@@H]1C(=O)N(C)c2cnc(Nc3ccc(C(=O)N[C@H]4C[C@@H]5CN(C)C[C@@H]5C4)c4c3OCC4)nc2N1C1CCCC1]<br>(cis-endo)-N-[2-Methyl-3,3α,4,5,6,6α-hexahydro-1H-cyclopenta[c]pyrrol-5-yl]-7-[[(7R)-8-cyclopentyl-7-ethyl-5-methyl-6-oxo-7H-pteridin-2-yl]amino]-2,3-dihydrobenzofuran-4-carboxamide |
| 12 | 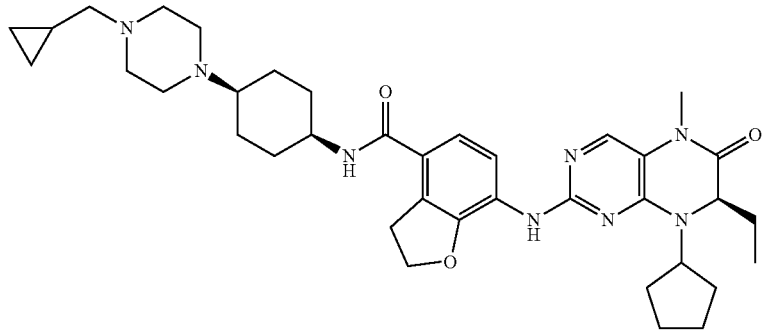 [SMILES: CC[C@@H]1C(=O)N(C)c2cnc(Nc3ccc(C(=O)N[C@H]4CC[C@@H](N5CCN(CC6CC6)CC5)CC4)c4c3OCC4)nc2N1C1CCCC1]<br>7-[[(7R)-8-Cyclopentyl-7-ethyl-5-methyl-6-oxo-7H-pteridin-2-yl]amino]-N-[(cis)-4-[4-(cyclopropylmethyl)piperazin-1-yl]cyclohexyl]-2,3-hydrobenzofuran-4-carboxamide |
| 13 | 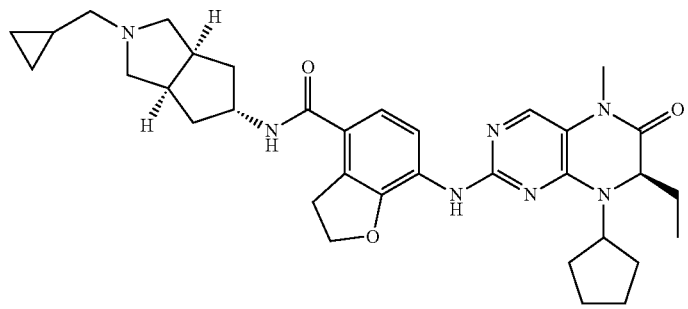 [SMILES: CC[C@@H]1C(=O)N(C)c2cnc(Nc3ccc(C(=O)N[C@H]4C[C@@H]5CN(CC6CC6)C[C@@H]5C4)c4c3OCC4)nc2N1C1CCCC1]<br>(cis-endo)-N-[2-(Cyclopropylmethyl)-3,3α,4,5,6,6α-hexahydro-1H-cyclopenta[c]pyrrol-5-yl]-7-[[(7R)-8-cyclopentyl-7-ethyl-5-methyl-6-oxo-7H-pteridin-2-yl]amino]-2,3-dihydrobenzofuran-4-carboxamide |
| 14 | 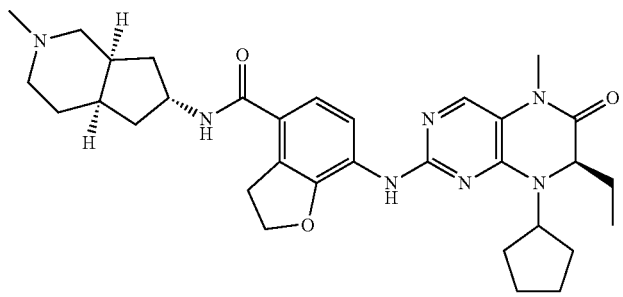 [SMILES: CC[C@@H]1C(=O)N(C)c2cnc(Nc3ccc(C(=O)N[C@@H]4C[C@H]5CCN(C)C[C@H]5C4)c4c3OCC4)nc2N1C1CCCC1]<br>(cis-endo)-N-[2-Methyl-1,3,3α,4,5,6,7,7α-octahydrocyclopenta[c]pyridin-6-yl]-7-[[(7R)-8-cyclopentyl-7-ethyl-5-methyl-6-oxo-7H-pteridin-2-yl]amino]-2,3-dihydrobenzofuran-4-carboxamide |

-continued

| Example No. | Structure and Name |
|---|---|
| 15 | 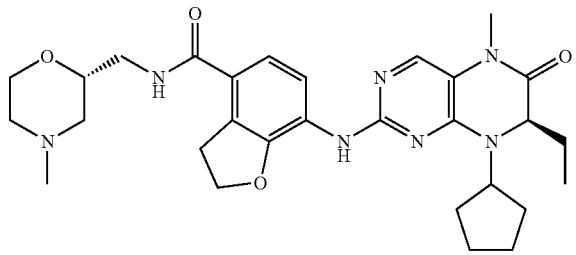 [SMILES: CC[C@@H]1C(=O)N(C)c2cnc(Nc3ccc(C(=O)NC[C@@H]4CN(C)CCO4)c4c3OCC4)nc2N1C1CCCC1]

7-[[(7R)-8-Cyclopentyl-7-ethyl-5-methyl-6-oxo-7H-pteridin-2-yl]amino]-N-[[(2R)-4-methylmorpholin-2-yl]methyl]-2,3-dihydrobenzofuran-4-carboxamide |
| 16 | 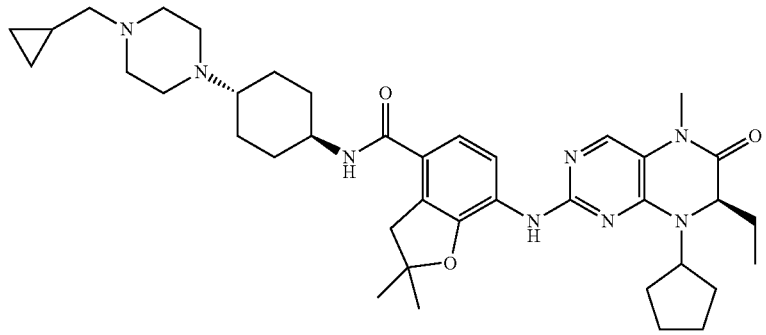 [SMILES: CC[C@@H]1C(=O)N(C)c2cnc(Nc3ccc(C(=O)N[C@H]4CC[C@H](N5CCN(CC6CC6)CC5)CC4)c4c3OC(C)(C)C4)nc2N1C1CCCC1]

7-[[(7R)-8-Cyclopentyl-7-ethyl-5-methyl-6-oxo-7H-pteridin-2-yl]amino]-N-[(trans)-4-[4-(cyclopropylmethyl)piperazin-1-yl]cyclohexyl]-2,2-dimethyl-3H-benzofuran-4-carboxamide |
| 17 | 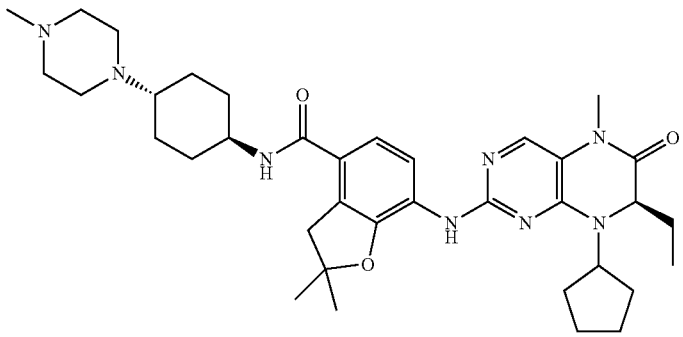 [SMILES: CC[C@@H]1C(=O)N(C)c2cnc(Nc3ccc(C(=O)N[C@H]4CC[C@H](N5CCN(C)CC5)CC4)c4c3OC(C)(C)C4)nc2N1C1CCCC1]

7-[[(7R)-8-Cyclopentyl-7-ethyl-5-methyl-6-oxo-7H-pteridin-2-yl]amino]-2,2-dimethyl-N-[(trans)-4-(4-methylpiperazin-1-yl)cyclohexyl]-3H-benzofuran-4-carboxamide |
| 18 | 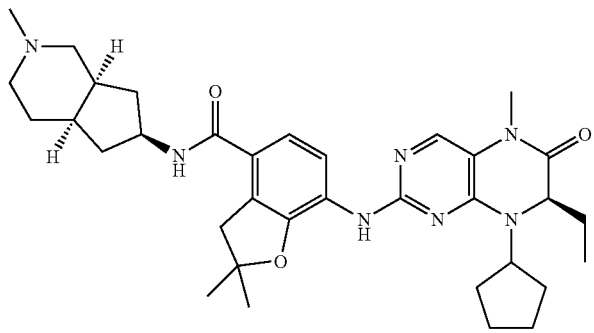 [SMILES: CC[C@@H]1C(=O)N(C)c2cnc(Nc3ccc(C(=O)N[C@H]4C[C@H]5CCN(C)C[C@H]5C4)c4c3OC(C)(C)C4)nc2N1C1CCCC1]

(cis-exo)-N-[2-Methyl-1,3,4,4α,5,6,7,7α-octahydrocyclopenta[c]pyridin-6-yl]-7-[((7R)-8-cyclopentyl-7-ethyl-5-methyl-6-oxo-7H-pteridin-2-yl)amino]-2,2-dimethyl-3H-benzofuran-4-carboxamide |

| Example No. | Structure and Name |
|---|---|
| 19 | 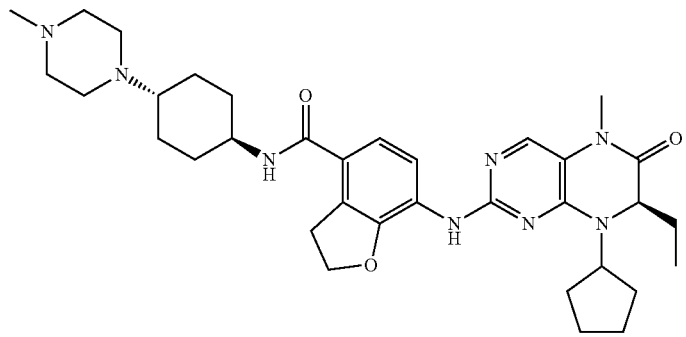 [SMILES: CC[C@@H]1C(=O)N(C)c2cnc(Nc3ccc(C(=O)N[C@H]4CC[C@H](N5CCN(C)CC5)CC4)c4c3OCC4)nc2N1C1CCCC1]<br>7-[[(7R)-8-Cyclopentyl-7-ethyl-5-methyl-6-oxo-7H-pteridin-2-yl]amino]-N-[(trans)-4-(4-methylpiperazin-1-yl)cyclohexyl]-2,3-dihydrobenzofuran-4-carboxamide |
| 20 | 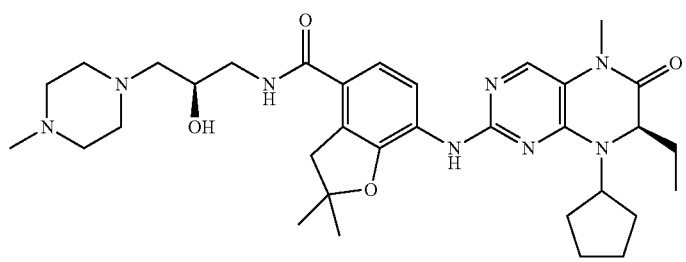 [SMILES: CC[C@@H]1C(=O)N(C)c2cnc(Nc3ccc(C(=O)NC[C@@H](O)CN4CCN(C)CC4)c4c3OC(C)(C)C4)nc2N1C1CCCC1]<br>7-[[(7R)-8-Cyclopentyl-7-ethyl-5-methyl-6-oxo-7H-pteridin-2-yl]amino]-N-[(2R)-3-(4-methylpiperazin-1-yl)-2-hydroxy-propyl]-2,2-dimethyl-3H-benzofuran-4-carboxamide |
| 21 | 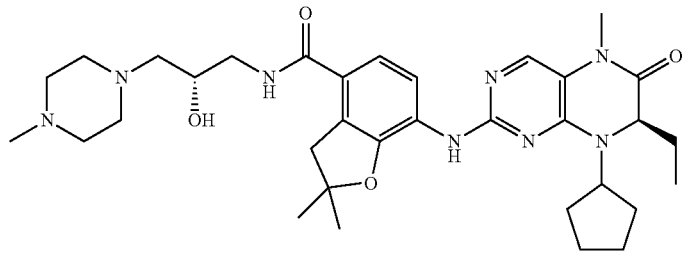 [SMILES: CC[C@@H]1C(=O)N(C)c2cnc(Nc3ccc(C(=O)NC[C@H](O)CN4CCN(C)CC4)c4c3OC(C)(C)C4)nc2N1C1CCCC1]<br>7-[[(7R)-8-Cyclopentyl-7-ethyl-5-methyl-6-oxo-7H-pteridin-2-yl]amino]-N-[(2S)-3-(4-methylpiperazin-1-yl)-2-hydroxy-propyl]-2,2-dimethyl-3H-benzofuran-4-carboxamide |
| 22 | 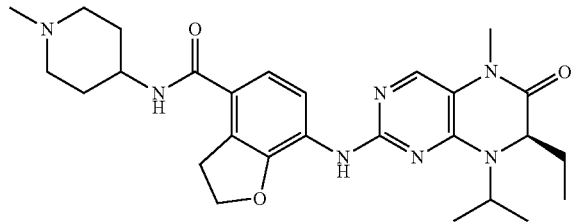 [SMILES: CC[C@@H]1C(=O)N(C)c2cnc(Nc3ccc(C(=O)NC4CCN(C)CC4)c4c3OCC4)nc2N1C(C)C]<br>7-[[(7R)-7-Ethyl-8-isopropyl-5-methyl-6-oxo-7H-pteridin-2-yl]amino]-N-(1-methyl-4-piperidyl)-2,3-dihydrobenzofuran-4-carboxamide |

-continued

| Example No. | Structure and Name |
|---|---|
| 23 | 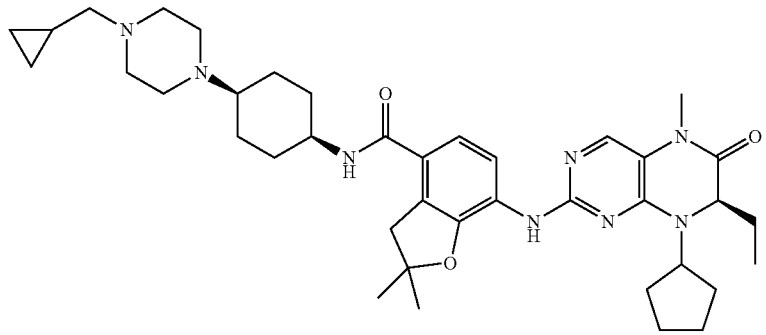 [SMILES: CC[C@@H]1C(=O)N(C)c2cnc(Nc3ccc(C(=O)N[C@H]4CC[C@@H](N5CCN(CC6CC6)CC5)CC4)c4c3OC(C)(C)C4)nc2N1C1CCCC1]

7-[[(7R)-8-Cyclopentyl-7-ethyl-5-methyl-6-oxo-7H-pteridin-2-yl]amino]-N-[(cis)-4-[4-(cyclopropylmethyl)piperazin-1-yl]cyclohexyl]-2,2-dimethyl-3H-benzofuran-4-carboxamide |
| 24 | 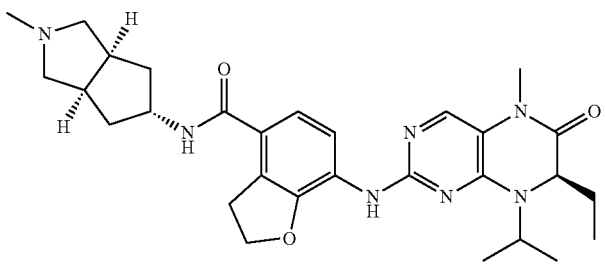 [SMILES: CC[C@@H]1C(=O)N(C)c2cnc(Nc3ccc(C(=O)N[C@H]4C[C@@H]5CN(C)C[C@@H]5C4)c4c3OCC4)nc2N1C(C)C]

(cis-endo)-N-[2-Methyl-3,3α,4,5,6,6α-hexahydro-1H-cyclopenta[c]pyrrol-5-yl]-7-[[(7R)-7-ethyl-8-isopropyl-5-methyl-6-oxo-7H-pteridin-2-yl]amino]-2,3-dihydrobenzofuran-4-carboxamide |
| 25 | 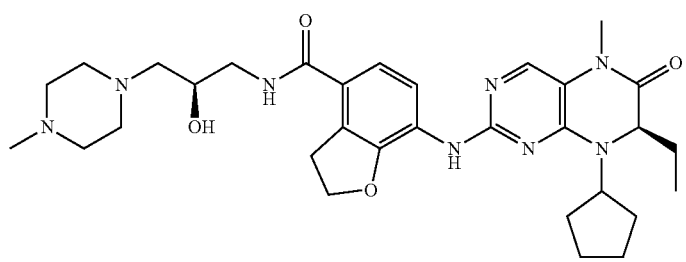 [SMILES: CC[C@@H]1C(=O)N(C)c2cnc(Nc3ccc(C(=O)NC[C@@H](O)CN4CCN(C)CC4)c4c3OCC4)nc2N1C1CCCC1]

7-[[(7R)-8-Cyclopentyl-7-ethyl-5-methyl-6-oxo-7H-pteridin-2-yl]amino]-N-[(2R)-2-hydroxy-3-(4-methylpiperazin-1-yl)propyl]-2,3-dihydrobenzofuran-4-carboxamide |
| 26 | 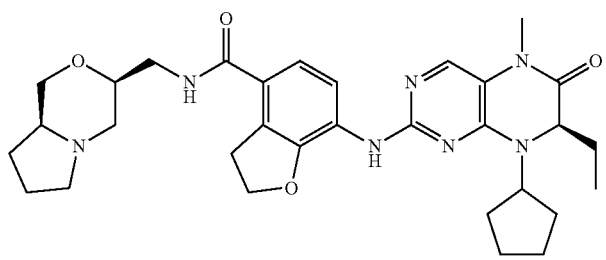 [SMILES: CC[C@@H]1C(=O)N(C)c2cnc(Nc3ccc(C(=O)NC[C@H]4CN5CCC[C@H]5CO4)c4c3OCC4)nc2N1C1CCCC1]

N-[[(3S,8aS)-3,4,6,7,8,8a-Hexahydro-1H-pyrrolo[2,1-c][1,4]oxazin-3-yl]methyl]-7-[[(7R)-8-cyclopentyl-7-ethyl-5-methyl-6-oxo-7H-pteridin-2-yl]amino]-2,3-dihydrobenzofuran-4-carboxamide |

-continued

| Example No. | Structure and Name |
|---|---|
| 27 | 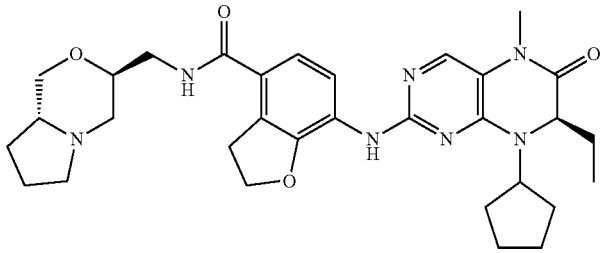 [SMILES: CC[C@@H]1C(=O)N(C)c2cnc(Nc3ccc(C(=O)NC[C@H]4CN5CCC[C@@H]5CO4)c4c3OCC4)nc2N1C1CCCC1]
N-[[(3S,8aR)-3,4,6,7,8,8a-Hexahydro-1H-pyrrolo[2,1-c][1,4]oxazin-3-yl]methyl]-7-[[(7R)-8-cyclopentyl-7-ethyl-5-methyl-6-oxo-7H-pteridin-2-yl]amino]-2,3-dihydrobenzofuran-4-carboxamide |
| 28 | 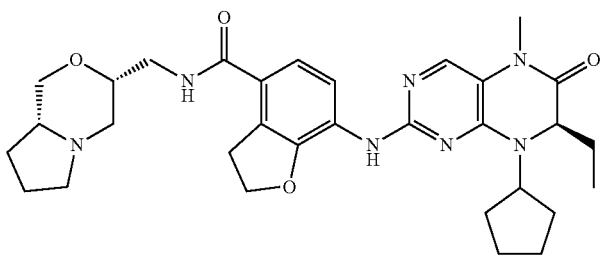 [SMILES: CC[C@@H]1C(=O)N(C)c2cnc(Nc3ccc(C(=O)NC[C@@H]4CN5CCC[C@@H]5CO4)c4c3OCC4)nc2N1C1CCCC1]
N-[[(3R,8aR)-3,4,6,7,8,8a-Hexahydro-1H-pyrrolo[2,1-c][1,4]oxazin-3-yl]methyl]-7-[[(7R)-8-cyclopentyl-7-ethyl-5-methyl-6-oxo-7H-pteridin-2-yl]amino]-2,3-dihydrobenzofuran-4-carboxamide |
| 29 | 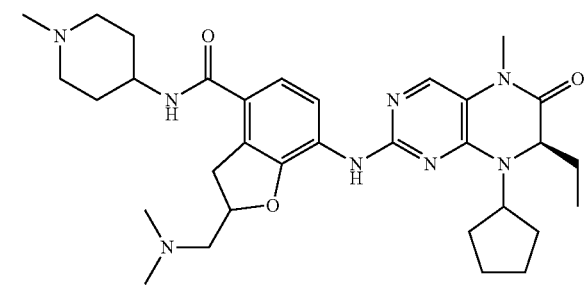 [SMILES: CC[C@@H]1C(=O)N(C)c2cnc(Nc3ccc(C(=O)NC4CCN(C)CC4)c4c3OC(CN(C)C)C4)nc2N1C1CCCC1]
7-[[(7R)-8-Cyclopentyl-7-ethyl-5-methyl-6-oxo-7H-pteridin-2-yl]amino]-2-(dimethylaminomethyl)-N-(1-methyl-4-piperidyl)-2,3-dihydrobenzofuran-4-carboxamide |
| 30 | 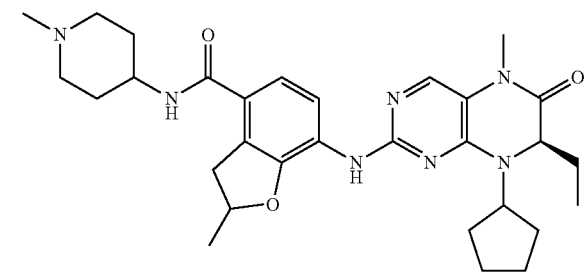 [SMILES: CC[C@@H]1C(=O)N(C)c2cnc(Nc3ccc(C(=O)NC4CCN(C)CC4)c4c3OC(C)C4)nc2N1C1CCCC1]
7-[[(7R)-8-Cyclopentyl-7-ethyl-5-methyl-6-oxo-7H-pteridin-2-yl]amino]-2-methyl-N-(1-methyl-4-piperidyl)-2,3-dihydrobenzofuran-4-carboxamide |

| Example No. | Structure and Name |
|---|---|
| 31 | 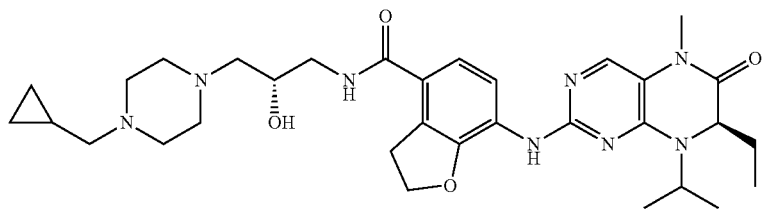 [SMILES: CC[C@@H]1C(=O)N(C)c2cnc(Nc3ccc(C(=O)NC[C@H](O)CN4CCN(CC5CC5)CC4)c4c3OCC4)nc2N1C(C)C]
N-[(2S)-3-[4-(Cyclopropylmethyl)piperazin-1-yl]-2-hydroxy-propyl]-7-[[(7R)-7-ethyl-8-isopropyl-5-methyl-6-oxo-7H-pteridin-2-yl]amino]-2,3-dihydrobenzofuran-4-carboxamide |
| 32 | 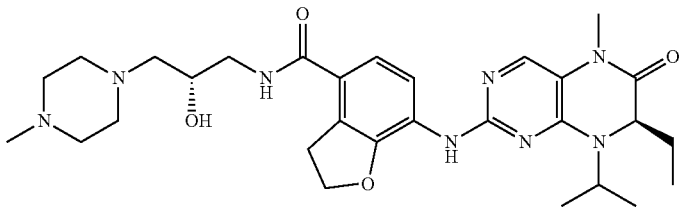 [SMILES: CC[C@@H]1C(=O)N(C)c2cnc(Nc3ccc(C(=O)NC[C@H](O)CN4CCN(C)CC4)c4c3OCC4)nc2N1C(C)C]
7-[[(7R)-7-Ethyl-8-isopropyl-5-methyl-6-oxo-7H-pteridin-2-yl]amino]-N-[(2S)-2-hydroxy-3-(4-methylpiperazin-1-yl)propyl]-2,3-dihydro-benzofuran-4-carboxamide |
| 33 | 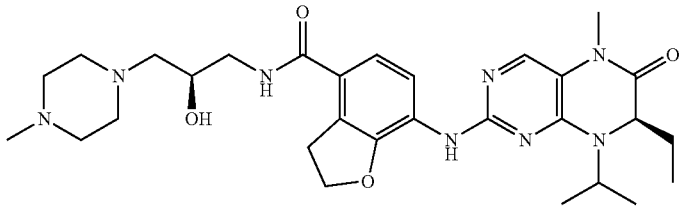 [SMILES: CC[C@@H]1C(=O)N(C)c2cnc(Nc3ccc(C(=O)NC[C@@H](O)CN4CCN(C)CC4)c4c3OCC4)nc2N1C(C)C]
7-[[(7R)-7-Ethyl-8-isopropyl-5-methyl-6-oxo-7H-pteridin-2-yl]amino]-N-[(2R)-2-hydroxy-3-(4-methylpiperazin-1-yl)propyl]-2,3-dihydro-benzofuran-4-carboxamide |
| 34 | 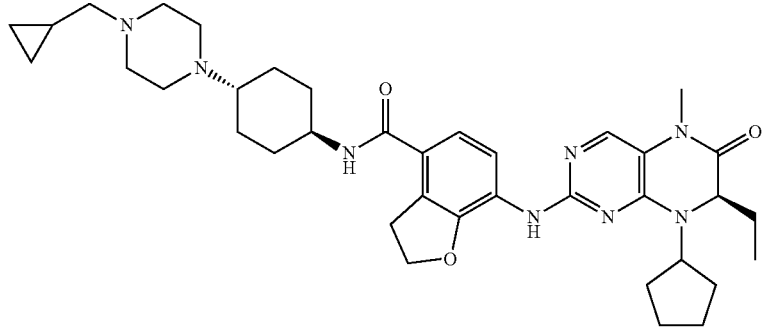 [SMILES: CC[C@@H]1C(=O)N(C)c2cnc(Nc3ccc(C(=O)N[C@H]4CC[C@H](N5CCN(CC6CC6)CC5)CC4)c4c3OCC4)nc2N1C1CCCC1]
7-[[(7R)-8-Cyclopentyl-7-ethyl-5-methyl-6-oxo-7H-pteridin-2-yl]amino]-N-[(trans)-4-[4-(cyclopropylmethyl)piperazin-1-yl]cyclohexyl]-2,3-dihydrobenzofuran-4-carboxamide |
| 35 | 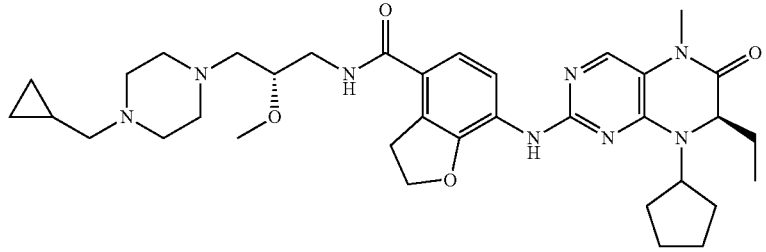 [SMILES: CC[C@@H]1C(=O)N(C)c2cnc(Nc3ccc(C(=O)NC[C@@H](CN4CCN(CC5CC5)CC4)OC)c4c3OCC4)nc2N1C1CCCC1]
7-[[(7R)-8-Cyclopentyl-7-ethyl-5-methyl-6-oxo-7H-pteridin-2-yl]amino]-N-[(2S)-3-[4-(cyclopropylmethyl)piperazin-1-yl]-2-methoxy-propyl]-2,3-dihydrobenzofuran-4-carboxamide |

| Example No. | Structure and Name |
|---|---|
| 36 | 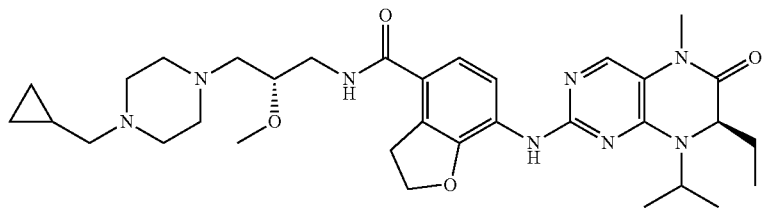 [SMILES: CC[C@@H]1C(=O)N(C)c2cnc(Nc3ccc(C(=O)NC[C@@H](CN4CCN(CC5CC5)CC4)OC)c4c3OCC4)nc2N1C(C)C]<br>N-[(2S)-3-[4-(Cyclopropylmethyl)piperazin-1-yl]-2-methoxy-propyl]-7-[[(7R)-7-ethyl-8-isopropyl-5-methyl-6-oxo-7H-pteridin-2-yl]amino]-2,3-dihydrobenzofuran-4-carboxamide |
| 37 | 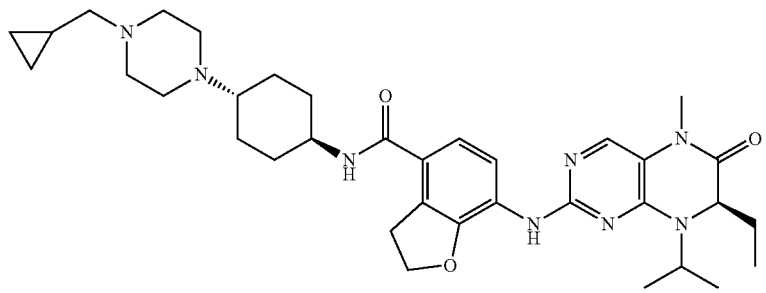 [SMILES: CC[C@@H]1C(=O)N(C)c2cnc(Nc3ccc(C(=O)N[C@H]4CC[C@H](N5CCN(CC6CC6)CC5)CC4)c4c3OCC4)nc2N1C(C)C]<br>N-[(trans)-4-[4-(Cyclopropylmethyl)piperazin-1-yl]cyclohexyl]-7-[[(7R)-7-ethyl-8-isopropyl-5-methyl-6-oxo-7H-pteridin-2-yl]amino]-2,3-dihydrobenzofuran-4-carboxamide |
| 38 | 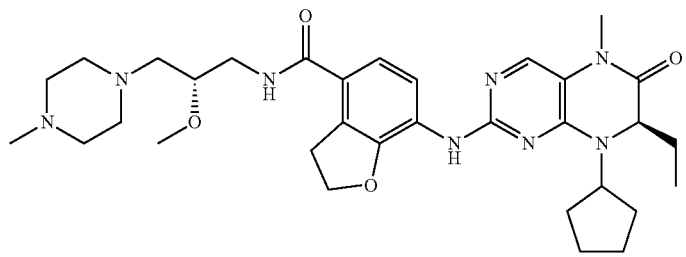 [SMILES: CC[C@@H]1C(=O)N(C)c2cnc(Nc3ccc(C(=O)NC[C@@H](CN4CCN(C)CC4)OC)c4c3OCC4)nc2N1C1CCCC1]<br>7-[[(7R)-8-Cyclopentyl-7-ethyl-5-methyl-6-oxo-7H-pteridin-2-yl]amino]-N-[(2S)-2-methoxy-3-(4-methylpiperazin-1-yl)propyl]-2,3-dihydrobenzofuran-4-carboxamide |
| 39 | 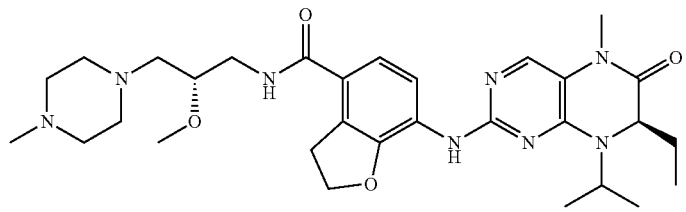 [SMILES: CC[C@@H]1C(=O)N(C)c2cnc(Nc3ccc(C(=O)NC[C@@H](CN4CCN(C)CC4)OC)c4c3OCC4)nc2N1C(C)C]<br>7-[[(7R)-7-Ethyl-8-isopropyl-5-methyl-6-oxo-7H-pteridin-2-yl]amino]-N-[(2S)-2-methoxy-3-(4-methylpiperazin-1-yl)propyl]-2,3-dihydrobenzofuran-4-carboxamide |

| Example No. | Structure and Name |
|---|---|
| 40 | 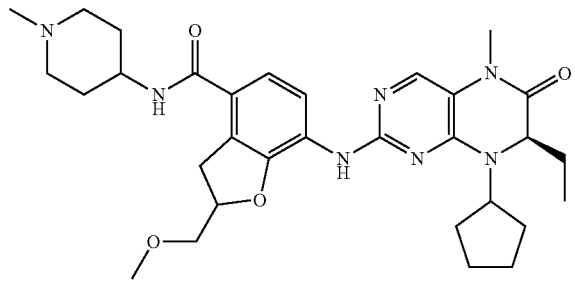 [SMILES: CC[C@@H]1C(=O)N(C)c2cnc(Nc3ccc(C(=O)NC4CCN(C)CC4)c4c3OC(COC)C4)nc2N1C1CCCC1]<br>7-[[(7R)-8-Cyclopentyl-7-ethyl-5-methyl-6-oxo-7H-pteridin-2-yl]amino]-2-(methoxymethyl)-N-(1-methyl-4-piperidyl)-2,3-dihydrobenzofuran-4-carboxamide |
| 41 | 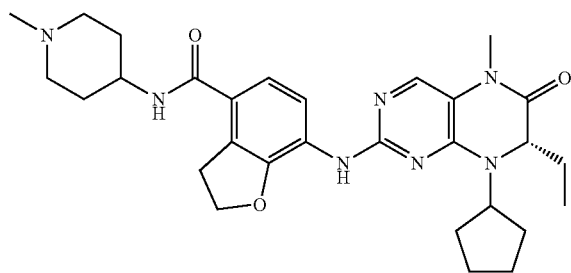 [SMILES: CC[C@H]1C(=O)N(C)c2cnc(Nc3ccc(C(=O)NC4CCN(C)CC4)c4c3OCC4)nc2N1C1CCCC1]<br>7-[[(7S)-8-Cyclopentyl-7-ethyl-5-methyl-6-oxo-7H-pteridin-2-yl]amino]-N-(1-methyl-4-piperidyl)-2,3-dihydrobenzofuran-4-carboxamide |
| 42 | 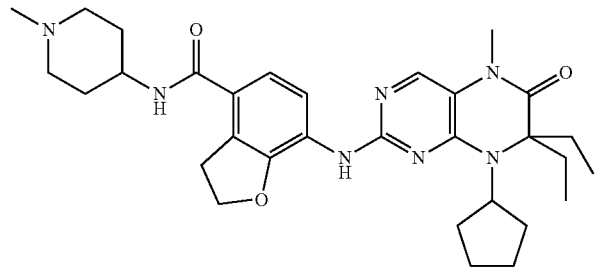 [SMILES: CCC1(CC)C(=O)N(C)c2cnc(Nc3ccc(C(=O)NC4CCN(C)CC4)c4c3OCC4)nc2N1C1CCCC1]<br>7-[(8-Cyclopentyl-7,7-diethyl-5-methyl-6-oxo-pteridin-2-yl)amino]-N-(1-methyl-4-piperidyl)-2,3-dihydrobenzofuran-4-carboxamide |
| 43 | 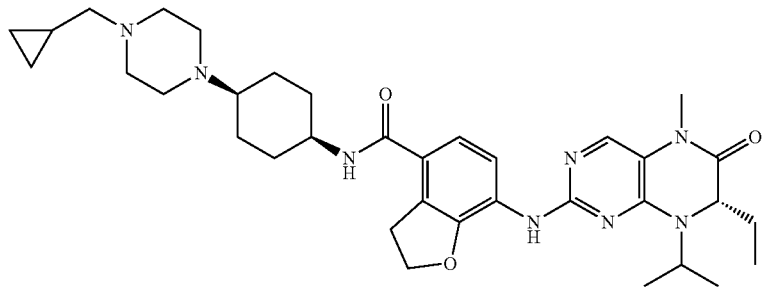 [SMILES: CC[C@H]1C(=O)N(C)c2cnc(Nc3ccc(C(=O)N[C@H]4CC[C@@H](N5CCN(CC6CC6)CC5)CC4)c4c3OCC4)nc2N1C(C)C]<br>N-[(cis)-4-[4-(Cyclopropylmethyl)piperazin-1-yl]cyclohexyl]-7-[[(7S)-7-ethyl-8-isopropyl-5-methyl-6-oxo-7H-pteridin-2-yl]amino]-2,3-dihydrobenzofuran-4-carboxamide |

| Example No. | Structure and Name |
|---|---|
| 44 | 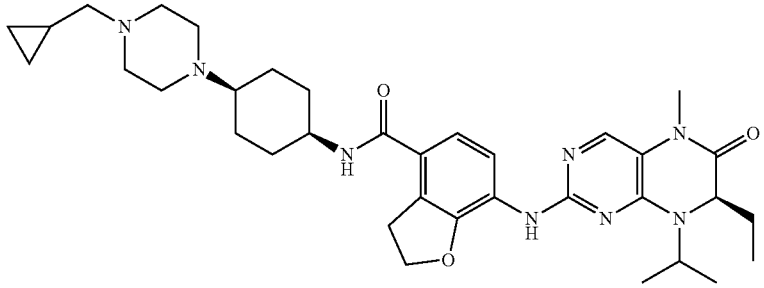 [SMILES: CC[C@@H]1C(=O)N(C)c2cnc(Nc3ccc(C(=O)N[C@H]4CC[C@@H](N5CCN(CC6CC6)CC5)CC4)c4c3OCC4)nc2N1C(C)C]<br>N-[(cis)-4-[4-(Cyclopropylmethyl)piperazin-1-yl]cyclohexyl]-7-[[(7R)-7-ethyl-8-isopropyl-5-methyl-6-oxo-7H-pteridin-2-yl]amino]-2,3-dihydrobenzofuran-4-carboxamide |
| 45 | 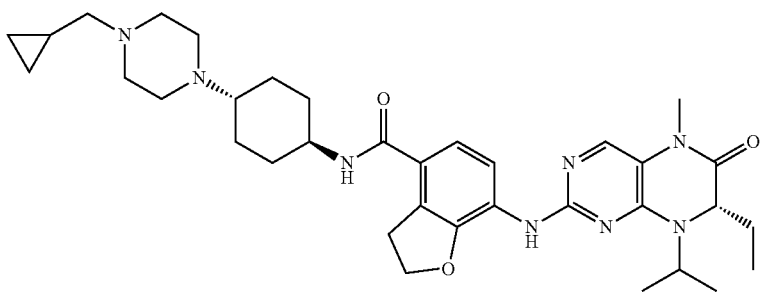 [SMILES: CC[C@H]1C(=O)N(C)c2cnc(Nc3ccc(C(=O)N[C@H]4CC[C@H](N5CCN(CC6CC6)CC5)CC4)c4c3OCC4)nc2N1C(C)C]<br>N-[(trans)-4-[4-(Cyclopropylmethyl)piperazin-1-yl]cyclohexyl]-7-[[(7S)-7-ethyl-8-isopropyl-5-methyl-6-oxo-7H-pteridin-2-yl]amino]-2,3-dihydrobenzofuran-4-carboxamide | or tautomers, racemates, enantiomers, diastereoisomers, and mixtures thereof, and pharmaceutically acceptable salts thereof.

In another aspect, this invention relates to the compounds of the following formula (IA) as intermediates in the synthesis of the compounds of formula (I):

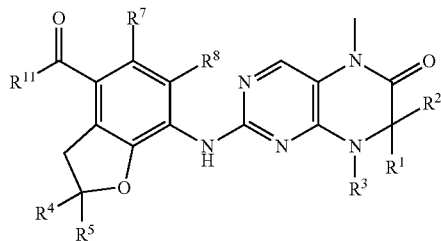

(IA)

wherein:

$R^1$ and $R^2$ are each independently selected from the group consisting of hydrogen, alkyl, alkenyl, alkynyl, cycloalkyl, heterocyclyl, aryl, heteroaryl, carboxy or carboxylic ester, wherein the alkyl, alkenyl, alkynyl, cycloalkyl, heterocyclyl, aryl or heteroaryl is each optionally substituted with one or more groups selected from the group consisting of alkyl, halogen, hydroxyl, aryl, sulfuryl, carboxy or carboxylic ester;

or, $R^1$ and $R^2$ are taken together with the attached atom to form a 3 to 6 membered ring, wherein the 3 to 6 membered ring optionally contains 1 to 2 N, O or S(O)n heteroatoms;

$R^3$ is selected from the group consisting of hydrogen, alkyl, alkenyl, alkynyl, cycloalkyl, heterocyclyl, aryl or heteroaryl, wherein the alkyl, alkenyl, alkynyl, cycloalkyl, heterocyclyl, aryl or heteroaryl is each optionally substituted with one or more groups selected from the group consisting of alkyl, alkoxyl, halogen, hydroxyl, aryl, sulfuryl, carboxy or carboxylic ester;

or, $R^1$ and $R^3$ or $R^2$ and $R^3$ are taken together with the attached atom to form a 3 to 6 membered ring, wherein the 3 to 6 membered ring contains 1 to 2 N, O or S(O)n heteroatoms, and the 3 to 6 membered ring is each optionally substituted with one or more groups selected from the group consisting of alkyl, alkoxyl, halogen, carbonyl, aryl, benzyl, —C(O)$R^9$, —C(O)N$R^9R^{10}$, —N$R^9R^{10}$, carboxy or carboxylic ester;

$R^4$ and $R^5$ are each independently selected from the group consisting of hydrogen, alkyl, alkoxyl, cyano, hydroxyl, halogen, alkenyl, alkynyl, cycloalkyl, heterocyclyl, aryl, heteroaryl, carboxy or carboxylic ester, wherein the alkyl, alkoxyl, alkenyl, alkynyl, cycloalkyl, heterocyclyl, aryl or heteroaryl is each optionally substituted with one or more groups selected from the group consisting of alkyl, alkoxyl, halogen, hydroxyl, aryl, sulfuryl, —N$R^9R^{10}$, carboxy or carboxylic ester;

$R^7$ and $R^8$ are each independently selected from the group consisting of hydrogen, alkyl or halogen;

$R^9$ and $R^{10}$ are each independently selected from the group consisting of hydrogen, alkyl, cycloalkyl, heterocyclyl, aryl, heteroaryl, carboxy or carboxylic ester, wherein the alkyl, cycloalkyl, heterocyclyl, aryl or heteroaryl is each optionally substituted with one or more groups selected from the group consisting of alkyl, halogen, hydroxyl, cyano, alkoxyl, aryloxyl, cycloalkyl, cycloalkylalkyl, heterocyclyl, aryl, heteroaryl, sulfuryl, carboxy or carboxylic ester;

or, $R^9$ and $R^{10}$ are taken together with the attached N atom to form a 4 to 8 membered heterocycle, wherein the 4 to 8 membered heterocycle contains one or more N, O or S(O)n heteroatoms, and the 4 to 8 membered heterocycle is each optionally substituted with one or more groups selected from the group consisting of alkyl, halogen, hydroxyl, haloalkyl, cyano, alkoxyl, aryloxyl, hydroxyl alkyl, cycloalkyl, cycloalkylalkyl, heterocyclyl, aryl, heteroaryl, sulfuryl, carboxy or carboxylic ester;

$R^{11}$ is selected from the group consisting of hydroxyl or alkoxyl; and n is 0, 1 or 2.

Preferably, the compounds of formula (IA), wherein $R^1$ and $R^2$ are each independently selected from the group consisting of hydrogen or alkyl; $R^3$ is selected from the group consisting of hydrogen, alkyl or cycloalkyl.

Preferably, the compounds of formula (IA), wherein $R^1$ and $R^2$ are each independently selected from the group consisting of hydrogen or alkyl;

$R^3$ is selected from the group consisting of alkyl or cycloalkyl;

$R^4$ and $R^5$ are each independently selected from the group consisting of hydrogen or alkyl, wherein the alkyl is optionally substituted with one or more groups selected from alkoxyl or $-NR^9R^{10}$;

$R^6$ is selected from the group consisting of alkyl, cycloalkyl or heterocyclyl, wherein the alkyl, cycloalkyl or heterocyclyl is each optionally substituted with one or more groups selected from the group consisting of alkyl, hydroxyl, cycloalkylalkyl, heterocyclyl, $-NR^9R^{10}$, carboxy or carboxylic ester;

$R^7$ and $R^8$ are independently hydrogen;

$R^9$ and $R^{10}$ are each independently selected from the group consisting of hydrogen, alkyl, cycloalkyl, heterocyclyl, aryl, heteroaryl, carboxy or carboxylic ester, wherein the alkyl, cycloalkyl, heterocyclyl, aryl or heteroaryl is each optionally substituted with one or more groups selected from the group consisting of alkyl, halogen, hydroxyl, cyano, alkoxyl, aryloxyl, heterocyclyl, aryl, heteroaryl, sulfuryl, carboxy or carboxylic ester;

or, $R^9$ and $R^{10}$ are taken together with the attached N atom to form a 4 to 8 membered heterocycle, wherein the 4 to 8 membered heterocycle contains one or more N, O or S(O)n heteroatoms, and the 4 to 8 membered heterocycle is each optionally substituted with one or more groups selected from the group consisting of alkyl, halogen, hydroxyl, haloalkyl, cyano, alkoxyl, aryloxyl, hydroxyl alkyl, cycloalkyl, cycloalkylalkyl, heterocyclyl, aryl, heteroaryl, sulfuryl, carboxy or carboxylic ester;

$R^{11}$ is selected from the group consisting of hydroxyl or alkoxyl; and n is 0, 1 or 2.

In another aspect, this invention relates to a preparation process of the compound of formula (I), comprising the following steps of:

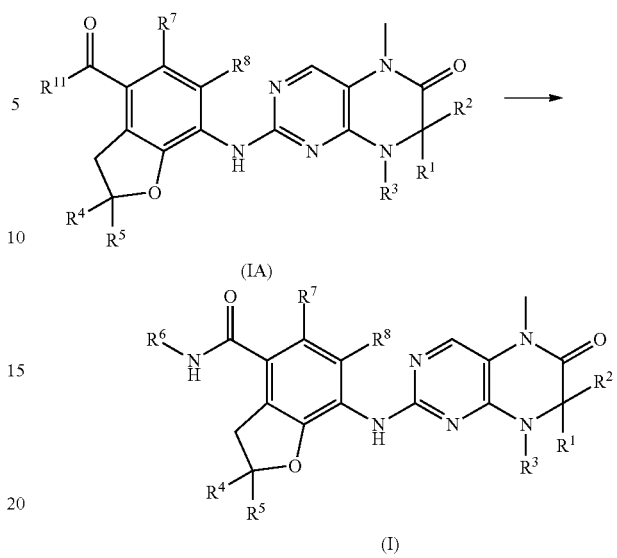

reacting the compounds of formula (IA) with $R^6NH_2$ to obtain the compounds of formula (I);

wherein $R^1$ to $R^8$ are defined as those in formula (I), and $R^{11}$ is defined as that in formula (IA).

In another aspect, this invention relates to a use of the compounds of formula (I) or tautomers, racemates, enantiomers, diastereoisomers, and mixtures thereof, and pharmaceutically acceptable salts thereof, in the preparation of a medicament for the treatment of cell proliferation disorder, wherein the cell proliferation disorder is selected from the group consisting of cancer, infection, inflammation or autoimmune disease; wherein the cancer is selected from the group consisting of non small-cell lung cancer, squamous cell carcinoma, breast cancer, ovarian cancer, uterine cervix cancer, papillary carcinoma or colorectal carcinoma; preferably uterine cervix cancer or colorectal carcinoma.

Furthermore, this invention also relates to a use of compounds of formula (I) or tautomers, racemates, enantiomers, diastereoisomers, and mixtures thereof, and pharmaceutically acceptable salts thereof, in the preparation of a medicament as a Plk inhibitor.

In still another aspect, the present invention relates to a pharmaceutical composition comprising a therapeutically effective amount of the compounds of formula (I) according to the present invention, or tautomers, racemates, enantiomers, diastereoisomers, and mixtures thereof, and pharmaceutically acceptable salts thereof, together with pharmaceutically acceptable carriers or excipients. And the present invention relates to a use of the said pharmaceutical composition in the preparation of a medicament for the treatment of cancer, infection, inflammation and autoimmune disease; wherein the cancer is selected from the group consisting of non small-cell lung cancer, squamous cell carcinoma, breast cancer, ovarian cancer, uterine cervix cancer, papillary carcinoma or colorectal carcinoma; preferably uterine cervix cancer or colorectal carcinoma. And the present invention relates to a use of the said pharmaceutical composition in the preparation of a medicament as a Plk inhibitor. And the present invention relates to the said pharmaceutical composition for use as a medicament for the treatment of cancer. And the present invention relates to a preparation process of the said pharmaceutical composition, comprising the step of combinating the compounds of formula (I) with the pharmaceutically acceptable carrier or excipient.

The present invention relates to a method for the treatment of cell proliferation disorder, wherein the method comprises administrating to the subject in need thereof a therapeutically effective amount of the compounds of formula (I), tautomers, racemates, enantiomers, diastereoisomers, and mixtures thereof, and pharmaceutically acceptable salts thereof or a pharmaceutical composition containing the same; wherein cell proliferation disorder is selected from the group consisting of cancer, infection, inflammation or autoimmune disease, wherein the cancer is selected from the group consisting of non small-cell lung cancer, squamous cell carcinoma, breast cancer, ovarian cancer, uterine cervix cancer, papillary carcinoma or colorectal carcinoma, preferably uterine cervix cancer or colorectal carcinoma.

The present invention relates to a method of modulating the activity of Plk kinase, wherein the method comprises administrating to the subject in need thereof a therapeutically effective amount of the compounds of formula (I), or tautomers, racemates, enantiomers, diastereoisomers, and mixtures thereof, and pharmaceutically acceptable salts thereof, or a pharmaceutical composition containing the same.

The present invention relates to the compound of formula (I) or tautomers, racemates, enantiomers, diastereoisomers, and mixtures thereof, and pharmaceutically acceptable salts thereof or a pharmaceutical composition thereof, for use as a medicament for the treatment of cell proliferation disorder, wherein cell proliferation disorder is selected from the group consisting of cancer, infection, inflammation or autoimmune disease, wherein the cancer is selected from the group consisting of non small-cell lung cancer, squamous cell carcinoma, breast cancer, ovarian cancer, uterine cervix cancer, papillary carcinoma or colorectal carcinoma, preferably uterine cervix cancer or colorectal carcinoma.

DETAILED DESCRIPTION OF THE INVENTION

Unless otherwise stated, the following terms used in the specification and claims have the meanings described below.

"Alkyl" refers to a saturated aliphatic hydrocarbon group including $C_1$-$C_{20}$ straight chain and branched chain groups. Preferably an alkyl group is an alkyl having 1 to 12 carbon atoms. Representative examples include, but are not limited to methyl, ethyl, n-propyl, isopropyl, n-butyl, isobutyl, tert-butyl, sec-butyl, n-pentyl, 1,1-dimethyl propyl, 1,2-dimethyl propyl, 2,2-dimethyl propyl, 1-ethyl propyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and the isomers of branched chain thereof. More preferably an alkyl group is a lower alkyl having 1 to 6 carbon atoms. Representative examples include, but are not limited to methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl and etc. The alkyl group may be substituted or unsubstituted. When substituted, the substituent group(s) is preferably one or more groups independently selected from the group consisting of alkyl, alkenyl, alkynyl, alkyxoyl, alkylsulfo, alkylamino, halogen, thiol, hydroxyl, nitro, cyano, cycloalkyl, heterocyclyl, aryl, heteroaryl, cycloalkyoxyl, heterocylic alkyoxyl, cycloalkylthio, heterocylic alkylthio, carbonyl, —C(O)$R^9$, —C(O)N$R^9R^{10}$, —N$R^9R^{10}$, carboxy or carboxylic ester.

"Alkenyl" refers to an alkyl defined as above that have at least two carbon atoms and at least one carbon-carbon double bond. For example, vinyl, 1-propenyl, 2-propenyl, 1-, 2- or 3-butenyl and etc. The alkenyl group may be substituted or unsubstituted. When substituted, the substituent group(s) is preferably one or more independently selected from the group consisting of alkyl, alkenyl, alkynyl, alkyxoyl, alkylsulfo, alkylamino, halogen, thiol, hydroxyl, nitro, cyano, cycloalkyl, heterocyclyl, aryl, heteroaryl, cycloalkyoxyl, heterocylic alkyoxyl, cycloalkylthio, heterocylic alkylthio, carbonyl, —C(O)$R^9$, —C(O)N$R^9R^{10}$, —N$R^9R^{10}$, carboxy or carboxylic ester.

"Alkynyl" refers to an alkyl defined as above that have at least two carbon atoms and at least one carbon-carbon triple bond. For example, ethynyl, 1-propynyl, 2-propynyl, 1-, 2- or 3-butynyl and etc. The alkynyl group may be substituted or unsubstituted. When substituted, the substituent group(s) is preferably one or more independently selected from the group consisting of alkyl, alkenyl, alkynyl, alkyxoyl, alkylsulfo, alkylamino, halogen, thiol, hydroxyl, nitro, cyano, cycloalkyl, heterocyclyl, aryl, heteroaryl, cycloalkyoxyl, heterocylic alkyoxyl, cycloalkylthio, heterocylic alkylthio, carbonyl, —C(O)$R^9$, —C(O)N$R^9R^{10}$, —N$R^9R^{10}$, carboxy or carboxylic ester.

"Cycloalkyl" refers to saturated and/or partially unsaturated monocyclic or polycyclic hydrocarbon group and have 3 to 20 carbon atoms. Preferably a cycloalkyl group is a cycloalkyl having 3 to 12 carbon atoms. More preferably a cycloalkyl group is a cycloalkyl having 3 to 10 carbon atoms. Representative examples of monocyclic cycloalkyl include, but are not limited to cyclopropyl, cyclobutyl, cyclopentyl, cyclopentenyl, cyclohexyl, cyclohexenyl, cyclohexadienyl, cycloheptyl, cycloheptatrienyl, cyclooctyl and etc. Polycyclic cycloalkyl includes the cycloalkyl having spiro ring, fused ring bridged ring.

"Spiro Cycloalkyl" refers to 5 to 20 membered polycyclic hydrocarbon group with rings connected through one common carbon atom (called as spiro atom), wherein one or more rings may contain one or more double bonds, but none of the rings has a completely conjugated pi-electron system. Preferably a spiro cycloalkyl is 6 to 14 membered, more preferably is 7 to 10 membered. According to the number of the common spiro atom, spiro cycloalkyl is divided into monocyclic spiro ring, bicyclic spiro ring or multicyclic spiro ring, preferably refers to monocyclic spiro ring or bicyclic spiro ring. More preferably spiro cycloalkyl is 4-membered/4-membered, 4-membered/5-membered, 4-membered/6-membered, 5-membered/5-membered, or 5-membered/6-membered monocyclic spiro ring. Representative examples of spiro cycloalkyl include, but are not limited to the following groups:

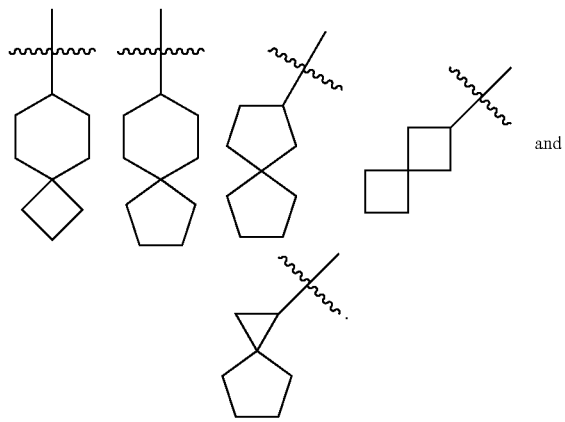

"Fused Cycloalkyl" refers to 5 to 20 membered polycyclic hydrocarbon group, wherein each ring in the system shares an adjacent pair of carbon atoms with other ring, wherein one or more rings may contain one or more double bonds, but none of the rings has a completely conjugated pi-electron system. Preferably an fused cycloalkyl group is 6 to 14 membered, more preferably is 7 to 10 membered. According to the number of membered ring, fused cycloalkyl is divided into fused bicyclic ring, tricyclic ring, tetracyclic ring or multicyclic ring, preferably refers to fused bicyclic ring or tricyclic ring. More preferably fused cycloalkyl is 5-membered/5-membered, or 5-membered/6-membered fused bicyclic ring. Representative examples of fused cycloalkyl include, but are not limited to the following groups:

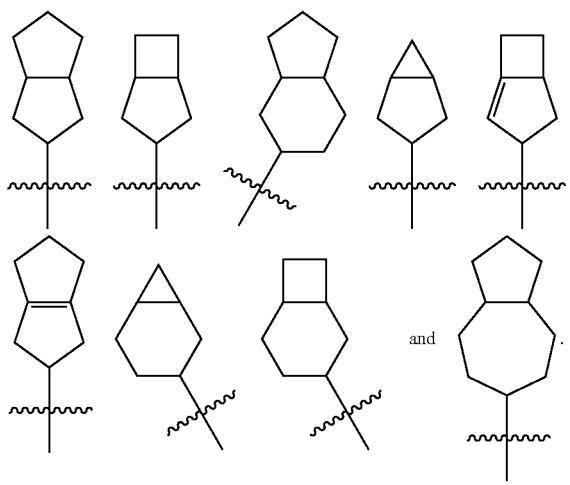

"Bridged Cycloalkyl" refers to 5 to 20 membered polycyclic hydrocarbon group, wherein every two rings in the system share with two disconnected carbon atoms. The said rings could have one or more double bonds but have no completely conjugated pi-electron system. Preferably an bridged cycloalkyl is 6 to 14 membered, more preferably is 7 to 10 membered. According to the number of membered ring, bridged cycloalkyl is divided into bridged bicyclic ring, tricyclic ring, tetracyclic ring or multicyclic ring, preferably refers to bicyclic ring, tricyclic ring or tetracyclic ring bridged cycloalkyl, more preferably refers to bicyclic ring or tricyclic ring bridged cycloalkyl. Representative examples of bridged cycloalkyl include, but are not limited to the following groups:

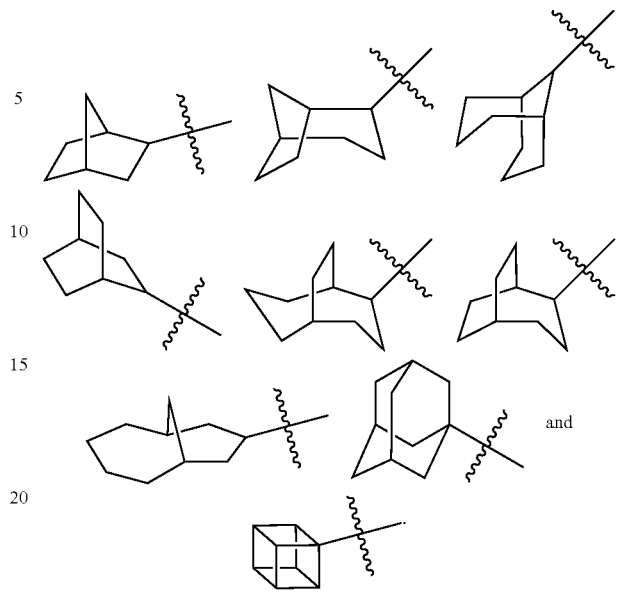

The said cycloalkyl can be fused to aryl, heteroaryl or heterocyclyl, wherein the ring connected with parent structure is cycloalkyl. Representative examples of bridged cycloalkyl include, but are not limited to indanylacetic, tetrahydronaphthalene, benzocycloheptyl and so on. Said cycloalkyl may be substituted or unsubstituted. When substituted, the substituent group(s) is preferably one or more groups independently selected from the group consisting of alkyl, alkenyl, alkynyl, alkyxoyl, alkylsulfo, alkylamino, halogen, thiol, hydroxyl, nitro, cyano, cycloalkyl, heterocyclyl, aryl, heteroaryl, cycloalkyoxyl, heterocyclic alkyoxyl, cycloalkylthio, heterocylic alkylthio, carbonyl, —C(O)R$^9$, —C(O)NR$^9$R$^{10}$, —NR$^9$R$^{10}$, carboxy or carboxylic ester.

"Heterocyclyl" refers to 3 to 20 membered saturated and/or partially unsaturated monocyclic or polycyclic hydrocarbon group having one or more heteroatoms selected from the group consisting of N, O, or S(O)n (wherein n is 0, 1 or 2) as ring atoms, but excluding —O—O—, —O—S— or —S—S— in the ring, the remaining ring atoms being C. Preferably, heterocyclyl is 3 to 12 membered having 1 to 4 said heteroatoms; more preferably, is 3 to 10 membered. Representative examples of monocyclic heterocyclyl include, but are not limited to pyrrolidyl, piperidyl, piperazinyl, morpholinyl, sulfo-morpholinyl, homopiperazinyl and so on. Polycyclic heterocyclyl includes the heterocyclyl having spiro ring, fused ring and bridged ring. "Spiro Heterocyclo alkyl" refers to 5 to 20 membered polycyclic heterocyclyl group with rings connected through one common carbon atom (called as spiro atom), wherein said rings have one or more heteroatoms selected from the group consisting of N, O, or S(O)$_p$ (wherein p is 0, 1 or 2) as ring atoms, the remaining ring atoms being C, wherein one or more rings may contain one or more double bonds, but none of the rings has a completely conjugated pi-electron system. Preferably an spiro heterocyclyl is 6 to 14 membered, more preferably is 7 to 10 membered. According to the number of common atom, spiro heterocyclyl is divided into monocyclic spiro heterocyclo alkyl, bicyclic spiro heterocyclyl or multicyclic spiro heterocyclo alkyl, preferably refers to monocyclic spiro heterocyclyl or bicyclic spiro heterocyclo alkyl. More preferably spiro heterocyclyl is 4-membered/4-membered, 4-membered/5-membered, 4-membered/6-membered, 5-membered/5-membered, or 5-membered/6-membered monocyclic spiro heterocyclo alkyl. Representative examples of spiro heterocyclyl include, but are not limited to the following groups:

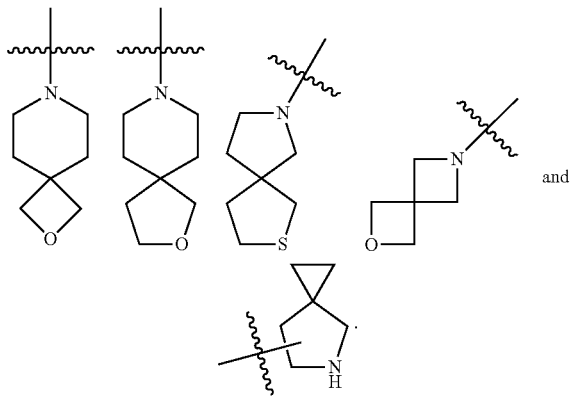

"Fused Heterocyclyl" refers to 5 to 20 membered polycyclic heterocyclyl group, wherein each ring in the system shares an adjacent pair of carbon atoms with other ring, wherein one or more rings may contain one or more double bonds, but none of the rings has a completely conjugated pi-electron system, and wherein said rings have one or more heteroatoms selected from the group consisting of N, O, or $S(O)_p$ (wherein p is 0, 1 or 2) as ring atoms, the remaining ring atoms being C. Preferably an fused heterocyclyl is 6 to 14 membered, more preferably is 7 to 10 membered. According to the number of membered ring, fused heterocyclyl is divided into fused bicyclic ring, tricyclic ring, tetracyclic ring or multicyclic ring, preferably refers to fused bicyclic ring or tricyclic ring. More preferably fused heterocyclyl is 5-membered/5-membered, or 5-membered/6-membered fused bicyclic ring. Representative examples of fused heterocyclyl include, but are not limited to the following groups:

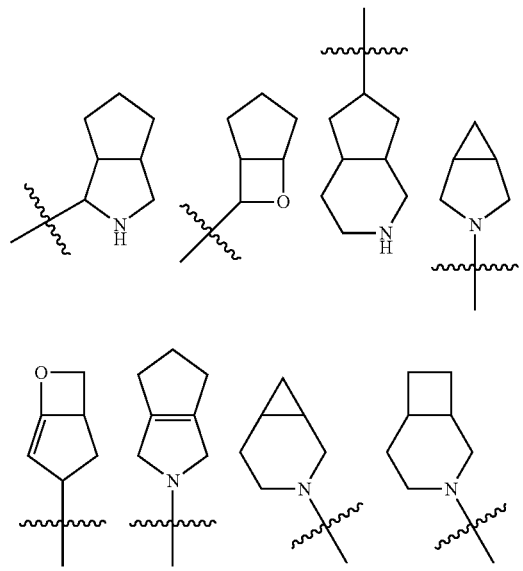

-continued

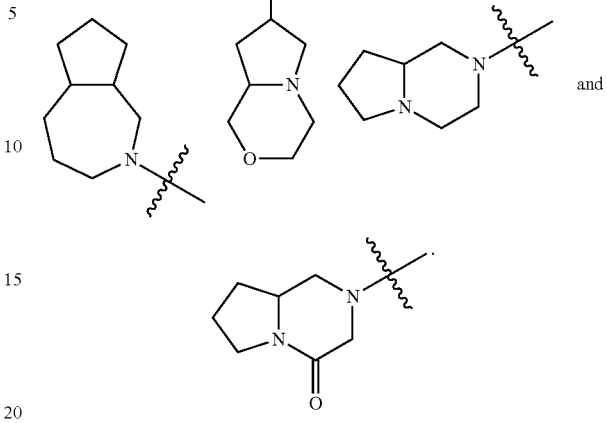

"Bridged Heterocyclyl" refers to 5 to 14 membered polycyclic heterocyclyl group, wherein every two rings in the system share with two disconnected carbon atoms, said rings could have one or more double bonds but have no completely conjugated pi-electron system, and said rings have one or more heteroatoms selected from the group consisting of N, O, or $S(O)_p$ (wherein p is 0, 1 or 2) as ring atoms, the remaining ring atoms being C. Preferably an bridged heterocyclyl is 6 to 14 membered, more preferably is 7 to 10 membered. According to the number of membered ring, bridged heterocyclyl is divided into bridged bicyclic ring, tricyclic ring, tetracyclic ring or multicyclic ring, preferably refers to bicyclic ring, tricyclic ring or tetracyclic ring bridged heterocyclo alkyl, more preferably refers to bicyclic ring or tricyclic ring bridged heterocyclo alkyl. Representative examples of bridged heterocyclyl include, but are not limited to the following groups:

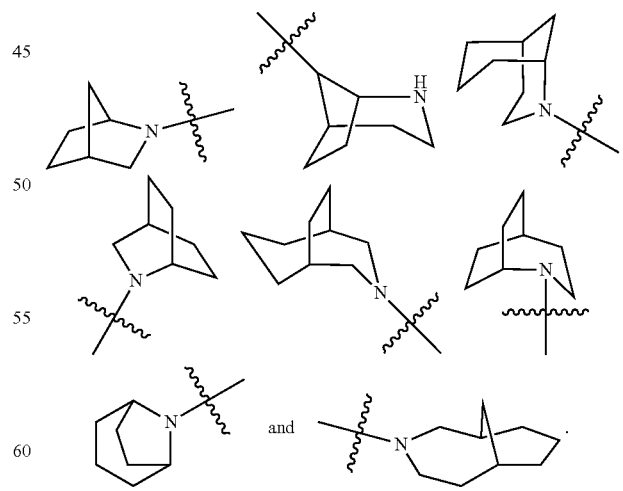

The said heterocyclyl can be fused to aryl, heterocyclyl or cycloalkyl, wherein the ring connected with parent structure is heterocyclo alkyl. Representative examples of heterocyclyl include, but are not limited to the following groups:

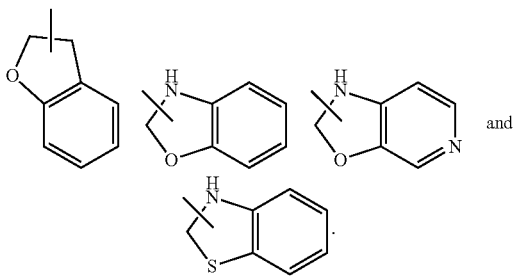

The heterocyclyl may be substituted or unsubstituted. When substituted, the substituent group(s) is preferably one or more groups independently selected from the group consisting of alkyl, alkenyl, alkynyl, alkyxoyl, alkylsulfo, alkylamino, halogen, thiol, hydroxyl, nitro, cyano, cycloalkyl, heterocyclyl, aryl, heteroaryl, cycloalkyoxyl, heterocylic alkyoxyl, cycloalkylthio, heterocylic alkylthio, carbonyl, —C(O)R$^9$, —C(O)NR$^9$R$^{10}$, —NR$^9$R$^{10}$, carboxy or carboxylic ester.

"Aryl" refers to refers to a 6 to 14 membered all-carbon monocyclic ring or a multicyclic fused ring (a "fused" ring system means that each ring in the system shares an adjacent pair of carbon atoms with other ring in the system) group, and has a completely conjugated pi-electron system. Preferably aryl is 6 to 10 membered, such as phenyl and naphthyl. The said aryl can be fused to heteroaryl, heterocyclyl or cycloalkyl, wherein the ring connected with parent structure is aryl. Representative examples of aryl include, but are not limited to the following groups:

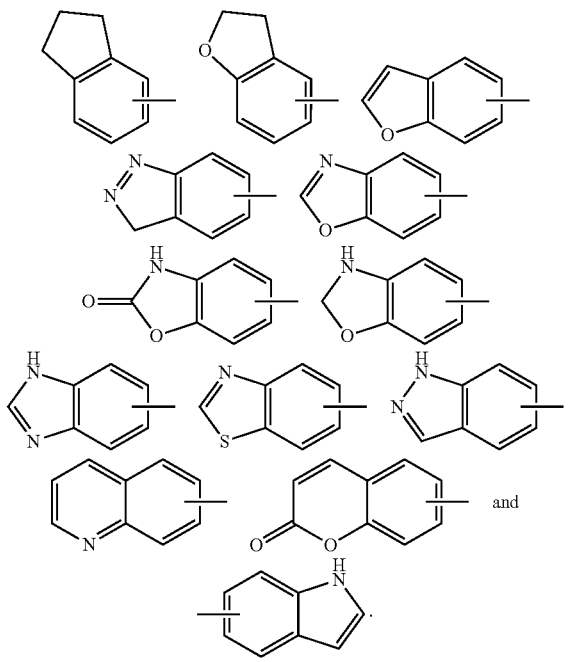

The aryl group may be substituted or unsubstituted. When substituted, the substituent group(s) is preferably one or more groups independently selected from the group consisting of alkyl, alkenyl, alkynyl, alkyxoyl, alkylsulfo, alkylamino, halogen, thiol, hydroxyl, nitro, cyano, cycloalkyl, heterocyclyl, aryl, heteroaryl, cycloalkyoxyl, heterocylic alkyoxyl, cycloalkylthio, heterocylic alkylthio, carbonyl, —C(O)R$^9$, —C(O)NR$^9$R$^{10}$, —NR$^9$R$^{10}$, carboxy or carboxylic ester.

"Heteroaryl" refers to an heteroaryl having 1 to 4 heteroatoms selected from the group consisting of N, O, or S as ring atoms and have 5 to 14 annular atoms, preferably 6- to 10-membered ring. More preferably 5- or 6-membered ring. The examples of heteroaryl groups include furyl, thienyl, pyridyl, pyrrolyl, N-alkyl pyrrolyl, pyrimidinyl, pyrazinyl, imidazolyl, and the like. The said heteroaryl can be fused with the ring of aryl, heterocylic group or cycloalkyl, wherein the ring connected with parent structure is heteroaryl. Representative examples include, but are not limited to the following groups,

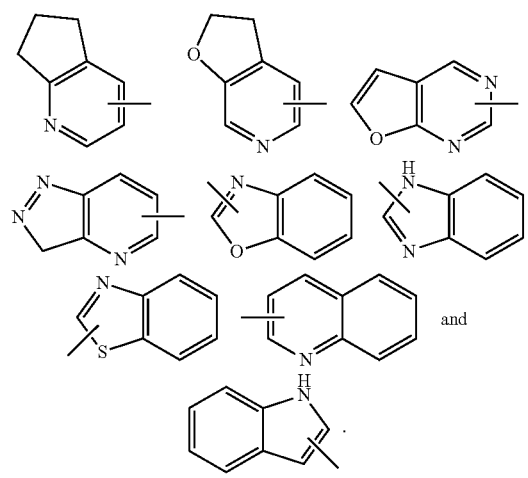

The heteroaryl group may be substituted or unsubstituted. When substituted, the substituent group(s) is preferably one or more groups independently selected from the group consisting of alkyl, alkenyl, alkynyl, alkyxoyl, alkylsulfo, alkylamino, halogen, thiol, hydroxyl, nitro, cyano, cycloalkyl, heterocyclyl, aryl, heteroaryl, cycloalkyoxyl, heterocylic alkyoxyl, cycloalkylthio, heterocylic alkylthio, carbonyl, —C(O)R$^9$, —C(O)NR$^9$R$^{10}$, —NR$^9$R$^{10}$, carboxy or carboxylic ester.

"Alkoxyl" refers to both an —O-(alkyl) and an —O-(unsubstituted cycloalkyl) group, wherein the alkyl is defined as above. Representative examples include, but are not limited to, methoxy, ethoxy, propoxy, butoxy, cyclopropyloxy, cyclobutyloxy, cyclopentyloxy, cyclohexyloxy, and the like. The alkoxyl may be substituted or unsubstituted. When substituted, the substituent is preferably one or more groups independently selected from the group consisting of alkyl, alkenyl, alkynyl, alkyxoyl, alkylsulfo, alkylamino, halogen, thiol, hydroxyl, nitro, cyano, cycloalkyl, heterocyclyl, aryl, heteroaryl, cycloalkyoxyl, heterocylic alkyoxyl, cycloalkylthio, heterocylic alkylthio, carbonyl, —C(O)R$^9$, —C(O)NR$^9$R$^{10}$, —NR$^9$R$^{10}$, carboxy or carboxylic ester.

"Aryoxyl" refers to both an —O-(aryl) and an —O-(heteroaryl) group, wherein the aryl and heteroaryl is defined as above. Representative examples include phenoxy, pyridinyl oxy, furyl oxy, thienyl oxy, pyrimidinyl oxy, pyrazinyl oxy and the derivatives thereof.

"Hydroxy" refers to an —OH group.

"Halogen" refers to fluoro, chloro, bromo or iodo.

"Amino" refers to a —NH$_2$ group.

"Cyano" refers to a —CN group.

"Nitro" refers to a -NO$_2$ group.

"sulfuryl" refers to a (group)-S(=O)$_2$-(group) group.

"Carbonyl" refers to a (group)-C(=O)-(group) group.

"Hydroxylalkyl" refers to a -alkyl-OH group, wherein the alkyl is defined as above.

"Benzyl" refers to a —CH₂-(pentyl) group, wherein the phenyl is defined as above.

"Carboxy" refers to a (alkyl) C(=O)OH group, wherein the alkyl is defined as above.

"Carboxylic ester" refers to a (alkyl) C(=O)O (alkyl), wherein the alkyl is defined as above.

A "pharmaceutical composition" refers to a mixture of one or more of the compounds described herein or physiologically/pharmaceutically acceptable salts or prodrugs thereof, with other chemical components such as physiologically/pharmaceutically acceptable carriers and excipients. The purpose of a pharmaceutical composition is to facilitate administration of a compound to an organism.

Synthesis Method of the Invention Compound

In order to complete the purpose of the invention, the invention applies the following technical solution:

A preparation process of the compounds of formula (I) of the invention, comprising the following steps of:

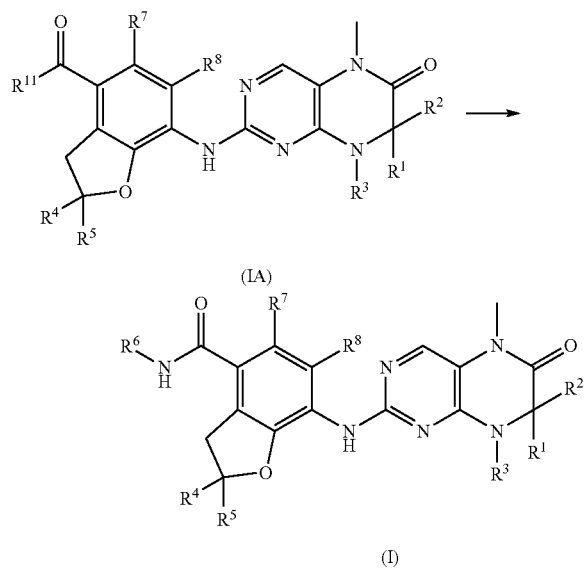

the compounds of formula (I) being optionally hydrolyzed and then condensated with R⁶NH₂ in the presence of O-(benzotriazol-1-yl)-N,N,N',N'-tetramethyluronium tetrafluoroborate to obtain the compounds of formula (I).

Wherein R¹ to R⁸ are defined as those in formula (I), and R¹¹ is defined as that in formula (IA).

Preferred Embodiments

The following examples serve to illustrate the invention, but the examples should not be considered as limiting the scope of the invention.

Examples

The compound's structure was indentified by NMR and/or MS. NMR chemical shifts (δ) were given in ppm. NMR is determined by a Bruker AVANCE-400 machine. The solvents were deuterated-dimethyl sulfoxide (DMSO-d₆), deuterated-chloroform (CDCl₃) and deuterated-methanol (CD₃OD) with tetramethylsilane (TMS) as an internal standard.

MS was determined by a FINNIGAN LCQAd (ESI) mass spectrometer (manufacturer: Thermo, type: Finnigan LCQ advantage MAX);

HPLC was determined on an Agilent 1200DAD high pressure liquid chromatography spectrometer (Sunfire C18 150× 4.6 mm chromatographic column) and a Waters 2695-2996 high pressure liquid chromatography spectrometer (Gimini C18 150×4.6 mm chromatographic column).

IC₅₀ was determined by a NovoStar ELIASA (BMG Co., German);

The thin-layer silica gel used Yantai Huanghai HSGF254 or Qingdao GF254 silica gel plate. The dimension of the plates used in TLC was 0.15 mm to 0.2 mm, and the dimension of the plates used in product purification was 0.4 mm to 0.5 mm.

Column chromatography generally used Yantai Huanghai 200 to 300 mesh silica gel as carrier.

The known starting material of the invention can be prepared by the conventional synthesis method in the prior art, or be purchased from ABCR GmbH & Co. KG, Acros Organics, Aldrich Chemical Company, Accela ChemBio Inc or Dari chemical Company, etc.

Unless otherwise stated, the following reactions were placed under nitrogen atmosphere or argon atmosphere.

The term "nitrogen atmosphere" or "argon atmosphere" refers to that a reaction flask is equipped with a 1 L nitrogen or argon balloon.

The term "hydrogen atmosphere" refers to that a reaction flask is equipped with a 1 L hydrogen balloon.

Pressured hydrogenation reactions were performed with a Parr 3916EKX hydrogenation spectrometer and a QL-500 hydrogen generator.

In hydrogenation reactions, the reaction system was generally vacuumed and filled with hydrogen, repeat the above operation three times.

HPLC preparative chromatography: Gilson GX-281.

Microwave reactions were performed with a CEM Discover-S 908860 microwave reactor.

Unless otherwise stated, the solution used in following reaction refers to an aqueous solution.

Unless otherwise stated, the reaction temperature in the following reaction was room temperature.

Room temperature was the most ambient reaction temperature, which was 20° C.-30° C.

The reaction process was monitored by thin layer chromatography (TLC), the system of developing solvent included: dichloromethane and methanol, hexane and ethyl acetate, petroleum ether and ethyl acetate, acetone. The ratio of the volume of the solvent was adjusted according to the polarity of the compounds.

The elution system of purification the compounds by the column chromatography and thin layer chromatography included: A: dichloromethane and methanol system, B: hexane and ethyl acetate system, C: ethyl acetate and methanol system, D: hexane, E: ethyl acetate. The volume of the solvent was adjusted according to the polar of the compounds, and sometimes a little alkaline reagent such as triethylamine and acidic reagent such as acetic acid was also added.
PREPARATION EXAMPLES
Example 1
7-[[(7R)-8-Cyclopentyl-7-ethyl-5-methyl-6-oxo-7H-pteridin-2-yl]amino]-N-(1-methyl-piperidyl)-2,3-dihydrobenzofuran-4-carboxamide
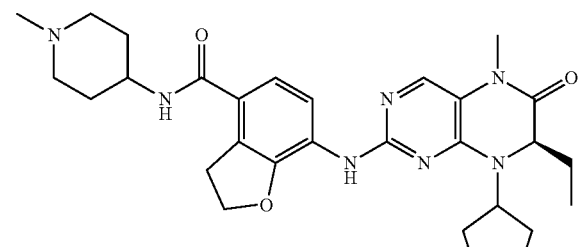
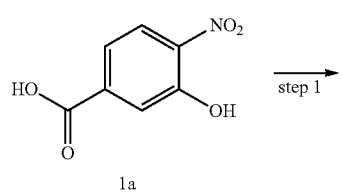
1a
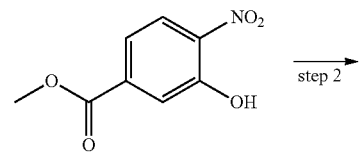
1b
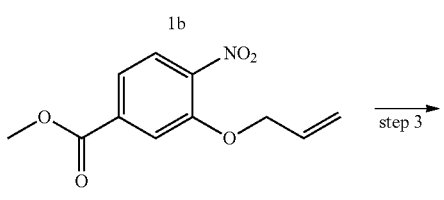
1c
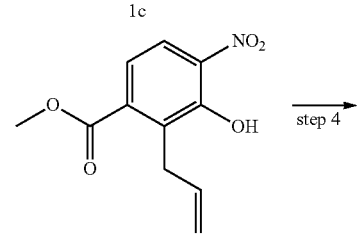
1d
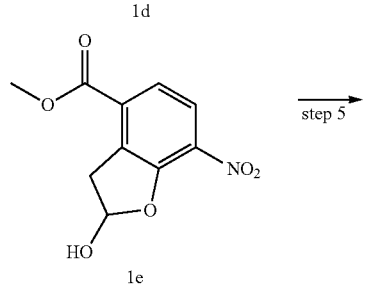
1e
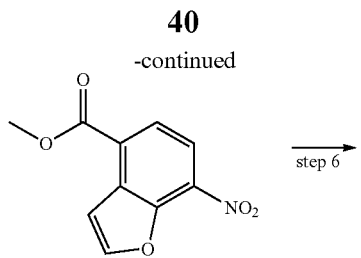
1f
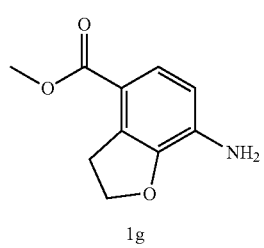
1g
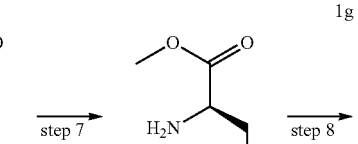
1h    1j
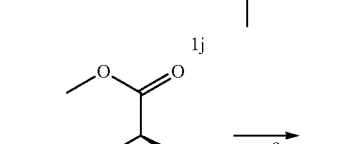
1k
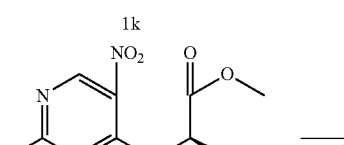
1m
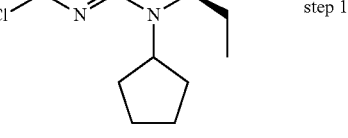
1n
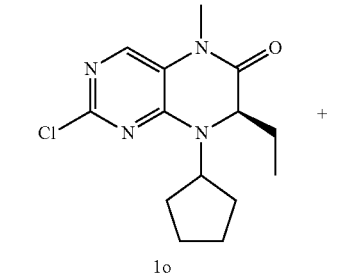
1o -continued

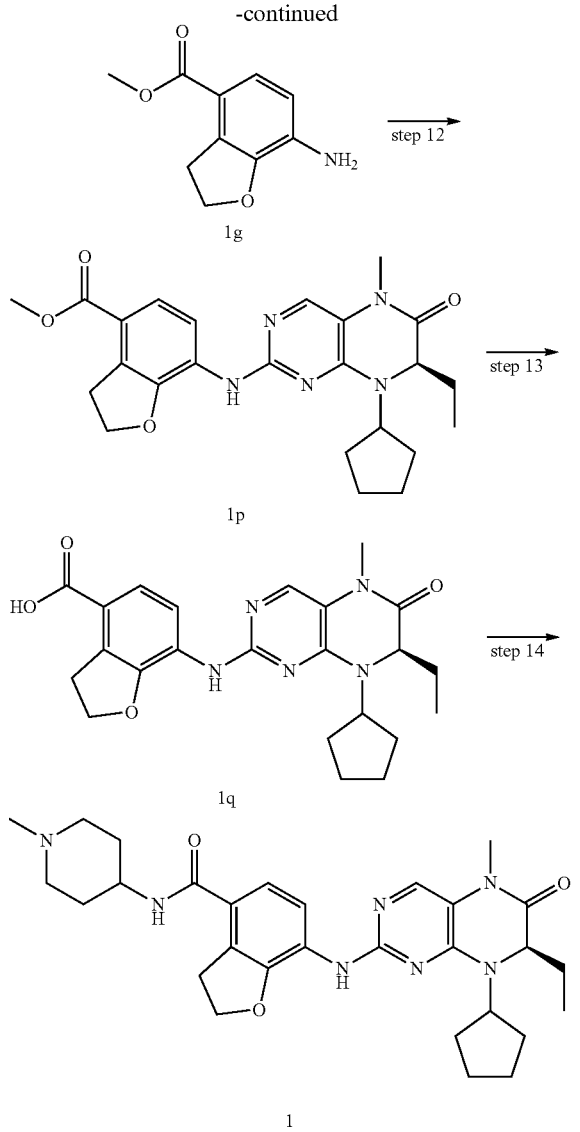

Step 1

Methyl 3-hydroxy-4-nitro-benzoate

3-Hydroxy-4-nitro-benzoic acid 1a (3.17 g, 17.32 mmol) was dissolved in 40 mL of anhydrous methanol. The reaction solution was cooled down to 0° C. and added dropwise with thionyl chloride (3.09 g, 25.98 mmol) with stirring. Upon the completion of the addition, the resulting solution was heated to reflux for 2 hours. The reaction solution was concentrated under reduced pressure, extracted with ethyl acetate (200 mL). The combined organic phase was washed with saturated sodium bicarbonate solution (100 mL×3), saturated sodium chloride solution (100 mL×3) successively, then dried over anhydrous magnesium sulfate, filtered and the filtrate was concentrated under reduced pressure to obtain the title compound methyl 3-hydroxy-4-nitro-benzoate 1b (3.30 g as a yellow solid) yield: 96.7%.

MS m/z (ESI): 195.8 [M−1]

Step 2

Methyl 3-allyloxy-4-nitro-benzoate

Methyl 3-hydroxy-4-nitro-benzoate 1b (7 g, 35.50 mmol) was dissolved in 100 mL of anhydrous acetonitrile followed by the addition of potassium carbonate (14.70 g, 106.50 mmol) and 3-bromopropene (6.2 mL, 71 mmol) successively, the reaction mixture was heated to reflux for 3 hours with stirring. The resulting mixture was filtered and the filtrate was concentrated under reduced pressure. The crude residue was added with 150 mL of ethyl acetate, washed with water (100 mL×3) and saturated sodium chloride solution (100 mL×3) successively, then dried over anhydrous magnesium sulfate, filtered and the filtrate was concentrated under reduced pressure. The resulting residue was purified by silica gel column chromatography to obtain the title compound methyl 3-allyloxy-4-nitro-benzoate 1c (7.45 g, yield: 89.0%) as a yellow solid.

MS m/z (ESI): 235.9 [M−1]

Step 3

Methyl 2-allyl-3-hydroxy-4-nitro-benzoate

Methyl 3-allyloxy-4-nitro-benzoate 1c (6 g, 25.30 mmol) was added into a three-necked flask, heated to 190° C. for 3 hours and cooled down to room temperature. The resulting mixture was added with 150 mL of ethyl acetate, concentrated under reduced pressure. The resulting residue was purified by silica gel column chromatography to obtain the title compound methyl 2-allyl-3-hydroxy-4-nitro-benzoate 1d (4.06 g, yield: 68.0%) as a yellow liquid.

MS m/z (ESI): 235.9 [M−1]

Step 4

Methyl 2-hydroxy-7-nitro-2,3-dihydrobenzofuran-4-carboxylate

Methyl 2-allyl-3-hydroxy-4-nitro-benzoate 1d (5.39 g, 22.70 mmol) was dissolved in 110 mL of the mixture solvent of dichloromethane and methanol (V/V=10:1), the reaction solution was cooled down to −78° C. and filled with oxone. After stirring for 50 minutes, oxone was removed from filling with. The reaction mixture was stirred for another 20 minutes, then filled with argon and stirred for 10 minutes. Triphenyl phosphine (17.80 g, 68.10 mmol) was added. After removing the dry ice bath, the resulting mixture was allowed to room temperature and stirred for 3 hours. The reaction solution was concentrated under reduced pressure, added with 200 mL of ethyl acetate, washed with water (100 mL×3) and saturated sodium chloride solution (100 mL×3) successively, then dried over anhydrous magnesium sulfate, filtered and the filtrate was concentrated under reduced pressure. The resulting residue was purified by silica gel column chromatography to obtain the title compound methyl 2-hydroxy-7-nitro-2,3-dihydrobenzofuran-4-carboxylate 1e (5.20 g, yield: 96.0%) as a brown solid.

MS m/z (ESI): 237.9 [M−1]

Step 5

Methyl 7-nitrobenzofuran-4-carboxylate

Methyl 2-hydroxy-7-nitro-2,3-dihydrobenzofuran-4-carboxylate 1e (2 g, 8.40 mmol) was suspended in 250 mL of 85% phosphoric acid, stirred for 10 minutes, puted into a 100° C. oil bath and stirred for another 20 minutes. The resulting reaction mixture was added with 50 mL of water, extracted with ethyl acetate (50 mL×3). The combined organic phase was washed with saturated sodium carbonate solution (50 mL×3) and saturated sodium chloride solution (50 mL×3) successively, then dried over anhydrous sodium sulfate, filtered and the filtrate was concentrated under reduced pressure. The resulting residue was purified by silica gel column chromatography to obtain the title compound methyl 7-nitrobenzofuran-4-carboxylate 1f (0.63 g, yield: 34.0%) as a light yellow solid.

MS m/z (ESI): 220.7 [M−1]

Step 6

Methyl 7-amino-2,3-dihydrobenzofuran-4-carboxylate

Methyl 7-nitrobenzofuran-4-carboxylate 1f (820 mg, 3.70 mmol) was dissolved in 150 mL of methanol in an ice-water bath, added with (164 mg, 10%) palladium/carbon, methanol (0.3 mL). The resulting solution was subjected to hydrogenation for 16 hours at 3 atmosphere at room temperature. The resulting mixture was filtered and washed with 50 mL of methanol, concentrated under reduced pressure. The crude residue was recrystallised by the mixture solvent of 25 mL ethyl acetate and n-hexane (V/V=1:4) to obtain the title compound methyl 7-amino-2,3-dihydrobenzofuran-4-carboxylate 1g (446 mg, yield: 62.0%) as a gray solid.

MS m/z (ESI): 194.1 [M+1]

Step 7

Methyl (2R)-2-aminobutanoate (R)-2-Aminobutanoic acid 1 h (10 g, 0.10 mol) was dissolved in 50 mL of methanol. The solution was cooled down to −10° C. in an ice-salt bath, added dropwise with thionyl chloride (13 mL, 0.17 mol). Upon the completion of the addition, the resulting mixture was heated to reflux for 1 hour with stirring and cooled down to room temperature. The reaction mixture was concentrated under reduced pressure to obtain the crude title compound methyl (2R)-2-aminobutanoate 1j as a colourless oil liquid, which was used in the next step without further furification.

MS m/z (ESI): 118.0 [M+1]

Step 8

Methyl (2R)-2-(cyclopentylamino)butanoate

The crude compound methyl (2R)-2-aminobutanoate 1j (11.24 g, 0.10 mol) and cyclopentanone (8.24 g, 0.10 mol) were dissolved in 150 mL of dichloromethane, stirred for 1.5 hours followed by the addition of sodium acetate (8.04 g, 0.10 mol) and sodium triacetoxyborohydride (30.52 g, 0.14 mol), and stirred for 3 hours. The reaction solution was poured into 150 mL 10% sodium bicarbonate solution, extracted with dichloromethane (100 mL×3). The combined organic phase was washed with saturated sodium chloride solution (100 mL×3), then dried over anhydrous magnesium sulfate, filtered and the filtrate was concentrated under reduced pressure. The resulting residue was purified by silica gel column chromatography to obtain the title compound methyl (2R)-2-(cyclopentylamino)butanoate 1k (6.04 g, yield: 34.0%) as a light liquid.

MS m/z (ESI): 186.1 [M+1]

Step 9

Methyl (2R)-2-[(2-chloro-5-nitro-pyrimidin-4-yl)-(1-cyclopentyl)amino]butanoate

Methyl (2R)-2-(cyclopentylamino)butanoate 1k (2.50 g, 13.50 mmol) and sodium bicarbonate (4.54 g, 54 mmol) were dissolved in 100 mL of cyclohexane, stirred for 30 minutes followed by the addition of 2,4-dichloro-5-nitro-pyrimidine (2.88 g, 14.84 mmol), heated to 60° C. and stirred for another 12 hours. The reaction mixture was filtered, washed with dichloromethane (50 mL), and the filtrate was concentrated under reduced pressure, the resulting residue was recrystallized by 150 mL of the mixture solvent of ethyl acetate and n-hexane (V/V=1:4) to obtain the title compound methyl (2R)-2-[(2-chloro-5-nitro-pyrimidin-4-yl)-(1-cyclopentyl)amino]butanoate 1m (3.36 g, yield: 72.6%) as a light yellow solid.

MS m/z (ESI): 343.1 [M+1]

Step 10

(7R)-2-chloro-8-cyclopentyl-7-ethyl-7,8-dihydro-5H-pteridin-6-one

Methyl (2R)-2-[(2-chloro-5-nitro-pyrimidin-4-yl)-cyclopentyl-amino]butanoate 1m (1 g, 3 mmol) was dissolved in 10 mL of acetic acid followed by the addition of Raney nickel (0.50 g), filled with hydrogen three times, then heated to 75-80° C. and stirred for 12 hours. The reaction mixture was filtered, washed with dichloromethane (50 mL). The filtrate was concentrated under reduced pressure, added with 100 mL ethyl acetate, washed with water (50 mL×3) and saturated sodium chloride solution (50 mL×3) successively. The combined organic phase was dried over anhydrous magnesium sulfate, filtered and the filtrate was concentrated under reduced pressure. The resulting residue was purified by silica gel column chromatography to obtain the title compound (7R)-2-chloro-8-cyclopentyl-7-ethyl-7,8-dihydro-5H-pteridin-6-one 1n (0.56 g, yield: 66.7%) as a white solid.

MS m/z (ESI): 281.2 [M+1]

Step 11

(7R)-2-chloro-8-cyclopentyl-7-ethyl-5-methyl-5H-pteridin-6-one (7R)-2-Chloro-8-cyclopentyl-7-ethyl-7,8-dihydro-5H-pteridin-6-one 1n (3.50 g, 12.50 mmol) was dissolved in 80 mL of acetone followed by the addition of methyl p-toluenesulfonate (3.40 g, 18.70 mmol) and potassium carbonate (3.45 g, 25 mmol). The resulting mixture was heated to reflux for 2 hours with stirring and then cooled down to room temperature. The reaction mixture was filtered and the filtrate was concentrated under reduced pressure. The resulting residue was purified by silica gel column chromatography to obtain the title compound (7R)-2-chloro-8-cyclopentyl-7-ethyl-5-methyl-5H-pteridin-6-one 1o (3.40 g, yield: 93.0%) as a white solid.

MS m/z (ESI): 295.4 [M+1]

Step 12 methyl 7-[[(7R)-8-cyclopentyl-7-ethyl-5-methyl-6-oxo-7H-pteridin-2-yl]amino]-2,3-dihydrobenzofuran-4-carboxylate (7R)-2-Chloro-8-cyclopentyl-7-ethyl-5-methyl-5H-pteridin-6-one 1o (670 mg, 2.30 mmol), methyl 7-amino-2,3-dihydrobenzofuran-4-carboxylate 1g (440 mg, 2.30 mmol) and p-toluenesulfonic acid (700 mg, 3.68 mmol) were dissolved in 25 mL 4-methyl-2-pentanol. The resulting solution was heated to reflux for 6 hours with stirring. The reaction solution was added with 25 mL of saturated sodium bicarbonate solution, extracted with ethyl acetate (50 mL×3). The combined organic phase was washed with water (50 mL×3) and saturated sodium chloride solution (50 mL×3) successively, then dried over anhydrous sodium sulfate, filtered and the filtrate was concentrated under reduced pressure. The resulting residue was purified by silica gel column chromatography to obtain the title compound methyl 7-[[(7R)-8-cyclopentyl-7-ethyl-5-methyl-6-oxo-7H-pteridin-2-yl]amino]-2,3-dihydrobenzofuran-4-carboxylate 1p (0.77 g, yield: 74.0%) as a light yellow solid.

MS m/z (ESI): 452.3 [M+1]

Step 13

7-[[(7R)-8-cyclopentyl-7-ethyl-5-methyl-6-oxo-7H-pteridin-2-yl]amino]-2,3-dihydrobenzofuran-4-carboxylic acid Methyl 7-[[(7R)-8-cyclopentyl-7-ethyl-5-methyl-6-oxo-7H-pteridin-2-yl]amino]-2,3-dihydrobenzofuran-4-carboxylate 1p (5 g, 11 mmol) was dissolved in 180 mL mixture solution of 1 mol/L lithium hydroxide solution and methanol (V/V=1:1). The resulting mixture was heated to reflux for 3 hours with stirring. The reaction solution was added with 50 mL of water, concentrated under reduced pressure and extracted with ethyl acetate (50 mL×3). 1 M hydrochloric acid was added dropwise to adjust the aqueous phase pH to 2 resulting in the formation of precipitate. The precipitate was filtered, and dried to obtain the title compound 7-[[(7R)-8-cyclopentyl-7-ethyl-5-methyl-6-oxo-7H-pteridin-2-yl]amino]-2,3-dihydrobenzofuran-4-carboxylic acid 1q (4.70 g, yield: 97.0%) as a white solid.

MS m/z (ESI): 436.3 [M−1]

Step 14

7-[[(7R)-8-cyclopentyl-7-ethyl-5-methyl-6-oxo-7H-pteridin-2-yl]amino]-N-(1-methyl-piperidyl)-2,3-dihydrobenzofuran-4-carboxamide 7-[[(7R)-8-Cyclopentyl-7-ethyl-5-methyl-6-oxo-7H-pteridin-2-yl]amino]-2,3-dihydrobenzofuran-4-carboxylic acid 1q (300 mg, 0.68 mmol) and O-(benzotriazol-1-yl)-N,N,N',N'-tetra methyluronium tetrafluoroborate (148 mg, 0.46 mmol) were dissolved in 30 mL of dichloromethane, followed by the addition of diisopropylethylamine (131 mg, 1 mmol). The reaction solution was stirred for 10 minutes followed by the addition of 1-methyl-piperidin-4-yl amine (52 mg, 0.46 mmol), and stirred for another 3 hours. The reaction mixture was added with 30 mL of saturated sodium chloride solution and 30 mL of dichloromethane successively, then seperated. The organic phase was washed with saturated sodium carbonate solution (50 mL×2), water (50 mL) and saturated sodium chloride solution (50 mL) successively, then dried over anhydrous sodium sulfate, filtered and the filtrate was concentrated under reduced pressure. The resulting residue was purified by silica gel column chromatography to obtain the title compound 7-[[(7R)-8-cyclopentyl-7-ethyl-5-methyl-6-oxo-7H-pteridin-2-yl]amino]-N-(1-methyl-piperidyl)-2,3-dihydrobenzofuran-4-carboxamide 1 (194 mg, yield: 79%) as a white solid.

MS m/z (ESI): 534.4[M+1]

$^{1}$H NMR (400 MHz, CDCl$_3$) δ 8.28 (d, 1H), 7.67 (s, 1H), 7.10 to 7.00 (m, 2H), 5.89 (d, 1H), 4.68 (t, 2H), 4.47 (t, 1H), 4.21 (dd, 1H), 4.07 to 3.91 (m, 1H), 3.58 (t, 2H), 3.32 (s, 3H), 2.91 (d, 2H), 2.36 (s, 3H), 2.24 (t, 2H), 2.16 to 1.83 (m, 4H), 1.86 to 1.78 (m, 4H), 1.76 to 1.62 (m, 6H), 0.88 (t, 3H)

Example 2

7-[[(7R)-8-cyclopentyl-7-ethyl-5-methyl-6-oxo-7H-pteridin-2-yl]amino]-N-[(4-methylmorpholin-2-yl)methyl]-2,3-dihydrobenzofuran-4-carboxamide

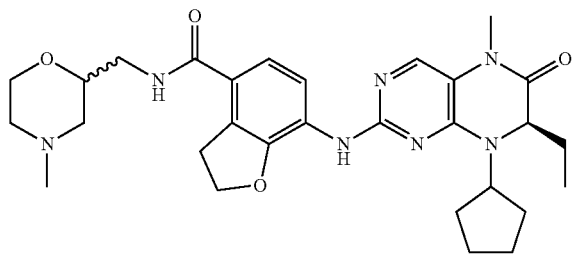

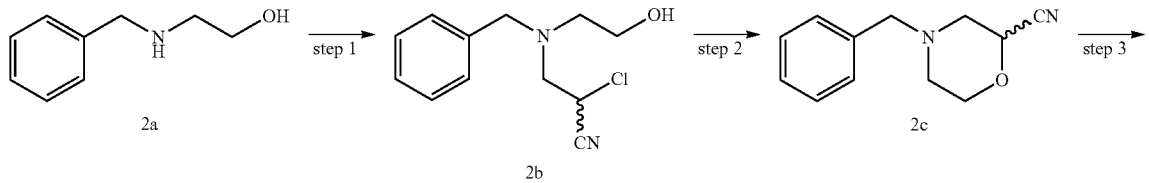

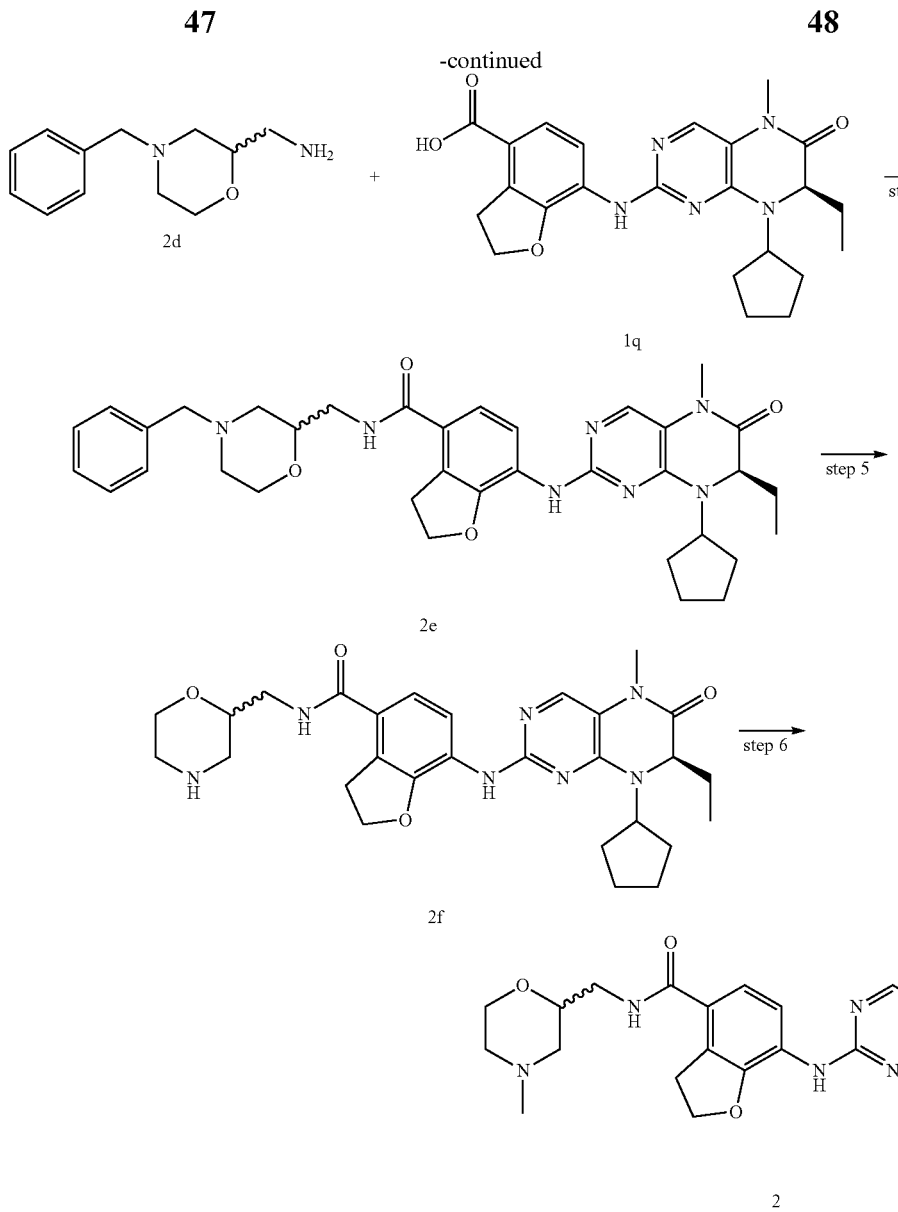

Step 1

3-(benzyl(2-hydroxyethyl)amino)-2-chloro-propanenitrile 2-(benzylamino)ethanol 2a (5 g, 0.03 mol) and 2-chloro-propenenitrile (3 g, 0.03 mol) were dissolved in 50 mL of anhydrous ethyl ether in an ice-water bath, heated to room temperature and stirred for 12 hours. The reaction solution was concentrated under reduced pressure to obtain the crude title compound 3-(benzyl(2-hydroxyethyl)amino)-2-chloro-propanenitrile 2b (7 g) as a red oil liquid, which was used in the next step without further furification.

Step 2

4-benzylmorpholine-2-carbonitrile

The crude compound 3-(benzyl(2-hydroxyethyl)amino)-2-chloro-propanenitrile 2b (8 g, 0.03 mol) was dissolved in 70 mL of tetrahydrofuran followed by the addition of potassium tert-butanolate (5.50 g, 0.05 mol) in an ice-water bath. The resulting solution was stirred for 2 hours, heated to reflux for 1 hour, added with 50 mL of saturated sodium carbonate solution, and extracted with ethyl acetate (40 mL×3). The combined organic phase was washed with saturated sodium chloride solution (50 mL×3), then dried over anhydrous magnesium sulfate, filtered and the filtrate was concentrated under reduced pressure. The resulting residue was purified by silica gel column chromatography to obtain the title compound 4-benzylmorpholine-2-carbonitrile 2c (2.71 g, yield: 41.0%) as a yellow oil liquid.

MS m/z (ESI): 203.2 [M+1]

Step 3

(4-benzylmorpholin-2-yl)methanamine 4-benzylmorpholine-2-carbonitrile 2c (0.80 g, 4 mmol) was dissolved in 30 mL of methanol followed by the addition of Raney nickel (0.50 g), filled with hydrogen two times and the resulting solution was stirred for 12 hours, filtered. The filtrate was concentrated under reduced pressure to obtain the crude title compound (4-benzylmorpholin-2-yl)methanamine 2d (0.60 g) as a colorless oil liquid, which was used in the next step without further furification.

Step 4

N-[(4-benzylmorpholin-2-yl)methyl]-7-[[(7R)-8-cyclopentyl-7-ethyl-5-methyl-6-oxo-7H-pteridin-2-yl]amino]-2,3-dihydrobenzofuran-4-carboxamide The crude compound (4-benzylmorpholin-2-yl)methanamine 2d (141 mg, 0.69 mmol), 7-[[(7R)-8-cyclopentyl-7-ethyl-5-methyl-6-oxo-7H-pteridin-2-yl]amino]-2,3-dihydrobenzofuran-4-carboxylic acid 1q (300 mg, 0.69 mmol), O-(benzotriazol-1-yl)-N,N,N',N'-tetra methyluronium tetrafluoroborate (221 mg, 0.69 mmol) and diisopropylethylamine (260 mL, 1.52 mmol) were dissolved in 40 mL of dichloromethane, stirred for 12 hours. The resulting mixture was added with 50 mL of saturated sodium bicarbonate solution, extracted with dichloromethane (50 mL×3). The combined organic phase was washed with saturated sodium chloride solution (50 mL×3), then dried over anhydrous magnesium sulfate, filtered and the filtrate was concentrated under reduced pressure. The resulting residue was purified by silica gel column chromatography to obtain the title compound N-[(4-benzylmorpholin-2-yl)methyl]-7-[[(7R)-8-cyclopentyl-7-ethyl-5-methyl-6-oxo-7H-pteridin-2-yl]amino]-2,3-dihydrobenzofuran-4-carboxamide 2e (190 mg, yield: 44.0%) as a white solid.
MS m/z (ESI): 626.5 [M+1]

Step 5

7-[[(7R)-8-cyclopentyl-7-ethyl-5-methyl-6-oxo-7H-pteridin-2-yl]amino]-N-(morpholin-2-ylmethyl)-2,3-dihydrobenzofuran-4-carboxamide N-[(4-benzylmorpholin-2-yl)methyl]-7-[[(7R)-8-cyclopentyl-7-ethyl-5-methyl-6-oxo-7H-pteridin-2-yl]amino]-2,3-dihydrobenzofuran-4-carboxamide 2e (0.19 g, 0.30 mmol) was dissolved in 30 mL of methanol followed by the addition of palladium/carbon (40 mg, 10%), filled with hydrogen two times. The reaction solution was stirred for 2 hours and filtered. The filtrate was concentrated under reduced pressure to obtain the crude title compound 7-[[(7R)-8-cyclopentyl-7-ethyl-5-methyl-6-oxo-7H-pteridin-2-yl]amino]-N-(morpholin-2-ylmethyl)-2,3-dihydrobenzofuran-4-carboxamide 2f (163 mg) as a white solid, which was used in the next step without further furification.

Step 6

7-[[(7R)-8-cyclopentyl-7-ethyl-5-methyl-6-oxo-7H-pteridin-2-yl]amino]-N-[(4-methylmorpholin-2-yl)methyl]-2,3-dihydrobenzofuran-4-carboxamide The crude compound 7-[[(7R)-8-cyclopentyl-7-ethyl-5-methyl-6-oxo-7H-pteridin-2-yl]amino]-N-(morpholin-2-ylmethyl)-2,3-dihydrobenzofuran-4-carboxamide 2f (163 mg, 0.30 mmol) was dissolved in 60 mL of the mixture solvent of acetonitrile and water (V/V=1:1) in an ice-water bath, the reaction solution was cooled down to 0° C. followed by the addition of formaldehyde (18 mg, 0.60 mmol) and sodium triacetoxyborohydride (191 mg, 0.90 mmol), warmed up slowly to room temperature and stirred for 2 hours. The resulting mixture was added dropwise with saturated sodium bicarbonate solution to adjust pH to 9 to 10, extracted with dichloromethane (50 mL×3). The combined organic phase was washed with saturated sodium chloride solution (50 mL×3), then dried over anhydrous magnesium sulfate, filtered and the filtrate was concentrated under reduced pressure. The resulting residue was purified by silica gel column chromatography to obtain the title compound 7-[[(7R)-8-cyclopentyl-7-ethyl-5-methyl-6-oxo-7H-pteridin-2-yl]amino]-N-[(4-methylmorpholin-2-yl)methyl]-2,3-dihydrobenzofuran-4-carboxamide 2 (62 mg, yield: 38.0%) as a white solid.
MS m/z (ESI): 550.5 [M+1]
$^1$H NMR (400 MHz, CDCl$_3$) δ 8.29 (d, 1H), 7.67 (s, 1H), 7.13 (d, 1H), 7.04 (s, 1H), 6.46 to 6.35 (m, 1H), 4.68 (t, 2H), 4.47 (t, 1H), 4.21 (dd, 1H), 3.96 to 3.86 (m, 1H), 3.78 to 3.66 (m, 3H), 3.59 (t, 2H), 3.37 (td, 1H), 3.32 (s, 3H), 2.80 (d, 1H), 2.69 (d, 1H), 2.32 (s, 3H), 2.21 to 2.07 (m, 2H), 2.04 to 1.90 (m, 2H), 1.89 to 1.76 (m, 4H), 1.76 to 1.62 (m, 4H), 0.87 (t, 3H)

Example 3

[(1R,2R,4R,5R)-4-Acetoxy-2-[[7-[[(7R)-8-cyclopentyl-7-ethyl-5-methyl-6-oxo-7H-pteridin-2-yl]amino]-2,3-dihydrobenzofuran-4-carbonyl]amino]-5-dimethylamino-cyclohexyl]acetate

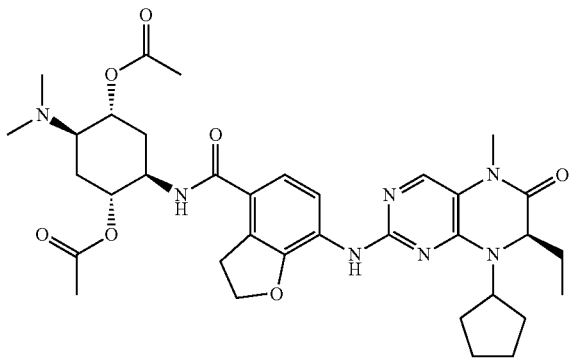

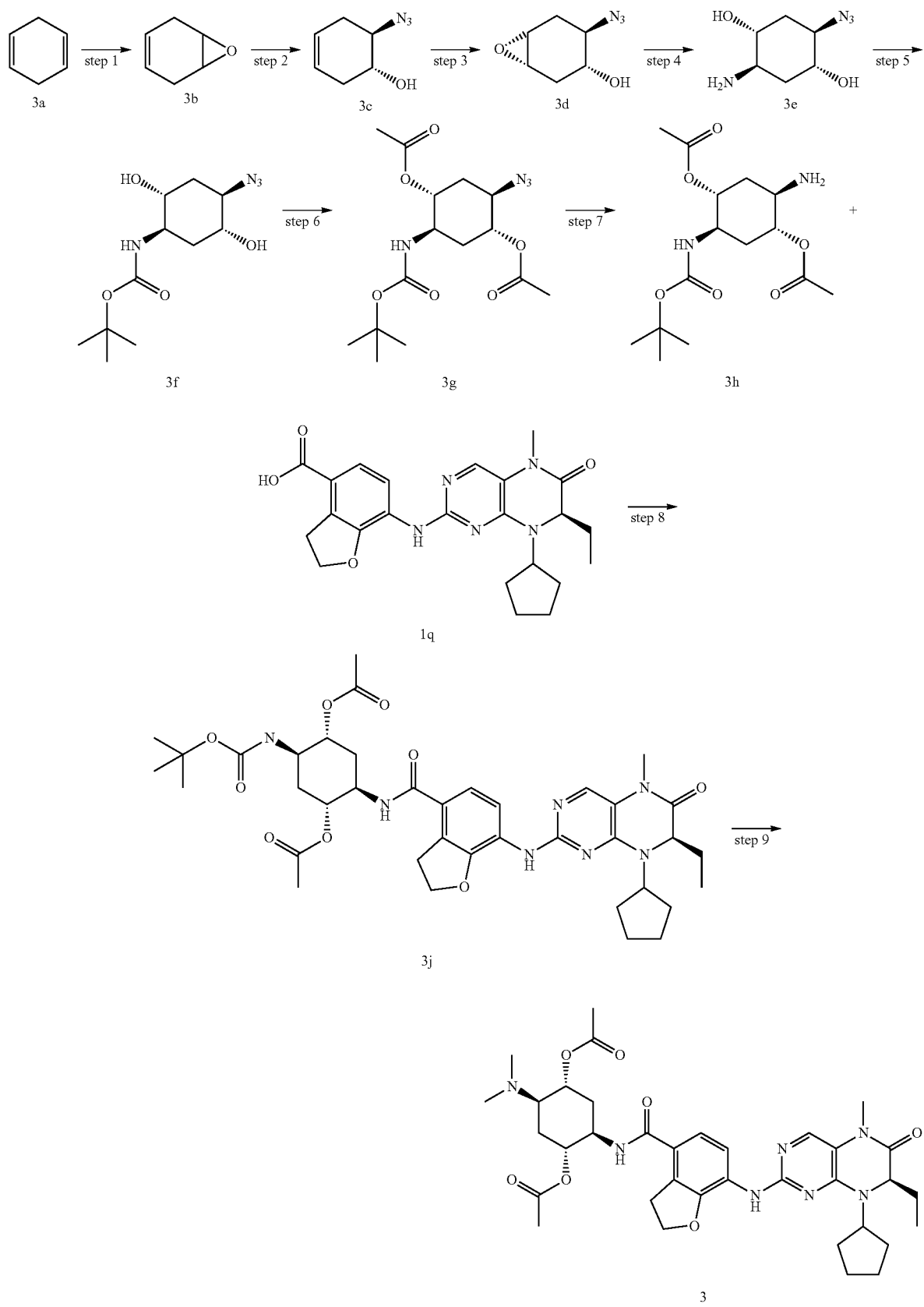

Step 1

7-Oxabicyclo[4.1.0]hept-3-ene 1,4-Cyclohexanediene 3a (8 g, 0.10 mol), 75% m-chloroperbenzoic acid (16.40 g, 0.10 mol) and sodium bicarbonate (8.80 g, 0.11 mol) were dissolved in 400 mL of dichloromethane, stirred for 12 hours. The resulting solution was added with 100 mL of dichloromethane and 20 mL of water, extracted and separated. The organic phase was dried over anhydrous magnesium sulfate, filtered and the filtrate was concentrated under normal pressure, the crude oil was distilled, and the distillate of 119-122° C. was collected to obtain the title compound 7-oxabicyclo[4.1.0]hept-3-ene 3b (4 g, yield: 41.7%) as a colorless oil liquid.

Step 2

(1R,6R)-6-Azidocyclohex-3-en-1-ol

7-Oxabicyclo[4.1.0]hept-3-ene 3b (3.50 g, 36.40 mmol), ammonium chloride (4.90 g, 91 mmol) and sodium azide (5.90 g, 91 mmol) were dissolved in 200 mL of the mixture solvent of methanol and water (V/V=9:1), the reaction solution was heated to reflux for 2 hours. The resulting solution was added with 500 mL of ethyl acetate, 200 mL of ethyl ether and 50 mL of water successively, seperated. The organic phase was dried over anhydrous magnesium sulfate, filtered and the filtrate was concentrated under reduced pressure to obtain the title compound (1R,6R)-6-azidocyclohex-3-en-1-ol 3c (3 g, yield: 60.0%) as a yellow oil.

Step 3

(1S,3R,4R)-4-Azido-7-oxabicyclo[4.1.0]heptan-3-ol (1R,6R)-6-Azidocyclohex-3-en-1-ol 3c (500 mg, 3.60 mmol) was dissolved in 150 mL of dichloromethane followed by the addition of sodium bicarbonate (600 mg, 7.20 mmol) and m-Chloroperbenzoic acid (2.40 g, 9.60 mmol), the reaction solution was stirred for 12 hours. The resulting solution was washed with saturated sodium bicarbonate solution (50 mL), saturated sodium thiosulfate solution (50 mL) and saturated sodium chloride solution (50 mL×3) successively, then dried over anhydrous magnesium sulfate, filtered and the filtrate was concentrated under reduced pressure, the residue was purified by HPLC to obtain the title compound (1S,3R,4R)-4-azido-7-oxabicyclo[4.1.0]heptan-3-ol 3d (360 mg, yield: 64.6%) as a white solid.

Step 4

(1R,2R,4R,5R)-2-Amino-5-azido-cyclohexane-1,4-diol (1S,3R,4R)-4-Azido-7-oxabicyclo[4.1.0]heptan-3-ol 3d (600 mg, 3.87 mmol) was dissolved in 20 mL ethanol followed by the addition of 10 mL of aqueous ammonia. The resulting solution was heated to reflux for 4 hours, then cooled down to room temperature and stirred for another 12 hours. The reaction solution was concentrated under reduced pressure to obtain the crude title compound (1R,2R,4R,5R)-2-amino-5-azido-cyclohexane-1,4-diol 3e (665 mg, as a yellow oil), which was used in the next step without further furification.

MS m/z (ESI): 173.1 [M+1]

Step 5

Tert-butyl N-[(1R,2R,4R,5R)-4-azido-2,5-dihydroxy-cyclohexyl]carbamate

The crude compound (1R,2R,4R,5R)-2-amino-5-azido-cyclohexane-1,4-diol 3e (665 mg, 3.87 mmol), di-tert-butyl dicarbonate (1.10 g, 5 mmol) and triethylamine (1.6 mL, 11.60 mmol) were dissolved in 40 mL of dichloromethane, then the reaction solution was stirred for 3 hours. The reaction solution was concentrated under reduced pressure, added with 50 mL ethyl acetate and 20 mL of water, then added dropwise with 1 M hydrochloric acid to adjust pH to 3 to 4, seperated. The organic phase was dried over anhydrous magnesium sulfate, filtered and the filtrate was concentrated under reduced pressure, the residue was purified by HPLC to obtain the title compound tert-butyl N-[(1R,2R,4R,5R)-4-azido-2,5-dihydroxy-cyclohexyl]carbamate 3f (350 mg, yield: 35.0%) as a white solid.

Step 6

[(1R,2R,4R,5R)-4-acetoxy-2-azido-5-(tert-butoxycarbonylamino)cyclohexyl]acetate Tert-butyl N-[(1R,2R,4R,5R)-4-azido-2,5-dihydroxy-cyclohexyl]carbamate 3f (350 mg, 1.28 mmol) was dissolved in 10 mL of acetic anhydride followed by the addition of 2 mL of pyridine, and stirred for 3 hours. The reaction solution was concentrated under reduced pressure, added with 50 mL ethyl acetate and 10 mL of water, then added dropwise with 1 M hydrochloric acid to adjust pH to 3 to 4, seperated, the organic phase was dried over anhydrous magnesium sulfate, filtered and the filtrate was concentrated under reduced pressure to obtain the title compound [(1R,2R,4R,5R)-4-acetoxy-2-azido-5-(tert-butoxycarbonylamino)cyclohexyl]acetate 3g (450 mg, yield: 100.0%) as a yellow oil.

MS m/z (ESI): 379.2 [M+23]

Step 7

[(1R,2R,4R,5R)-4-Acetoxy-2-amino-5-(tert-butoxycarbonylamino)cyclohexyl]acetate

[(1R,2R,4R,5R)-4-Acetoxy-2-azido-5-(tert-butoxycarbonylamino)cyclohexyl]acetate 3g (450 mg, 1.26 mmol) was dissolved in 30 mL of methanol followed by the addition of palladium/carbon (50 mg, 10%), filled with hydrogen three times. The reaction mixture was stirred for 1.5 hours and filtered. The filtrate was concentrated under reduced pressure to obtain the title compound [(1R,2R,4R,5R)-4-acetoxy-2-amino-5-(tert-butoxycarbonylamino)cyclohexyl]acetate 3h (350 mg, yield: 84.3%) as a white solid.

MS m/z (ESI): 331.0 [M+1]

Step 8

[(1R,2R,4R,5R)-4-Acetoxy-5-(tert-butoxycarbonylamino)-2-[[7-[[(7R)-8-cyclopentyl-7-ethyl-5-methyl-6-oxo-7H-pteridin-2-yl]amino]-2,3-dihydrobenzofuran-4-carbonyl]amino]cyclohexyl]acetate

[(1R,2R,4R,5R)-4-Acetoxy-2-amino-5-(tert-butoxycarbonylamino)cyclohexyl]acetate 3h (100 mg, 0.30 mmol), 7-[[(7R)-8-cyclopentyl-7-ethyl-5-methyl-6-oxo-7H-pteridin-2-yl]amino]-2,3-dihydrobenzofuran-4-carboxylic acid 1q (132 mg, 0.30 mmol), O-(benzotriazol-1-yl)-N,N,N',N'-tetramethyluronium tetrafluoroborate (96 mg, 0.30 mmol) and diisopropylethylamine (0.1 mL, 0.66 mmol) were dissolved in 30 mL of dichloromethane. The resulting solution was stirred for 2 hours, added with 10 mL of water, extracted with dichloromethane (30 mL×3). The combined organic phase was washed with saturated sodium chloride solution (20 mL×3), then dried over anhydrous magnesium sulfate, filtered and the filtrate was concentrated under reduced pressure. The resulting residue was purified by silica gel column chromatography to obtain the title compound [(1R,2R,4R,5R)-4-acetoxy-5-(tert-butoxycarbonylamino)-2-[[7-[[(7R)-8-cyclopentyl-7-ethyl-5-methyl-6-oxo-7H-pteridin-2-yl]amino]-2,3-dihydrobenzofuran-4-carbonyl]amino]cyclohexyl]acetate 3j (130 mg, yield: 58.0%) as a white solid.

MS m/z (ESI): 750.6 [M+1]

Step 9

[(1R,2R,4R,5R)-4-Acetoxy-2-[[7-[[(7R)-8-cyclopentyl-7-ethyl-5-methyl-6-oxo-7H-pteridin-2-yl]amino]-2,3-dihydrobenzofuran-4-carbonyl]amino]-5-dimethylamino-cyclohexyl]acetate

[(1R,2R,4R,5R)-4-Acetoxy-5-(tert-butoxycarbonylamino)-2-[[7-[[(7R)-8-cyclopentyl-7-ethyl-5-methyl-6-oxo-7H-pteridin-2-yl]amino]-2,3-dihydrobenzofuran-4-carbonyl]amino]cyclohexyl]acetate 3j (130 mg, 0.17 mmol) was dissolved in 20 mL of dichloromethane followed by the addition of 20 mL solution of 4 M 1,4-dioxane in hydrochloric acid solution, stirred for 0.5 hours. The reaction solution was concentrated under reduced pressure. The residue was dissolved in the mixture solvent of 60 mL of acetonitrile and 30 mL of water (V/V=1:1), added with 30% formaldehyde (68 mg, 0.68 mmol), stirred 0.5 hours followed by the addition of sodium triacetoxyborohydride (216 mg, 1.02 mmol), stirred for 12 hours. The resulting solution was added with 10 mL of aqueous ammonia, extracted with dichloromethane (50 mL×3). The combined organic phase was washed with saturated sodium chloride solution (50 mL×3), then dried over anhydrous magnesium sulfate, filtered and the filtrate was concentrated under reduced pressure. The resulting residue was purified by silica gel column chromatography to obtain the title compound [(1R,2R,4R,5R)-4-acetoxy-2-[[7-[[(7R)-8-cyclopentyl-7-ethyl-5-methyl-6-oxo-7H-pteridin-2-yl]amino]-2,3-dihydrobenzofuran-4-carbonyl]amino]-5-dimethylamino-cyclohexyl]acetate 3 (40 mg, yield: 34.8%) as a white solid.

MS m/z (ESI): 678.4 [M+1]

$^1$H NMR (400 MHz, CDCl$_3$) δ 8.27 (d, 1H), 7.67 (s, 1H), 7.10 to 7.01 (m, 2H), 5.32 to 5.27 (m, 1H), 4.67 (t, 2H), 4.46 (d, 2H), 4.21 (dd, 1H), 3.59 (dd, 2H), 3.32 (s, 3H), 2.45 to 2.30 (m, 6H), 2.27 to 2.17 (m, 2H), 2.18 to 2.08 (m, 6H), 2.05 to 1.91 (m, 7H), 1.86 (d, 4H), 1.71 (dd, 4H), 0.88 (t, 3H)

Example 4

7-[[(7R)-8-Cyclopentyl-7-ethyl-5-methyl-6-oxo-7H-pteridin-2-yl]amino]-2,2-dimethyl-N-(1-methyl-4-piperidyl)-3H-benzofuran-4-carboxamide

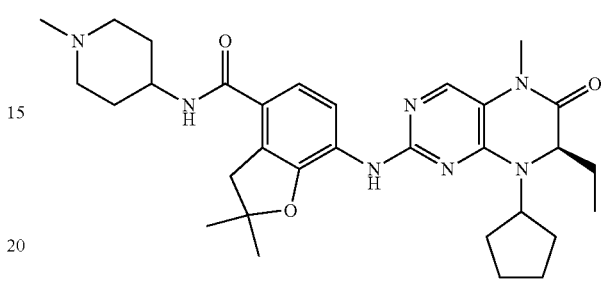

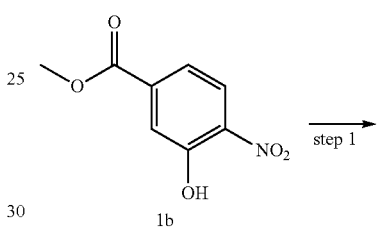

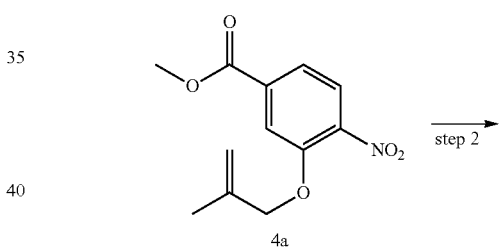

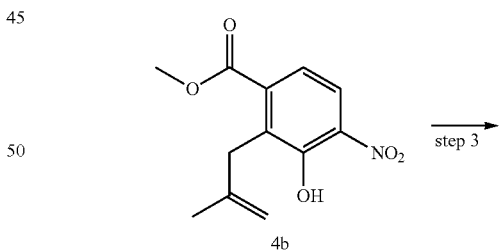

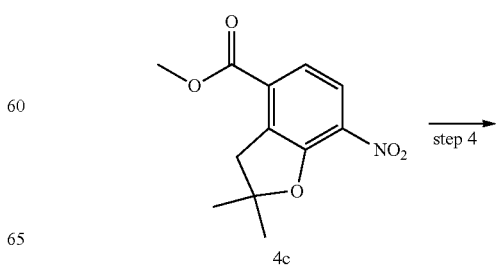

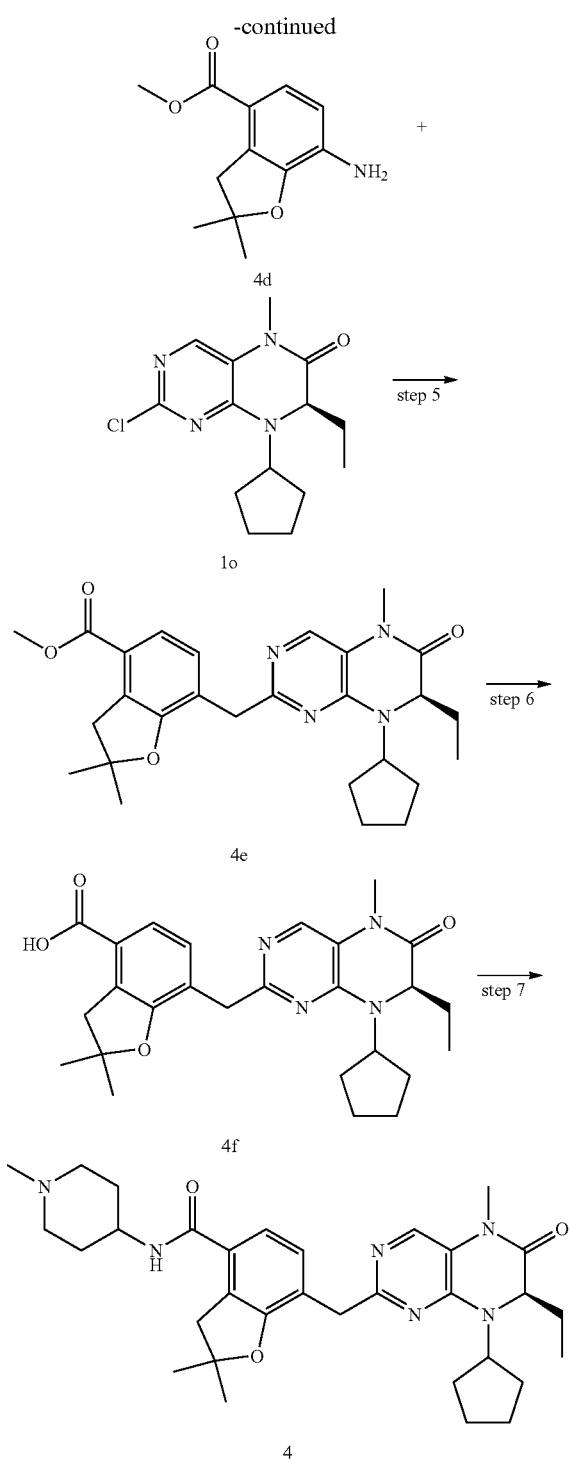

Step 1

Methyl 3-(2-methylallyloxy)-4-nitro-benzoate

Triphenyl phosphine (7.87 g, 30 mmol) was dissolved in 80 mL of tetrahydrofuran followed by the addition of diethyl azodicarboxylate (5.23 g, 30 mmol) in a dry ice bath. The reaction mixture was stirred 30 minutes, added dropwise with a solution of methyl 3-hydroxy-4-nitro-benzoate 1b (2.96 g, 15 mmol) in tetrahydrofuran, and stirred 10 minutes followed by the addition of 2-methyl-allyl alcohol (1.41 g, 19.50 mmol), then stirred for another 1 hour. The resulting mixture was heated to room temperature and stirred for 12 hours. The resulting mixture was added with 10 mL of water, added dropwise with 1 M hydrochloric acid to adjust pH to 2 to 3 and extracted with ethyl acetate (50 mL×3). The combined organic phase was added dropwise with 1 M sodium hydroxide solution to adjust pH to 9 to 10, extracted with ethyl acetate (50 mL×2). The combined organic phase was dried over anhydrous magnesium sulfate, filtered and the filtrate was concentrated under reduced pressure. The resulting residue was purified by silica gel column chromatography to obtain the title compound methyl 3-(2-methylallyloxy)-4-nitro-benzoate 4a (3 g, yield: 79.6%) as a light yellow solid.

MS m/z (ESI): 252.1 [M+1]

Step 2

Methyl 3-hydroxy-2-(2-methylallyl)-4-nitro-benzoate

Methyl 3-(2-methylallyloxy)-4-nitro-benzoate 4a (4.52 g, 18 mmol) was heated to 190° C. and stirred for 3 hours. The reaction mixture was cooled down to room temperature followed by the addition of 50 mL of dichloromethane. The reaction solution was concentrated under reduced pressure. The resulting residue was purified by silica gel column chromatography to obtain the title compound methyl 3-hydroxy-2-(2-methylallyl)-4-nitro-benzoate 4b (2.60 g, yield: 57.7%) as a yellow oil.

MS m/z (ESI): 252.1 [M+1]

Step 3

Methyl 2,2-dimethyl-7-nitro-3H-benzofuran-4-carboxylate

Methyl 3-hydroxy-2-(2-methylallyl)-4-nitro-benzoate 4b (2.58 g, 10.30 mmol) was dissolved in 50 mL 1,2-dichloroethane followed by the addition of trifluoromethanesulfonic acid (77 mg, 0.50 mmol). The reaction solution was stirred for 2 hours and concentrated under reduced pressure. The resulting residue was purified by silica gel column chromatography to obtain the title compound methyl 2,2-dimethyl-7-nitro-3H-benzofuran-4-carboxylate 4c (0.83 g, yield: 32.1%) as a yellow solid.

MS m/z (ESI): 252.1 [M+1]

Step 4

Methyl 7-amino-2,2-dimethyl-3H-benzofuran-4-carboxylate 2,2-Dimethyl-7-nitro-3H-benzofuran-4-carboxylate 4c (1.20 g, 4.77 mmol) and iron powder (0.80 g, 14.32 mmol) were dissolved in 25 mL of acetic acid. The reaction mixture was stirred for 12 hours. The resulting mixture was added with sodium carbonate and solid sodium bicarbonate to adjust pH to 7 to 8, extracted with ethyl acetate (50 mL×3). The combined organic phase was washed with water (30 mL) and saturated sodium chloride solution (20 mL) successively, then dried over anhydrous magnesium sulfate, filtered and the filtrate was concentrated under reduced pressure. The resulting residue was purified by silica gel column chromatography to obtain the title compound methyl 7-amino-2,2-dimethyl-3H-benzofuran-4-carboxylate 4d (789 mg, yield: 74.6%) as a white solid.

MS m/z (ESI): 222.2 [M+1]

Step 5

Methyl 7-[[(7R)-8-cyclopentyl-7-ethyl-5-methyl-6-oxo-7H-pteridin-2-yl]amino]-2,2-dimethyl-3H-benzofuran-4-carboxylate Methyl 7-amino-2,2-dimethyl-3H-benzofuran-4-carboxylate 4d (770 mg, 3.48 mmol) was dissolved in 20 mL of 1,3-dimethyl-butanol followed by the addition of (7R)-2-chloro-8-cyclopentyl-7-ethyl-5-methyl-5H-pteridin-6-one 1o (1.23 g, 4.18 mmol) and p-toluenesulfonic acid (1.06 g, 5.57 mmol) successively. The reaction solution was heated to reflux for 2 hours with stirring. The resulting solution was added with 50 mL of saturated sodium bicarbonate solution, extracted with ethyl acetate (50 mL×3). The combined organic phase was washed with water (30 mL), saturated sodium chloride solution (20 mL) successively and dried over anhydrous magnesium sulfate. The filtrate was concentrated under reduced pressure. The resulting residue was purified by silica gel column chromatography to obtain the title compound methyl 7-[[(7R)-8-cyclopentyl-7-ethyl-5-methyl-6-oxo-7H-pteridin-2-yl]amino]-2,2-dimethyl-3H-benzofuran-4-carboxylate 4e (1.78 g, yield: 100%) as a light yellow solid.

MS m/z (ESI): 480.4 [M+1]

Step 6

7-[[(7R)-8-Cyclopentyl-7-ethyl-5-methyl-6-oxo-7H-pteridin-2-yl]amino]-2,2-dimethyl-3H-benzofuran-4-carboxylic acid Methyl 7-[[(7R)-8-cyclopentyl-7-ethyl-5-methyl-6-oxo-7H-pteridin-2-yl]amino]-2,2-dimethyl-3H-benzofuran-4-carboxylate 4e (1.67 g, 3.48 mmol) was dissolved in 50 mL of methanol followed by the addition of 1 M lithium hydroxide solution (17.4 mL, 17.40 mmol). The reaction solution was heated to 50° C. and stirred for 12 hours. The resulting solution was added with 10 mL of water, and added dropwise with 1 M hydrochloric acid to adjust pH to 2 to 3. The reaction solution was concentrated under reduced pressure to obtain the title compound 7-[[(7R)-8-cyclopentyl-7-ethyl-5-methyl-6-oxo-7H-pteridin-2-yl]amino]-2,2-dimethyl-3H-benzofuran-4-carboxylic acid 4f (1.89 g, yield: 100%) as a white solid.

MS m/z (ESI): 464.3 [M−1]

Step 7

7-[[(7R)-8-Cyclopentyl-7-ethyl-5-methyl-6-oxo-7H-pteridin-2-yl]amino]-2,2-dimethyl-N-(1-methyl-4-piperidyl)-3H-benzofuran-4-carboxamide 7-[[(7R)-8-Cyclopentyl-7-ethyl-5-methyl-6-oxo-7H-pteridin-2-yl]amino]-2,2-dimethyl-3H-benzofuran-4-carboxylic acid 4f (931 mg, 2 mmol) was dissolved in 50 mL of dichloromethane followed by the addition of 1-methyl-piperidyl-4-yl-amine (228 mg, 2 mmol), O-(benzotriazol-1-yl)-N,N,N',N'-tetra methyluronium tetrafluoroborate (642 mg, 2 mmol) and diisopropylethylamine (775 mg, 6 mmol). The reaction solution was stirred for 1.5 hours. The resulting mixture was added with 50 mL of saturated sodium bicarbonate solution, extracted with dichloromethane (50 mL×3). The combined organic phase was washed with water (15 mL), saturated sodium chloride solution (15 mL) successively, dried over anhydrous magnesium sulfate. The filtrate was concentrated under reduced pressure. The resulting residue was purified by silica gel column chromatography to obtain the title compound 7-[[(7R)-8-cyclopentyl-7-ethyl-5-methyl-6-oxo-7H-pteridin-2-yl]amino]-2,2-dimethyl-N-(1-methyl-4-piperidyl)-3H-benzofuran-4-carboxamide 4 (793 mg, yield: 70.8%) as a white solid.

MS m/z (ESI): 562.4 [M+1]

$^1$H NMR (400 MHz, CDCl$_3$) δ 8.27 (d, 1H), 7.67 (s, 1H), 7.11 to 7.00 (m, 2H), 5.85 (d, 1H), 4.56 (t, 1H), 4.21 (dd, 1H), 3.95 (dd, 1H), 3.38 (s, 2H), 3.33 (s, 3H), 2.84 (d, 2H), 2.32 (s, 3H), 2.25 to 2.10 (m, 3H), 2.08 to 1.95 (m, 3H), 1.89 to 1.75 (m, 4H), 1.75 to 1.64 (m, 4H), 1.64 to 1.54 (m, 2H), 1.51 (s, 6H), 0.88 (t, 3H)

Example 5

(cis-exo)-N-2-Methyl-3,3a,4,5,6,6a-hexahydro-1H-cyclopenta[c]pyrrol-5-yl]-7-[[(7R)-8-cyclopentyl-7-ethyl-5-methyl-6-oxo-7H-pteridin-2-yl]amino]-2,3-dihydrobenzofuran-4-carboxamide

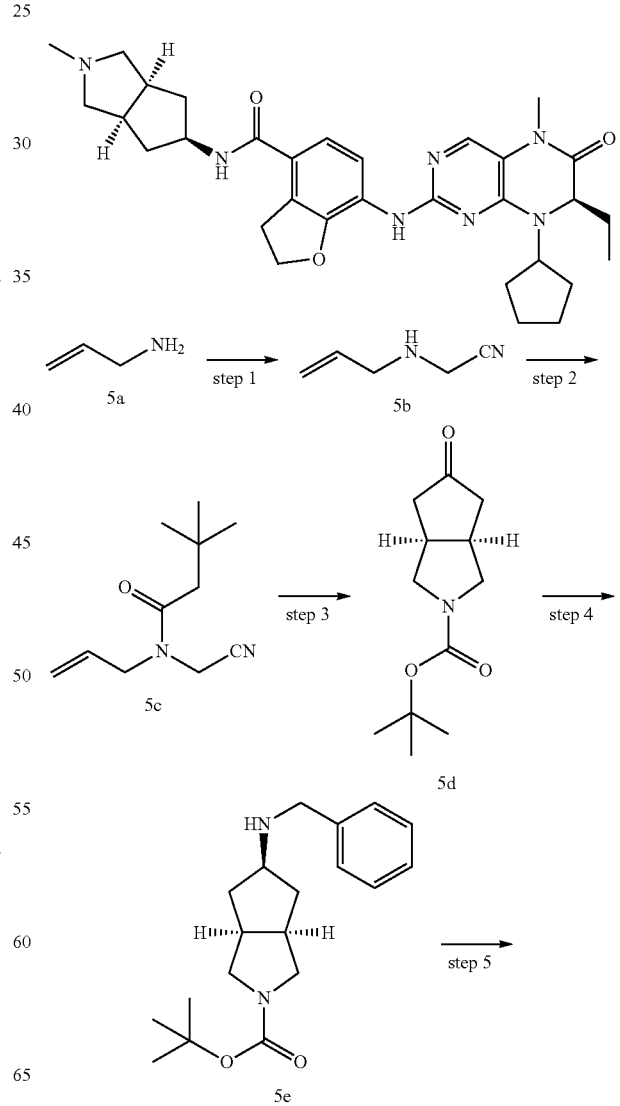

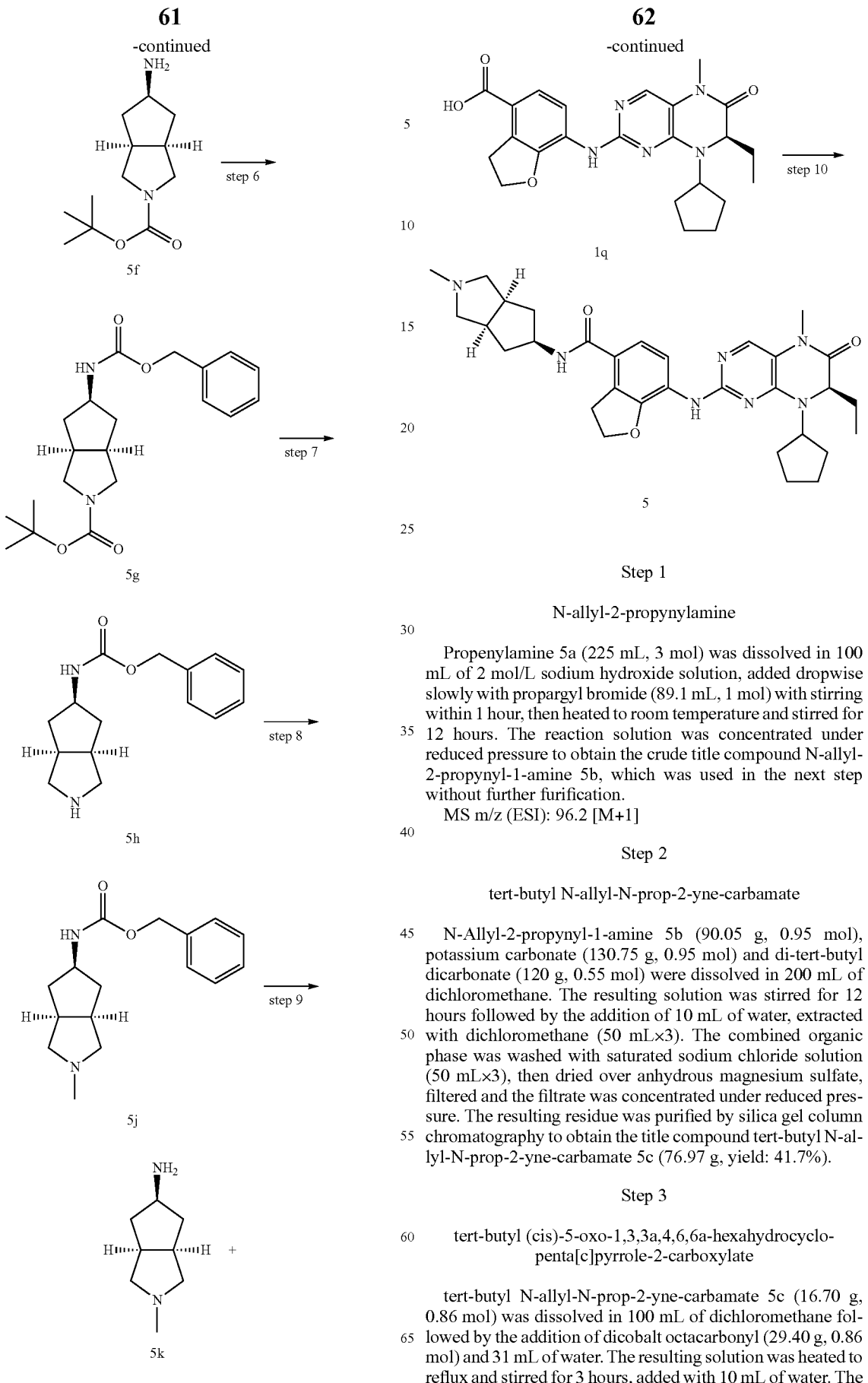

Step 1

N-allyl-2-propynylamine

Propenylamine 5a (225 mL, 3 mol) was dissolved in 100 mL of 2 mol/L sodium hydroxide solution, added dropwise slowly with propargyl bromide (89.1 mL, 1 mol) with stirring within 1 hour, then heated to room temperature and stirred for 12 hours. The reaction solution was concentrated under reduced pressure to obtain the crude title compound N-allyl-2-propynyl-1-amine 5b, which was used in the next step without further furification.

MS m/z (ESI): 96.2 [M+1]

Step 2 tert-butyl N-allyl-N-prop-2-yne-carbamate

N-Allyl-2-propynyl-1-amine 5b (90.05 g, 0.95 mol), potassium carbonate (130.75 g, 0.95 mol) and di-tert-butyl dicarbonate (120 g, 0.55 mol) were dissolved in 200 mL of dichloromethane. The resulting solution was stirred for 12 hours followed by the addition of 10 mL of water, extracted with dichloromethane (50 mL×3). The combined organic phase was washed with saturated sodium chloride solution (50 mL×3), then dried over anhydrous magnesium sulfate, filtered and the filtrate was concentrated under reduced pressure. The resulting residue was purified by silica gel column chromatography to obtain the title compound tert-butyl N-allyl-N-prop-2-yne-carbamate 5c (76.97 g, yield: 41.7%).

Step 3 tert-butyl (cis)-5-oxo-1,3,3a,4,6,6a-hexahydrocyclopenta[c]pyrrole-2-carboxylate tert-butyl N-allyl-N-prop-2-yne-carbamate 5c (16.70 g, 0.86 mol) was dissolved in 100 mL of dichloromethane followed by the addition of dicobalt octacarbonyl (29.40 g, 0.86 mol) and 31 mL of water. The resulting solution was heated to reflux and stirred for 3 hours, added with 10 mL of water. The reaction solution was concentrated under reduced pressure, added with 100 mL of ethyl acetate, 100 mL of water and 50 mL of 1 M hydrochloric acid, extracted with ethyl acetate (100 mL×3). The combined organic phase was washed with saturated sodium chloride solution (50 mL×3), then dried over anhydrous magnesium sulfate, filtered and the filtrate was concentrated under reduced pressure. The resulting residue was purified by silica gel column chromatography to obtain the title compound tert-butyl (cis)-5-oxo-1,3,3a,4,6,6a-hexahydrocyclopenta[c]pyrrole-2-carboxylate 5d (7.69 g, yield: 40.0%).

Step 4

Tert-butyl (cis-exo)-5-(benzylamino)-3,3a,4,5,6,6a-hexahydro-1H-cyclopenta[c]pyrrole-2-carboxylate Tert-butyl (cis)-5-oxo-1,3,3a,4,6,6a-hexahydrocyclopenta[c]pyrrole-2-carboxylate 5d (3.37 g, 15 mmol), benzylamine (1.60 g, 15 mmol) and acetic acid (0.90 g, 15 mmol) were dissolved in 60 mL of dichloromethane in an ice-water bath, stirred for 0.5 hours followed by the addition of sodium triacetoxyborohydride (6.40 g, 30 mmol), stirred for 12 hours. The resulting solution was added with 50 mL of saturated sodium bicarbonate solution and 100 mL of dichloromethane, seperated. The organic phase was washed with saturated sodium chloride solution (50 mL×3), then dried over anhydrous magnesium sulfate, filtered and the filtrate was concentrated under reduced pressure. The resulting residue was purified by silica gel column chromatography to obtain the title compound tert-butyl (cis-exo)-5-(benzylamino)-3,3a,4,5,6,6a-hexahydro-1H-cyclopenta[c]pyrrole-2-carboxylate 5e (4.70 g, yield: 100%) as a white solid.
MS m/z (ESI): 317.3 [M+1]

Step 5

Tert-butyl (cis-exo)-5-(amino)-3,3a,4,5,6,6a-hexahydro-1H-cyclopenta[c]pyrrole-2-carboxylate Tert-butyl (cis-exo)-5-(benzylamino)-3,3a,4,5,6,6a-hexahydro-1H-cyclopenta[c]pyrrole-2-carboxylate 5e (4.70 g, 14.80 mmol) and acetic acid (1 g, 14.80 mmol) were dissolved in 100 mL of methanol followed by the addition of palladium/carbon (500 mg, 10%), filled with hydrogen three times. The reaction mixture was stirred for 12 hours and filtered. The reaction solution was concentrated under reduced pressure, added with 50 mL of saturated sodium bicarbonate solution and 100 mL of dichloromethane, seperated. The organic phase was washed with saturated sodium chloride solution (50 mL×3), then dried over anhydrous magnesium sulfate, filtered and the filtrate was concentrated under reduced pressure to obtain the title compound tert-butyl (cis-exo)-5-(amino)-3,3a,4,5,6,6a-hexahydro-1H-cyclopenta[c]pyrrole-2-carboxylate 5f (1.70 g, yield: 51.5%) as a white solid.

Step 6

Tert-butyl (cis-exo)-5-benzyloxycarbonylamino-3,3a,4,5,6,6a-hexahydro-1H-cyclopenta[c]pyrrole-2-carboxylate Tert-butyl (cis-exo)-5-(amino)-3,3a,4,5,6,6a-hexahydro-1H-cyclopenta[c]pyrrole-2-carboxylate 5f (1.70 g, 7.50 mmol) was dissolved in 60 mL of dichloromethane followed by the addition of benzyloxy chloride (1.41 g, 8.26 mmol) and triethylamine (1.52 g, 15 mmol), stirred for 3 hours. The resulting solution was added with 50 mL of saturated sodium bicarbonate solution and 100 mL of dichloromethane. The organic phase was washed with saturated sodium chloride solution (50 mL×3), then dried over anhydrous magnesium sulfate, filtered and the filtrate was concentrated under reduced pressure. The resulting residue was purified by silica gel column chromatography to obtain the title compound tert-butyl (cis-exo)-5-benzyloxycarbonylamino-3,3a,4,5,6,6a-hexahydro-1H-cyclopenta[c]pyrrole-2-carboxylate 5g (1.98 g, yield: 73.3%) as a colorless viscous liquid.

Step 7

Benzyl (cis-exo)-N-[1,2,3,3a,4,5,6,6a-octahydrocyclopenta[c]pyrrol-5-yl]carbamate Tert-butyl (cis-exo)-5-benzyloxycarbonylamino-3,3a,4,5,6,6a-hexahydro-1H-cyclopenta[c]pyrrole-2-carboxylate 5g (1.96 g, 5.44 mmol) was dissolved in 10 mL of 1,4-dioxane followed by the addition of 10 mL of 2 M hydrochloric acid, heated to 50° C., stirred for 12 hours. The reaction solution was concentrated under reduced pressure, added dropwise with 2 M sodium hydroxide solution to adjust pH to 2, extracted with dichloromethane (50 mL). The organic phase was washed with saturated sodium chloride solution (50 mL×3), then dried over anhydrous magnesium sulfate, filtered and the filtrate was concentrated under reduced pressure to obtain the title compound benzyl (cis-exo)-N-[1,2,3,3a,4,5,6,6a-octahydrocyclopenta[c]pyrrol-5-yl]carbamate 5h (635 mg, yield: 45.0%) as a light yellow oil liquid.
MS m/z (ESI): 261.2 [M+1]

Step 8

Benzyl (cis-exo)-N-[2-methyl-3,3a,4,5,6,6a-hexahydro-1H-cyclopenta[c]pyrrol-5-yl]carbamate Benzyl (cis-exo)-N-[1,2,3,3a,4,5,6,6a-octahydrocyclopenta[c]pyrrol-5-yl]carbamate 5h (635 mg, 2.40 mmol) was dissolved in 20 mL of the mixture solvent of acetonitrile and water (V/V=9:1) in an ice-water bath followed by the addition of 37% aqueous formaldehyde solution (110 mg, 3.66 mmol), stirred 10 minutes, added with sodium triacetoxyborohydride (1.52 g, 7.20 mmol), stirred for 2 hours. The reaction solution was concentrated under reduced pressure, added with 50 mL of saturated sodium bicarbonate solution and 100 mL of dichloromethane, seperated. The organic phase was washed with saturated sodium chloride solution (50 mL×3), then dried over anhydrous magnesium sulfate, filtered and the filtrate was concentrated under reduced pressure. The resulting residue was purified by silica gel column chromatography to obtain the title compound benzyl (cis-exo)-N-[2-methyl-3,3a,4,5,6,6a-hexahydro-1H-cyclopenta[c]pyrrol-5-yl]carbamate 5j (559 mg, yield: 85%) as a yellow oil liquid.

Step 9

(cis-exo)-2-Methyl-3,3a,4,5,6,6a-hexahydro-1H-cyclopenta[c]pyrrol-5-amine

Benzyl (cis-exo)-N-[2-methyl-3,3a,4,5,6,6a-hexahydro-1H-cyclopenta[c]pyrrol-5-yl]carbamate 5j (550 mg, 2 mmol) was dissolved in 20 mL of methanol followed by the addition of palladium/carbon (55 mg, 10%), filled with hydrogen three times. The reaction mixture was stirred for 1 hour. The reaction solution was concentrated under reduced pressure to obtain the title compound (cis-exo)-2-methyl-3,3a,4,5,6,6a-hexahydro-1H-cyclopenta[c]pyrrol-5-amine 5k (246 mg, yield: 87.9%) as a colorless oil liquid.

MS m/z (ESI): 141.2 [M+1]

Step 10

(cis-exo)-N-2-Methyl-3,3a,4,5,6,6a-hexahydro-1H-cyclopenta[c]pyrrol-5-yl]-7-[[(7R)-8-cyclopentyl-7-ethyl-5-methyl-6-oxo-7H-pteridin-2-yl]amino]-2,3-dihydrobenzofuran-4-carboxamide 7-[[(7R)-8-Cyclopentyl-7-ethyl-5-methyl-6-oxo-7H-pteridin-2-yl]amino]-2,3-dihydrobenzofuran-4-carboxylic acid 1q (187 mg, 0.43 mmol) and O-(benzotriazol-1-yl)-N,N,N',N'-tetra methyluronium tetrafluoroborate (138 mg, 0.43 mmol) were dissolved in 40 mL of anhydrous dichloromethane followed by the addition of diisopropylethylamine (0.2 mL, 0.95 mmol), stirred until the solution became clear, followed by the addition of 5 mL of a solution of (cis-exo)-2-methyl-3,3a,4,5,6,6a-hexahydro-1H-cyclopenta[c]pyrrol-5-amine 5k (60 mg, 0.43 mmol) in dichloromethane, and stirred for another 2 hours. The resulting solution was added with 30 mL of dichloromethane, washed with dilute aqueous ammonia (20 mL), water (20 mL) and saturated sodium chloride solution (20 mL) successively, then dried over anhydrous sodium sulfate, filtered and the filtrate was concentrated under reduced pressure. The resulting residue was purified by silica gel column chromatography to obtain the title compound (cis-exo)-N-2-methyl-3,3a,4,5,6,6a-hexahydro-1H-cyclopenta[c]pyrrol-5-yl]-7-[[(7R)-8-cyclopentyl-7-ethyl-5-methyl-6-oxo-7H-pteridin-2-yl]amino]-2,3-dihydrobenzofuran-4-carboxamide 5 (170 mg, yield: 71.0%) as a white solid.

MS m/z (ESI): 560.4 [M+1]

$^1$H NMR (400 MHz, CDCl$_3$) δ8.25 (d, 1H), 7.67 (s, 1H), 7.12 to 6.99 (m, 2H), 4.66 (t, 2H), 4.59 (dd, 1H), 4.58 to 4.35 (m, 1H), 4.20 (dd, 1H), 3.66 (t, 2H), 3.32 (s, 3H), 3.10 to 2.80 (m, 2H), 2.80 to 2.70 (m, 2H), 2.47 (s, 3H), 2.40 to 2.25 (m, 2H), 2.24 to 2.06 (m, 3H), 2.05 to 1.92 (m, 2H), 1.91 to 1.74 (m, 4H), 1.73 to 1.59 (m, 6H), 0.88 (t, 3H)

Example 6

(cis-exo)-N-[2-Methyl-3,3a,4,5,6,6a-hexahydro-1H-cyclopenta[c]pyrrol-5-yl]-7-[[(7R)-8-cyclopentyl-7-ethyl-5-methyl-6-oxo-7H-pteridin-2-yl]amino]-2,2-dimethyl-3H-benzofuran-4-carboxamide

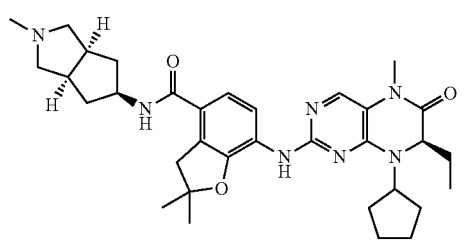

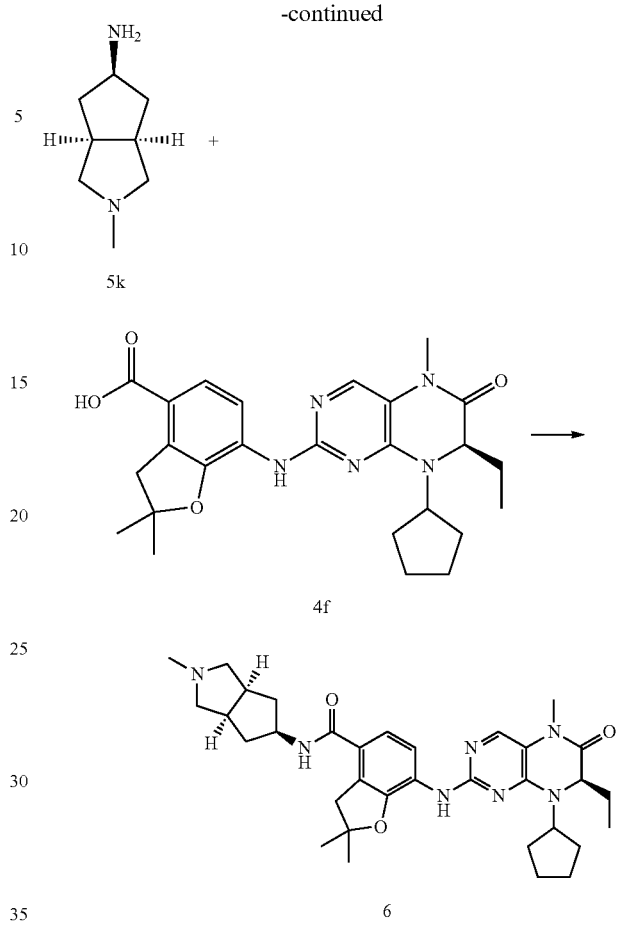

7-[[(7R)-8-Cyclopentyl-7-ethyl-5-methyl-6-oxo-7H-pteridin-2-yl]amino]-2,2-dimethyl-3H-benzofuran-4-carboxylic acid 4f (163 mg, 0.35 mmol) was dissolved in 15 mL of dichloromethane followed by the addition of (cis-exo)-2-methyl-3,3a,4,5,6,6a-hexahydro-1H-cyclopenta[c]pyrrol-5-amine 5k (59 mg, 0.42 mmol), O-(benzotriazol-1-yl)-N,N,N',N'-tetra methyluronium tetrafluoroborate (112 mg, 0.35 mmol) and diisopropylethylamine (135 mg, 1.05 mmol). The reaction solution was stirred for 1.5 hours. The resulting solution was added with 10 mL of saturated sodium bicarbonate solution, extracted with ethyl acetate (50 mL×3). The combined organic phase was washed with water (10 mL), saturated sodium chloride solution (10 mL) successively, and dried over anhydrous magnesium sulfate. The filtrate was concentrated under reduced pressure. The resulting residue was purified by silica gel column chromatography to obtain the title compound (cis-exo)-N-[2-methyl-3,3a,4,5,6,6a-hexahydro-1H-cyclopenta[c]pyrrol-5-yl]-7-[[(7R)-8-cyclopentyl-7-ethyl-5-methyl-6-oxo-7H-pteridin-2-yl]amino]-2,2-dimethyl-3H-benzofuran-4-carboxamide 6 (40 mg, yield: 19.5%) as a white solid.

MS m/z (ESI): 588.3 [M+1]

$^1$H NMR (400 MHz, CDCl$_3$) δ 8.21 (d, 1H), 7.65 (s, 1H), 7.26 to 7.16 (m, 2H), 6.99 (s, 1H), 4.59 to 4.41 (m, 2H), 4.22 (dd, 1H), 3.57 (s, 2H), 3.43 (s, 2H), 3.32 (s, 3H), 2.96 (s, 3H), 2.87 (s, 3H), 2.47 to 2.35 (m, 2H), 2.14 (s, 3H), 2.06 to 1.94 (m, 2H), 1.89 to 1.63 (m, 8H), 1.51 (s, 6H), 0.88 (t, 3H)

Example 7

7-[[(7R)-8-Cyclopentyl-7-ethyl-5-methyl-6-oxo-7H-pteridin-2-yl]amino]-N-[(2S)-3-[4-(cyclopropylmethyl)piperazin-1-yl]-2-hydroxy-propyl]-2,3-dihydrobenzofuran-4-carboxamide (R)-2-chloromethyl-oxirane (1.85 g, 20 mmol). The reaction solution was stirred for 5 hours and concentrated under reduced pressure. The resulting residue was purified by silica gel column chromatography to obtain the title compound tert-butyl 4-[[(2R)-oxiran-2-yl]methyl]piperazine-1-carboxylate 7b (3.55 g, yield: 74.0%) as a colorless oil.

MS m/z (ESI): 243.2 [M+1]

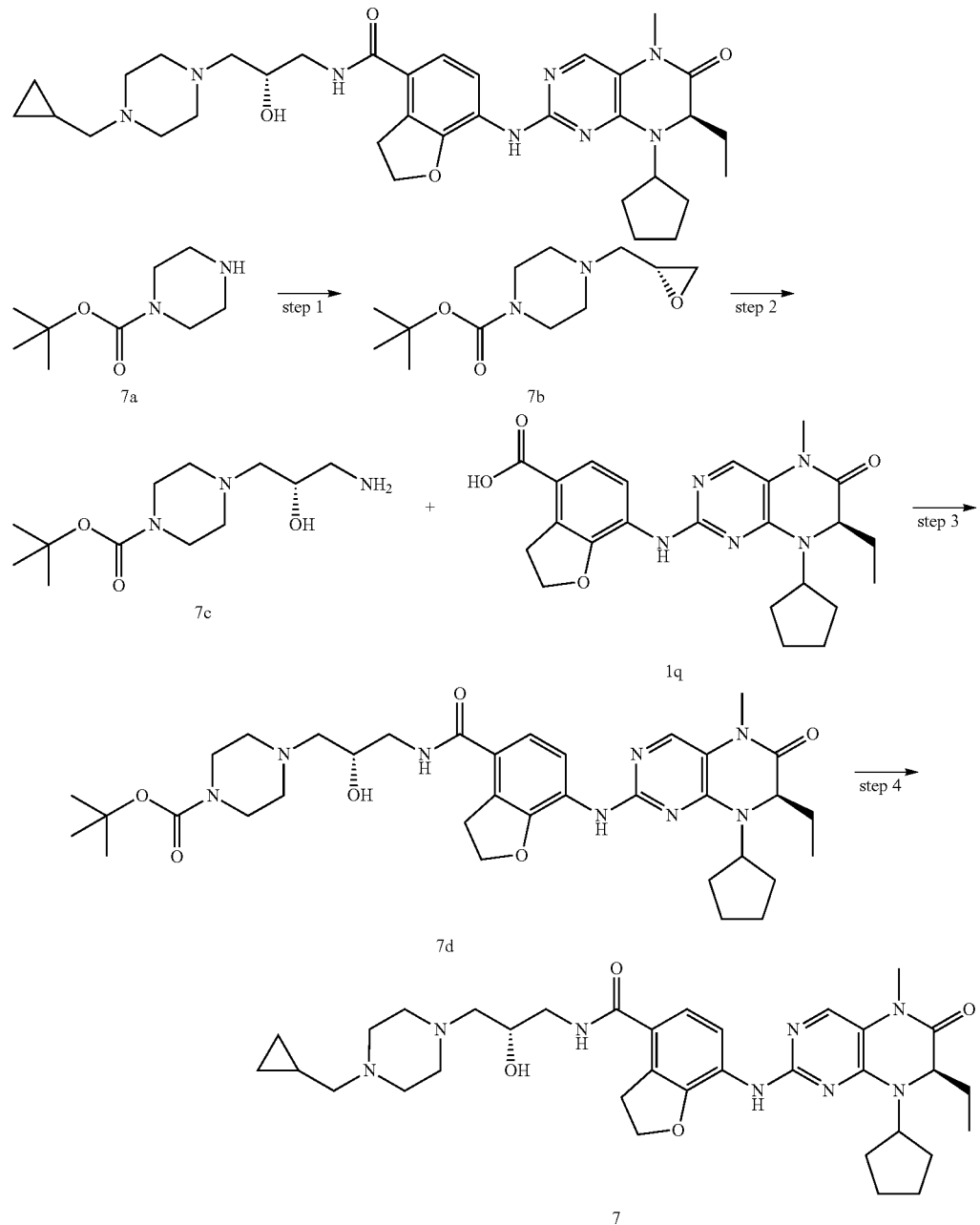

Step 1

Tert-butyl 4-[[(2R)-oxiran-2-yl]methyl]piperazine-1-carboxylate

Tert-butyl piperazine-1-carboxylate 7a (3.72 g, 20 mmol) was dissolved in 40 mL of ethanol followed by the addition of

Step 2

Tert-butyl 4-[(2S)-3-amino-2-hydroxy-propyl]piperazine-1-carboxylate

Tert-butyl 4-[[(2R)-oxiran-2-yl]methyl]piperazine-1-carboxylate 7b (3.55 g, 14.70 mmol) was dissolved in 40 mL of ethanol followed by the addition of 40 mL of aqueous ammonia, stirred for 12 hours. The resulting solution was heated to 50° C. and stirred for another 1 hour, then concentrated under reduced pressure to obtain the crude title compound tert-butyl 4-[(2S)-3-amino-2-hydroxy-propyl]piperazine-1-carboxylate 7c (3.40 g) as a light yellow solid, which was used in the next step without further furification.

Step 3

Tert-butyl 4-[(2S)-3-[[7-[[(7R)-8-cyclopentyl-7-ethyl-5-methyl-6-oxo-7H-pteridin-2-yl]amino]-2,3-dihydrobenzofuran-4-carbonyl]amino]-2-hydroxy-propyl]piperazine-1-carboxylate Tert-butyl 4-[(2S)-3-amino-2-hydroxy-propyl]piperazine-1-carboxylate 7c (355 mg, 1.37 mmol), 7-[[(7R)-8-cyclopentyl-7-ethyl-5-methyl-6-oxo-7H-pteridin-2-yl]amino]-2,3-dihydrobenzofuran-4-carboxylic acid 1q (600 mg, 1.37 mmol), O-(benzotriazol-1-yl)-N,N,N'-tetra methyluronium tetrafluoroborate (440 mg, 1.37 mmol) and diisopropylethylamine (390 mg, 3.01 mmol) were dissolved in 40 mL of dichloromethane. The reaction solution was stirred for 2 hours. The resulting solution was added with 50 mL of water and 10 mL of aqueous ammonia successively, stirred for 0.5 hours, extracted with dichloromethane (50 mL×3). The combined organic phase was washed with saturated sodium chloride solution (50 mL), dried over anhydrous magnesium sulfate. The filtrate was concentrated under reduced pressure. The resulting residue was purified by silica gel column chromatography to obtain the title compound tert-butyl 4-[(2S)-3-[[7-[[(7R)-8-cyclopentyl-7-ethyl-5-methyl-6-oxo-7H-pteridin-2-yl]amino]-2,3-dihydrobenzofuran-4-carbonyl]amino]-2-hydroxy-propyl]piperazine-1-carboxylate 7d (300 mg, yield: 32.3%) as a white solid.

MS m/z (ESI): 679.6 [M+1]

Step 4

7-[[(7R)-8-Cyclopentyl-7-ethyl-5-methyl-6-oxo-7H-pteridin-2-yl]amino]-N-[(2S)-3-[4-(cyclopropylmethyl)piperazin-1-yl]-2-hydroxy-propyl]-2,3-dihydrobenzofuran-4-carboxamide Tert-butyl 4-[(2S)-3-[[7-[[(7R)-8-cyclopentyl-7-ethyl-5-methyl-6-oxo-7H-pteridin-2-yl]amino]-2,3-dihydrobenzofuran-4-carbonyl]amino]-2-hydroxy-propyl]piperazine-1-carboxylate 7d (300 mg, 0.44 mmol) was dissolved in 40 mL of dichloromethane. The reaction solution was filled with gas of hydrogen chloride and stirred for 0.5 hours. The reaction solution was concentrated under reduced pressure. The resulting residue was dissolved in 41 mL of acetonitrile followed by the addition of 183 mL of triethylamine, sodium bicarbonate (148 mg, 1.76 mmol) and bromo-methyl-cyclopropane (130 mg, 0.97 mmol). The resulting solution was stirred for 12 hours and filtered. The filtrate was concentrated under reduced pressure. The resulting residue was purified by silica gel column chromatography to obtain the title compound 7-[[(7R)-8-cyclopentyl-7-ethyl-1-methyl-6-oxo-7H-pteridin-2-yl]amino]-N-[(2S)-3-[4-(cyclopropylmethyl)piperazin-1-yl]-2-hydroxy-propyl]-2,3-dihydrobenzofuran-4-carboxamide 7 (200 mg, yield: 72.0%) as a white solid.

MS m/z (ESI): 633.6 [M+1]

$^1$H NMR (400 MHz, CDCl$_3$) δ 8.26 (d, 1H), 7.65 (s, 1H), 7.25 (d, 1H), 7.13 (s, 1H), 7.04 (s, 1H), 4.67 (t, 2H), 4.44 (t, 1H), 4.21 (dd, 1H), 4.15 to 4.08 (m, 1H), 3.74 to 3.66 (m, 1H), 3.59 (t, 2H), 3.52 to 3.41 (m, 2H), 3.31 (s, 3H), 3.41 to 3.01 (m, 6H), 2.85 to 2.52 (m, 4H), 2.17 to 2.07 (m, 1H), 2.01 to 1.92 (m, 1H), 1.88 to 1.76 (m, 4H), 1.74 to 1.64 (m, 4H), 1.38 (t, 1H), 1.26 (t, 1H), 1.18 (s, 1H), 0.87 (t, 3H), 0.71 (d, 2H), 0.40 to 0.31 (m, 2H)

Example 8

7-[[(7R)-8-Cyclopentyl-7-ethyl-5-methyl-6-oxo-7H-pteridin-2-yl]amino]-N-[(2S)-2-hydroxy-3-(4-methylpiperazin-1-yl)propyl]-2,3-dihydrobenzofuran-4-carboxamide

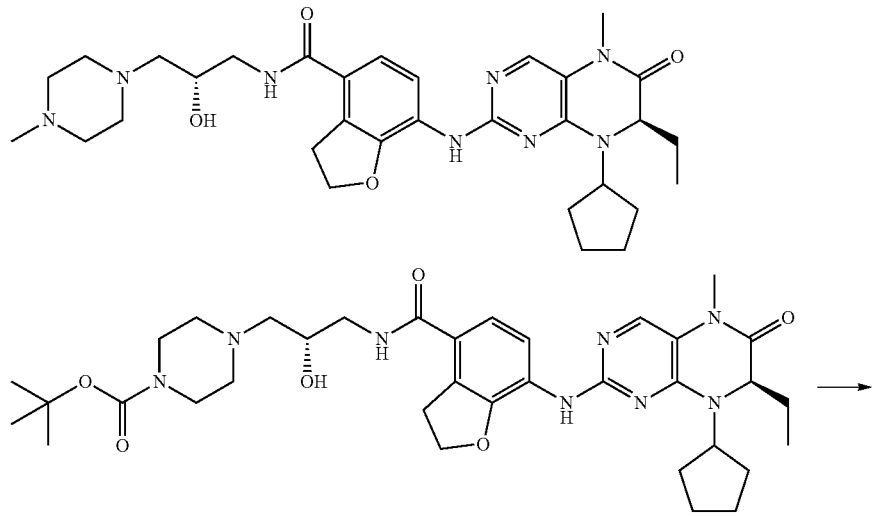

7d

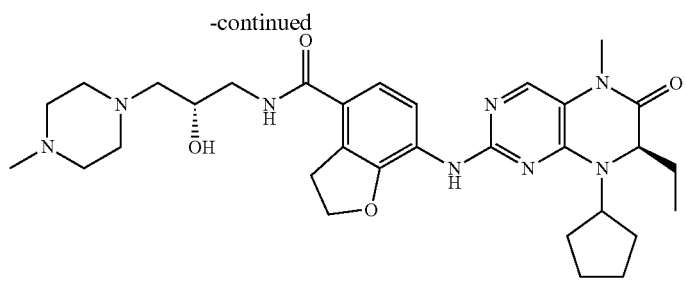

8

Tert-butyl 4-[(2S)-3-[[7-[[(7R)-8-cyclopentyl-7-ethyl-5-methyl-6-oxo-7H-pteridin-2-yl]amino]-2,3-dihydrobenzofuran-4-carbonyl]amino]-2-hydroxy-propyl]piperazine-1-carboxylate 7d (580 mg, 0.85 mmol) was dissolved in 50 mL of dichloromethane followed by the addition of 20 mL of a 4 M solution of hydrogen chloride in dioxane. The reaction solution was stirred for 0.5 hours and concentrated under reduced pressure. The resulting residue was dissolved in 40 mL of acetonitrile followed by the addition of sodium bicarbonate (285 mg, 3.40 mmol) and methyl p-toluenesulfonate (316 mg, 1.70 mmol) and stirred for 12 hours. The resulting solution was added with 50 mL of water and extracted with dichloromethane (50 mL×3). The combined organic phase was washed with saturated sodium chloride solution (50 mL×3), dried over anhydrous magnesium sulfate. The filtrate was concentrated under reduced pressure. The resulting residue was purified by silica gel column chromatography to obtain the title compound 7-[[(7R)-8-cyclopentyl-7-ethyl-5-methyl-6-oxo-7H-pteridin-2-yl]amino]-N-[(2S)-2-hydroxy-3-(4-methylpiperazin-1-yl)propyl]-2,3-dihydrobenzofuran-4-carboxamide 8 (150 mg, yield: 30.0%) as a white solid.

MS m/z (ESI): 593.5 [M+1]

$^1$H NMR (400 MHz, CDCl$_3$) δ 8.29 (d, 1H), 7.67 (s, 1H), 7.15 (d, 1H), 7.04 (s, 1H), 6.66 to 6.54 (m, 1H), 4.68 (t, 2H), 4.53 to 4.41 (m, 1H), 4.21 (dd, 1H), 4.02 to 3.90 (m, 1H), 3.75 to 3.65 (m, 1H), 3.61 to 3.55 (m, 2H), 3.45 to 3.36 (m, 1H), 3.32 (s, 3H), 2.90 to 2.76 (m, 2H), 2.70 to 2.45 (m, 7H), 2.38 (s, 3H), 2.20 to 2.08 (m, 2H), 2.04 to 1.92 (m, 2H), 1.90 to 1.79 (m, 4H), 1.77 to 1.63 (m, 4H), 0.88 (t, 3H)

Example 9

(cis-exo)-N-[2-Methyl-3,3a,4,5,6,6a-hexahydro-1H-cyclopenta[c]pyrrol-5-yl]-7-[[(7R)-8-cyclopentyl-7-ethyl-5-methyl-6-oxo-7H-pteridin-2-yl]amino]-2,2-dimethyl-3H-benzofuran-4-carboxamide

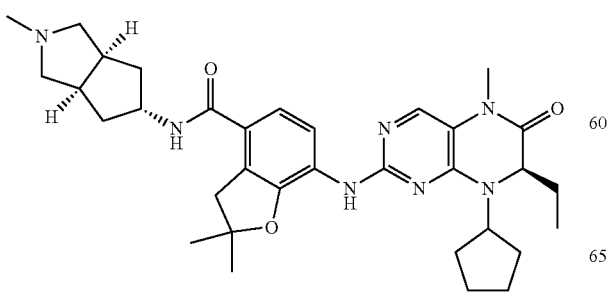

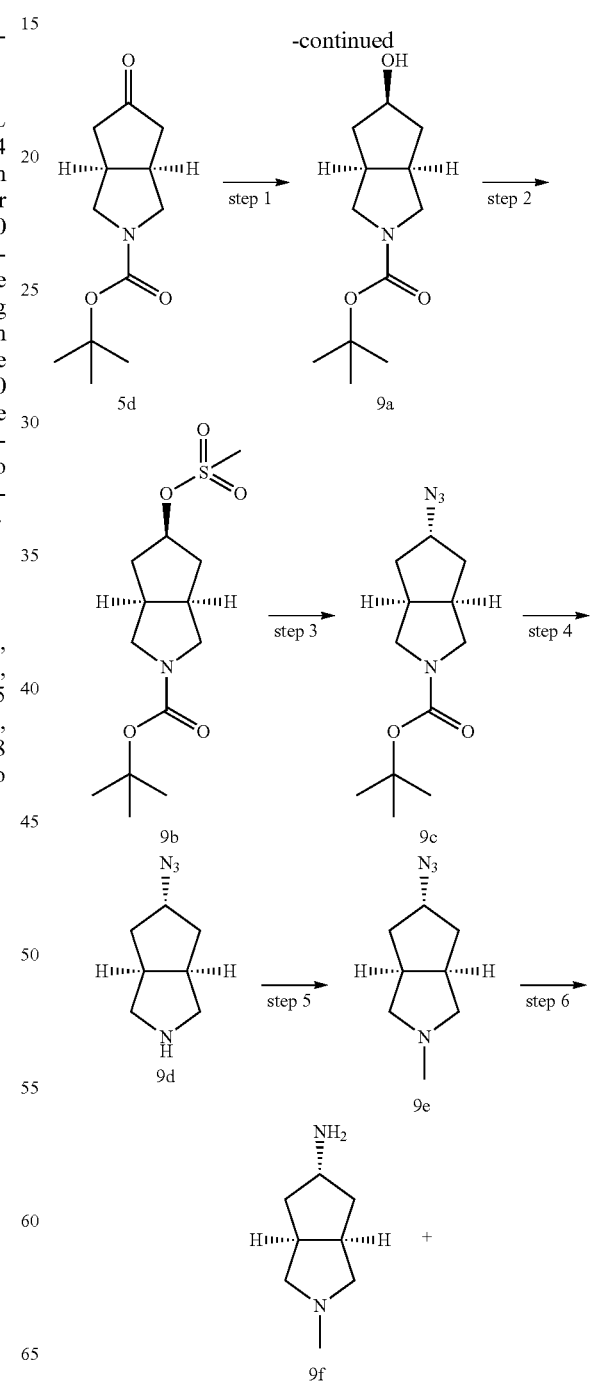

-continued

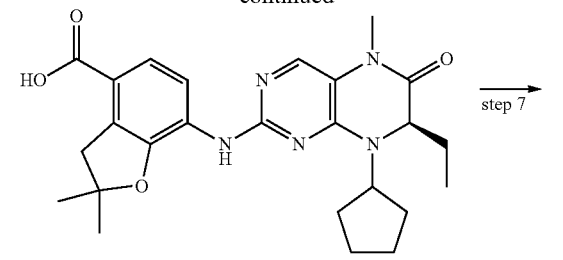

4f

9

Step 1

Tert-butyl (cis-exo)-5-hydroxyl-3,3a,4,5,6,6a-hexahydro-1H-cyclopenta[c]pyrrole-2-carboxylate Tert-butyl (cis)-5-oxo-1,3,3a,4,6,6a-hexahydrocyclopenta[c]pyrrole-2-carboxylate 5d (1.80 g, 8 mmol) was dissolved in 30 mL of tetrahydrofuran followed by the addition of sodium borohydride (0.60 g, 16 mmol), stirred for 12 hours. The resulting solution was added with 30 mL of saturated sodium bicarbonate solution and extracted with ethyl acetate (50 mL×3). The combined organic phase was washed with saturated sodium chloride solution (50 mL×3), then dried over anhydrous magnesium sulfate, filtered and the filtrate was concentrated under reduced pressure. The resulting residue was purified by silica gel column chromatography to obtain the title compound tert-butyl (cis-exo)-5-hydroxyl-3,3a,4,5,6,6a-hexahydro-1H-cyclopenta[c]pyrrole-2-carboxylate 9a (1.64 g, yield: 90.0%) as a yellow viscous liquid.

MS m/z (ESI): 228.1 [M+1]

Step 2

Tert-butyl (cis-exo)-5-methylsulfonyloxy-3,3a,4,5,6,6a-hexahydro-1H-cyclopenta[c]pyrrole-2-carboxylate Tert-butyl (cis-exo)-5-hydroxyl-3,3a,4,5,6,6a-hexahydro-1H-cyclopenta[c]pyrrole-2-carboxylate 9a (1.64 g, 7.20 mmol) was dissolved in 30 mL of dichloromethane followed by the addition of methanesulfonyl chloride (0.9 mL, 11 mmol) and triethylamine (2 mL, 14.40 mmol) in an ice-water bath, stirred for 2 hours. The resulting solution was added with 30 mL of saturated sodium bicarbonate solution and extracted with dichloromethane (50 mL×3). The combined organic phase was washed with saturated sodium chloride solution (50 mL×3), then dried over anhydrous magnesium sulfate, filtered and the filtrate was concentrated under reduced pressure. The resulting residue was purified by silica gel column chromatography to obtain the title compound tert-butyl (cis-exo)-5-methylsulfonyloxy-3,3a,4,5,6,6a-hexahydro-1H-cyclopenta[c]pyrrole-2-carboxylate 9b (1.76 g, yield: 80.0%) as yellow liquid.

MS m/z (ESI): 305.9 [M+1]

Step 3

Tert-butyl (cis-endo)-5-azido-3,3a,4,5,6,6a-hexahydro-1H-cyclopenta[c]pyrrole-2-carboxylate Tert-butyl (cis-exo)-5-methylsulfonyloxy-3,3a,4,5,6,6a-hexahydro-1H-cyclopenta[c]pyrrole-2-carboxylate 9b (1.76 g, 5.76 mmol) was dissolved in 20 mL of dichloromethane followed by the addition of sodium azide (0.94 g, 14.40 mmol), heated to 70-80° C. and stirred for 4 hours. The resulting solution was added with 5 mL of water and extracted with ethyl acetate (30 mL×3). The combined organic phase was washed with saturated sodium chloride solution (30 mL×3), then dried over anhydrous magnesium sulfate, filtered and the filtrate was concentrated under reduced pressure. The resulting residue was purified by silica gel column chromatography to obtain the title compound tert-butyl (cis-endo)-5-azido-3,3a,4,5,6,6a-hexahydro-1H-cyclopenta[c]pyrrole-2-carboxylate 9c (1.15 g, yield: 79.0%) as a white solid.

MS m/z (ESI): 253.0 [M+1]

Step 4

(cis-endo)-5-Azido-1,2,3,3a,4,5,6,6a-octahydrocyclopenta[c]pyrrole hydrochloride Tert-butyl (cis-endo)-5-azido-3,3a,4,5,6,6a-hexahydro-1H-cyclopenta[c]pyrrole-2-carboxylate 9c (0.62 g, 2.44 mmol) was dissolved in 10 mL of dichloromethane followed by the addition of 10 mL of a 4 M solution of [1,4]dioxane in hydrochloric acid solution and stirred for 0.5 hours. The reaction solution was concentrated under reduced pressure to obtain the title compound (cis-endo)-5-azido-1,2,3,3a,4,5,6,6a-octahydrocyclopenta[c]pyrrole hydrochloride 9d (0.47 g, yield: 100%) as a white solid.

MS m/z (ESI): 153.1 [M+1]

Step 5

(cis-endo)-5-Azido-2-methyl-3,3a,4,5,6,6a-hexahydro-1H-cyclopenta[c]pyrrole (cis-endo)-5-Azido-1,2,3,3a,4,5,6,6a-octahydrocyclopenta[c]pyrrole hydrochloride 9d (0.45 g, 2.38 mmol) was dissolved in 10 mL of the mixture solvent of acetonitrile and water (V:V=9:1). The reaction solution was cooled down to 0° C. followed by the addition of formaldehyde (0.4 mL, 4.76 mmol) and sodium triacetoxyborohydride (1.51 g, 7.14 mmol) and stirred for 2 hours. The resulting solution was added dropwise with saturated sodium carbonate solution to adjust pH to 10, stirred for 10 minutes and extracted with dichloromethane (20 mL×3). The combined organic phase was washed with saturated sodium chloride solution (20 mL×3), then dried over anhydrous magnesium sulfate, filtered and the filtrate was concentrated under reduced pressure. The resulting residue was purified by silica gel column chromatography to obtain the title compound (cis-endo)-5-azido-2-methyl-3,3a,4,5,6,6a-hexahydro-1H-cyclopenta[c]pyrrole 9e (0.28 g, yield: 71.0%) as a light yellow liquid.

MS m/z (ESI): 167.1 [M+1]

Step 6

(cis-endo)-2-Methyl-3,3a,4,5,6,6a-hexahydro-1H-cyclopenta[c]pyrrol-5-amine (cis-endo)-5-Azido-2-methyl-3,3a,4,5,6,6a-hexahydro-1H-cyclopenta[c]pyrrole 9e (150 mg, 0.90 mmol) was dissolved in 20 mL of methanol followed by the addition of palladium/carbon (30 mg, 10%), filled with hydrogen two times. The reaction mixture was stirred for 2 hours and filtered. The filter cake was washed with 10 mL of methanol. The combined filtrate was concentrated under reduced pressure to obtain the title compound (cis-endo)-2-methyl-3,3a,4,5,6,6a-hexahydro-1H-cyclopenta[c]pyrrol-5-amine 9f (0.08 g, yield: 63.0%) as a light yellow liquid.

MS m/z (ESI): 141.4 [M+1]

Step 7

(cis-exo)-N-[2-Methyl-3,3a,4,5,6,6a-hexahydro-1H-cyclopenta[c]pyrrol-5-yl]-7-[[(7R)-8-cyclopentyl-7-ethyl-5-methyl-6-oxo-7H-pteridin-2-yl]amino]-2,2-dimethyl-3H-benzofuran-4-carboxamide 7-[[(7R)-8-Cyclopentyl-7-ethyl-5-methyl-6-oxo-7H-pteridin-2-yl]amino]-2,2-dimethyl-3H-benzofuran-4-carboxylic acid 4f (163 mg, 0.35 mmol) was dissolved in 15 mL of dichloromethane followed by the addition of (cis-endo)-2-methyl-3,3a,4,5,6,6a-hexahydro-1H-cyclopenta[c]pyrrol-5-amine 9f (59 mg, 0.35 mmol), O-(benzotriazol-1-yl)-N,N,N',N'-tetra methyluronium tetrafluoroborate (112 mg, 0.35 mmol) and diisopropylethylamine (135 mg, 1.05 mmol), stirred for 2 hours. The resulting solution was added with 10 mL saturated sodium bicarbonate solution and extracted with dichloromethane (50 mL×3). The combined organic phase was washed with water (50 mL), saturated sodium chloride solution (50 mL), dried over anhydrous magnesium sulfate. The filtrate was concentrated under reduced pressure. The resulting residue was purified by silica gel column chromatography to obtain the title compound (cis-exo)-N-[2-methyl-3,3a,4,5,6,6a-hexahydro-1H-cyclopenta[c]pyrrol-5-yl]-7-[[(7R)-8-cyclopentyl-7-ethyl-5-methyl-6-oxo-7H-pteridin-2-yl]amino]-2,2-dim ethyl-3H-benzofuran-4-carboxamide 9 (141 mg, yield: 68.8%) as a white solid.

MS m/z (ESI): 588.5 [M+1]

$^1$H NMR (400 MHz, CDCl$_3$) δ 8.26 (d, 1H), 7.67 (s, 1H), 7.09 to 6.95 (m, 2H), 5.86 (d, 1H), 4.62 to 4.45 (m, 2H), 4.21 (dd, 1H), 3.39 (s, 2H), 3.32 (s, 3H), 2.86 to 2.68 (m, 4H), 2.33 (s, 3H), 2.26 to 2.08 (m, 4H), 2.01 (d, 1H), 1.93 (dd, 2H), 1.88 to 1.60 (m, 9H), 1.51 (s, 6H), 0.88 (t, 3H)

Example 10

N-[(cis-endo)-2-(Cyclopropylmethyl)-3,3a,4,5,6,6a-hexahydro-1H-cyclopenta[c]pyrrol-5-yl]-7-[[(7R)-8-cyclopentyl-7-ethyl-5-methyl-6-oxo-7H-pteridin-2-yl]amino]-2,2-dimethyl-3H-benzofuran-4-carboxamide

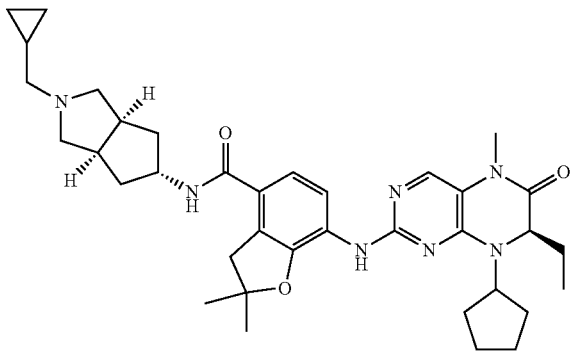

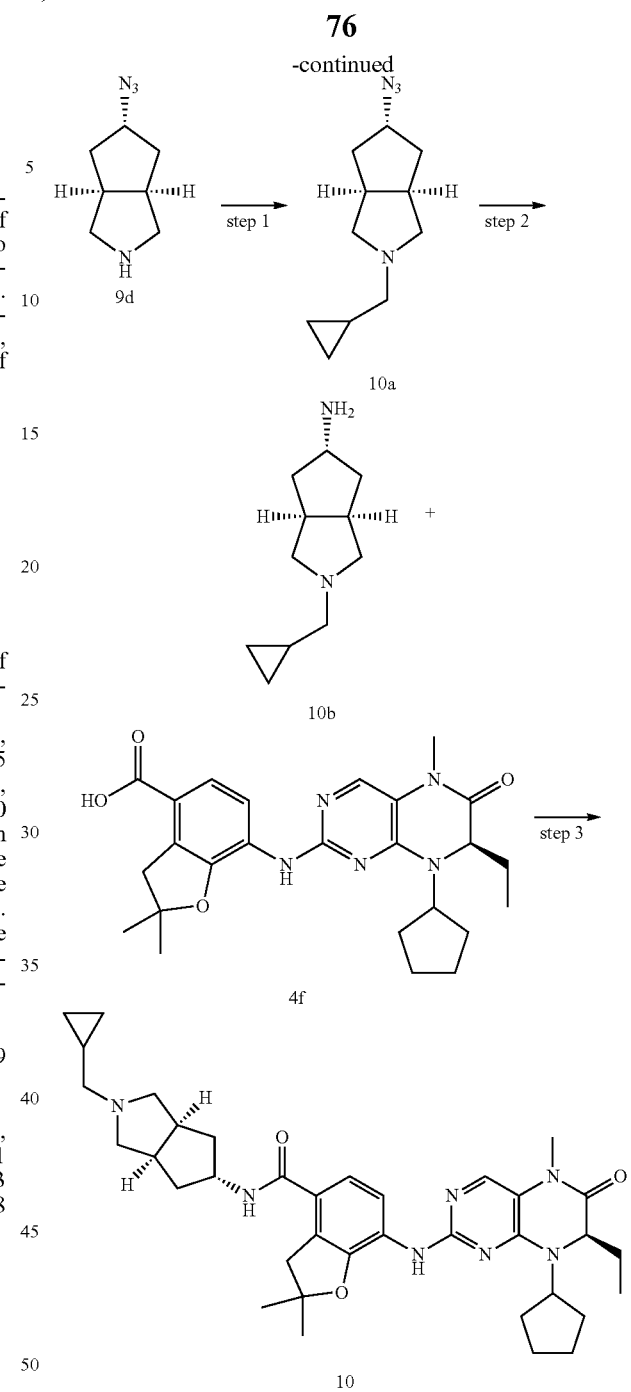

Step 1

(cis-endo)-5-Azido-2-(cyclopropylmethyl)-3,3a,4,5,6,6a-hexahydro-1H-cyclopenta[c]pyrrole (cis-endo)-5-Azido-1,2,3,3a,4,5,6,6a-octahydrocyclopenta[c]pyrrole hydrochloride 9d (693 mg, 3.67 mmol) was dissolved in 25 mL of acetonitrile followed by the addition of potassium carbonate (1.50 g, 11 mmol) and bromomethylcyclopropane (644 mg, 4.77 mmol). The reaction solution was heated to reflux for 2 hours. The resulting solution was concentrated under reduced pressure, added with 20 mL of water and extracted with ethyl acetate (50 mL×3). The combined organic phase was washed with water (50 mL), saturated sodium chloride solution (50 mL) successively and dried over anhydrous magnesium sulfate. The filtrate was concentrated under reduced pressure. The resulting residue was purified by silica gel column chromatography to obtain the title compound (cis-endo)-5-azido-2-(cyclopropylmethyl)-3,3a,4,5,6,6a-hexahydro-1H-cyclopenta[c]pyrrole 10a (0.54 g, yield: 70.9%) as a light yellow solid.

Step 2

(cis-endo)-2-(cyclopropylmethyl)-3,3a,4,5,6,6a-hexahydro-1H-cyclopenta[c]pyrrol-5-amine (cis-endo)-5-azido-2-(cyclopropylmethyl)-3,3a,4,5,6,6a-hexahydro-1H-cyclopenta[c]pyrrole 10a (517 mg, 2.51 mmol) was dissolved in 20 mL of methanol followed by the addition of palladium/carbon (60 mg, 10%), filled with hydrogen three times. The reaction mixture was stirred for 1.5 hours and filtered. The filter cake was washed with methanol. The combined filtrate was concentrated under reduced pressure to obtain the title compound (cis-endo)-2-(cyclopropylmethyl)-3,3a,4,5,6,6a-hexahydro-1H-cyclopenta[c]pyrrol-5-amine 10b (0.43 g, yield: 95.6%) as a yellow liquid.

MS m/z (ESI): 181.2 [M+1]

Step 3

N-[(cis-endo)-2-(Cyclopropylmethyl)-3,3a,4,5,6,6a-hexahydro-1H-cyclopenta[c]pyrrol-5-yl]-7-[[(7R)-8-cyclopentyl-7-ethyl-5-methyl-6-oxo-7H-pteridin-2-yl]amino]-2,2-dimethyl-3H-benzofuran-4-carboxamide 7-[[(7R)-8-Cyclopentyl-7-ethyl-5-methyl-6-oxo-7H-pteridin-2-yl]amino]-2,2-dimethyl-3H-benzofuran-4-carboxylic acid 4f (163 mg, 0.35 mmol) was dissolved in 15 mL of dichloromethane followed by the addition of (cis-endo)-2-(cyclopropylmethyl)-3,3a,4,5,6,6a-hexahydro-1H-cyclopenta[c]pyrrol-5-amine 10b (63 mg, 0.35 mmol), O-(benzotriazol-1-yl)-N,N,N',N'-tetra methyluronium tetrafluoroborate (112 mg, 0.35 mmol) and diisopropylethylamine (135 mg, 1.05 mmol). The reaction solution was stirred for 2 hours. The resulting solution was added with 10 mL of saturated sodium bicarbonate solution and extracted with dichloromethane (50 mL×3). The combined organic phase was washed with water (50 mL), saturated sodium chloride solution (50 mL) successively, then dried over anhydrous magnesium sulfate, filtered and the filtrate was concentrated under reduced pressure. The resulting residue was purified by silica gel column chromatography to obtain the title compound N-[(cis-endo)-2-(cyclopropylmethyl)-3,3a,4,5,6,6a-hexahydro-1H-cyclopenta[c]pyrrol-5-yl]-7-[[(7R)-8-cyclopentyl-7-ethyl-5-methyl-6-oxo-7H-pteridin-2-yl]amino]-2,2-dimethyl-3H-benzofuran-4-carboxamide 10 (153 mg, yield: 69.5%) as a white solid.

MS m/z (ESI): 628.5 [M+1]

$^1$H NMR (400 MHz, CDCl$_3$) δ 8.27 (d, 1H), 7.67 (s, 1H), 7.08 to 6.95 (m, 2H), 5.96 (d, 1H), 5.30 (s, 1H), 4.66-4.43 (m, 2H), 4.21 (dd, 1H), 3.55 to 3.36 (m, 4H), 3.32 (s, 3H), 3.01 (m, 2H), 2.56 (m, 2H), 2.33 (m, 2H), 2.15 (m, 1H), 2.01 (dd, 3H), 1.90 to 1.60 (m, 9H), 1.51 (s, 6H), 1.15 to 1.05 (m, 1H), 0.88 (t, 3H), 0.63 (d, 2H), 0.26 (d, 2H)

Example 11

(cis-endo)-N-[2-Methyl-3,3a,4,5,6,6a-hexahydro-1H-cyclopenta[c]pyrrol-5-yl]-7-[[(7R)-8-cyclopentyl-7-ethyl-5-methyl-6-oxo-7H-pteridin-2-yl]amino]-2,3-dihydrobenzofuran-4-carboxamide

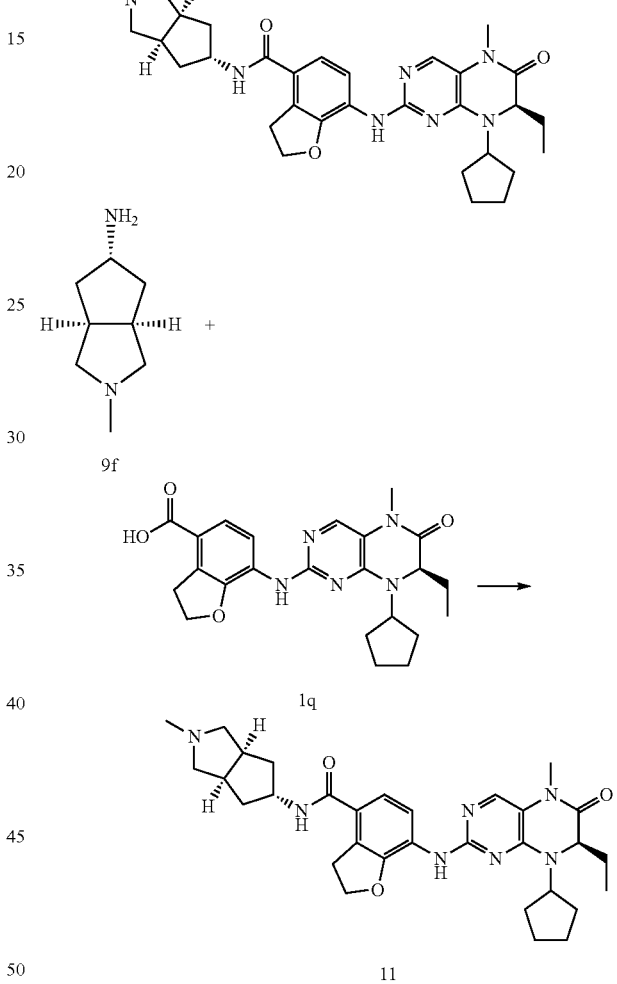

7-[[(7R)-8-Cyclopentyl-7-ethyl-5-methyl-6-oxo-7H-pteridin-2-yl]amino]-2,3-dihydrobenzofuran-4-carboxylic acid 1q (187 mg, 0.43 mmol) and O-(benzotriazol-1-yl)-N,N,N',N'-tetra methyluronium tetrafluoroborate (138 mg, 0.43 mmol) were dissolved in 20 mL of anhydrous dichloromethane followed by the addition of diisopropylethylamine (0.2 mL, 0.95 mmol), stirred until the solution became clear. Then the reaction solution was added with (cis-endo)-2-methyl-3,3a,4,5,6,6a-hexahydro-1H-cyclopenta[c]pyrrol-5-amine 9f (60 mg, 0.43 mmol) and stirred for another 3 hours. The resulting mixture was added with 10 mL of saturated sodium carbonate solution and 10 mL of dichloromethane. The organic phase was washed with saturated sodium carbonate solution (50 mL×2), water (50 mL) and saturated sodium chloride solution (50 mL) successively, then dried over anhydrous sodium sulfate and filtered. The filtrate was concentrated under reduced pressure. The resulting residue was purified by silica gel column chromatography to obtain the title compound (cis-endo)-N-[2-methyl-3,3a,4,5,6,6a-hexahydro-1H-cyclopenta[c]pyrrol-5-yl]-7-[[(7R)-8-cyclopentyl-7-ethyl-5-methyl-6-oxo-7H-pteridin-2-yl]amino]-2,3-dihydrobenzofuran-4-carboxamide 11 (160 mg, yield: 67.0%) as a white solid.

MS m/z (ESI): 560.4 [M+1]

$^1$H NMR (400 MHz, CDCl$_3$) δ 8.27 (d, 1H), 7.67 (s, 1H), 7.10 to 6.94 (m, 2H), 5.88 (d, 1H), 4.68 (t, 2H), 4.56 (d, 1H), 4.47 (t, 1H), 4.21 (dd, 1H), 3.59 (t, 2H), 3.32 (s, 3H), 2.90 to 2.67 (m, 4H), 2.33 (s, 3H), 2.25 to 2.19 (m, 2H), 2.18 to 2.05 (m, 2H), 2.05 to 1.89 (m, 3H), 1.89 to 1.60 (m, 9H), 0.88 (t, 3H)

Example 12

7-[[(7R)-8-Cyclopentyl-7-ethyl-5-methyl-6-oxo-7H-pteridin-2-yl]amino]-N-[(cis)-4-[4-(cyclopropylmethyl)piperazin-1-yl]cyclohexyl]-2,3-dihydrobenzofuran-4-carboxamide

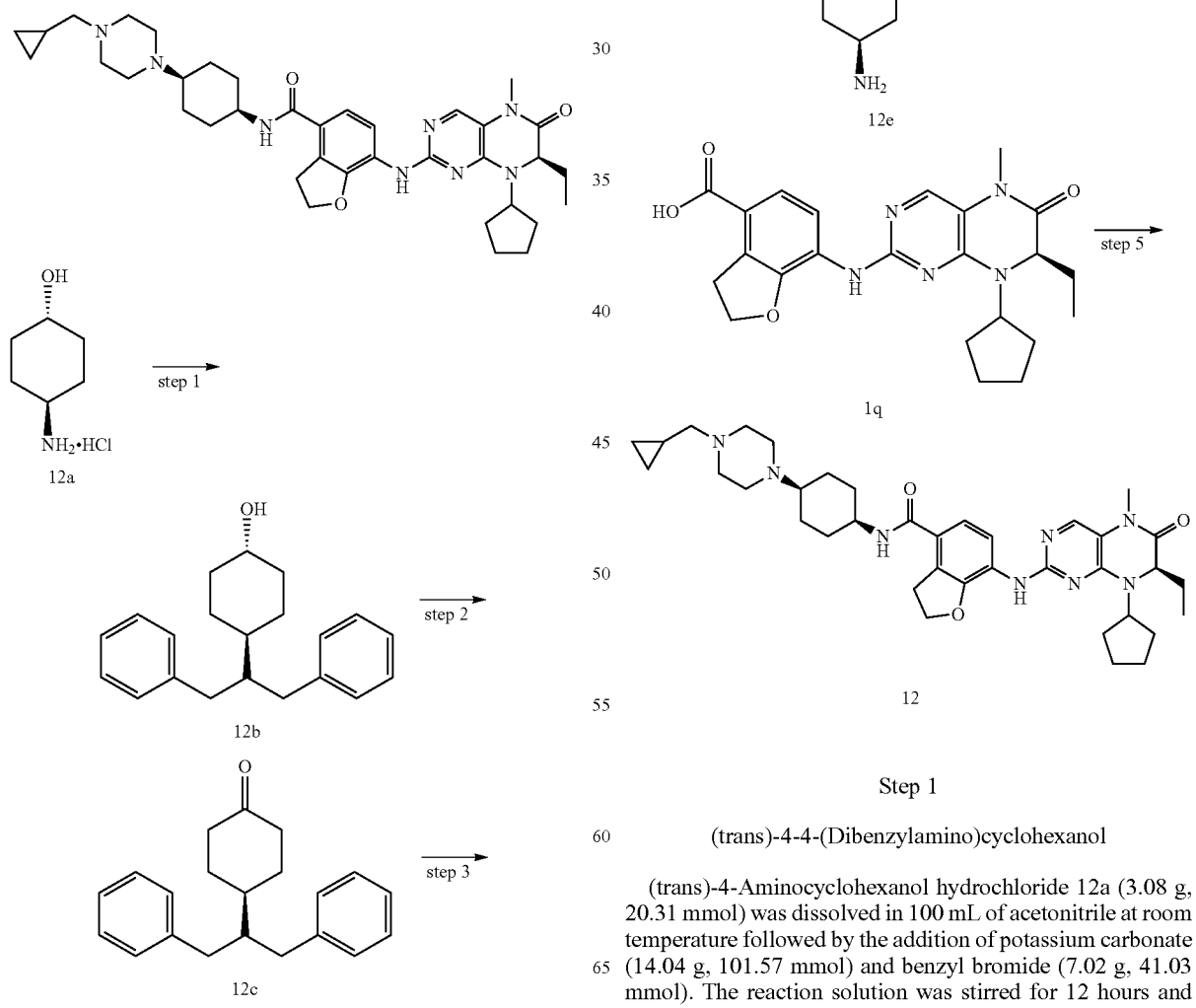

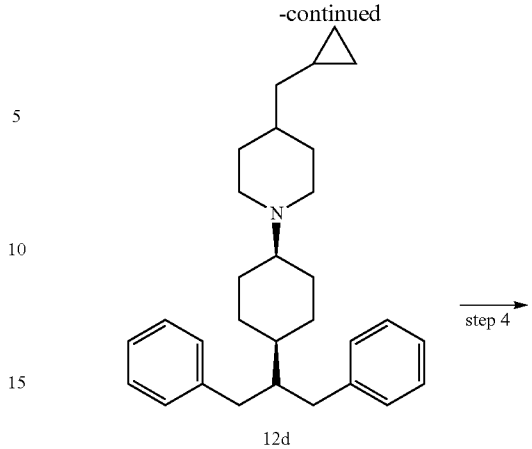

Step 1

(trans)-4-4-(Dibenzylamino)cyclohexanol (trans)-4-Aminocyclohexanol hydrochloride 12a (3.08 g, 20.31 mmol) was dissolved in 100 mL of acetonitrile at room temperature followed by the addition of potassium carbonate (14.04 g, 101.57 mmol) and benzyl bromide (7.02 g, 41.03 mmol). The reaction solution was stirred for 12 hours and filtered. The filter cake was washed with dichloromethane (20 mL×3). The filtrate was concentrated under reduced pressure, and the residue was dissolved by the dichloromethane above, washed successively with saturated ammonium chloride solution (50 mL) and saturated sodium chloride solution (50 mL), then dried over anhydrous magnesium sulfate, filtered and the filtrate was concentrated under reduced pressure to obtain the title compound (trans)-4-4-(dibenzylamino)cyclohexanol 12b (5.93 g, yield: 98.8%) as a white solid.

MS m/z (ESI): 296.3 [M+1]

Step 2

(R)-4-(Dibenzylamino)cyclohexanone (trans)-4-(Dibenzylamino)cyclohexanol 12b (5.93 g, 20 mmol) was dissolved in 120 mL of acetone in an ice-salt bath followed by the addition of a 2.5 mol/L solution of chromium trioxide in sulfuric acid solution (24 mL, 60 mmol), stirred for 5 minutes. The reaction solution was heated to room temperature and stirred for another 30 minutes. The resulting mixture was added with 400 mL of dichloromethane, added dropwise with saturated potassium carbonate solution to adjust pH to 8, filtered and seperated. The organic phase was concentrated under reduced pressure. The resulting residue was purified by silica gel column chromatography to obtain the title compound (R)-4-(dibenzylamino)cyclohexanone 12c (3.09 g, yield: 70.0%) as a white oil.

MS m/z (ESI): 294.3 [M+1]

Step 3

(cis)-N,N-Dibenzyl-4-[4-(cyclopropylmethyl)piperazin-1-yl]cyclohexanamine

Cyclopropylmethyl-piperizine dihydrochloride (5.16 g, 24.20 mmol) was dissolved in 280 mL of acetonitrile, added with solid sodium acetate to adjust pH to 6-7 followed by the addition of (R)-4-(dibenzylamino)cyclohexanone 12c (6.48 g, 22 mmol) and sodium triacetoxyborohydride (11.66 g, 55 mmol) successively, stirred for 12 hours. The resulting solution was added with 100 mL of water, then added with solid sodium carbonate to adjust pH to 8 and seperated. The aqueous phase was extracted with dichloromethane (250 mL×2). The combined organic phase was washed with saturated sodium bicarbonate solution (100 mL) and saturated sodium chloride solution (100 mL) successively, then dried over anhydrous magnesium sulfate, filtered and the filtrate was concentrated under reduced pressure. The resulting residue was purified by silica gel column chromatography to obtain the title compound (cis)-N,N-dibenzyl-4-[4-(cyclopropylmethyl)piperazin-1-yl]cyclohexanamine 12d (3.13 g, yield: 34.1%) as a white solid.

MS m/z (ESI): 418.4 [M+1]

Step 4

(cis)-4-[4-(Cyclopropylmethyl)piperazin-1-yl]cyclohexanamine (cis)-N,N-Dibenzyl-4-[4-(cyclopropylmethyl)piperazin-1-yl]cyclohexanamine 12d (2.44 g, 5.83 mmol) was dissolved in 30 mL mixture solvent of dichloromethane and methanol (V/V=1:2) followed by the addition of palladium/carbon (1.22 g, 10%) and 0.1 mL acetic acid, filled with hydrogen three times. The reaction mixture was reacted at 3 atmosphere for 12 hours. The resulting solution was added with 4 g alkaline aluminum oxide (200-300 mesh) and filtered. The filtrate was concentrated under reduced pressure to obtain the title compound (cis)-4-[4-(cyclopropylmethyl)piperazin-1-yl]cyclohexanamine 12e (2.38 g, yield: 98.0%) as a colorless solid.

Step 5

7-[[(7R)-8-Cyclopentyl-7-ethyl-5-methyl-6-oxo-7H-pteridin-2-yl]amino]-N-[(cis)-4-[4-(cyclopropylmethyl)piperazin-1-yl]cyclohexyl]-2,3-dihydrobenzofuran-4-carboxamide (cis)-4-[4-(Cyclopropylmethyl)piperazin-1-yl]cyclohexanamine 12e (139 mg, 0.40 mmol), 7-[[(7R)-8-cyclopentyl-7-ethyl-5-methyl-6-oxo-7H-pteridin-2-yl]amino]-2,3-dihydrobenzofuran-4-carboxylic acid 1q (175 mg, 0.40 mmol), O-(benzotriazol-1-yl)-N,N,N',N'-tetra methyluronium tetrafluoroborate (128 mg, 0.40 mmol) and diisopropylethylamine (258 mg, 2.08 mmol) were dissolved in 50 mL of dichloromethane. The reaction solution was stirred for 2 hours followed by the addition of 50 mL of water and 10 mL of aqueous ammonia successively, and stirred for another 0.5 hours. The resulting solution was extracted with dichloromethane (50 mL×3). The combined organic phase was washed with saturated sodium chloride solution (50 mL×3), dried over anhydrous magnesium sulfate. The filtrate was concentrated under reduced pressure. The resulting residue was purified by silica gel column chromatography to obtain the title compound 7-[[(7R)-8-cyclopentyl-7-ethyl-5-methyl-6-oxo-7H-pteridin-2-yl]amino]-N-[(cis)-4-[4-(cyclopropylmethyl)piperazin-1-yl]cyclohexyl]-2,3-dihydrobenzofuran-4-carboxamide 12 (160 mg, yield: 61.0%) as a white solid.

MS m/z (ESI): 657.6 [M+1]

$^1$H NMR (400 MHz, CDCl$_3$) δ 8.28 (d, 1H), 7.67 (s, 1H), 7.13 (d, 1H), 7.03 (s, 1H), 6.18 to 6.08 (m, 1H), 4.68 (t, 2H), 4.52 to 4.48 (m, 1H), 4.28 to 4.19 (m, 2H), 3.60 (t, 2H), 3.32 (s, 3H), 3.15 to 2.64 (m, 8H), 2.63 to 2.45 (m, 4H), 2.16 to 2.08 (m, 1H), 2.08 to 1.92 (m, 3H), 1.92 to 1.75 (m, 6H), 1.75 to 1.60 (m, 8H), 1.07 to 0.92 (m, 1H), 0.88 (t, 3H), 0.61 to 0.50 (m, 2H), 0.23 to 0.15 (m, 2H)

Example 13

(cis-endo)-N-[2-(Cyclopropylmethyl)-3,3a,4,5,6,6a-hexahydro-1H-cyclopenta[c]pyrrol-5-yl]-7-[[(7R)-8-cyclopentyl-7-ethyl-5-methyl-6-oxo-7H-pteridin-2-yl]amino]-2,3-dihydrobenzofuran-4-carboxamide

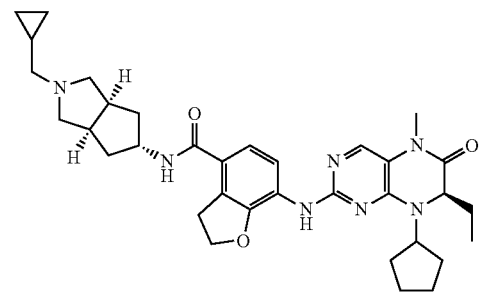

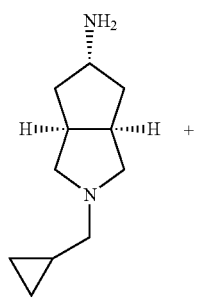

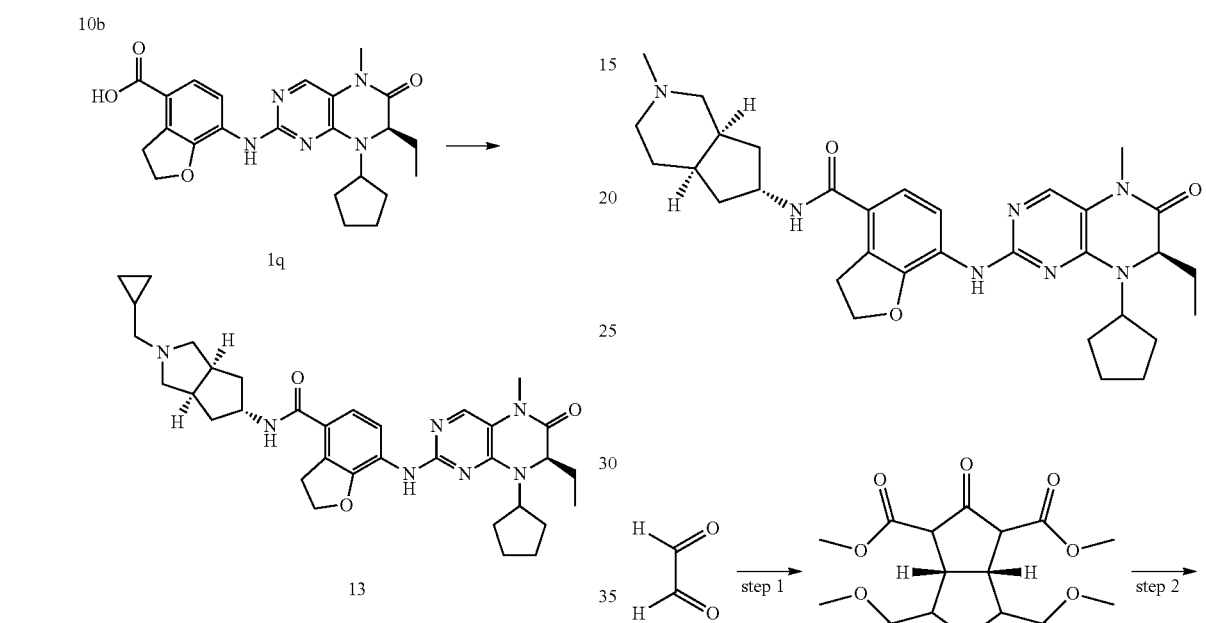

7-[[(7R)-8-Cyclopentyl-7-ethyl-5-methyl-6-oxo-7H-pteridin-2-yl]amino]-2,3-dihydrobenzofuran-4-carboxylic acid 1q (187 mg, 0.43 mmol) and O-(benzotriazol-1-yl)-N,N,N',N'-tetra methyluronium tetrafluoroborate (138 mg, 0.43 mmol) were dissolved in 20 mL of anhydrous dichloromethane followed by the addition of diisopropylethylamine (0.2 mL, 0.95 mmol), stirred until the solution became clear, then added with (cis-endo)-2-(cyclopropylmethyl)-3,3a,4,5,6,6a-hexahydro-1H-cyclopenta[c]pyrrol-5-amine 10b (77 mg, 0.43 mmol), stirred for 3 hours. The resulting solution was added with 10 mL of saturated sodium carbonate solution and 20 mL of dichloromethane, and seperated. The organic phase was washed with saturated sodium carbonate solution (20 mL×2), and water (30 mL) and saturated sodium chloride solution (30 mL) successively, then dried over anhydrous sodium sulfate, filtered and the filtrate was concentrated under reduced pressure. The resulting residue was purified by silica gel column chromatography to obtain the title compound (cis-endo)-N-[2-(cyclopropylmethyl)-3,3a,4,5,6,6a-hexahydro-1H-cyclopenta[c]pyrrol-5-yl]-7-[[(7R)-8-cyclopentyl-7-ethyl-5-methyl-6-oxo-7H-pteridin-2-yl]amino]-2,3-dihydrobenzofuran-4-carboxamide 13 (210 mg, yield: 81.0%) as a white solid.

MS m/z (ESI): 600.5 [M+1]

$^1$H NMR (400 MHz, CDCl$_3$) δ 8.27 (d, 1H), 7.67 (s, 1H), 7.10 to 6.92 (m, 2H), 5.90 (d, 1H), 4.68 (t, 2H), 4.47 (s, 2H), 4.21 (dd, 1H), 3.59 (t, 2H), 3.32 (s, 3H), 3.06 (s, 2H), 2.80 (s, 2H), 2.31 (d, 2H), 2.23 to 2.06 (m, 3H), 2.06 to 1.91 (m, 3H), 1.91 to 1.77 (m, 4H), 1.77 to 1.52 (m, 6H), 1.39 to 1.15 (m, 1H), 0.88 (t, 3H), 0.58 to 0.36 (m, 2H), 0.20 to 0.08 (m, 2H)

Example 14

(cis-endo)-N-[2-Methyl-1,3,3a,4,5,6,7,7a-octahydro-cyclopenta[c]pyridin-6-yl]-7-[[(7R)-8-cyclopentyl-7-ethyl-5-methyl-6-oxo-7H-pteridin-2-yl]amino]-2,3-dihydrobenzofuran-4-carboxamide

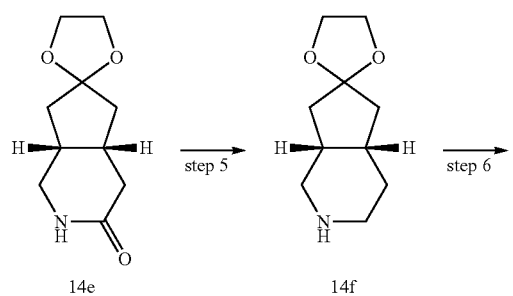

85
-continued

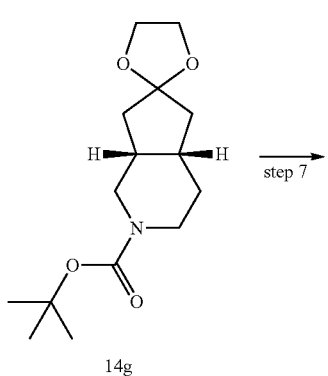
14g step 7

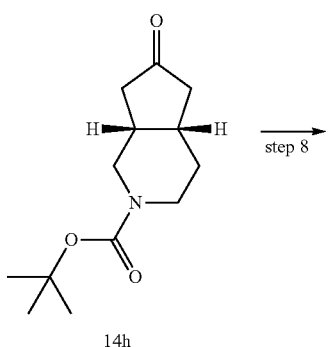
14h step 8

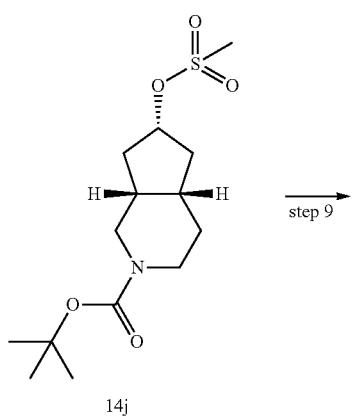
14j step 9

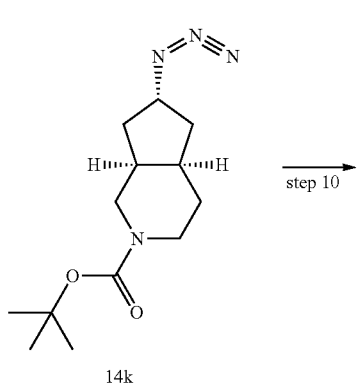
14k step 10

86
-continued

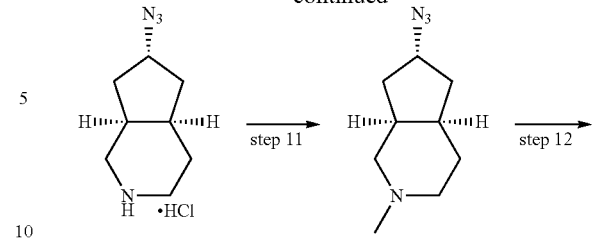
14m → step 11 → 14n → step 12

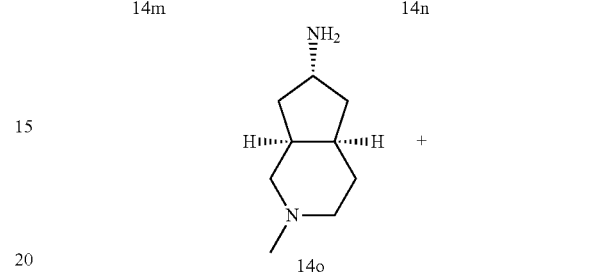
14o +

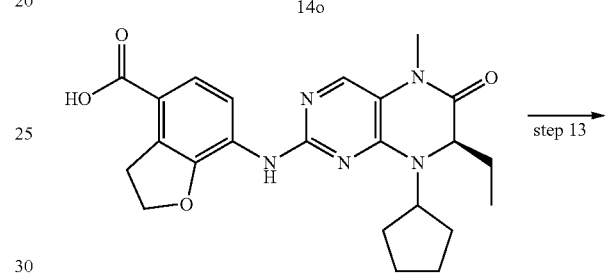
1q step 13

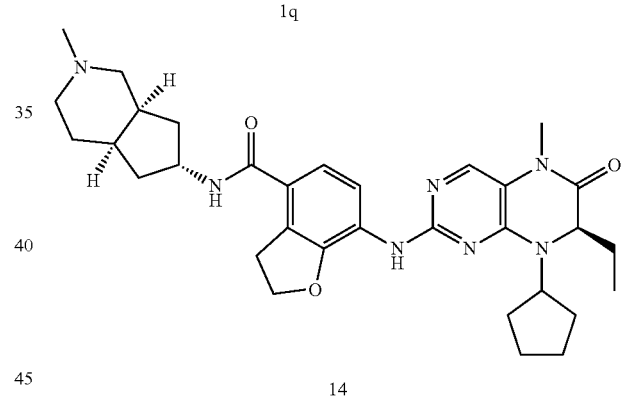
14

Step 1

(cis)-Tetramethyl bicyclo[3.3.0]octane-3,7-dioxo-2,4,6,8-tetracarboxylate

Sodium hydroxide (6.40 g, 0.16 mol) was dissolved in 115 mL of methanol in an ice-water bath, added dropwise with dimethyl 1,3-acetone-dicarboxylate (22.6 mL, 0.16 mol) with stirring. The reaction solution was heated to reflux until the salt was dissolved completely, added dropwise quickly with glyoxal 14a (12.85 g, 0.09 mol) at 65° C., then cooled down to room temperature, stirred for 12 hours and filtered. The filter cake was washed with 50 mL of methanol and dissolved in 180 mL of the mixture solvent of dichloromethane and water (V/V=5:4). The resulting solution was cooled down to 0° C., added dropwise with 1 M hydrochloric acid to adjust pH to 6 and extracted with dichloromethane (50 mL×3). The combined organic phase was washed with saturated sodium chloride solution (50 mL×3), then dried over anhydrous magnesium sulfate, filtered and the filtrate was concentrated under reduced pressure to obtain the title compound (cis)-tetramethyl bicyclo[3.3.0]octane-3,7-dioxo-2,4,6,8-tetracarboxylate 14b (20 g, yield: 61.0%) as a white solid.

MS m/z (ESI): 371.3 [M+1]

Step 2

(cis)-Bicyclo[3.3.0]octane-3,7-dione (cis)-Tetramethyl bicyclo[3.3.0]octane-3,7-dioxo-2,4,6,8-tetracarboxylate 14b (6.75 g, 0.02 mol) was dissolved in 3.3 mL of acetic acid followed by the addition of 30 mL of 1 M hydrochloric acid. The reaction solution was heated to reflux for 3.5 hours and then cooled down to room temperature. The reaction solution was extracted with dichloromethane (50 mL×3). The combined organic phase was concentrated under reduced pressure, added with 100 mL of dichloromethane, added dropwise with saturated sodium bicarbonate solution to adjust pH to 7 and seperated. The organic phase was dried over anhydrous magnesium sulfate, filtered and the filtrate was concentrated under reduced pressure to obtain the title compound (cis)-bicyclo[3.3.0]octane-3,7-dione 14c (2 g, yield: 80.0%) as a white solid.

Step 3

(cis)-2,4,4a,5,7,7a-hexahydro-1H-cyclopenta[c]pyridine-3,6-dione (cis)-Bicyclo[3.3.0]octane-3,7-dione 14c (1.80 g, 13 mmol) was dissolved in 25 mL of concentrated hydrochloric acid in an ice-water bath, added with sodium azide (1.10 g, 16.90 mmol) in batches, then heated to room temperature and stirred for 12 hours. The reaction solution was added dropwise with 20% sodium hydroxide solution to adjust pH to 10 to 11, extracted with dichloromethane (50 mL×3). The combined organic phase was washed with saturated sodium chloride solution (50 mL×3), then dried over anhydrous magnesium sulfate, filtered and the filtrate was concentrated under reduced pressure to obtain the title compound (cis)-2,4,4a,5,7,7a-hexahydro-1H-cyclopenta[c]pyridine-3,6-dione 14d (3 g, yield: 100.0%) as a white solid.

MS m/z (ESI): 154.1 [M+1]

Step 4

(cis)-spiro[1,3-dioxolane-2,6'-2,4,4a,5,7,7a-hexahydro-1H-cyclopenta[c]pyridine]-3'-one (cis)-2,4,4a,5,7,7a-hexahydro-1H-cyclopenta[c]pyridine-3,6-dione 14d (1.20 g, 7.80 mmol), ethanediol (1.34 g, 21.50 mmol) and p-toluenesulfonic acid (24 mg, 0.13 mmol) were dissolved in 60 mL of toluene, heated to reflux for 8 hours with stirring, then added dropwise with saturated sodium bicarbonate solution to adjust pH to 7 around and extracted with dichloromethane (50 mL). The aqueous phase was extracted with dichloromethane (50 mL×3). The combined organic phase was washed with saturated sodium chloride solution (50 mL×3), then dried over anhydrous magnesium sulfate, filtered and the filtrate was concentrated under reduced pressure. The resulting residue was purified by silica gel column chromatography to obtain the title compound (cis)-spiro[1,3-dioxolane-2,6'-2,4,4a,5,7,7a-hexahydro-1H-cyclopenta[c]pyridine]-3'-one 14e (1.10 g, yield: 70.0%) as a white solid.

MS m/z (ESI): 198.1 [M+1]

Step 5

(cis)-spiro[1,2,3,4,4a,5,7,7a-octahydrocyclopenta[c]pyridine-6,2'-1,3-dioxolane]

In an ice-water bath, lithium aluminium hydride (47 mg, 1.27 mmol) was dissolved in 10 mL of tetrahydrofuran followed by the addition of 10 mL of a solution of (cis)-spiro[1,3-dioxolane-2,6'-2,4,4a,5,7,7a-hexahydro-1H-cyclopenta[c]pyridine]-3'-one 14e (120 mg, 0.60 mmol) in tetrahydrofuran. The resulting solution was stirred for 1 hour, added with 1 μL of water, 1 μL of 15% sodium hydroxide solution in batches, extracted with dichloromethane (50 mL×3). The combined organic phase was washed with saturated sodium chloride solution (50 mL×3), then dried over anhydrous magnesium sulfate, filtered and the filtrate was concentrated under reduced pressure to obtain the crude title compound (cis)-spiro[1,2,3,4,4a,5,7,7a-octahydrocyclopenta[c]pyridine-6,2'-1,3-dioxolane] 14f (150 mg) as a yellow oil liquid, which was used in the next step without further furification.

MS m/z (ESI): 184.2 [M+1]

Step 6

(cis)-tert-butyl-spiro[1,3-dioxolane-2,6'-3,4,4a,5,7,7a-hexahydro-1H-cyclopenta[c]pyridine]-2'-carboxylate (cis)-spiro[1,2,3,4,4a,5,7,7a-octahydrocyclopenta[c]pyridine-6,2'-1,3-dioxolane] 14f (100 mg, 0.54 mmol) was dissolved in 15 mL of dichloromethane in an ice-water bath. The resulting solution was added with triethylamine (109 mg, 1.08 mmol) and di-tert-butyl dicarbonate (130 mg, 0.60 mmol) successively, stirred for 2 hours, then added dropwise with saturated sodium bicarbonate solution to adjust pH to 8 to 9, extracted with dichloromethane (50 mL×3). The combined organic phase was washed with saturated sodium chloride solution (50 mL×3), then dried over anhydrous magnesium sulfate, filtered and the filtrate was concentrated under reduced pressure. The resulting residue was purified by silica gel column chromatography to obtain the title compound (cis)-tert-butyl-spiro[1,3-dioxolane-2,6'-3,4,4a,5,7,7a-hexahydro-1H-cyclopenta[c]pyridine]-2'-carboxylate 14g (100 mg, yield: 66.0%) as a colorless oil liquid.

Step 7

(cis)-tert-butyl-6-oxo-3,4,4a,5,7,7a-hexahydro-1H-cyclopenta[c]pyridine-2-carboxylate (cis)-tert-butyl-spiro[1,3-dioxolane-2,6'-3,4,4a,5,7,7a-hexahydro-1H-cyclopenta[c]pyridine]-2'-carboxylate 14g (620 mg, 2.20 mmol) was dissolved in 50 mL of acetone followed by the addition of p-toluenesulfonic acid (200 mg, 1.10 mmol). The resulting solution was heated to reflux for 30 minutes, then cooled down to room temperature, added dropwise with saturated sodium bicarbonate solution to adjust pH to 8 to 9, extracted with dichloromethane (50 mL×3). The combined organic phase was washed with saturated sodium chloride solution (50 mL×3), then dried over anhydrous magnesium sulfate, filtered and the filtrate was concentrated under reduced pressure. The resulting residue was purified by silica gel column chromatography to obtain the title compound (cis)-tert-butyl-6-oxo-3,4,4a,5,7,7a-hexahydro-1H- cyclopenta[c]pyridine-2-carboxylate 14h (450 mg, yield: 85.0%) as a colorless oil liquid.

Step 8

(cis-exo)-tert-butyl-6-methylsulfonyloxy-1,3,4,4a,5,6,7,7a-octahydrocyclopenta[c]pyridine-2-carboxylate (cis)-tert-butyl-6-oxo-3,4,4a,5,7,7a-hexahydro-1H-cyclopenta[c]pyridine-2-carboxylate 14h (22 mg, 0.10 mmol) was dissolved in 10 mL of tetrahydrofuran followed by the addition of sodium borohydride (10 mg, 0.14 mmol), stirred for 12 hours. The reaction solution was concentrated under reduced pressure followed by the addition of 20 mL of dichloromethane, then added with triethylamine (40 μL, 0.29 mmol) and methanesulfonyl chloride (20 μL, 0.14 mmol), stirred for 2 hours. The resulting solution was added dropwise with saturated sodium bicarbonate solution to adjust pH to 8 to 9, extracted with dichloromethane (50 mL×3). The combined organic phase was washed with saturated sodium chloride solution (50 mL×3), then dried over anhydrous magnesium sulfate, filtered and the filtrate was concentrated under reduced pressure. The resulting residue was purified by silica gel column chromatography to obtain the title compound (cis-exo)-tert-butyl-6-methylsulfonyloxy-1,3,4,4a,5,6,7,7a-octahydrocyclopenta[c]pyridine-2-carboxylate 14j (28 mg, yield: 98.0%) as a colorless oil liquid.

Step 9

(cis-endo)-tert-butyl-6-azido-1,3,4,4a,5,6,7,7a-octahydrocyclopenta[c]pyridine-2-carboxylate (cis-exo)-tert-butyl-6-methylsulfonyloxy-1,3,4,4a,5,6,7,7a-octahydrocyclopenta[c]pyridine-2-carboxylate 14j (32 mg, 0.10 mmol) was dissolved in 10 mL of N,N-Dimethylformamide, added slowly with sodium azide (20 mg, 0.25 mmol), then heated to 70-80° C. and stirred for 3.5 hours. The resulting solution was added dropwise with saturated sodium bicarbonate solution to adjust pH to 8 to 9, extracted with dichloromethane (50 mL×3). The combined organic phase was washed with saturated sodium chloride solution (50 mL×3), then dried over anhydrous magnesium sulfate, filtered and the filtrate was concentrated under reduced pressure. The resulting residue was purified by silica gel column chromatography to obtain the title compound (cis-endo)-tert-butyl-6-azido-1,3,4,4a,5,6,7,7a-octahydrocyclopenta[c]pyridine-2-carboxylate 14k (40 mg, yield: 100.0%) as a colorless oil liquid.

Step 10

(cis-endo)-6-azido-2,3,4,4a,5,6,7,7a-octahydro-1H-cyclopenta[c]pyridine hydrochloride (cis-endo)-tert-butyl-6-azido-1,3,4,4a,5,6,7,7a-octahydrocyclopenta[c]pyridine-2-carboxylate 14k (1.15 g, 4.32 mmol) was dissolved in 5 mL of dichloromethane followed by the addition of 10 mL of a 4 M solution of hydrogen chloride dioxane in dioxane, stirred for 2 hours. The reaction solution was concentrated under reduced pressure to obtain the crude title compound (cis-endo)-6-azido-2,3,4,4a,5,6,7,7a-octahydro-1H-cyclopenta[c]pyridine hydrochloride 14m (880 mg) as a colorless oil liquid, which was used in the next step without further furification.
MS m/z (ESI): 167.2 [M+1]

Step 11

(cis-endo)-6-azido-2-methyl-1,3,4,4a,5,6,7,7a-octahydrocyclopenta[c]pyridine (cis-endo)-6-azido-2,3,4,4a,5,6,7,7a-octahydro-1H-cyclopenta[c]pyridine hydrochloride 14m (880 mg, 4.32 mmol) was dissolved in 20 mL of the mixture solvent of acetonitrile and water (V/V=1:1) in an ice-water bath, added with formaldehyde (0.7 mL, 8.64 mmol) and sodium triacetoxyborohydride (2.70 g, 12.96 mmol) successively, then stirred for 2 hours followed by the addition of 10 mL of 1 M hydrochloric acid, and added dropwise with 15 mL of 5% sodium hydroxide solution to adjust pH to 9. The resulting solution was stirred 10 minutes, extracted with dichloromethane (50 mL×3). The combined organic phase was washed with saturated sodium chloride solution (50 mL×3), then dried over anhydrous magnesium sulfate, filtered and the filtrate was concentrated under reduced pressure. The resulting residue was purified by silica gel column chromatography to obtain the title compound (cis-endo)-6-azido-2-methyl-1,3,4,4a,5,6,7,7a-octahydrocyclopenta[c]pyridine 14n (650 mg, yield: 84.0%) as a colorless oil.
MS m/z (ESI): 181.1 [M+1]

Step 12

(cis-endo)-2-methyl-1,3,4,4a,5,6,7,7a-octahydrocyclopenta[c]pyridin-6-amine (cis-endo)-6-azido-2-methyl-1,3,4,4a,5,6,7,7a-octahydrocyclopenta[c]pyridine 14n (650 mg, 3.60 mmol) was dissolved in 20 mL of methanol followed by the addition of palladium/carbon (70 mg, 10%), filled with hydrogen three times. The reaction mixture was stirred for 2 hours and filtered. The filtrate was concentrated under reduced pressure to obtain the title compound (cis-endo)-2-methyl-1,3,4,4a,5,6,7,7a-octahydrocyclopenta[c]pyridin-6-amine 14o (505 mg, yield: 91.0%) as a light yellow oil liquid.
MS m/z (ESI): 155.2 [M+1]

Step 13

N-[(cis-endo)-2-methyl-1,3,3a,4,5,6,7,7a-octahydrocyclopenta[c]pyridin-6-yl]-7-[[(7R)-8-cyclopentyl-7-ethyl-5-methyl-6-oxo-7H-pteridin-2-yl]amino]-2,3-dihydrobenzofuran-4-carboxamide 7-[[(7R)-8-cyclopentyl-7-ethyl-5-methyl-6-oxo-7H-pteridin-2-yl]amino]-2,3-dihydrobenzofuran-4-carboxylic acid 1q (187 mg, 0.43 mmol) and O-(benzotriazol-1-yl)-N,N,N',N'-tetra methyluronium tetrafluoroborate (138 mg, 0.43 mmol) were dissolved in 30 mL of anhydrous dichloromethane, added with diisopropylethylamine (0.2 mL, 0.95 mmol) and (cis-endo)-2-methyl-1,3,4,4a,5,6,7,7a-octahydrocyclopenta[c]pyridin-6-amine 14o (66 mg, 0.43 mmol) successively, stirred for 3 hours. The resulting solution was added with 10 mL of saturated sodium carbonate solution and 30 mL of dichloromethane, seperated. The organic phase was washed with sodium carbonate solution (50 mL×2), water (50 mL) and saturated sodium chloride solution (50 mL) successively, then dried over anhydrous sodium sulfate, filtered and the filtrate was concentrated under reduced pressure. The resulting residue was purified by silica gel column chromatography to obtain the title compound N-[(cis-endo)-2-methyl-1,3,3a,4,5,6,7,7a-octahydrocyclopenta[c]pyridin-6-yl]-7-[[(7R)-8-cyclopentyl-7-ethyl-5-methyl-6-oxo-7H-pteridin-2-yl]amino]-2,3-dihydrobenzofuran-4-carboxamide 14 (120 mg, yield: 48.0%) as a white solid.

MS m/z (ESI): 574.3 [M+1]

¹H NMR (400 MHz, CDCl₃) δ 8.27 (d, 1H), 7.67 (s, 1H), 7.10 to 6.94 (m, 2H), 6.04 (d, 1H), 4.67 (t, 2H), 4.58 (d, 1H), 4.47 (t, 1H), 4.21 (dd, 1H), 3.58 (t, 2H), 3.32 (s, 3H), 2.70 to 2.45 (m, 4H), 2.41 (s, 3H), 2.36 to 2.07 (m, 5H), 2.06 to 1.92 (m, 2H), 1.90 to 1.60 (m, 11H), 0.88 (t, 3H)

Example 15

7-[[(7R)-8-Cyclopentyl-7-ethyl-5-methyl-6-oxo-7H-pteridin-2-yl]amino]-N-[[(2R)-4-methylmorpholin-2-yl]methyl]-2,3-dihydrobenzofuran-4-carboxamide

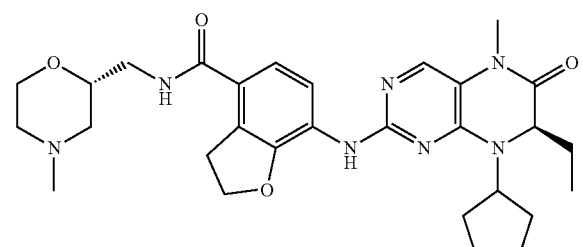

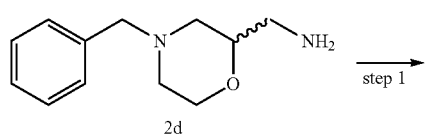

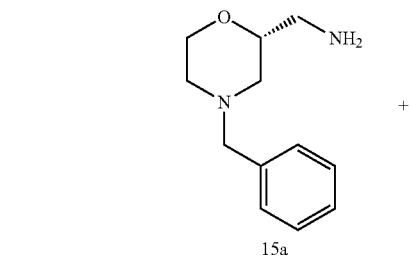

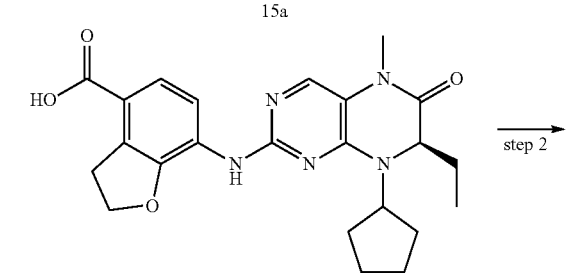

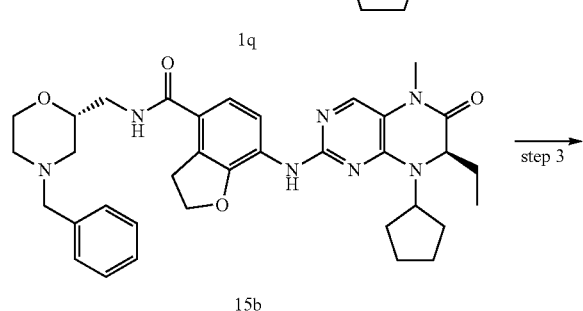

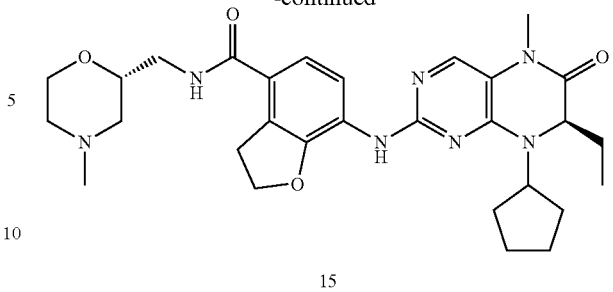

15

Step 1

[(2R)-4-Benzylmorpholin-2-yl]methanamine (4-Benzylmorpholin-2-yl)methanamine 2d (1.35 g, 6.50 mmol) was dissolved in 30 mL of ethanol followed by the addition of L-(−)-dibenzoyltartaric acid (2.34 g, 6.50 mmol). The reaction solution was heated to reflux for 10 minutes, then cooled down to room temperature, placed for 16 hours resulting in the formation of crystal and filtered. The filter cake was dissolved in 10 mL of water, added with 1 M aqueous sodium hydroxide solution to adjust pH to 9 and extracted with dichloromethane (30 mL×3). The combined organic phase was dried over anhydrous sodium sulfate, filtered and the filtrate was concentrated under reduced pressure to obtain the title compound [(2R)-4-benzylmorpholin-2-yl]methanamine 15a (0.28 g, yield: 28.0%) as a light yellow oil liquid.

MS m/z (ESI): 207.2 [M+1]

Step 2

N-[[(2R)-4-Benzylmorpholin-2-yl]methyl]-7-[[(7R)-8-cyclopentyl-7-ethyl-5-methyl-6-oxo-7H-pteridin-2-yl]amino]-2,3-dihydrobenzofuran-4-carboxamide 7-[[(7R)-8-Cyclopentyl-7-ethyl-5-methyl-6-oxo-7H-pteridin-2-yl]amino]-2,3-dihydrobenzofuran-4-carboxylic acid 1q (276 mg, 0.63 mmol) and O-(benzotriazol-1-yl)-N,N,N',N'-tetra methyluronium tetrafluoroborate (202 mg, 0.63 mmol) were dissolved in 20 mL of anhydrous dichloromethane, added with diisopropylethylamine (0.2 mL, 1.4 mmol), [(2R)-4-benzylmorpholin-2-yl]methanamine 15a (130 mg, 0.63 mmol) successively with stirring. The reaction solution was stirred for 3 hours. The resulting solution was added with 10 mL saturated sodium carbonate solution and 10 mL of dichloromethane successively, and seperated. The organic phase was washed with sodium carbonate solution (50 mL×2), water (50 mL) and saturated sodium chloride solution (50 mL) successively, then dried over anhydrous sodium sulfate, filtered and the filtrate was concentrated under reduced pressure. The resulting residue was purified by silica gel column chromatography to obtain the title compound N-[[(2R)-4-benzylmorpholin-2-yl]methyl]-7-[[(7R)-8-cyclopentyl-7-ethyl-5-methyl-6-oxo-7H-pteridin-2-yl]amino]-2,3-dihydrobenzofuran-4-carboxamide 15b (370 mg, yield: 94.0%) as a white solid.

MS m/z (ESI): 626.5 [M+1]

Step 3

7-[[(7R)-8-Cyclopentyl-7-ethyl-5-methyl-6-oxo-7H-pteridin-2-yl]amino]-N-[[(2R)-4-methylmorpholin-2-yl]methyl]-2,3-dihydrobenzofuran-4-carboxamide N-[[(2R)-4-Benzylmorpholin-2-yl]methyl]-7-[[(7R)-8-cyclopentyl-7-ethyl-5-methyl-6-oxo-7H-pteridin-2-yl]amino]-2,3-dihydrobenzofuran-4-carboxamide 15b (370 mg, 0.59 mmol) was dissolved in 30 mL of methanol. The reaction solution was hydrogenated with H-Cube (column of catalyst: 10% palladium/carbon; the pressure of hydrogen: 10 atmosphere; temperature: 40° C.) for 8 hours. The reaction solution was concentrated under reduced pressure to obtain the title compound 7-[[(7R)-8-cyclopentyl-7-ethyl-5-methyl-6-oxo-7H-pteridin-2-yl]amino]-N-[[(2R)-4-methylmorpholin-2-yl]methyl]-2,3-dihydrobenzofuran-4-carboxamide 15 (60 mg, yield: 18.5%) as a white solid.

MS m/z (ESI): 550.3 [M+1]

$^1$H NMR (400 MHz, CDCl$_3$) δ 8.25 (d, 1H), 7.67 (s, 1H), 7.11 to 7.02 (m, 2H), 4.66 (t, 2H), 4.62 to 4.53 (m, 1H), 4.50 (t, 1H), 4.20 (dd, 1H), 3.66 (t, 2H), 3.32 (s, 3H), 2.91 (s, 2H), 2.78 (s, 2H), 2.47 (s, 3H), 2.34 (s, 2H), 2.24 to 2.06 (m, 3H), 2.06 to 1.94 (m, 1H), 1.89 to 1.75 (m, 4H), 1.72 to 1.62 (m, 5H), 0.88 (t, 3H)

Example 16

7-[[(7R)-8-Cyclopentyl-7-ethyl-5-methyl-6-oxo-7H-pteridin-2-yl]amino]-N-[(trans)-4-[4-(cyclopropylmethyl)piperazin-1-yl]cyclohexyl]-2,2-dimethyl-3H-benzofuran-4-carboxamide

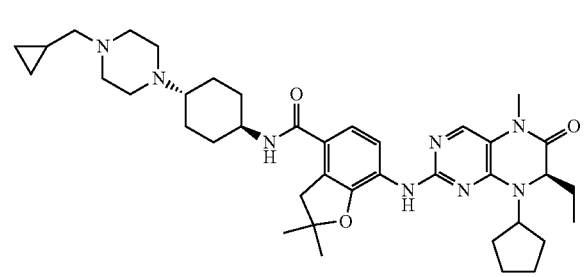

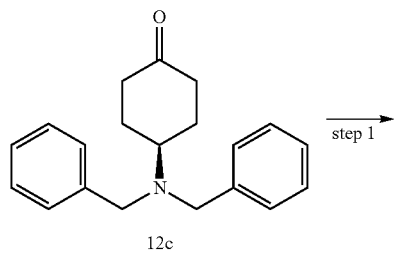

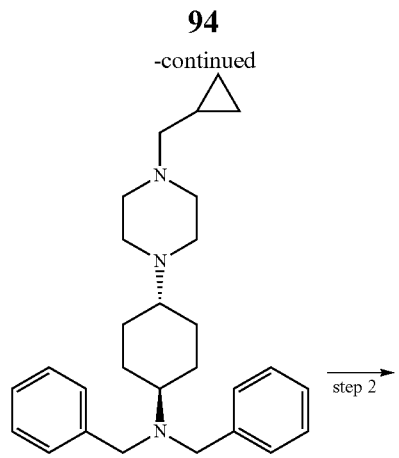

step 2 →

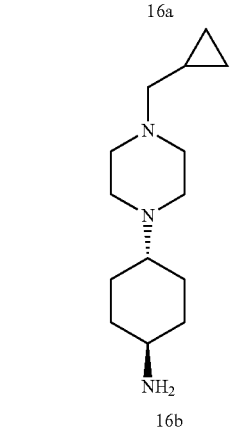

+

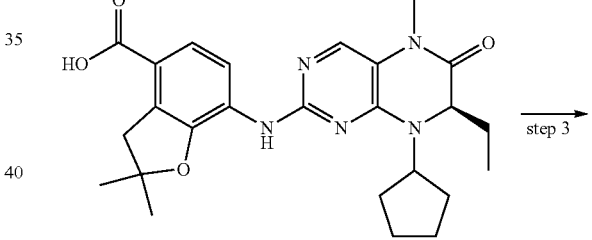

step 3 →

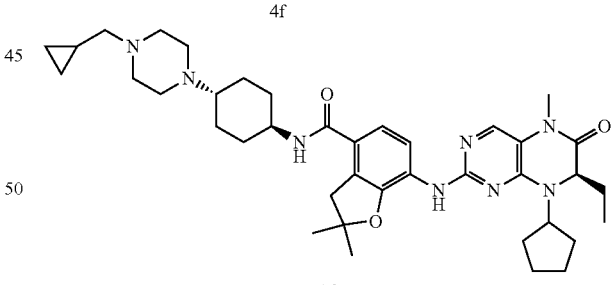

Step 1

(trans)-N,N-Dibenzyl-4-[4-(cyclopropylmethyl)piperazin-1-yl]cyclohexanamine

Cyclopropylmethylpiperazine dihydrochloride (5.16 g, 24.20 mmol) was dissolved in 280 mL of acetonitrile followed by the addition of 5 g solid sodium acetate to adjust pH to 6-7, then added with (R)-4-(dibenzylamino)cyclohexanone 12c (6.48 g, 22 mmol) and sodium triacetoxyborohydride (11.66 g, 55 mmol) successively. The reaction solution was stirred for 12 hours. The resulting solution was added with 100 mL of water and solid sodium carbonate successively to adjust pH to 8, seperated. The aqueous phase was extracted with dichloromethane (250 mL×2). The combined organic phase was washed with saturated sodium bicarbonate solution (50 mL×3) and saturated sodium chloride solution (50 mL×3) successively, then dried over anhydrous magnesium sulfate, filtered and the filtrate was concentrated under reduced pressure. The resulting residue was purified by silica gel column chromatography to obtain the title compound (trans)-N,N-dibenzyl-4-[4-(cyclopropylmethyl)piperazin-1-yl]cyclohexanamine 16a (1.14 g, yield: 15.4%) as a white solid.

MS m/z (ESI): 418.4 [M+1]

Step 2

(trans)-4-[4-(Cyclopropylmethyl)piperazin-1-yl]cyclohexanamine (trans)-N,N-Dibenzyl-4-[4-(cyclopropylmethyl)piperazin-1-yl]cyclohexanamine 16a (1.41 g, 3.38 mmol) was dissolved in 15 mL of methanol followed by the addition of palladium/carbon (706 mg, 10%) and 0.1 mL of acetic acid, filled with hydrogen three times. The reaction mixture was reacted for 12 hours at 3 atmosphere of hydrogen, added with 3 g alkaline aluminum oxide (200-300 mesh) and filtered. The filtrate was concentrated under reduced pressure to obtain the title compound (trans)-4-[4-(cyclopropylmethyl)piperazin-1-yl]cyclohexanamine 16b (900 mg, yield: 100%) as a colorless solid.

MS m/z (ESI): 238.2 [M+1]

Step 3

7-[[(7R)-8-Cyclopentyl-7-ethyl-5-methyl-6-oxo-7H-pteridin-2-yl]amino]-N-[(trans)-4-[4-(cyclopropylmethyl)piperazin-1-yl]cyclohexyl]-2,2-dimethyl-3H-benzofuran-4-carboxamide 7-[[(7R)-8-Cyclopentyl-7-ethyl-5-methyl-6-oxo-7H-pteridin-2-yl]amino]-2,2-dimethyl-3H-benzofuran-4-carboxylic acid 4f (150 mg, 0.32 mmol), (trans)-4-[4-(cyclopropylmethyl)piperazin-1-yl]cyclohexanamine 16b (76 mg, 0.32 mmol) and O-(benzotriazol-1-yl)-N,N,N',N'-tetra methyluronium tetrafluoroborate (103 mg, 0.32 mmol) were dissolved in 20 mL of dichloromethane followed by the addition of diisopropylethylamine (103 mg, 0.80 mmol). The reaction solution was stirred for 2 hours. The resulting solution was added with 20 mL of saturated ammonium chloride solution, seperated, the organic phase was dried over anhydrous magnesium sulfate, filtered and the filtrate was concentrated under reduced pressure. The residue was purified by preparation plate to obtain the title compound 7-[[(7R)-8-cyclopentyl-7-ethyl-5-methyl-6-oxo-7H-pteridin-2-yl]amino]-N-[(trans)-4-[4-(cyclopropylmethyl)piperazin-1-yl]cyclohexyl]-2,2-dimethyl-3H-benzofuran-4-carboxamide 16 (130 mg, yield: 59.0%) as a white solid.

MS m/z (ESI): 685.4 [M+1]

$^1$H NMR (400 MHz, CDCl$_3$) δ 8.28 (d, 1H), 7.70 (s, 1H), 7.23 to 7.00 (m, 2H), 5.92 (d, 1H), 4.58 (t, 1H), 4.25 (dd, 1H), 4.00-3.81 (m, 1H), 3.41 (s, 2H), 3.35 (s, 3H), 3.10 (s, 5H), 2.80 to 2.55 (m, 3H), 2.30 to 2.11 (m, 5H), 2.07 to 1.97 (m, 2H), 1.93 to 1.66 (m, 8H), 1.54 (s, 6H), 1.48 (s, 1H), 1.44 to 1.21 (m, 5H), 1.21 to 1.05 (m, 1H), 0.91 (t, 3H), 0.71 (d, 2H), 0.34 (d, 2H)

Example 17

7-[[(7R)-8-Cyclopentyl-7-ethyl-5-methyl-6-oxo-7H-pteridin-2-yl]amino]-2,2-dimethyl-N-[(trans)-4-(4-methylpiperazin-1-yl)cyclohexyl]-3H-benzofuran-4-carboxamide

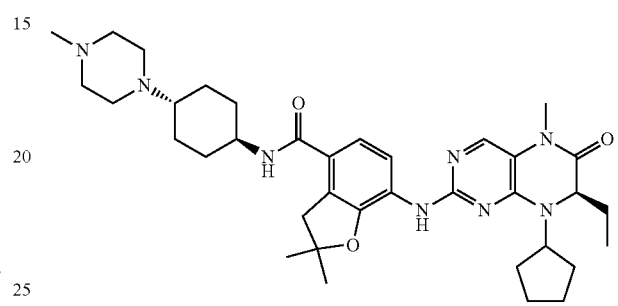

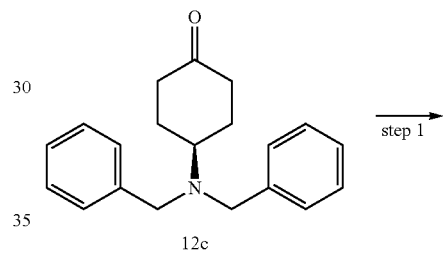

12c

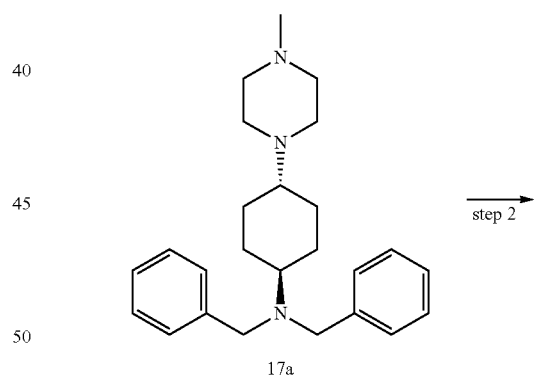

17a

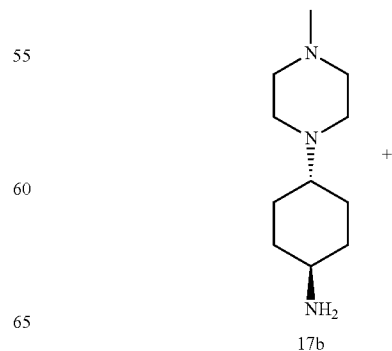

17b

-continued

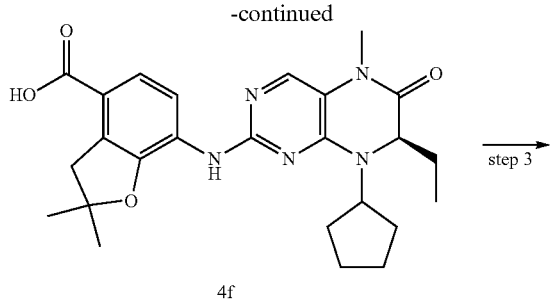

4f

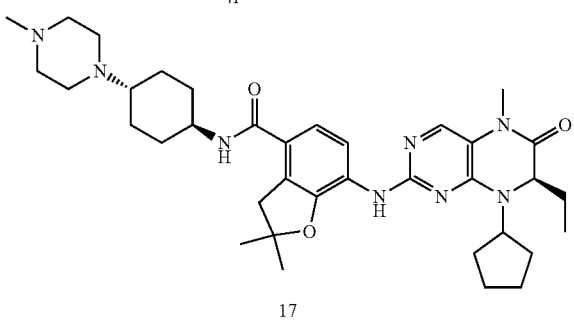

17

Step 1

(trans)-N,N-Dibenzyl-4-(4-methylpiperazin-1-yl)cyclohexanamine (R)-4-(Dibenzylamino)cyclohexanone 12c (4.61 g, 15.71 mmol) was dissolved in 150 mL of dichloromethane followed by the addition of 1-methyl-piperizine (1.73 g, 17.28 mmol), added dropwise with 0.1 mL of acetic acid successively, then added with sodium triacetoxyborohydride (6.66 g, 31.42 mmol). The reaction solution was stirred for 12 hours. The resulting solution was added with 15 mL of 1 M dilute hydrochloric acid and dropwise with saturated sodium carbonate solution to adjust pH to 8 and seperated. The organic phase was washed with saturated sodium chloride solution (50 mL×3), then dried over anhydrous magnesium sulfate, filtered and the filtrate was concentrated under reduced pressure. The resulting residue was purified by silica gel column chromatography to obtain the title compound (trans)-N,N-dibenzyl-4-(4-methylpiperazin-1-yl)cyclohexanamine 17a (3.80 g, yield: 64.0%) as a white solid.

MS m/z (ESI): 378.4 [M+1]

Step 2

(trans)-4-(4-Methylpiperazin-1-yl)cyclohexanamine (trans)-N,N-dibenzyl-4-(4-methylpiperazin-1-yl)cyclohexanamine 17a (3.35 g, 8.90 mmol) was dissolved in 20 mL of methanol followed by the addition of palladium/carbon (335 mg, 10%), filled with hydrogen three times. The reaction solution was reacted at 3 atmosphere for 12 hours and filtered. The filtrate was concentrated under reduced pressure followed by the addition of 10 mL of 1 M hydrochloric acid and extracted with dichloromethane (30 mL×3). The aqueous phase was added dropwise with saturated aqueous sodium carbonate solution to adjust pH to 11, extracted with dichloromethane (50 mL×3). The combined organic phase was dried over anhydrous magnesium sulfate, filtered and was concentrated under reduced pressure to obtain the crude title compound (trans)-4-(4-methylpiperazin-1-yl)cyclohexan-amine 17b (0.82 g, yield: 46.7%) as a yellow oil liquid, which was used in the next step without further furification.

Step 3

7-[[(7R)-8-Cyclopentyl-7-ethyl-5-methyl-6-oxo-7H-pteridin-2-yl]amino]-2,2-dimethyl-N-[(trans)-4-(4-methylpiperazin-1-yl)cyclohexyl]-3H-benzofuran-4-carboxamide The crude compound (trans)-4-(4-methylpiperazin-1-yl)cyclohexanamine 17b (60 mg, 0.30 mmol), 7-[[(7R)-8-cyclopentyl-7-ethyl-5-methyl-6-oxo-7H-pteridin-2-yl]amino]-2,2-dimethyl-3H-benzofuran-4-carboxylic acid 4f (153 mg, 0.33 mmol), O-(benzotriazol-1-yl)-N,N,N',N'-tetra methyluronium tetrafluoroborate (96 mg, 0.30 mmol) and diisopropylethylamine (96 mg, 0.75 mmol) were dissolved in 25 mL of dichloromethane. The reaction solution was stirred for 2 hours. The resulting solution was added dropwise with saturated sodium bicarbonate solution to adjust pH to 8 to 9, extracted with dichloromethane (30 mL×3), then dried over anhydrous magnesium sulfate, filtered and the filtrate was concentrated under reduced pressure. The resulting residue was purified by silica gel column chromatography to obtain the title compound 7-[[(7R)-8-cyclopentyl-7-ethyl-5-methyl-6-oxo-7H-pteridin-2-yl]amino]-2,2-dimethyl-N-[(trans)-4-(4-methylpiperazin-1-yl)cyclohexyl]-3H-benzofuran-4-carboxamide 17 (70 mg, yield: 33.0%) as a white solid.

MS m/z (ESI): 645.4 [M+1]

$^1$H NMR (400 MHz, CDCl$_3$) δ 8.26 (d, 1H), 7.68 (s, 1H), 7.13 to 7.91 (m, 2H), 6.08 (d, 1H), 4.58 (t, 1H), 4.22 (dd, 2H), 3.39 (s, 2H), 3.33 (s, 3H), 2.75 to 2.35 (m, 8H), 2.31 (s, 3H), 2.30 to 2.10 (m, 2H), 2.09 to 1.95 (m, 2H), 1.93 to 1.63 (m, 12H), 1.50 (s, 6H), 0.88 (t, 6H)

Example 18

(cis-exo)-N-[2-Methyl-1,3,4,4a,5,6,7,7a-octahydro-cyclopenta[c]pyridin-6-yl]-7-[[(7R)-8-cyclopentyl-7-ethyl-5-methyl-6-oxo-7H-pteridin-2-yl]amino]-2,2-dimethyl-3H-benzofuran-4-carboxamide

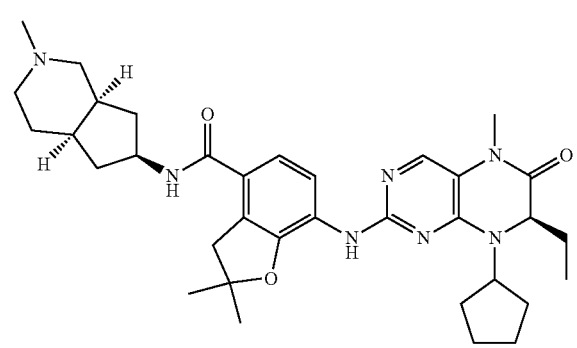

99
-continued

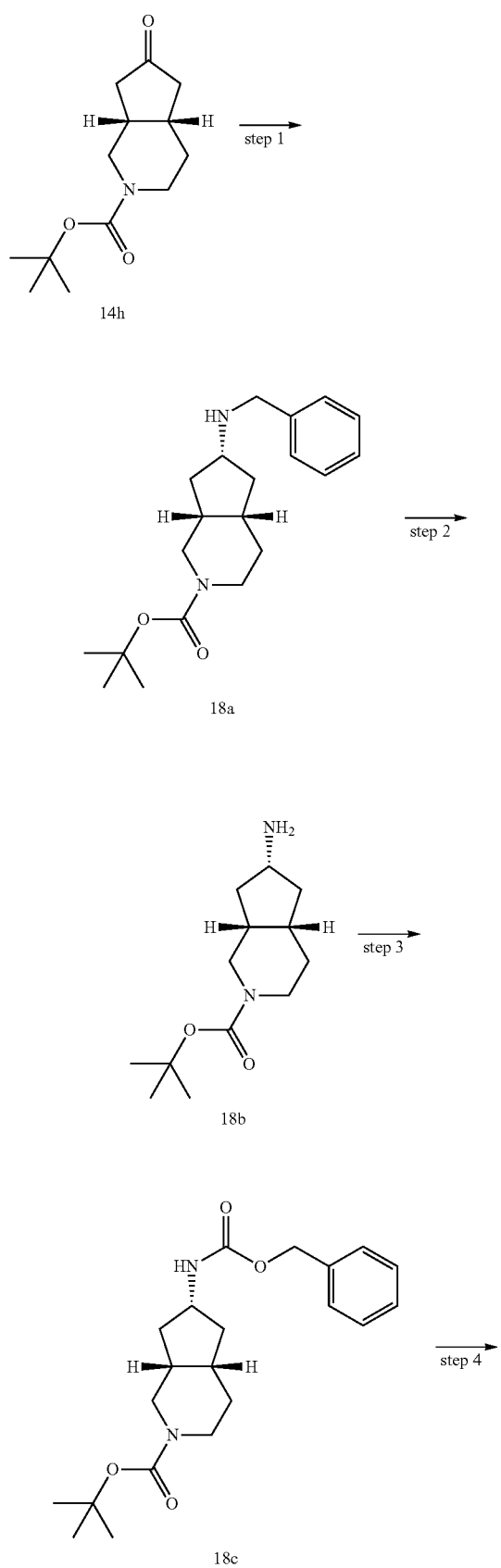

100
-continued

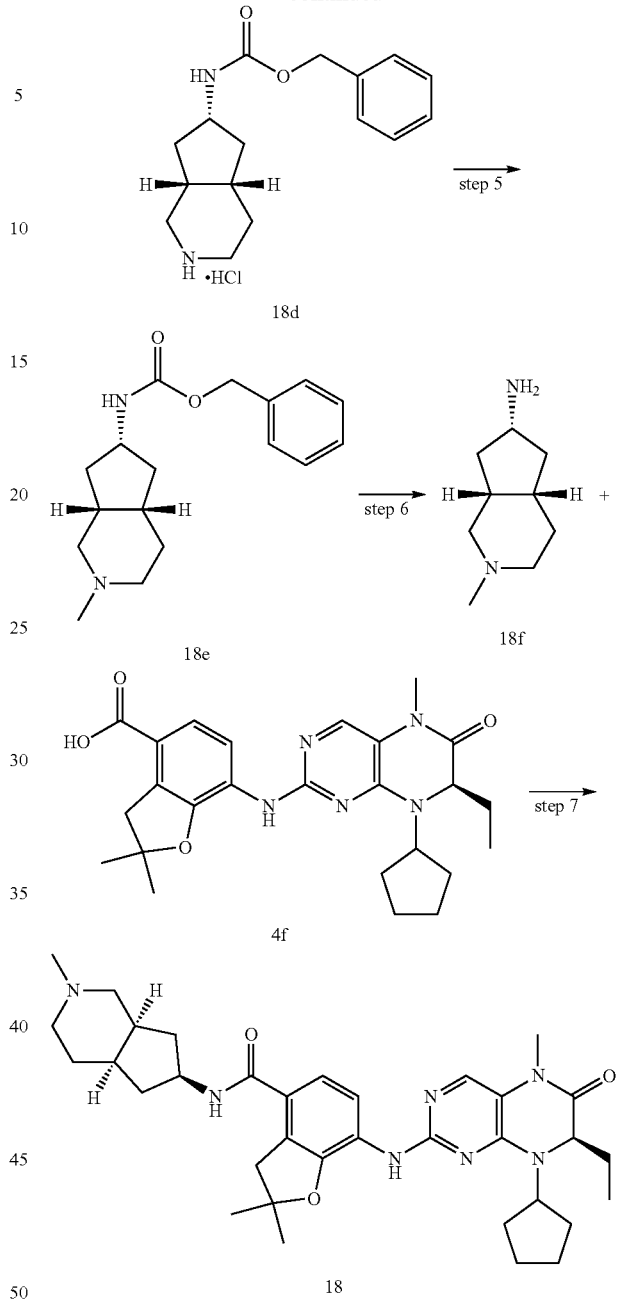

Step 1

Tert-butyl (cis-exo)-6-(benzylamino)-1,3,4,4a,5,6,7,7a-octahydrocyclopenta[c]pyridine-2-carboxylate Tert-butyl (cis)-6-oxo-3,4,4a,5,7,7a-hexahydro-1H-cyclopenta[c]pyridine-2-carboxylate 14h (1.10 g, 4.60 mmol) and benzylamine (492 mg, 4.60 mmol) were dissolved in 50 mL of dichloromethane in an ice-water bath followed by the addition of acetic acid (276 mg, 4.60 mmol), stirred for 30 minutes. The reaction solution was added with sodium triacetoxyborohydride (1.95 g, 9.20 mmol), heated to room temperature and stirred for another 12 hours. The resulting solution was added dropwise with saturated sodium carbonate solution to adjust pH to 9 and extracted with dichloromethane (50 mL×3). The combined organic phase was dried over anhydrous magnesium sulfate, filtered and the filtrate was concentrated under reduced pressure. The resulting residue was purified by silica gel column chromatography to obtain the title compound tert-butyl (cis-exo)-6-(benzylamino)-1,3,4,4a,5,6,7,7a-octahydrocyclopenta[c]pyridine-2-carboxylate 18a (1.25 g, yield: 83.0%) as a light yellow oil.

MS m/z (ESI): 331.3 [M+1]

Step 2

Tert-butyl (cis-exo)-6-amino-1,3,4,4a,5,6,7,7a-octahydrocyclopenta[c]pyridine-2-carboxylate Tert-butyl (cis-exo)-6-(benzylamino)-1,3,4,4a,5,6,7,7a-octahydrocyclopenta[c]pyridine-2-carboxylate 18a (1.25 g, 3.78 mmol) was dissolved in 20 mL of methanol followed by the addition of palladium/carbon (125 mg, 10%), filled with hydrogen three times. The reaction mixture was stirred for 12 hours and filtered. The filtrate was concentrated under reduced pressure to obtain the title compound tert-butyl (cis-exo)-6-amino-1,3,4,4a,5,6,7,7a-octahydrocyclopenta[c]pyridine-2-carboxylate 18b (910 mg, yield: 100.0%) as a light yellow oil.

MS m/z (ESI): 241.2 [M+1]

Step 3

Tert-butyl (cis-exo)-6-benzyloxycarbonylamino-1,3,4,4a,5,6,7,7a-octahydrocyclopenta[c]pyridine-2-carboxylate Tert-butyl (cis-exo)-6-amino-1,3,4,4a,5,6,7,7a-octahydrocyclopenta[c]pyridine-2-carboxylate 18b (909 mg, 3.78 mmol) was dissolved in 25 mL of dichloromethane followed by the addition of triethylamine (763 mg, 7.56 mmol) and benzyl chloroformate (707 mg, 4.16 mmol) in an ice-water bath, then heated to room temperature and stirred for 2 hours. The resulting solution was added dropwise with saturated sodium bicarbonate solution to adjust pH to 8-9 and extracted with dichloromethane (30 mL×3). The combined organic phase was dried over anhydrous magnesium sulfate, filtered and the filtrate was concentrated under reduced pressure. The resulting residue was purified by silica gel column chromatography to obtain the title compound tert-butyl (cis-exo)-6-benzyloxycarbonylamino-1,3,4,4a,5,6,7,7a-octahydrocyclopenta[c]pyridine-2-carboxylate 18c (520 mg, yield: 37.0%) as a colorless oil.

Step 4

Benzyl (cis-exo)-N-[2,3,4,4a,5,6,7,7a-octahydro-1H-cyclopenta[c]pyridin-6-yl]carbamate hydrochloride Tert-butyl (cis-exo)-6-benzyloxycarbonylamino-1,3,4,4a,5,6,7,7a-octahydrocyclopenta[c]pyridine-2-carboxylate 18c (513 mg, 1.37 mmol) was dissolved in 6 mL of dichloromethane followed by the addition of 6 mL of a 4 M solution of 1,4-dioxane in hydrogen chloride. The reaction solution was stirred for 30 minutes. The resulting solution was concentrated under reduced pressure to obtain the crude title compound benzyl (cis-exo)-N-[2,3,4,4a,5,6,7,7a-octahydro-1H-cyclopenta[c]pyridin-6-yl]carbamate hydrochloride 18d (430 mg) as a white viscous liquid, which was used in the next step without further furification.

MS m/z (ESI): 275.2 [M+1]

Step 5

Benzyl (cis-exo)-N-[2-methyl-1,3,4,4a,5,6,7,7a-octahydrocyclopenta[c]pyridin-6-yl]carbamate The crude compound benzyl (cis-exo)-N-[2,3,4,4a,5,6,7,7a-octahydro-1H-cyclopenta[c]pyridin-6-yl]carbamate hydrochloride 18d (425 mg, 1.37 mmol) was dissolved in 20 mL of the mixture solvent of acetonitrile and water (V/V=1:1) in an ice-water bath followed by the addition of sodium triacetoxyborohydride (871 mg, 4.11 mmol), then heated to room temperature and stirred for 12 hours. The resulting solution was added dropwise with saturated sodium bicarbonate solution to adjust pH to about 9, and extracted with dichloromethane (20 mL×3), washed with water (20 mL), saturated sodium chloride solution (20 mL) successively, then dried over anhydrous magnesium sulfate, filtered and the filtrate was concentrated under reduced pressure to obtain the crude title compound benzyl (cis-exo)-N-[2-methyl-1,3,4,4a,5,6,7,7a-octahydrocyclopenta[c]pyridin-6-yl]carbamate 18e (374 mg) as a light yellow oil, which was used in the next step without further furification.

MS m/z (ESI): 289.2 [M+1]

Step 6

(cis-exo)-2-Methyl-1,3,4,4a,5,6,7,7a-octahydrocyclopenta[c]pyridin-6-amine

The crude compound benzyl (cis-exo)-N-[2-methyl-1,3,4,4a,5,6,7,7a-octahydrocyclopenta[c]pyridin-6-yl]carbamate 18e (374 mg, 1.29 mmol) was dissolved in 25 mL of methanol followed by the addition of palladium/carbon (40 mg, 10%), filled with hydrogen three times. The reaction mixture was stirred for 2 hours and filtered. The filtrate was concentrated under reduced pressure to obtain the crude title compound (cis-exo)-2-methyl-1,3,4,4a,5,6,7,7a-octahydrocyclopenta[c]pyridin-6-amine 18f (198 mg) as a white solid, which was used in the next step without further furification.

MS m/z (ESI): 155.2 [M+1]

Step 7

(cis-exo)-N-[2-Methyl-1,3,4,4a,5,6,7,7a-octahydrocyclopenta[c]pyridin-6-yl]-7-[[(7R)-8-cyclopentyl-7-ethyl-5-methyl-6-oxo-7H-pteridin-2-yl]amino]-2,2-dimethyl-3H-benzofuran-4-carboxamide The crude compound (cis-exo)-2-methyl-1,3,4,4a,5,6,7,7a-octahydrocyclopenta[c]pyridin-6-amine 18f (60 mg, 0.39 mmol), 7-[[(7R)-8-cyclopentyl-7-ethyl-5-methyl-6-oxo-7H-pteridin-2-yl]amino]-2,2-dimethyl-3H-benzofuran-4-carboxylic acid 4f (199 mg, 0.43 mmol), O-(benzotriazol-1-yl)-N,N,N',N'-tetramethyluronium tetrafluoroborate (125 mg, 0.39 mmol) and diisopropylethylamine (125 mg, 0.98 mmol) were dissolved in 25 mL of dichloromethane. The reaction solution was stirred for 2 hours. The resulting solution was added with 25 mL saturated sodium bicarbonate solution and extracted with dichloromethane (30 mL×3), washed with water (30 mL), saturated sodium chloride solution (30 mL) successively, then dried over anhydrous magnesium sulfate, filtered and the filtrate was concentrated under reduced pressure. The resulting residue was purified by silica gel column chromatography to obtain the title compound (cis-exo)-N-[2-methyl-1,3,4,4a,5,6,7,7a-octahydrocyclopenta[c]pyridin-6- yl]-7-[[(7R)-8-cyclopentyl-7-ethyl-5-methyl-6-oxo-7H-pteridin-2-yl]amino]-2,2-dimethyl-3H-benzofuran-4-carboxamide 18 (120 mg, yield: 50.0%) as a white solid.

MS m/z (ESI): 602.3 [M+1]

¹H NMR (400 MHz, CDCl₃) δ 8.29 (d, 1H), 7.71 (s, 1H), 7.11 to 7.03 (m, 2H), 6.12 (d, 1H), 4.60 (t, 1H), 4.55 to 4.46 (m, 1H), 4.25 (dd, 1H), 3.43 (s, 2H), 3.36 (s, 3H), 2.57 to 2.45 (m, 2H), 2.43 to 2.33 (m, 2H), 2.32 to 2.28 (m, 4H), 2.25 to 2.13 (m, 4H), 2.11 to 1.96 (m, 3H), 1.91 to 1.62 (m, 8H), 1.53 (s, 6H), 1.51 to 1.45 (m, 2H), 0.92 (t, 3H)

Example 19

7-[[(7R)-8-Cyclopentyl-7-ethyl-5-methyl-6-oxo-7H-pteridin-2-yl]amino]-N-[(trans)-4-(4-methylpiperazin-1-yl)cyclohexyl]-2,3-dihydrobenzofuran-4-carboxamide

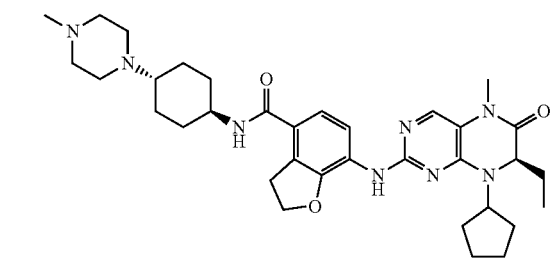

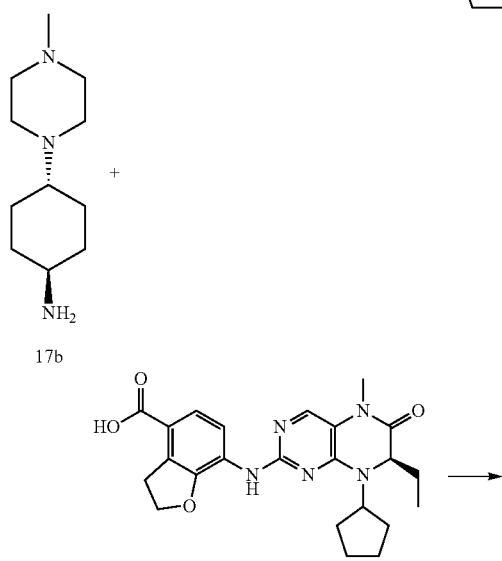

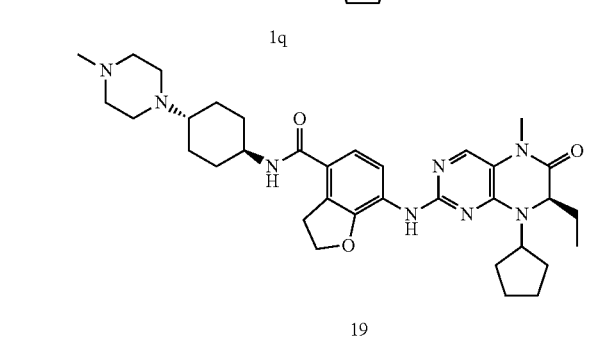

7-[[(7R)-8-Cyclopentyl-7-ethyl-5-methyl-6-oxo-7H-pteridin-2-yl]amino]-2,3-dihydrobenzofuran-4-carboxylic acid 1q (200 mg, 0.46 mmol) and O-(benzotriazol-1-yl)-N,N,N',N'-tetramethyluronium tetrafluoroborate (147 mg, 0.46 mmol) were dissolved in 25 mL of anhydrous dichloromethane followed by the addition of diisopropylethylamine (0.2 mL, 1 mmol) and (trans)-4-(4-methylpiperazin-1-yl)cyclohexanamine 17b (90 mg, 0.46 mmol) successively. The reaction solution was stirred for 3 hours. The resulting solution was added with 20 mL of saturated sodium carbonate solution and extracted with dichloromethane (30 mL×3). The combined organic phase was washed with saturated sodium carbonate solution (30 mL×2), water (30 mL) and saturated sodium chloride solution (30 mL) successively, then dried over anhydrous sodium sulfate, filtered and the filtrate was concentrated under reduced pressure. The resulting residue was purified by silica gel column chromatography to obtain the title compound 7-[[(7R)-8-cyclopentyl-7-ethyl-5-methyl-6-oxo-7H-pteridin-2-yl]amino]-N-[(trans)-4-(4-methylpiperazin-1-yl)cyclohexyl]-2,3-dihydrobenzofuran-4-carboxamide 19 (190 mg, yield: 67.0%) as a white solid.

MS m/z (ESI): 617.4 [M+1]

¹H NMR (400 MHz, CDCl₃) δ 8.28 (d, 1H), 7.67 (s, 1H), 7.11 (d, 1H), 7.03 (s, 1H), 6.14 (s, 1H), 4.68 (t, 2H), 4.49 (t, 1H), 4.21 (dd, 2H), 3.60 (t, 2H), 3.32 (s, 3H), 2.90 to 2.55 (m, 8H), 2.37 (s, 3H), 2.38 to 2.30 (m, 1H), 2.12 (d, 1H), 2.08 to 1.94 (m, 2H), 1.94 to 1.78 (m, 7H), 1.78 to 1.55 (m, 8H), 0.88 (t, 3H)

Example 20

7-[[(7R)-8-Cyclopentyl-7-ethyl-5-methyl-6-oxo-7H-pteridin-2-yl]amino]-N-[(2R)-3-(4-methylpiperazin-1-yl)-2-hydroxy-propyl]-2,2-dimethyl-3H-benzofuran-4-carboxamide

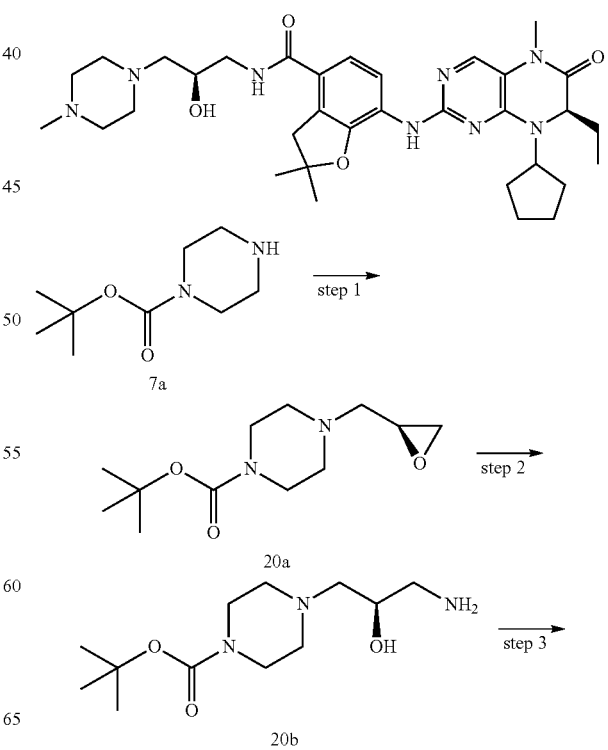

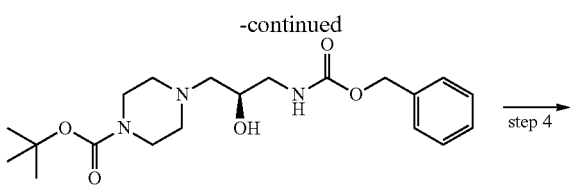

20c

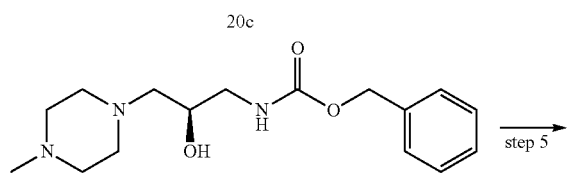

20d

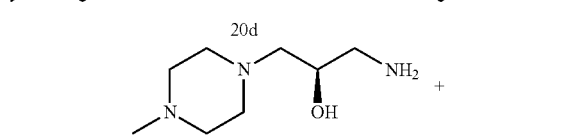

20e

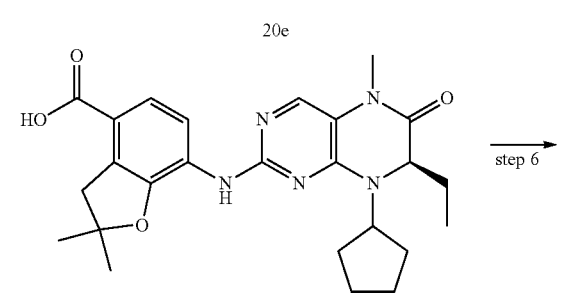

4f

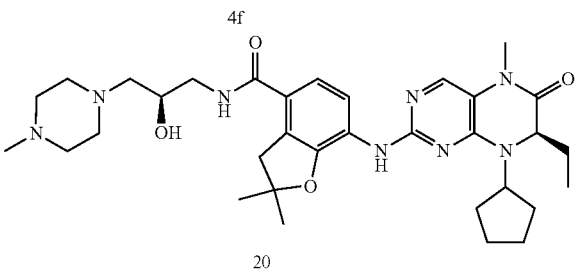

20

Step 1

Tert-butyl 4-[[(2S)-oxiran-2-yl]methyl]piperazine-1-carboxylate

Tert-butyl piperazine-1-carboxylate 7a (7.44 g, 40 mmol) and (S)-2-chloromethyl-oxirane (3.70 g, 40 mmol) were dissolved in 60 mL of ethanol. The reaction solution was stirred for 12 hours. The resulting solution was concentrated under reduced pressure. The resulting residue was purified by silica gel column chromatography to obtain the title compound tert-butyl 4-[[(2S)-oxiran-2-yl]methyl]piperazine-1-carboxylate 20a (9.20 g, yield: 95.0%) as a white solid.

Step 2

Tert-butyl 4-[(2R)-3-amino-2-hydroxy-propyl]piperazine-1-carboxylate

Tert-butyl 4-[[(2S)-oxiran-2-yl]methyl]piperazine-1-carboxylate 20a (9.20 g, 38 mmol) was dissolved in 60 mL of ethanol followed by the addition of 50 mL of aqueous ammonia. The reaction solution was stirred for 12 hours. The reaction solution was concentrated under reduced pressure to obtain the crude title compound tert-butyl 4-[(2R)-3-amino-2-hydroxy-propyl]piperazine-1-carboxylate 20b (9 g, as a white solid), which was used in the next step without further furification.

MS m/z (ESI): 260.2 [M+1]

Step 3

Tert-butyl 4-[(2R)-3-benzyloxycarbonylamino-2-hydroxy-propyl]piperazine-1-carboxylate The crude compound tert-butyl 4-[(2R)-3-amino-2-hydroxy-propyl]piperazine-1-carboxylate 20b (4.50 g, 17.40 mmol) was dissolved in 80 mL of dichloromethane in an ice-water bath followed by the addition of diisopropylethylamine (2.50 g, 19.10 mmol) and dropwise addition of 20 mL of a solution of carbobenzoxy chloride (2 g, 19.10 mmol) in dichloromethane successively, stirred for 12 hours. The resulting mixture was added with 20 mL of water and stirred for 10 minutes. The reaction solution was concentrated under reduced pressure, added with 100 mL of water and extracted with ethyl acetate (100 mL×3). The combined organic phase was washed with saturated sodium chloride solution (50 mL×3), then dried over anhydrous magnesium sulfate, filtered and the filtrate was concentrated under reduced pressure. The resulting residue was purified by silica gel column chromatography to obtain the title compound tert-butyl 4-[(2R)-3-benzyloxycarbonylamino-2-hydroxy-propyl]piperazine-1-carboxylate 20c (1.80 g, yield: 26.0%) as a light yellow oil.

MS m/z (ESI): 394.3 [M+1]

Step 4

Benzyl N-[(2R)-2-hydroxy-3-(4-methylpiperazin-1-yl)propyl]carbamate

Tert-butyl 4-[(2R)-3-benzyloxycarbonylamino-2-hydroxy-propyl]piperazine-1-carboxylate 20c (1.80 g, 4.80 mmol) was dissolved in 30 mL of dichloromethane followed by the addition of 20 mL of a solution of hydrogen chloride in dioxane. The reaction solution was stirred for 0.5 hours. The reaction solution was concentrated under reduced pressure, added with 30 mL of water and 30 mL of acetonitrile, formaldehyde (288 mg, 9.6 mmol) and dropwise with 0.1 mL of acetic acid. The resulting solution was stirred for 0.5 hours followed by the addition of sodium triacetoxyborohyride (3.05 g, 14.40 mmol). The reaction solution was stirred for 12 hours, added dropwise with saturated sodium carbonate solution to adjust pH to 10 and extracted with ethyl acetate (50 mL×3). The combined organic phase was washed with saturated sodium chloride solution (50 mL×3), then dried over anhydrous magnesium sulfate, filtered and the filtrate was concentrated under reduced pressure. The resulting residue was purified by silica gel column chromatography to obtain the title compound benzyl N-[(2R)-2-hydroxy-3-(4-methylpiperazin-1-yl)propyl]carbamate 20d (830 mg, yield: 56.0%) as a yellow oil.

MS m/z (ESI): 308.2 [M+1]

Step 5

(2R)-1-Amino-3-(4-methylpiperazin-1-yl)propan-2-ol

Benzyl N-[(2R)-2-hydroxy-3-(4-methylpiperazin-1-yl)propyl]carbamate 20d (830 mg, 2.70 mmol) was dissolved in 40 mL of methanol followed by the addition of palladium/carbon (85 mg, 10%), filled with hydrogen three times. The reaction solution was stirred for 12 hours and filtered. The filtrate was concentrated under reduced pressure to obtain the crude title compound (2R)-1-amino-3-(4-methylpiperazin-1-yl)propan-2-ol 20e (500 mg) as a light yellow oil, which was used in the next step without further furification.

MS m/z (ESI): 174.2 [M+1]

Step 6

7-[[(7R)-8-Cyclopentyl-7-ethyl-5-methyl-6-oxo-7H-pteridin-2-yl]amino]-N-[(2R)-3-(4-methylpiperazin-1-yl)-2-hydroxy-propyl]-2,2-dimethyl-3H-benzofuran-4-carboxamide 7-[[(7R)-8-Cyclopentyl-7-ethyl-5-methyl-6-oxo-7H-pteridin-2-yl]amino]-2,2-dimethyl-3H-benzofuran-4-carboxylic acid 4f (116 mg, 0.25 mmol) was dissolved in 15 mL of dichloromethane followed by the addition of (2R)-1-amino-3-(4-methylpiperazin-1-yl)propan-2-ol 20e (48 mg, 0.28 mmol), O-(benzotriazol-1-yl)-N,N,N',N'-tetra methyluronium tetrafluoroborate (80 mg, 0.25 mmol) and diisopropylethylamine (97 mg, 0.75 mmol). The reaction solution was stirred for 2 hours. The resulting solution was added with 20 mL of saturated sodium bicarbonate solution and extracted with dichloromethane (50 mL×3). The combined organic phase was washed with water (50 mL), saturated sodium chloride solution (50 mL) successively, then dried over anhydrous magnesium sulfate, filtered and the filtrate was concentrated under reduced pressure. The resulting residue was purified by silica gel column chromatography to obtain the title compound 7-[[(7R)-8-cyclopentyl-7-ethyl-5-methyl-6-oxo-7H-pteridin-2-yl]amino]-N-[(2R)-3-(4-methylpiperazin-1-yl)-2-hydroxy-propyl]-2,2-dimethyl-3H-benzofuran-4-carboxamide 20 (120 mg, yield: 77.4%) as a white solid.

MS m/z (ESI): 621.4 [M+1]

$^1$H NMR (400 MHz, CDCl$_3$) δ 8.27 (d, 1H), 7.67 (s, 1H), 7.13 (d, 1H), 7.05 (s, 1H), 6.56 (s, 1H), 4.55 (t, 1H), 4.22 (dd, 1H), 3.91 (d, 1H), 3.76 to 3.61 (m, 1H), 3.45 to 3.28 (m, 6H), 2.80 to 2.65 (m, 2H), 2.62 to 2.34 (m, 7H), 2.30 (s, 3H), 2.20 to 2.10 (m, 2H), 2.01 (dd, 2H), 1.92 to 1.62 (m, 8H), 1.51 (s, 6H), 0.88 (t, 3H)

Example 21

7-[[(7R)-8-Cyclopentyl-7-ethyl-5-methyl-6-oxo-7H-pteridin-2-yl]amino]-N-[(2S)-3-(4-methylpiperazin-1-yl)-2-hydroxy-propyl]-2,2-dimethyl-3H-benzofuran-4-carboxamide

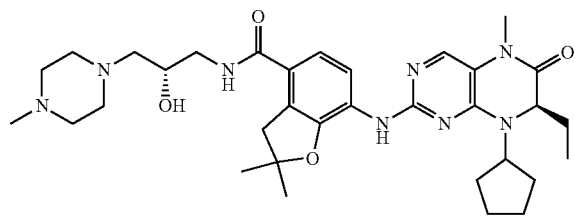

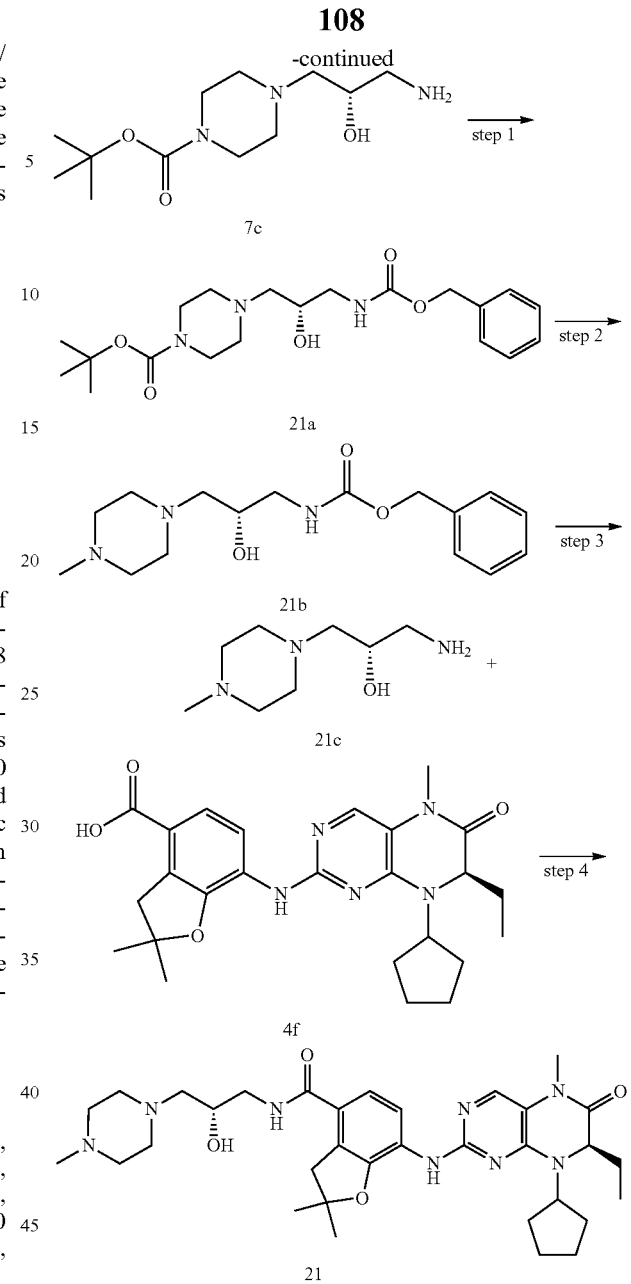

Step 1

Tert-butyl 4-[(2S)-3-benzyloxycarbonylamino-2-hydroxy-propyl]piperazine-1-carboxylate Tert-butyl 4-[(2S)-3-amino-2-hydroxy-propyl]piperazine-1-carboxylate 7c (1.24 g, 4.80 mmol) was dissolved in 60 mL of dichloromethane followed by the addition of triethylamine (970 mg, 9.60 mmol) and carbobenzoxy chloride (0.90 g, 5.28 mmol). The reaction solution was stirred for 2 hours. The resulting solution was added with 50 mL of saturated sodium bicarbonate solution and extracted with dichloromethane (50 mL×3). The combined organic phase was washed with saturated sodium chloride solution (50 mL×3), then dried over anhydrous magnesium sulfate, filtered and the filtrate was concentrated under reduced pressure. The resulting residue was purified by silica gel column chromatography to obtain the title compound tert-butyl 4-[(2S)-3-benzyloxycarbonylamino-2-hydroxy-propyl]piperazine-1-carboxylate 21a (1.45 g, yield: 76.0%) as a colorless oil.
MS m/z (ESI): 394.3 [M+1]

Step 2

Benzyl N-[(2S)-2-hydroxy-3-(4-m ethylpiperazin-1-yl)propyl]carbamate

Tert-butyl 4-[(2S)-3-benzyloxycarbonylamino-2-hydroxy-propyl]piperazine-1-carboxylate 21a (1.45 g, 3.70 mmol) was dissolved in 30 mL of dichloromethane followed by the addition of 20 mL of a 4 M solution of hydrogen chloride in dioxane. The reaction solution was stirred for 0.5 hours and concentrated under reduced pressure. The residue was added with 40 mL of dichloromethane, formaldehyde (222 mg, 7.40 mmol) and 0.1 mL of acetic acid successively. The resulting solution was stirred for 0.5 hours followed by the addition of sodium triacetoxyborohydride (2.35 g, 11.10 mmol), stirred for another 12 hours. The resulting solution was added with 50 mL of water and extracted with dichloromethane (50 mL×3). The combined organic phase was washed with saturated sodium chloride solution (50 mL×3), then dried over anhydrous magnesium sulfate, filtered and the filtrate was concentrated under reduced pressure. The resulting residue was purified by silica gel column chromatography to obtain the title compound benzyl N-[(2S)-2-hydroxy-3-(4-methylpiperazin-1-yl)propyl]carbamate 21b (840 mg, yield: 74.0%) as a yellow oil.
MS m/z (ESI): 308.3 [M+1]

Step 3

(2S)-1-Amino-3-(4-methylpiperazin-1-yl)propan-2-ol

Benzyl N-[(2S)-2-hydroxy-3-(4-methylpiperazin-1-yl)propyl]carbamate 21b (840 mg, 2.70 mmol) was dissolved in 50 mL of methanol to prepare a 0.01 mol/L solution. The reaction solution was hydrogenated with H-Cube (column of catalyst: 10% palladium/carbon; temperature: 30° C.; flow rate: 1 mL/min; pressure: 1 atmosphere) for 50 minutes. The reaction solution was concentrated under reduced pressure to obtain the crude title compound (2S)-1-amino-3-(4-methylpiperazin-1-yl)propan-2-ol 21c (500 mg) as a yellow oil which was used in the next step without further purification.
MS m/z (ESI): 174.2 [M+1]

Step 4

7-[[(7R)-8-Cyclopentyl-7-ethyl-5-methyl-6-oxo-7H-pteridin-2-yl]amino]-N-[(2S)-2-hydroxy-3-(4-methylpiperazin-1-yl)propyl]-2,2-dimethyl-3H-benzofuran-4-carboxamide The crude compound 7-[[(7R)-8-cyclopentyl-7-ethyl-5-methyl-6-oxo-7H-pteridin-2-yl]amino]-2,2-dimethyl-3H-benzofuran-4-carboxylic acid 4f (160 mg, 0.35 mmol), (2S)-1-amino-3-(4-methylpiperazin-1-yl)propan-2-ol 21c (60 mg, 0.35 mmol), O-(benzotriazol-1-yl)-N,N,N',N'-tetra methyluronium tetrafluoroborate (111 mg, 0.35 mmol) and diisopropylethylamine (89 mg, 0.69 mmol) were dissolved in 25 mL of dichloromethane. The reaction solution was stirred for 2 hours. The resulting solution was added dropwise with saturated sodium bicarbonate solution to adjust pH to 8-9 and extracted with dichloromethane (50 mL×3). The combined organic phase was washed with water (50 mL), saturated sodium chloride solution (50 mL) successively, then dried over anhydrous magnesium sulfate, filtered and the filtrate was concentrated under reduced pressure. The resulting residue was purified by silica gel column chromatography to obtain the title compound 7-[[(7R)-8-cyclopentyl-7-ethyl-5-methyl-6-oxo-7H-pteridin-2-yl]amino]-N-[(2S)-3-(4-methylpiperazin-1-yl)-2-hydroxy-propyl]-2,2-dimethyl-3H-benzofuran-4-carboxamide 21 (90 mg, yield: 45.0%) as a white solid.
MS m/z (ESI): 621.4 [M+1]
$^1$H NMR (400 MHz, CDCl$_3$) δ 8.26 (d, 1H), 7.67 (s, 1H), 7.19 to 6.97 (m, 2H), 6.61 (s, 1H), 4.55 (t, 1H), 4.22 (dd, 1H), 3.99 to 3.83 (m, 1H), 3.77 to 3.62 (m, 1H), 3.45 to 3.27 (m, 6H), 2.80 to 2.65 (m, 2H), 2.63 to 2.34 (m, 8H), 2.30 (s, 3H), 2.20 to 2.10 (m, 2H), 2.08 to 1.92 (m, 1H), 1.90 to 1.61 (m, 8H), 1.51 (s, 6H), 0.88 (t, 3H)

Example 22

7-[[(7R)-7-Ethyl-8-isopropyl-5-methyl-6-oxo-7H-pteridin-2-yl]amino]-N-(1-methyl-4-piperidyl)-2,3-dihydrobenzofuran-4-carboxamide

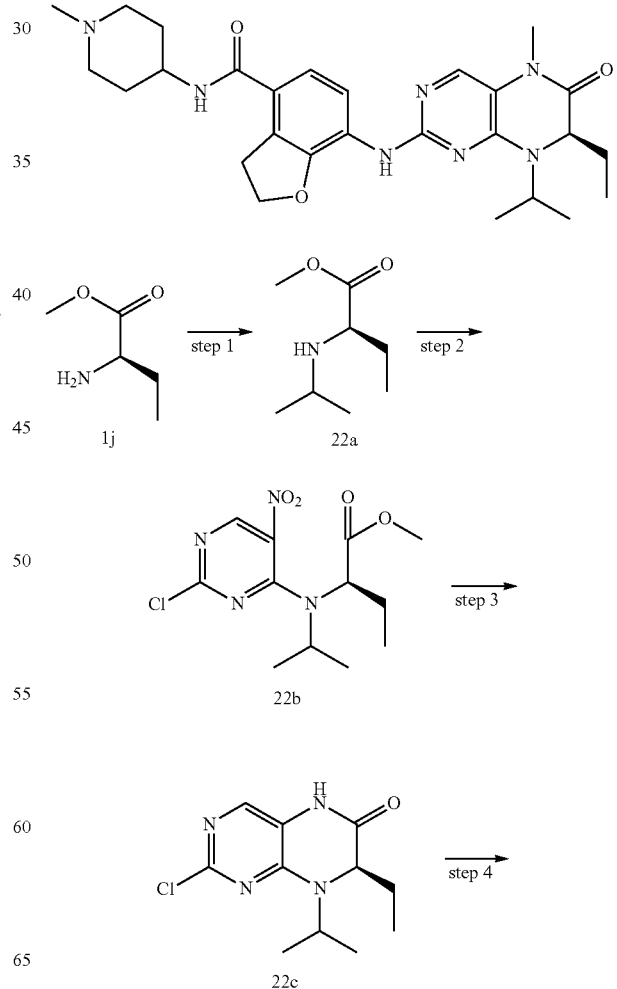

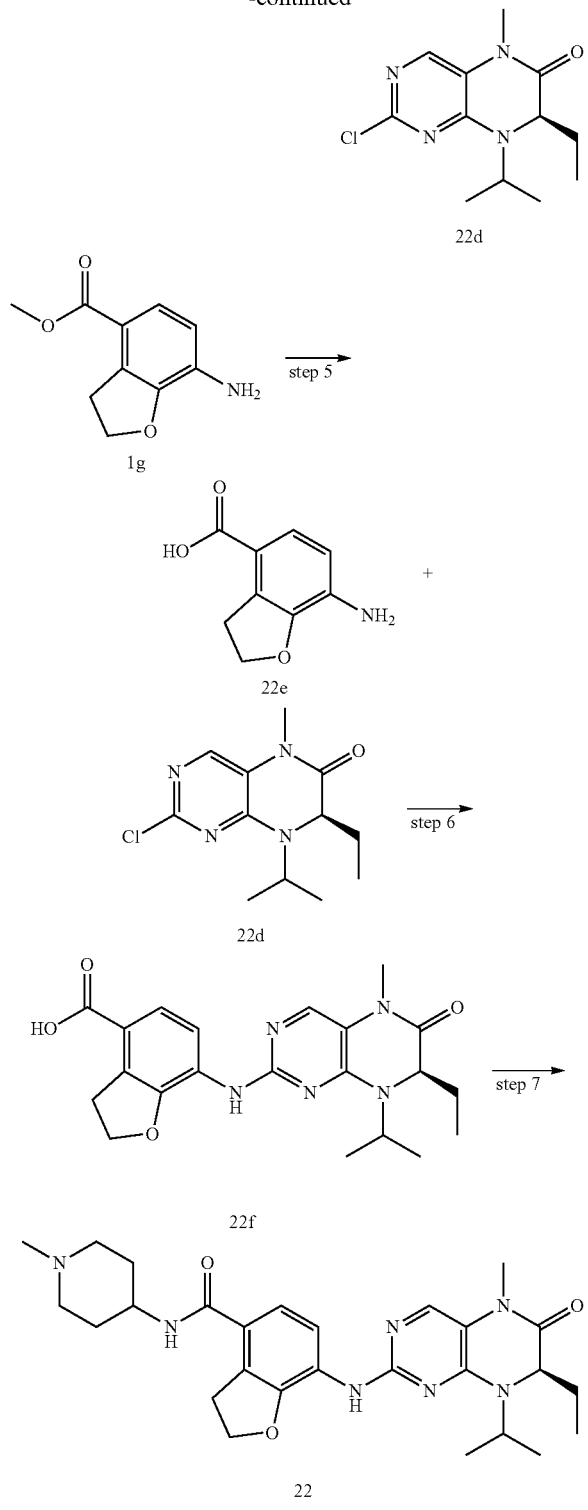

Step 1

Methyl (2R)-2-(isopropylamino)butanoate

Methyl (2R)-2-amino-butanoate 1j (28.78 g, 0.19 mol) was dissolved in 200 mL of dichloromethane followed by the addition of acetone (11.96 g, 0.21 mol) and sodium acetate (30.76 g, 0.38 mol), stirred 3 hours. Sodium triacetoxyborohydride (59.61 g, 0.28 mol) was added. The reaction solution was stirred for 12 hours followed by the addition of 100 mL of 1 M hydrochloric acid and dropwise addition of saturated sodium carbonate solution to adjust pH to 8 to 9, extracted with dichloromethane (100 mL×3). The combined organic phase was washed with saturated sodium chloride solution (50 mL×3), then dried over anhydrous magnesium sulfate, filtered and the filtrate was concentrated under reduced pressure. The resulting residue was purified by silica gel column chromatography to obtain the title compound methyl (2R)-2-(isopropylamino)butanoate 22a (16.40 g, yield: 55.0%) as a light yellow oil liquid.

Step 2

Methyl (2R)-2-[(2-chloro-5-nitro-pyrimidin-4-yl)-isopropyl-amino]butanoate 2,4-Dichloro-5-nitro-pyrimidine (19.90 g, 103 mmol) was dissolved in 300 mL of cyclohexane followed by the addition of methyl (2R)-2-(isopropylamino)butanoate 22a (16.40 g, 103 mmol) and sodium bicarbonate (36.61 g, 412 mmol). The reaction solution was heated to 80° C., stirred for 4 hours and filtered. The filtrate was concentrated under reduced pressure, added with 100 mL of water and extracted with dichloromethane (100 mL×3). The combined organic phase was washed with saturated sodium chloride solution (100 mL), then dried over anhydrous magnesium sulfate, filtered and the filtrate was concentrated under reduced pressure. The resulting residue was purified by silica gel column chromatography to obtain the title compound methyl (2R)-2-[(2-chloro-5-nitro-pyrimidin-4-yl)-isopropyl-amino]butanoate 22b (20.50 g, yield: 62.8%) as a yellow solid.

Step 3

(7R)-2-Chloro-7-ethyl-8-isopropyl-5,7-dihydropteridin-6-one

Methyl (2R)-2-[(2-chloro-5-nitro-pyrimidin-4-yl)-isopropyl-amino]butanoate 22b (7.30 g, 23 mmol) was dissolved in 100 mL acetic acid followed by the addition of 5 g Raney nickel, repeated filled with hydrogen for three times. The reaction mixture was heated to 75° C., stirred for 2 hours and filtered. The filtrate was concentrated under reduced pressure, added with 30 mL of ice water resulting in the formation of precipitate. The precipitate was filtered. the filter cake was dried by heat to obtain the crude title compound (7R)-2-chloro-7-ethyl-8-isopropyl-5,7-dihydropteridin-6-one 22c (12.10 g, yield: 71.7%) as a gray solid, which was used in the next step without further furification.

MS m/z (ESI): 255.1 [M+1]

Step 4

(7R)-2-Chloro-7-ethyl-8-isopropyl-5-methyl-7H-pteridin-6-one

The crude compound (7R)-2-chloro-7-ethyl-8-isopropyl-5,7-dihydropteridin-6-one 22c (12.10 g, 47.50 mmol) was dissolved in 180 mL of acetone followed by the addition of methyl p-toluenesulfonate (13.28 g, 71.30 mmol) and potassium carbonate (13.11 g, 95 mmol). The reaction solution was heated to reflux for 3 hours with stirring and filtered. The filtrate was concentrated under reduced pressure, added with 100 mL of water and extracted with dichloromethane (100 mL×3). The combined organic phase was washed with saturated sodium chloride solution (100 mL), then dried over anhydrous magnesium sulfate, filtered and the filtrate was concentrated under reduced pressure. The resulting residue was purified by silica gel column chromatography to obtain the title compound (7R)-2-chloro-7-ethyl-8-isopropyl-5-methyl-7H-pteridin-6-one 22d (10.80 g, yield: 84.7%) as a white solid.

Step 5

7-Amino-2,3-dihydrobenzofuran-4-carboxylic acid

Methyl 7-amino-2,3-dihydrobenzofuran-4-carboxylate 1g (2.30 g, 11.90 mmol) was dissolved in 80 mL of the mixture solvent of methanol and tetrahydrofuran (V/V=1:1) followed by the addition of a 1 M solution of lithium hydroxide solution (47.6 mL, 47.60 mmol) in tetrahydrofuran. The reaction solution was heated to reflux for 5 hours, then cooled down to room temperature, stirred for 12 hours. The reaction solution was added with 20 mL of water and concentrated under reduced pressure. The resulting residue was added with 100 mL of water, extracted with ethyl acetate (50 mL×2), the combined aqueous phase was added dropwise with 1 M hydrochloric acid to adjust pH to 3 resulting in the formation of precipitate. The precipitate was filtered to obtain the title compound 7-amino-2,3-dihydrobenzofuran-4-carboxylic acid 22e (1.70 g, yield: 80.0%) as a gary solid.

MS m/z (ESI): 178.1 [M−1]

Step 6

7-[[(7R)-7-Ethyl-8-isopropyl-5-methyl-6-oxo-7H-pteridin-2-yl]amino]-2,3-dihydrobenzofuran-4-carboxylic acid (7R)-2-Chloro-7-ethyl-8-isopropyl-5-methyl-7H-pteridin-6-one 22d (82 mg, 3.07 mmol) and 7-amino-2,3-dihydrobenzofuran-4-carboxylic acid 22e (500 mg, 2.80 mmol) were dissolved in 34 mL of the mixture solvent of ethanol and water (V/V=1:2.4) followed by the addition of 0.4 mL of concentrated hydrochloric acid. The reaction solution was heated to reflux for 15 hours and cooled down resulting in the formation of precipitate. The precipitate was filtered to obtain the title compound 7-[[(7R)-7-ethyl-8-isopropyl-5-methyl-6-oxo-7H-pteridin-2-yl]amino]-2,3-dihydrobenzofuran-4-carboxylic acid 22f (0.75 g, yield: 65.0%) as a white solid.

MS m/z (ESI): 410.2 [M−1]

Step 7

7-[[(7R)-7-Ethyl-8-isopropyl-5-methyl-6-oxo-7H-pteridin-2-yl]amino]-N-(1-methyl-4-piperidyl)-2,3-dihydrobenzofuran-4-carboxamide 7-[[(7R)-7-Ethyl-8-isopropyl-5-methyl-6-oxo-7H-pteridin-2-yl]amino]-2,3-dihydrobenzofuran-4-carboxylic acid 22f (120 mg, 0.29 mmol) and O-(benzotriazol-1-yl)-N,N,N',N'-tetra methyluronium tetrafluoroborate (93 mg, 0.29 mmol) were dissolved in 30 mL of dichloromethane followed by addition of diisopropylethylamine (83 mg, 0.64 mmol) and 1-methyl-piperidyl-4-yl amine (33 mg, 0.29 mmol) successively. The reaction solution was stirred for 3 hours. The resulting solution was washed with saturated sodium carbonate solution (30 mL) and saturated sodium chloride solution (30 mL) successively. The organic phase was dried over anhydrous sodium sulfate, filtered and the filtrate was concentrated under reduced pressure. The resulting residue was purified by silica gel column chromatography to obtain the title compound 7-[[(7R)-7-ethyl-8-isopropyl-5-methyl-6-oxo-7H-pteridin-2-yl]amino]-N-(1-methyl-4-piperidyl)-2,3-dihydrobenzofuran-4-carboxamide 22 (117 mg, yield: 80.0%) as a white solid.

MS m/z (ESI): 508.3 [M+1]

$^1$H NMR (400 MHz, CDCl$_3$) δ 8.31 (d, 1H), 7.67 (s, 1H), 7.13 to 7.01 (m, 2H), 5.96 (d, 1H), 4.82 to 4.61 (m, 3H), 4.29 (dd, 1H), 4.06 (d, 1H), 3.59 (t, 2H), 3.32 (s, 3H), 3.06 (d, 2H), 2.54 to 2.30 (m, 5H), 2.10 (d, 2H), 1.98 to 1.80 (m, 2H), 1.73 (td, 2H), 1.43 (d, 3H), 1.36 (d, 3H), 0.88 (t, 3H)

Example 23

7-[[(7R)-8-Cyclopentyl-7-ethyl-5-methyl-6-oxo-7H-pteridin-2-yl]amino]-N-[(cis)-4-[4-(cyclopropylmethyl)piperazin-1-yl]cyclohexyl]-2,2-dimethyl-3H-benzofuran-4-carboxamide

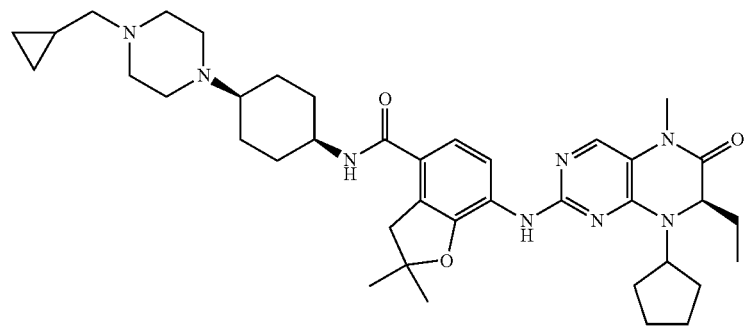

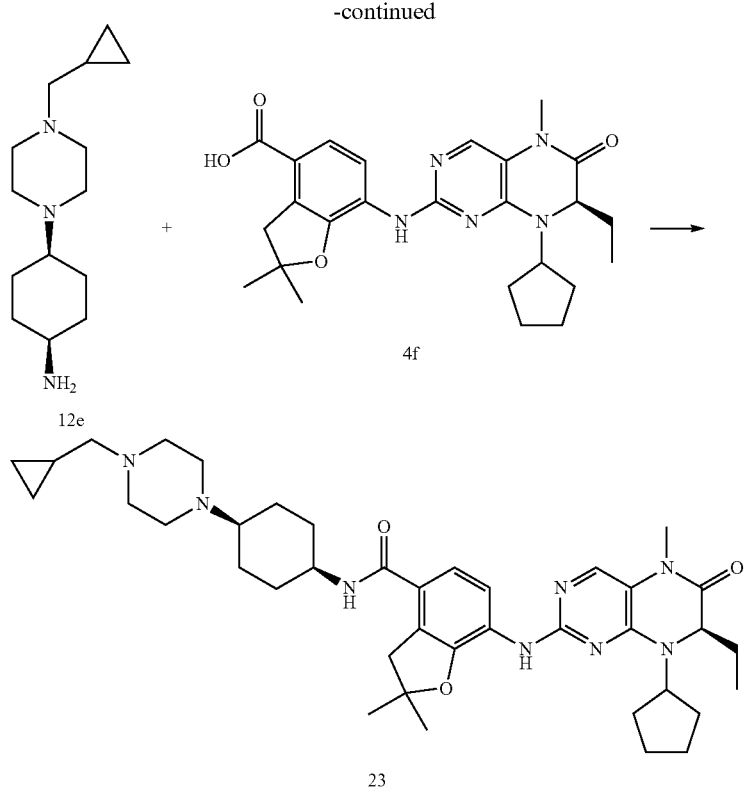

7-[[(7R)-8-Cyclopentyl-7-ethyl-5-methyl-6-oxo-7H-pteridin-2-yl]amino]-2,2-dimethyl-3H-benzofuran-4-carboxylic acid 4f (116 mg, 0.25 mmol) was dissolved in 15 mL of dichloromethane followed by the addition of (cis)-4-[4-(cyclopropylmethyl)piperazin-1-yl]cyclohexanamine 12e (65 mg, 0.28 mmol), O-(benzotriazol-1-yl)-N,N,N',N'-tetramethyluronium tetrafluoroborate (80 mg, 0.25 mmol) and diisopropylethylamine (97 mg, 0.75 mmol). The reaction solution was stirred for 3 hours. The resulting solution was added with 20 mL of saturated sodium bicarbonate solution and extracted with dichloromethane (50 mL×3). The combined organic phase was washed with water (50 mL), saturated sodium chloride solution (50 mL) successively, then dried over anhydrous magnesium sulfate, filtered and the filtrate was concentrated under reduced pressure. The resulting residue was purified by silica gel column chromatography to obtain the title compound 7-[[(7R)-8-cyclopentyl-7-ethyl-5-methyl-6-oxo-7H-pteridin-2-yl]amino]-N-[(cis)-4-[4-(cyclopropylmethyl)piperazin-1-yl]cyclohexyl]-2,2-dimethyl-3H-benzofuran-4-carboxamide 23 (135 mg, yield: 78.9%) as a white solid.

MS m/z (ESI): 685.4 [M+1]

$^1$H NMR (400 MHz, CDCl$_3$) δ 8.27 (d, 1H), 7.68 (s, 1H), 7.08 to 6.98 (m, 2H), 6.09 (d, 1H), 4.58 (t, 1H), 4.22 (dd, 2H), 3.40 (s, 2H), 3.33 (s, 3H), 2.95 to 2.40 (m, 7H), 2.33 to 2.24 (m, 3H), 2.19 to 2.13 (m, 1H), 2.13 to 1.95 (m, 1H), 1.94 to 1.64 (m, 16H), 1.62 to 1.55 (m, 2H), 1.51 (s, 6H), 0.87 (t, 3H), 0.57 to 0.48 (m, 2H), 0.19 to 0.10 (m, 2H)

Example 24

(cis-endo)-N-[2-Methyl-3,3a,4,5,6,6a-hexahydro-1H-cyclopenta[c]pyrrol-5-yl]-7-[[(7R)-7-ethyl-8-isopropyl-5-methyl-6-oxo-7H-pteridin-2-yl]amino]-2,3-dihydrobenzofuran-4-carboxamide

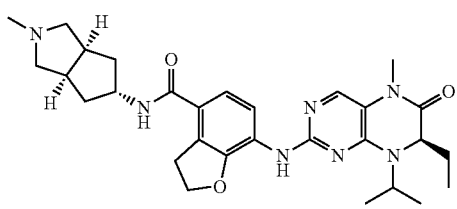

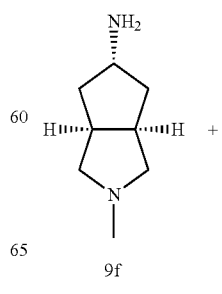

117

-continued

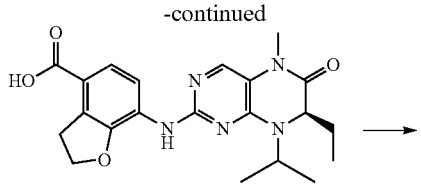

22f

118

-continued

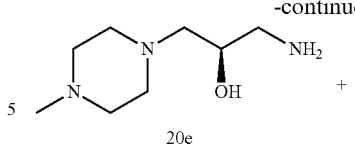

20e +

7-[[(7R)-7-Ethyl-8-isopropyl-5-methyl-6-oxo-7H-pteridin-2-yl]amino]-2,3-dihydrobenzofuran-4-carboxylic acid 22f (120 mg, 0.29 mmol) and O-(benzotriazol-1-yl)-N,N,N',N'-tetra methyluronium tetrafluoroborate (93 mg, 0.29 mmol) were dissolved in 30 mL of anhydrous dichloromethane followed by addition of diisopropylethylamine (0.1 mL, 0.64 mmol) and (cis-endo)-2-methyl-3,3a,4,5,6,6a-hexahydro-1H-cyclopenta[c]pyrrol-5-amine 9f (41 mg, 0.29 mmol). The reaction solution was stirred for 2 hours. The resulting solution was added with 30 mL of saturated sodium carbonate solution, stirred 10 minutes and extracted with dichloromethane (50 mL×3). The combined organic phase was washed with saturated sodium carbonate solution (50 mL), water (50 mL) and saturated sodium chloride solution (50 mL) successively, then dried over anhydrous sodium sulfate, filtered and the filtrate was concentrated under reduced pressure. The resulting residue was purified by silica gel column chromatography to obtain the title compound (cis-endo)-N-[2-methyl-3,3a,4,5,6,6a-hexahydro-1H-cyclopenta[c]pyrrol-5-yl]-7-[[(7R)-7-ethyl-8-isopropyl-5-methyl-6-oxo-7H-pteridin-2-yl]amino]-2,3-dihydrobenzofuran-4-carboxamide 24 (80 mg, yield: 52.0%) as a light yellow solid.

MS m/z (ESI): 534.4 [M+1]

$^1$H NMR (400 MHz, CDCl$_3$) δ 8.29 (d, 1H), 7.66 (s, 1H), 7.11 to 7.00 (m, 2H), 5.98 (d, 1H), 4.73 to 4.67 (m, 3H), 4.62 to 4.54 (m, 1H), 4.28 (dd, 1H), 3.59 (t, 2H), 3.32 (s, 3H), 3.22 to 3.12 (m, 2H), 3.05 to 2.90 (m, 2H), 2.52 (s, 3H), 2.39 (dd, 2H), 1.98 (dd, 2H), 1.91 (ddd, 1H), 1.79 to 1.66 (m, 3H), 1.42 (d, 3H), 1.25 (d, 3H), 0.88 (t, 3H)

Example 25

7-[[(7R)-8-Cyclopentyl-7-ethyl-5-methyl-6-oxo-7H-pteridin-2-yl]amino]-N-[(2R)-2-hydroxy-3-(4-methylpiperazin-1-yl)propyl]-2,3-dihydrobenzofuran-4-carboxamide

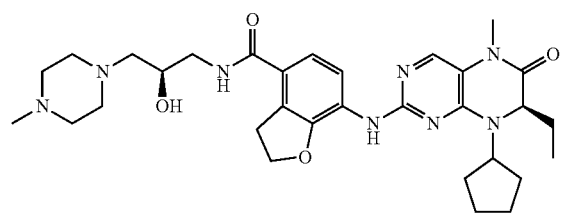

25

7-[[(7R)-8-Cyclopentyl-7-ethyl-5-methyl-6-oxo-7H-pteridin-2-yl]amino]-2,3-dihydrobenzofuran-4-carboxylic acid 1q (150 mg, 0.34 mmol) and O-(benzotriazol-1-yl)-N,N,N',N'-tetra methyluronium tetrafluoroborate (110 mg, 0.34 mmol) were dissolved in 30 mL of anhydrous dichloromethane, followed by the addition of diisopropylethylamine (0.1 mL, 0.75 mmol) and (2R)-1-amino-3-(4-methylpiperazin-1-yl)propan-2-ol 20e (59 mg, 0.34 mmol). The reaction solution was stirred for 3 hours. The resulting solution was added with 30 mL of saturated sodium carbonate solution and extracted with dichloromethane (50 mL×3). The combined organic phase was washed with saturated sodium carbonate solution (50 mL×3), water (50 mL) and saturated sodium chloride solution (50 mL) successively, then dried over anhydrous sodium sulfate, filtered and the filtrate was concentrated under reduced pressure. The resulting residue was purified by silica gel column chromatography to obtain the title compound 7-[[(7R)-8-cyclopentyl-7-ethyl-5-methyl-6-oxo-7H-pteridin-2-yl]amino]-N-[(2R)-2-hydroxy-3-(4-methylpiperazin-1-yl)propyl]-2,3-dihydrobenzofuran-4-carboxamide 25 (120 mg, yield: 60.0%) as a white solid.

MS m/z (ESI): 593.4 [M+1]

$^1$H NMR (400 MHz, CDCl$_3$) δ 8.29 (d, 1H), 7.67 (s, 1H), 7.15 (d, 1H), 7.05 (s, 1H), 6.62 (t, 1H), 4.68 (t, 2H), 4.47 (t, 1H), 4.21 (dd, 1H), 3.98 to 3.92 (m, 1H), 3.72 to 3.65 (m, 1H), 3.60 (t, 2H), 3.42 to 3.35 (m, 1H), 3.32 (s, 3H), 2.85 to 2.70 (m, 3H), 2.62 to 2.43 (m, 8H), 2.34 (s, 3H), 2.15 to 2.08 (m, 1H), 2.03 to 1.94 (m, 1H), 1.88 to 1.78 (m, 4H), 1.70 (m, 4H), 0.88 (t, 3H)

Example 26

N-[[(3S,8aS)-3,4,6,7,8,8a-Hexahydro-1H-pyrrolo[2,1-c][1,4]oxazin-3-yl]methyl]-7-[[(7R)-8-cyclopentyl-7-ethyl-5-methyl-6-oxo-7H-pteridin-2-yl]amino]-2,3-dihydrobenzofuran-4-carboxamide

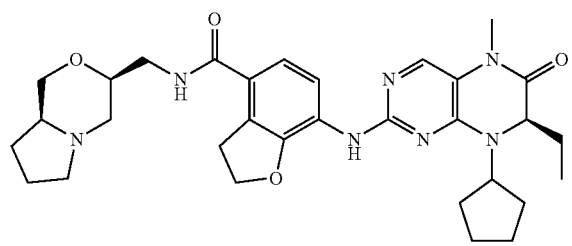

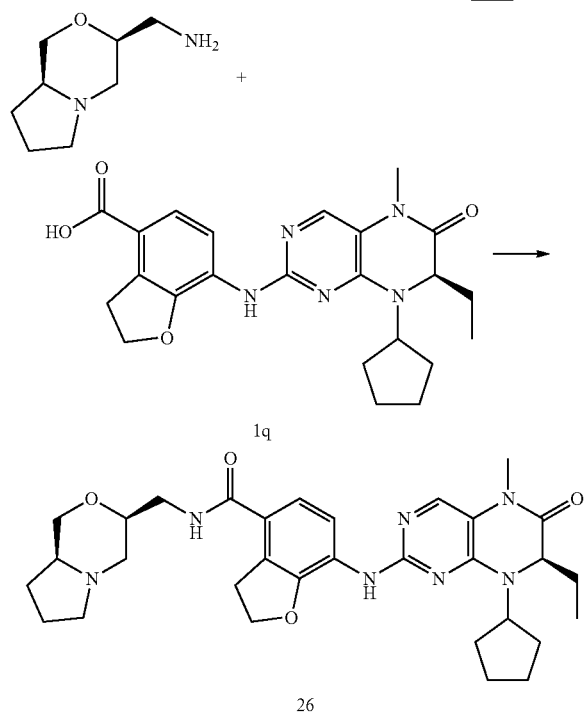

7-[[(7R)-8-Cyclopentyl-7-ethyl-5-methyl-6-oxo-7H-pteridin-2-yl]amino]-2,3-dihydrobenzofuran-4-carboxylic acid 1q (160 mg, 0.36 mmol) and O-(benzotriazol-1-yl)-N,N,N',N'-tetra methyluronium tetrafluoroborate (117 mg, 0.36 mmol) were dissolved in 30 mL of anhydrous dichloromethane followed by the addition of diisopropylethylamine (0.1 mL, 0.80 mmol) and (3S,8aS)-hexahydro-pyrrolo[2,1-c][1,4]oxazin-3-yl]methanamine (57 mg, 0.36 mmol, prepared by a well-known method disclose in "patent application CN101392001"). The reaction solution was stirred for 2 hours. The resulting solution was washed with saturated sodium carbonate solution (30 mL), saturated sodium chloride solution (30 mL) successively, then dried over anhydrous sodium sulfate, filtered and the filtrate was concentrated under reduced pressure. The resulting residue was purified by silica gel column chromatography to obtain the title compound N-[[(3S,8aS)-3,4,6,7,8,8a-hexahydro-1H-pyrrolo[2,1-c][1,4]oxazin-3-yl]methyl]-7-[[(7R)-8-cyclopentyl-7-ethyl-5-methyl-6-oxo-7H-pteridin-2-yl]amino]-2,3-dihydrobenzofuran-4-carboxamide 26 (140 mg, yield: 67.0%) as a white solid.

MS m/z (ESI): 576.3 [M+1]

$^1$H NMR (400 MHz, CDCl$_3$) δ 8.29 (d, 1H), 7.67 (s, 1H), 7.13 (d, 1H), 7.04 (s, 1H), 6.45 to 6.37 (m, 1H), 4.68 (t, 2H), 4.47 (t, 1H), 4.21 (dd, 1H), 4.05 (dd, 1H), 3.78 to 3.69 (m, 2H), 3.59 (t, 2H), 3.50 to 3.38 (m, 2H), 3.32 (s, 3H), 3.14 (s, 2H), 2.31 to 2.08 (m, 3H), 2.05 to 1.95 (m, 2H), 1.89 to 1.76 (m, 6H), 1.69 (m, 6H), 0.88 (m, 3H)

Example 27

N-[[(3S,8aR)-3,4,6,7,8,8a-Hexahydro-1H-pyrrolo[2,1-c][1,4]oxazin-3-yl]methyl]-7-[[(7R)-8-cyclopentyl-7-ethyl-5-methyl-6-oxo-7H-pteridin-2-yl]amino]-2,3-dihydrobenzofuran-4-carboxamide

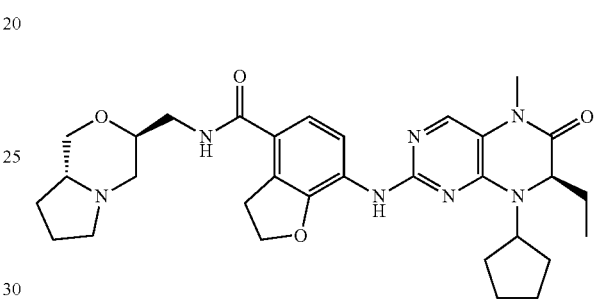

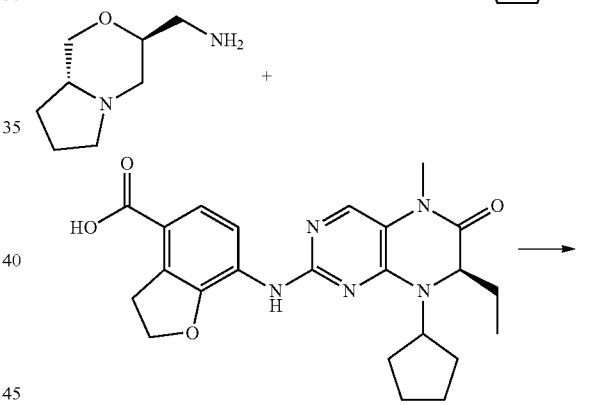

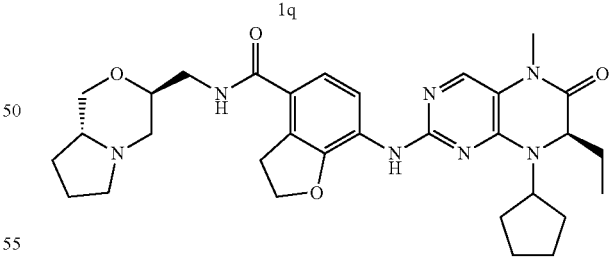

7-[[(7R)-8-Cyclopentyl-7-ethyl-5-methyl-6-oxo-7H-pteridin-2-yl]amino]-2,3-dihydrobenzofuran-4-carboxylic acid 1q (160 mg, 0.36 mmol) and O-(benzotriazol-1-yl)-N,N,N',N'-tetra methyluronium tetrafluoroborate (117 mg, 0.36 mmol) were dissolved in 30 mL of anhydrous dichloromethane followed by the addition of diisopropylethylamine (0.1 mL, 0.80 mmol) and (3S,8aR)-hexahydro-pyrrolo[2,1-c][1,4]oxazin-3-yl]methanamine (57 mg, 0.36 mmol, prepared by a well-known method disclosed in "patent application CN101392001"). The reaction solution was stirred for 12 hours. The resulting solution was washed with saturated sodium carbonate solution (30 mL), saturated sodium chloride solution (30 mL) successively, then dried over anhydrous sodium sulfate, filtered and the filtrate was concentrated under reduced pressure. The resulting residue was purified by silica gel column chromatography to obtain the title compound N-[[(3S,8aR)-3,4,6,7,8,8a-hexahydro-1H-pyrrolo[2,1-c][1,4]oxazin-3-yl]methyl]-7-[[(7R)-8-cyclopentyl-7-ethyl-5-methyl-6-oxo-7H-pteridin-2-yl]amino]-2,3-dihydrobenzofuran-4-carboxamide 27 (120 mg, yield: 57.4%) as a white solid.

MS m/z (ESI): 576.4 [M+1]

$^1$H NMR (400 MHz, CDCl$_3$) δ 8.28 (d, 1H), 7.67 (s, 1H), 7.11 (d, 1H), 7.04 (s, 1H), 6.86 to 6.74 (m, 1H), 4.68 (t, 2H), 4.48 (t, 1H), 4.21 (dd, 1H), 3.97 to 3.85 (m, 2H), 3.75 to 3.68 (m, 3H), 3.61 (t, 2H), 3.32 (s, 3H), 3.03 to 2.95 (m, 1H), 2.80 (dd, 1H), 2.55 (dd, 1H), 2.39 to 2.25 (m, 2H), 2.12 (m, 1H), 1.99 (m, 1H), 1.91 to 1.78 (m, 5H), 1.76 to 1.64 (m, 7H), 0.88 (t, 3H)

Example 28

N-[[(3R,8aR)-3,4,6,7,8,8a-Hexahydro-1H-pyrrolo[2,1-c][1,4]oxazin-3-yl]methyl]-7-[[(7R)-8-cyclopentyl-7-ethyl-5-methyl-6-oxo-7H-pteridin-2-yl]amino]-2,3-dihydrobenzofuran-4-carboxamide

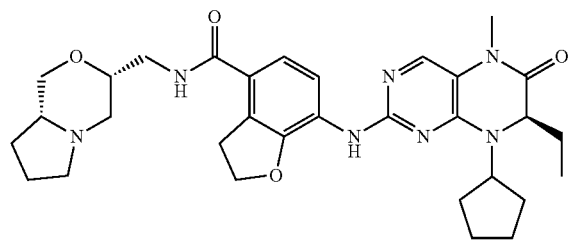

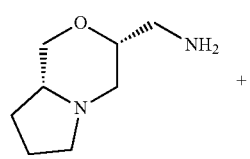

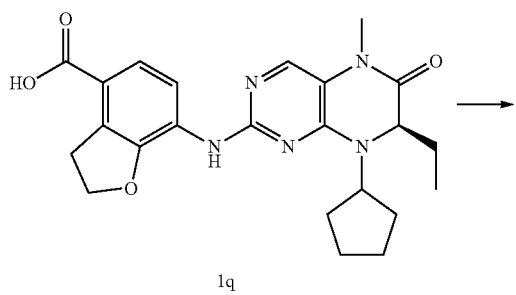

1q

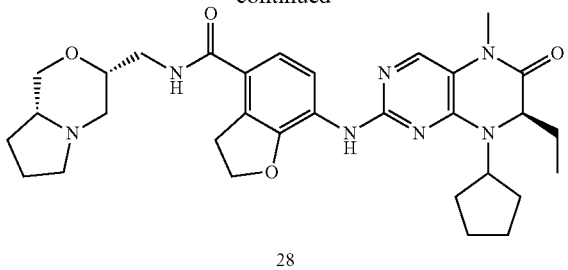

28

7-[[(7R)-8-Cyclopentyl-7-ethyl-5-methyl-6-oxo-7H-pteridin-2-yl]amino]-2,3-dihydrobenzofuran-4-carboxylic acid 1q (160 mg, 0.36 mmol) and O-(benzotriazol-1-yl)-N,N,N',N'-tetra methyluronium tetrafluoroborate (117 mg, 0.36 mmol) were dissolved in 30 mL of anhydrous dichloromethane followed by the addition of diisopropylethylamine (0.1 mL, 0.80 mmol) and (3R,8aR)-hexahydro-pyrrolo[2,1-c][1,4]oxazin-3-yl]methanamine (57 mg, 0.36 mmol, prepared by a well-known method disclosed in "patent application CN101392001") successively. The reaction solution was stirred for 12 hours. The resulting solution was washed with saturated sodium carbonate solution (30 mL), saturated sodium chloride solution (30 mL) successively, then dried over anhydrous sodium sulfate, filtered and the filtrate was concentrated under reduced pressure. The resulting residue was purified by silica gel column chromatography to obtain the title compound N-[[(3R,8aR)-3,4,6,7,8,8a-hexahydro-1H-pyrrolo[2,1-c][1,4]oxazin-3-yl]methyl]-7-[[(7R)-8-cyclopentyl-7-ethyl-5-methyl-6-oxo-7H-pteridin-2-yl]amino]-2,3-dihydrobenzofuran-4-carboxamide 28 (128 mg, yield: 61.2%) as a white solid.

MS m/z (ESI): 576.3 [M+1]

$^1$H NMR (400 MHz, CDCl$_3$) δ 8.29 (d, 1H), 7.67 (s, 1H), 7.13 (d, 1H), 7.04 (s, 1H), 6.42 (s, 1H), 4.68 (t, 2H), 4.46 (d, 1H), 4.21 (dd, 1H), 4.04 (dd, 1H), 3.79 to 3.67 (m, 2H), 3.59 (t, 2H), 3.41 (dd, 2H), 3.32 (s, 3H), 3.10 (d, 2H), 2.27 to 2.06 (m, 3H), 2.05 to 1.95 (m, 2H), 1.91 to 1.75 (m, 6H), 1.75 to 1.57 (m, 6H), 0.88 (t, 3H)

Example 29

7-[[(7R)-8-Cyclopentyl-7-ethyl-5-methyl-6-oxo-7H-pteridin-2-yl]amino]-2-(dimethylaminomethyl)-N-(1-methyl-4-piperidyl)-2,3-dihydrobenzofuran-4-carboxamide

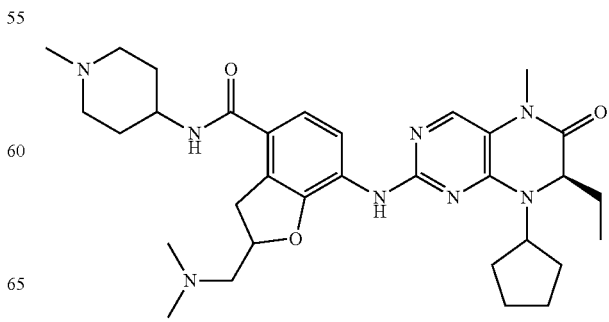

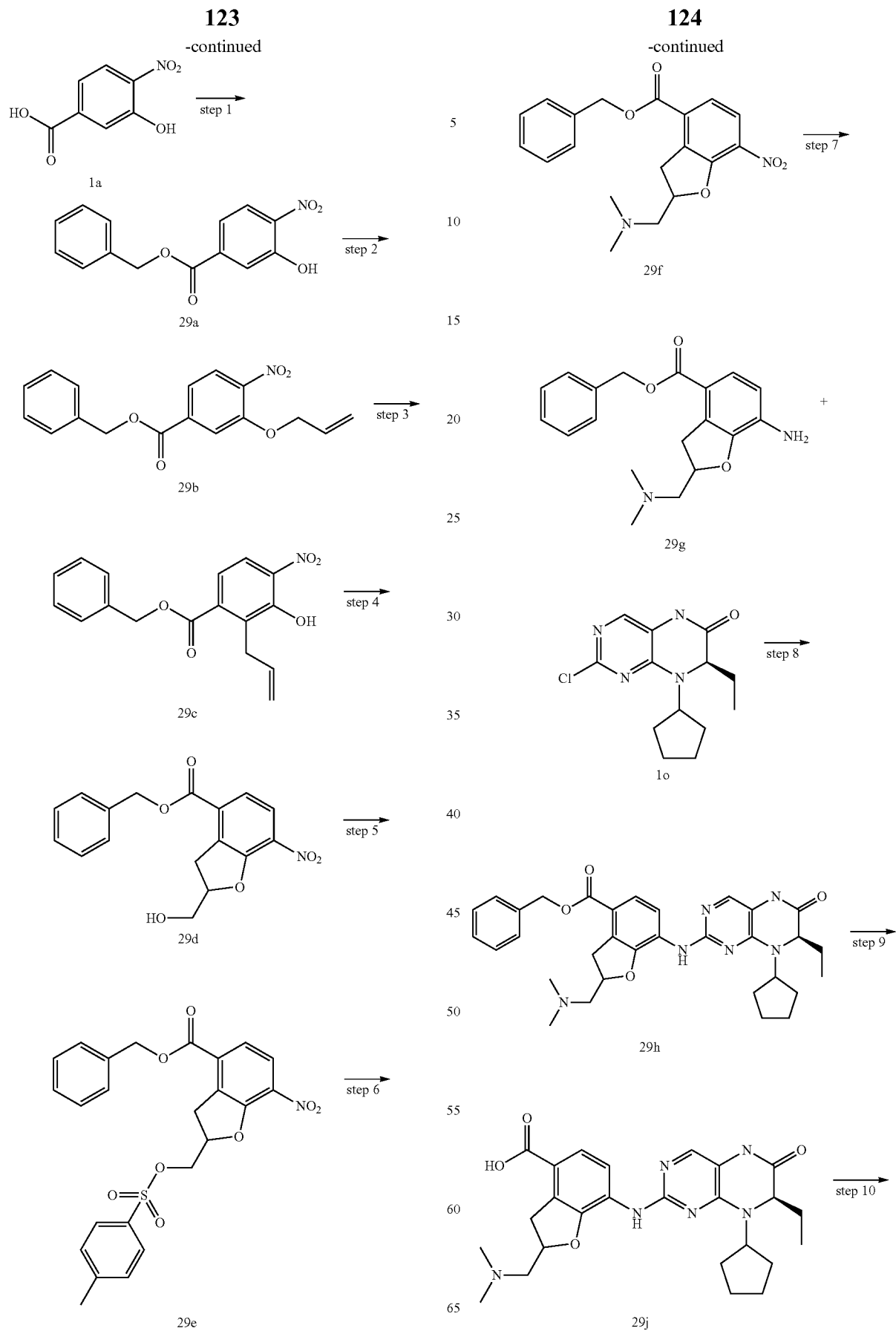

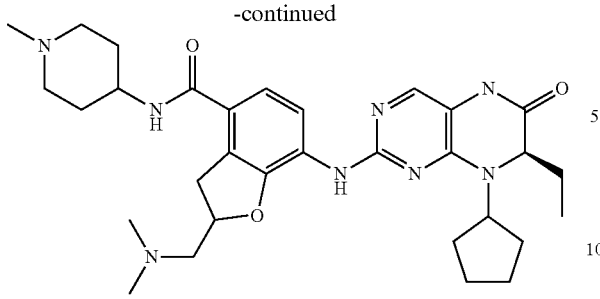

29

Step 1

Benzyl 3-hydroxy-4-nitro-benzoate

3-Hydroxy-4-nitro-benzoic acid 1a (10 g, 54.60 mmol) was dissolved in 125 mL of toluene followed by the addition of benzyl alcohol (9 g, 83.20 mmol) and p-toluenesulfonic acid (1 g, 5.30 mmol). The reaction solution was heated to reflux for 16 hours in water segregator. The resulting solution was added with 50 mL of ethyl acetate, washed with water (50 mL) and saturated sodium chloride solution (50 mL) successively, then dried over anhydrous magnesium sulfate, filtered and the filtrate was concentrated under reduced pressure. The resulting residue was purified by silica gel column chromatography to obtain the title compound benzyl 3-hydroxy-4-nitro-benzoate 29a (8 g, yield: 53.7%) as a yellow solid.

MS m/z (ESI): 272.1 [M−1]

Step 2

Benzyl 3-allyloxy-4-nitro-benzoate

Benzyl 3-hydroxy-4-nitro-benzoate 29a (4.50 g, 16.47 mmol) was dissolved in 75 mL of anhydrous acetonitrile. The resulting solution was added with potassium carbonate (6.83 g, 49.41 mmol) and 3-bromopropene (2.9 mL, 32.94 mmol) successively, heated to reflux for 3 hours, then filtered. The filtrate was concentrated under reduced pressure. The resulting residue was purified by silica gel column chromatography to obtain the title compound benzyl 3-allyloxy-4-nitro-benzoate 29b (4.86 g, yield: 94.2%) as a yellow solid.

$^1$H NMR (400 MHZ, CDCl$_3$) δ (ppm) 7.85 to 7.81 (d, 1H), 7.80 (s, 1H), 7.77 to 7.74 (m, 1H), 7.50 to 7.39 (m, 5H), 6.12 to 6.02 (m, 1H), 5.56 to 5.51 (d, 2H), 5.50 to 5.38 (m, 2H), 4.79 to 4.77 (m, 2H).

Step 3

Benzyl 2-allyl-3-hydroxy-4-nitro-benzoate

Benzyl 3-allyloxy-4-nitro-benzoate 29b (2.19 g, 7 mmol) was put into three-necked flask, heated to 190° C., and stirred for 3.5 hours. The resulting solution was cooled down to room temperature, added with 50 mL of dichloromethane and concentrated under reduced pressure. The resulting residue was purified by silica gel column chromatography to obtain the title compound benzyl 2-allyl-3-hydroxy-4-nitro-benzoate 29c (1.36 g, yield: 62.1%) as a yellow liquid.

MS m/z (ESI): 312.1 [M−1]

Step 4

Benzyl 2-(hydroxymethyl)-7-nitro-2,3-dihydrobenzofuran-4-carboxylate

Benzyl 2-allyl-3-hydroxy-4-nitro-benzoate 29c (1.36 g, 4.30 mmol) was dissolved in 100 mL of 1,2-dichloroethane followed by the addition of m-chloroperbenzoic acid (1.18 g, 4.77 mmol). The reaction solution was heated to 70° C. and stirred for 3 hours. The resulting solution was cooled down to room temperature, added with 20 mL of saturated sodium thiosulfate solution, stirred for 30 minutes and extracted with ethyl acetate (20 mL×3). The combined organic phase was washed with water (20 mL), saturated sodium chloride solution (20 mL) successively, then dried over anhydrous magnesium sulfate, filtered and the filtrate was concentrated under reduced pressure. The resulting residue was purified by silica gel column chromatography to obtain the title compound benzyl 2-(hydroxymethyl)-7-nitro-2,3-dihydrobenzofuran-4-carboxylate 29d (430 mg, yield: 30.1%) as a light yellow solid.

MS m/z (ESI): 330.2 [M+1]

Step 5

Benzyl 7-nitro-2-(tolyl-4-sulfonyloxymethyl)-2,3-dihydrobenzofuran-4-carboxylate Benzyl 2-(hydroxymethyl)-7-nitro-2,3-dihydrobenzofuran-4-carboxylate 29d (420 mg, 1.27 mmol) was dissolved in 25 mL of dichloromethane followed by the addition of p-toluenesulfonyl chloride (729 mg, 3.83 mmol) and triethylamine (514 mg, 5.08 mmol) in an ice-water bath. The reaction solution was warmed up to room temperature and stirred for 2 hours. The resulting solution was added with 5 mL of water and extracted with ethyl acetate (20 mL×3). The combined organic phase was washed with water (20 mL) and saturated sodium chloride solution (20 mL) successively, then dried over anhydrous magnesium sulfate, filtered and the filtrate was concentrated under reduced pressure. The resulting residue was purified by silica gel column chromatography to obtain the title compound benzyl 7-nitro-2-(tolyl-4-sulfonyloxymethyl)-2,3-dihydrobenzofuran-4-carboxylate 29e (524 mg, yield: 85.3%) as a white solid.

MS m/z (ESI): 501.3 [M+18]

Step 6

Benzyl 2-(dimethylaminomethyl)-7-nitro-2,3-dihydrobenzofuran-4-carboxylate

Dimethylamine hydrochloride (424 mg, 5.20 mmol) was dissolved in 20 mL of acetonitrile followed by the addition of triethylamine (737 mg, 7.28 mmol). The reaction solution was stirred at room temperature for 20 minutes followed by addition of benzyl 7-nitro-2-(tolyl-4-sulfonyloxymethyl)-2,3-dihydrobenzofuran-4-carboxylate 29e (510 mg, 1.04 mmol) and 10 mg potassium iodide. The reaction solution was heated to reflux for 3 hours. The resulting solution was added with 5 mL of water and extracted with ethyl acetate (50 mL×3). The combined organic phase was washed with water (50 mL) and saturated sodium chloride solution (50 mL) successively, then dried over anhydrous magnesium sulfate, filtered and the filtrate was concentrated under reduced pressure. The resulting residue was purified by silica gel column chromatography to obtain the title compound benzyl 2-(dimethylaminomethyl)-7-nitro-2,3-dihydrobenzofuran-4-carboxylate 29f (249 mg, yield: 67.1%) as a yellow oil liquid.

MS m/z (ESI): 357.2 [M+1]

Step 7

Benzyl 7-amino-2-(dimethylaminomethyl)-2,3-dihydrobenzofuran-4-carboxylate

Benzyl 2-(dimethylaminomethyl)-7-nitro-2,3-dihydrobenzofuran-4-carboxylate 29f (240 mg, 0.67 mmol) was dissolved in 30 mL of acetic acid followed by the addition of iron powder (189 mg, 3.37 mmol). The reaction solution was stirred for 2 hours. The resulting solution was concentrated under reduced pressure, added with 20 mL of water and 20 mL of dichloromethane, then added dropwise with 2 M sodium carbonate solution to adjust pH to about 10 and extracted with dichloromethane (30 mL×3). The combined organic phase was washed with water (20 mL) and saturated sodium chloride solution (20 mL) successively, then dried over anhydrous magnesium sulfate, filtered and the filtrate was concentrated under reduced pressure to obtain the title compound benzyl 7-amino-2-(dimethylaminomethyl)-2,3-dihydrobenzofuran-4-carboxylate 29g (212 mg, yield: 97.2%) as a yellow oil liquid.

MS m/z (ESI): 327.2 [M+1]

Step 8 benzyl 7-[[(7R)-8-Cyclopentyl-7-ethyl-5-methyl-6-oxo-7H-pteridin-2-yl]amino]-2-(dimethylaminomethyl)-2,3-dihydrobenzofuran-4-carboxylate Benzyl 7-amino-2-(dimethylaminomethyl)-2,3-dihydrobenzofuran-4-carboxylate 29g (212 mg, 0.65 mmol) was dissolved in 20 mL of 4-methyl-2-pentanol followed by the addition of (7R)-2-chloro-8-cyclopentyl-7-ethyl-5-methyl-7H-pteridin-6-one 1o (230 mg, 0.78 mmol) and p-toluenesulfonic acid monohydrate (198 mg, 1.04 mmol). The reaction solution was heated to reflux for 3 hours with stirring and concentrated under reduced pressure. The resulting residue was added with 30 mL of saturated sodium bicarbonate solution and extracted with dichloromethane (50 ml×3). The combined organic phase was washed with water (30 mL) and saturated sodium chloride solution (30 mL) successively, then dried over anhydrous magnesium sulfate, filtered and the filtrate was concentrated under reduced pressure. The resulting residue was purified by silica gel column chromatography to obtain the title compound benzyl 7-[[(7R)-8-cyclopentyl-7-ethyl-5-methyl-6-oxo-7H-pteridin-2-yl]amino]-2-(dimethylaminomethyl)-2,3-dihydrobenzofuran-4-carboxylate 29h (0.13 g, yield: 34.2%) as a white solid.

MS m/z (ESI): 585.5 [M+1]

Step 9

7-[[(7R)-8-Cyclopentyl-7-ethyl-5-methyl-6-oxo-7H-pteridin-2-yl]amino]-2-(dimethylaminomethyl)-2,3-dihydrobenzofuran-4-carboxylic acid Benzyl 7-[[(7R)-8-cyclopentyl-7-ethyl-5-methyl-6-oxo-7H-pteridin-2-yl]amino]-2-(dimethylaminomethyl)-2,3-dihydrobenzofuran-4-carboxylate 29h (120 mg, 0.20 mmol) was dissolved in 20 mL of methanol followed by the addition of palladium/carbon (12 mg, 10%). The reaction solution was stirred for 12 hours and filtered. The filtrate was concentrated under reduced pressure to obtain the title compound 7-[[(7R)-8-cyclopentyl-7-ethyl-5-methyl-6-oxo-7H-pteridin-2-yl]amino]-2-(dimethylaminomethyl)-2,3-dihydrobenzofuran-4-carboxylic acid 29j (30 mg, yield: 25.8%) as a white solid.

MS m/z (ESI): 493.3 [M−1]

Step 10

7-[[(7R)-8-Cyclopentyl-7-ethyl-5-methyl-6-oxo-7H-pteridin-2-yl]amino]-2-(dimethylaminomethyl)-N-(1-methyl-4-piperidyl)-2,3-dihydrobenzofuran-4-carboxamide 7-[[(7R)-8-Cyclopentyl-7-ethyl-5-methyl-6-oxo-7H-pteridin-2-yl]amino]-2-(dimethylaminomethyl)-2,3-dihydrobenzofuran-4-carboxylic acid 29j (30 mg, 0.06 mmol) was dissolved in 10 mL of dichloromethane followed by the addition of 1-methyl-piperidyl-4-yl-amine (7 mg, 0.06 mmol), O-(benzotriazol-1-yl)-N,N,N',N'-tetra methyluronium tetrafluoroborate (20 mg, 0.06 mmol) and diisopropylethylamine (24 mg, 0.18 mmol). The reaction solution was stirred for 2 hours. The resulting solution was added with 10 mL of saturated sodium chloride solution and extracted with dichloromethane (10 mL×3). The combined organic phase was washed with water (10 mL) and saturated sodium chloride solution (10 mL) successively, then dried over anhydrous magnesium sulfate, filtered and the filtrate was concentrated under reduced pressure. The resulting residue was purified by silica gel column chromatography to obtain the title compound 7-[[(7R)-8-cyclopentyl-7-ethyl-5-methyl-6-oxo-7H-pteridin-2-yl]amino]-2-(dimethylaminomethyl)-N-(1-methyl-4-piperidyl)-2,3-dihydrobenzofuran-4-carboxamide 29 (27 mg, yield: 77.1%) as a white solid.

MS m/z (ESI): 591.5 [M+1]

$^1$H NMR (400 MHz, CDCl$_3$) δ 8.22 (d, 1H), 7.79 (s, 1H), 7.33 (d, 1H), 5.34 (d, 1H), 4.56 (d, 1H), 4.27 (dd, 1H), 4.11 (t, 1H), 3.78 (dd, 1H), 3.51 (d, 2H), 3.44 to 3.36 (m, 1H), 3.40 to 3.20 (m, 7H), 3.19 to 3.10 (m, 2H), 2.93 (s, 6H), 2.84 (s, 3H), 2.23 to 2.10 (m, 3H), 2.05 to 1.94 (m, 3H), 1.91 to 1.81 (m, 4H), 1.81 to 1.66 (m, 4H), 0.88 (t, 3H)

Example 30

7-[[(7R)-8-Cyclopentyl-7-ethyl-5-methyl-6-oxo-7H-pteridin-2-yl]amino]-2-methyl-N-(1-methyl-4-piperidyl)-2,3-dihydrobenzofuran-4-carboxamide

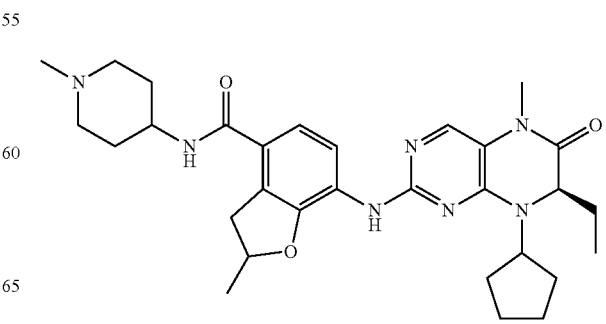

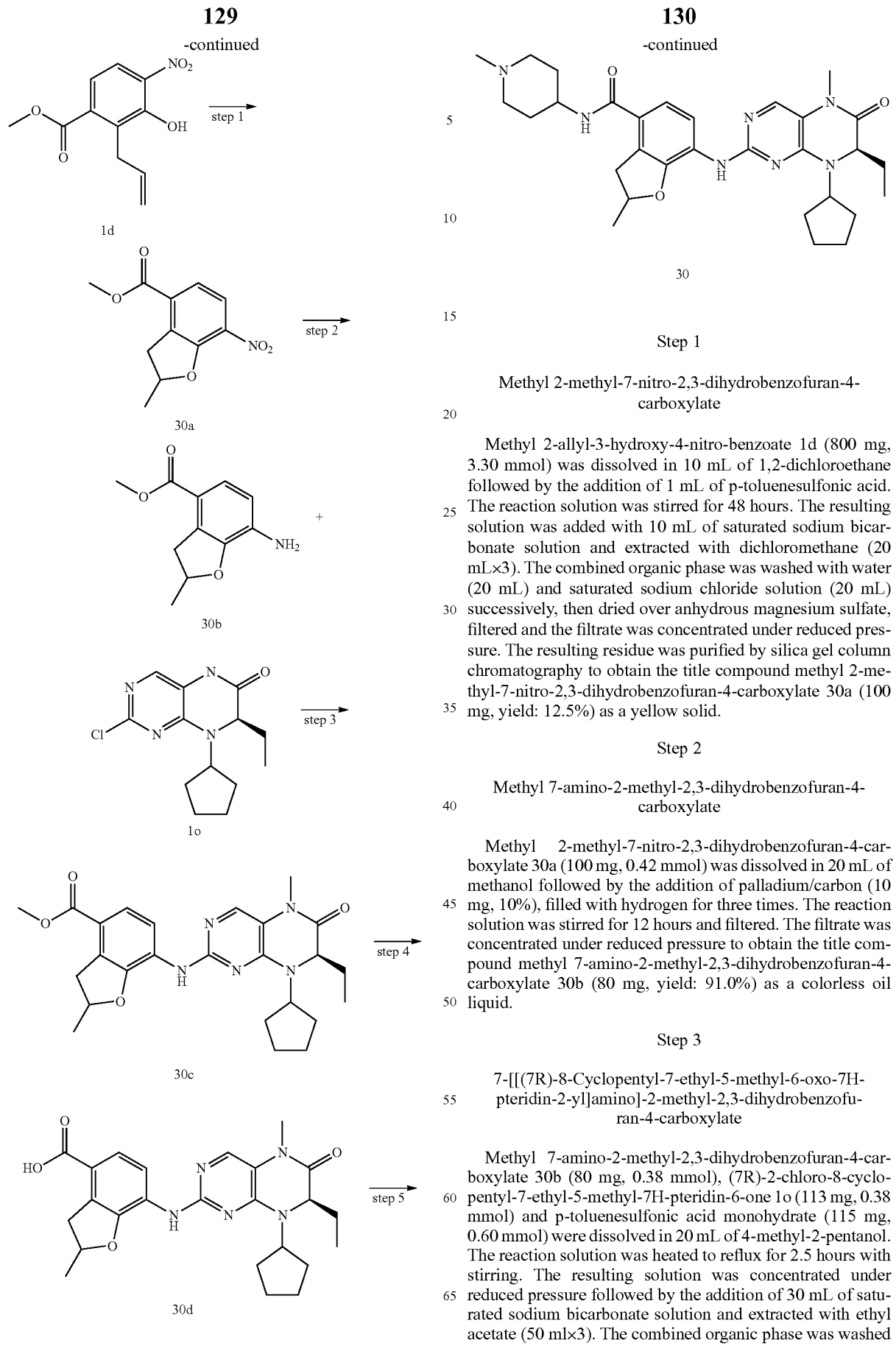

Step 1

Methyl 2-methyl-7-nitro-2,3-dihydrobenzofuran-4-carboxylate

Methyl 2-allyl-3-hydroxy-4-nitro-benzoate 1d (800 mg, 3.30 mmol) was dissolved in 10 mL of 1,2-dichloroethane followed by the addition of 1 mL of p-toluenesulfonic acid. The reaction solution was stirred for 48 hours. The resulting solution was added with 10 mL of saturated sodium bicarbonate solution and extracted with dichloromethane (20 mL×3). The combined organic phase was washed with water (20 mL) and saturated sodium chloride solution (20 mL) successively, then dried over anhydrous magnesium sulfate, filtered and the filtrate was concentrated under reduced pressure. The resulting residue was purified by silica gel column chromatography to obtain the title compound methyl 2-methyl-7-nitro-2,3-dihydrobenzofuran-4-carboxylate 30a (100 mg, yield: 12.5%) as a yellow solid.

Step 2

Methyl 7-amino-2-methyl-2,3-dihydrobenzofuran-4-carboxylate

Methyl 2-methyl-7-nitro-2,3-dihydrobenzofuran-4-carboxylate 30a (100 mg, 0.42 mmol) was dissolved in 20 mL of methanol followed by the addition of palladium/carbon (10 mg, 10%), filled with hydrogen for three times. The reaction solution was stirred for 12 hours and filtered. The filtrate was concentrated under reduced pressure to obtain the title compound methyl 7-amino-2-methyl-2,3-dihydrobenzofuran-4-carboxylate 30b (80 mg, yield: 91.0%) as a colorless oil liquid.

Step 3

7-[[(7R)-8-Cyclopentyl-7-ethyl-5-methyl-6-oxo-7H-pteridin-2-yl]amino]-2-methyl-2,3-dihydrobenzofuran-4-carboxylate Methyl 7-amino-2-methyl-2,3-dihydrobenzofuran-4-carboxylate 30b (80 mg, 0.38 mmol), (7R)-2-chloro-8-cyclopentyl-7-ethyl-5-methyl-7H-pteridin-6-one 1o (113 mg, 0.38 mmol) and p-toluenesulfonic acid monohydrate (115 mg, 0.60 mmol) were dissolved in 20 mL of 4-methyl-2-pentanol. The reaction solution was heated to reflux for 2.5 hours with stirring. The resulting solution was concentrated under reduced pressure followed by the addition of 30 mL of saturated sodium bicarbonate solution and extracted with ethyl acetate (50 ml×3). The combined organic phase was washed with water (30 mL) and saturated sodium chloride solution (30 mL) successively, then dried over anhydrous magnesium sulfate, filtered and the filtrate was concentrated under reduced pressure. The resulting residue was purified by the preparation plate to obtain the title compound 77-[[(7R)-8-cyclopentyl-7-ethyl-5-methyl-6-oxo-7H-pteridin-2-yl]amino]-2-methyl-2,3-dihydrobenzofuran-4-carboxylate 30c (0.10 g, yield: 56.0%) as a white solid.

Step 4

7-[[(7R)-8-Cyclopentyl-7-ethyl-5-methyl-6-oxo-7H-pteridin-2-yl]amino]-2-methyl-2,3-dihydrobenzofuran-4-carboxylic acid 7-[[(7R)-8-Cyclopentyl-7-ethyl-5-methyl-6-oxo-7H-pteridin-2-yl]amino]-2-methyl-2,3-dihydrobenzofuran-4-carboxylate 30c (100 mg, 0.21 mmol) and 1 M lithium hydroxide solution were dissolved in 50 mL of the mixture solvent of methanol and tetrahydrofuran (V/V=1:1). The reaction solution was stirred for 12 hours followed by the addition of 1 M hydrochloric acid to adjust pH to 6 to 7. The resulting solution was concentrated under reduced pressure. The residue was added dropwise with 1 M lithium hydroxide solution to adjust pH to 3 to 4 and extracted with ethyl acetate (30 mL×3). The combined organic phase was concentrated under reduced pressure to obtain the title compound 7-[[(7R)-8-cyclopentyl-7-ethyl-5-methyl-6-oxo-7H-pteridin-2-yl]amino]-2-methyl-2,3-dihydrobenzofuran-4-carboxylic acid 30d (90 mg, yield: 95.0%) as a white solid.

MS m/z (ESI): 450.2 [M−1]

Step 5

7-[[(7R)-8-Cyclopentyl-7-ethyl-5-methyl-6-oxo-7H-pteridin-2-yl]amino]-2-methyl-N-(1-methyl-4-piperidyl)-2,3-dihydrobenzofuran-4-carboxamide 7-[[(7R)-8-Cyclopentyl-7-ethyl-5-methyl-6-oxo-7H-pteridin-2-yl]amino]-2-methyl-2,3-dihydrobenzofuran-4-carboxylic acid 30d (70 mg, 0.20 mmol), 1-methyl-piperidyl-4-yl-amine (23 mg, 0.20 mmol), O-(benzotriazol-1-yl)-N,N,N',N'-tetra methyluronium tetrafluoroborate (64 mg, 0.20 mmol) and diisopropylethylamine (65 mg, 0.50 mmol) were dissolved in 30 mL of dichloromethane. The reaction solution was stirred for 2 hours. The resulting solution was added with 20 mL of saturated sodium bicarbonate solution and extracted with dichloromethane (50 mL×3). The combined organic phase was washed with water (30 mL) and saturated sodium chloride solution (30 mL) successively, then dried over anhydrous magnesium sulfate, filtered and the filtrate was concentrated under reduced pressure. The resulting residue was purified by silica gel column chromatography to obtain the title compound 7-[[(7R)-8-cyclopentyl-7-ethyl-5-methyl-6-oxo-7H-pteridin-2-yl]amino]-2-methyl-N-(1-methyl-4-piperidyl)-2,3-dihydrobenzofuran-4-carboxamide 30 (40 mg, yield: 36.0%) as a white solid.

MS m/z (ESI): 548.3 [M+1]

$^1$H NMR (400 MHz, CDCl$_3$) δ 8.32 to 8.23 (m, 1H), 7.67 (s, 1H), 7.11 to 7.01 (m, 2H), 5.94 to 5.84 (m, 1H), 5.10 to 4.97 (m, 1H), 4.59 to 4.45 (m, 1H), 4.28 to 4.16 (m, 1H), 3.99 (s, 1H), 3.78 to 3.61 (m, 2H), 3.33 (m, 3H), 3.23 to 3.12 (m, 1H), 2.97 to 2.81 (m, 2H), 2.34 (s, 3H), 2.29 to 2.15 (m, 2H), 2.13 to 1.89 (m, 6H), 1.88 to 1.78 (m, 3H), 1.77 to 1.57 (m, 4H), 1.50 (d, 3H), 0.88 (t, 3H)

Example 31

N-[(2S)-3-[4-(Cyclopropylmethyl)piperazin-1-yl]-2-hydroxy-propyl]-7-[[(7R)-7-ethyl-8-isopropyl-5-methyl-6-oxo-7H-pteridin-2-yl]amino]-2,3-dihydrobenzofuran-4-carboxamide

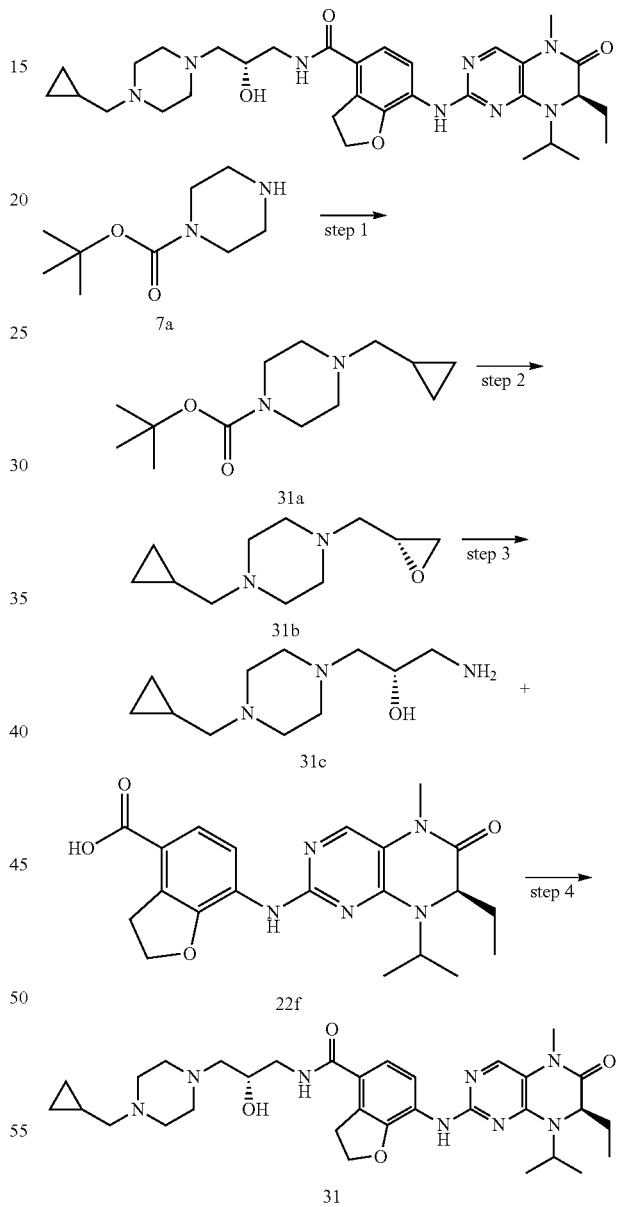

Step 1

Tert-butyl 4-(cyclopropylmethyl)piperazine-1-carboxylate

Tert-butyl piperazine-1-carboxylate 7a (6.14 g, 33 mmol), bromomethyl-cyclopropane (4.05 g, 30 mmol) and triethylamine (6.06 g, 60 mmol) were dissolved in 70 mL of dichloromethane. The reaction solution was stirred for 12 hours. The resulting solution was added with 50 mL of aqeuous saturated sodium bicarbonate solution and extracted with dichloromethane (50 mL×3). The combined organic phase was washed with saturated sodium chloride solution (50 mL), dried over anhydrous magnesium sulfate. The filtrate was concentrated under reduced pressure. The resulting residue was purified by silica gel column chromatography to obtain the title compound tert-butyl 4-(cyclopropylmethyl)piperazine-1-carboxylate 31a (4.50 g, yield: 62.5%) as a yellow oil.

MS m/z (ESI): 241.2 [M+1]

Step 2

1-(Cyclopropylmethyl)-4-[[(2R)-oxiran-2-yl]methyl]piperazine

Tert-butyl 4-(cyclopropylmethyl)piperazine-1-carboxylate 31a (2 g, 8.30 mmol) was dissolved in 40 mL of dichloromethane followed by the addition of 20 mL of a 4 M solution of hydrogen chloride in dioxane. The reaction solution was stirred for 0.5 hours. The reaction solution was concentrated under reduced pressure followed by the addition of 40 mL of dichloromethane and dropwise with 20 mL of triethylamine to adjust pH to 10 to 11. The resulting solution was concentrated under reduced pressure. The residue was added with 50 mL of ethyl acetate and filtered. The filtrate was concentrated under reduced pressure, added with 50 mL of ethyl acetate and 20 mL of water, then added with (R)-2-chloromethyl-oxirane (0.92 g, 9.96 mmol) and sodium hydroxide (0.66 g, 16.60 mmol). The reaction solution was stirred for 12 hours. The reaction solution was concentrated under reduced pressure, added with 50 mL of water and extracted with dichloromethane (50 mL×3). The combined organic phase was washed with saturated sodium chloride solution (50 mL), dried over anhydrous magnesium sulfate. The filtrate was concentrated under reduced pressure. The resulting residue was purified by silica gel column chromatography to obtain the title compound 1-(cyclopropylmethyl)-4-[[(2R)-oxiran-2-yl]methyl]piperazine 31b (0.91 g, yield: 57.0%) as a yellow oil.

MS m/z (ESI): 197.3 [M+1]

Step 3

(2S)-1-Amino-3-[4-(cyclopropylmethyl)piperazin-1-yl]-isopropanol 1-(Cyclopropylmethyl)-4-[[(2R)-oxiran-2-yl]methyl]piperazine 31b (908 mg, 4.62 mmol) was dissolved in 40 mL of ethanol followed by the addition of 10 mL of aqueous ammonia. The reaction solution was stirred for 12 hours. The resulting solution was concentrated under reduced pressure to obtain the crude title compound (2S)-1-amino-3-[4-(cyclopropylmethyl)piperazin-1-yl]-isopropanol 31c (0.74 g) as a light yellow oil, which was used in the next step without further furification.

MS m/z (ESI): 214.2 [M+1]

Step 4

N-[(2S)-3-[4-(Cyclopropylmethyl)piperazin-1-yl]-2-hydroxy-propyl]-7-[[(7R)-7-ethyl-8-isopropyl-5-methyl-6-oxo-7H-pteridin-2-yl]amino]-2,3-dihydrobenzofuran-4-carboxamide 7-[[(7R)-7-Ethyl-8-isopropyl-5-methyl-6-oxo-7H-pteridin-2-yl]amino]-2,3-dihydrobenzofuran-4-carboxylic acid 22f (150 mg, 0.36 mmol) and O-(benzotriazol-1-yl)-N,N,N',N'-tetra methyluronium tetrafluoroborate (117 mg, 0.36 mmol) were dissolved in 30 mL of anhydrous dichloromethane followed by the addition of diisopropylethylamine (0.1 mL, 0.80 mmol), stirred until the solution became clear, then added with the crude compound (2S)-1-amino-3-[4-(cyclopropylmethyl)piperazin-1-yl]-isopropanol 31c (78 mg, 0.36 mmol), stirred for 2 hours. The resulting solution was added with 30 mL of saturated sodium carbonate solution and extracted with dichloromethane (20 mL×3). The combined organic phase was washed with saturated sodium chloride solution (20 mL), then dried over anhydrous sodium sulfate, filtered and the filtrate was concentrated under reduced pressure. The resulting residue was purified by silica gel column chromatography to obtain the title compound N-[(2S)-3-[4-(cyclopropylmethyl)piperazin-1-yl]-2-hydroxy-propyl]-7-[[(7R)-7-ethyl-8-isopropyl-5-methyl-6-oxo-7H-pteridin-2-yl]amino]-2,3-dihydrobenzofuran-4-carboxamide 31 (50 mg, yield: 23.0%) as a light yellow solid.

MS m/z (ESI): 607.5 [M+1]

$^1$H NMR (400 MHz, CDCl$_3$) δ 8.30 (d, 1H), 7.67 (s, 1H), 7.16 (d, 1H), 7.08 (s, 1H), 6.54 to 6.61 (m, 1H), 4.74 to 4.62 (m, 3H), 4.29 (dd, 1H), 3.97 to 3.88 (m, 1H), 3.76 to 3.65 (m, 1H), 3.61 (t, 2H), 3.37 (td, 1H), 3.33 (s, 3H), 2.78 to 2.63 (m, 4H), 2.59 to 2.38 (m, 5H), 2.30 (d, 2H), 1.91 (m, 2H), 1.74 (qd, 2H), 1.43 (d, 3H), 1.35 (d, 3H), 1.32 to 1.23 (m, 1H), 0.88 (t, 3H), 0.58 to 0.49 (m, 2H), 0.13 (q, 2H)

Example 32

7-[[(7R)-7-Ethyl-8-isopropyl-5-methyl-6-oxo-7H-pteridin-2-yl]amino]-N-[(2S)-2-hydroxy-3-(4-methylpiperazin-1-yl)propyl]-2,3-dihydrobenzofuran-4-carboxamide

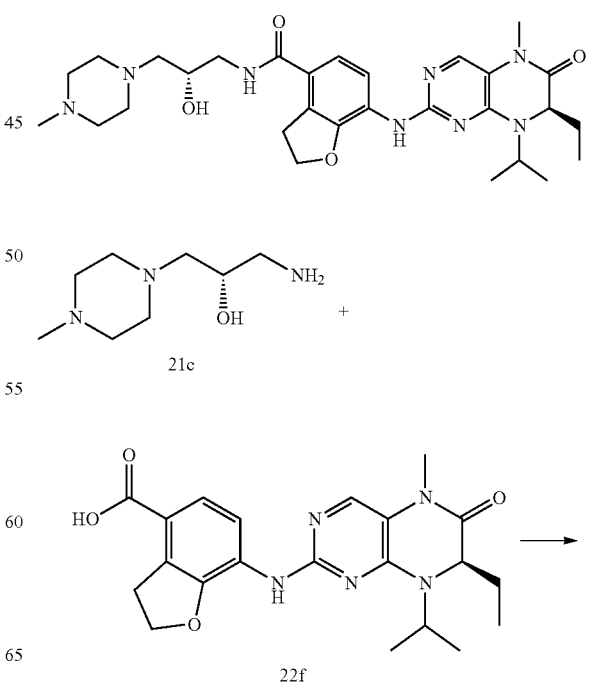

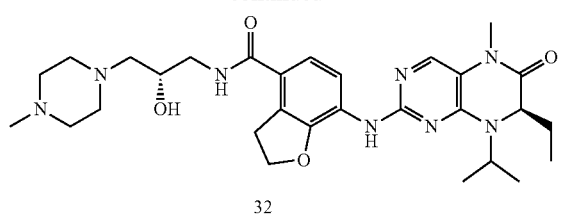

32

7-[[(7R)-7-Ethyl-8-isopropyl-5-methyl-6-oxo-7H-pteridin-2-yl]amino]-2,3-dihydrobenzofuran-4-carboxylic acid 22f (150 mg, 0.36 mmol) and O-(benzotriazol-1-yl)-N,N,N',N'-tetra methyluronium tetrafluoroborate (117 mg, 0.36 mmol) were dissolved in 30 mL of anhydrous dichloromethane followed by the addition of diisopropylethylamine (0.1 mL, 0.8 mmol) and (2S)-1-amino-3-(4-methylpiperazin-1-yl)propan-2-ol 21c (63 mg, 0.36 mmol) successively. The reaction solution was stirred for 2 hours. The resulting solution was added with 20 mL of saturated sodium carbonate solution and extracted with dichloromethane (20 mL×3). The combined organic phase was washed with saturated sodium chloride solution (20 mL), then dried over anhydrous sodium sulfate, filtered and the filtrate was concentrated under reduced pressure. The resulting residue was purified by silica gel column chromatography to obtain the title compound 7-[[(7R)-7-ethyl-8-isopropyl-5-methyl-6-oxo-7H-pteridin-2-yl]amino]-N-[(2S)-2-hydroxy-3-(4-methylpiperazin-1-yl)propyl]-2,3-dihydrobenzofuran-4-carboxamide 32 (40 mg, yield: 20.0%) as a white solid.

MS m/z (ESI): 567.5 [M+1]

$^1$H NMR (400 MHz, CDCl$_3$) δ 8.31 (d, 1H), 7.67 (s, 1H), 7.16 (d, 1H), 7.08 (s, 1H), 6.61 to 6.55 (m, 1H), 4.74 to 4.63 (m, 3H), 4.29 (dd, 1H), 3.94 (d, 1H), 3.74 to 3.65 (m, 1H), 3.61 (t, 2H), 3.42 to 3.29 (m, 4H), 2.77 to 2.53 (m, 2H), 2.66 to 2.39 (m, 7H), 2.34 (s, 3H), 1.91 (dtd, 2H), 1.74 (dt, 2H), 1.35 (d, 3H), 1.28 (d, 3H), 0.88 (t, 3H)

Example 33

7-[[(7R)-7-Ethyl-8-isopropyl-5-methyl-6-oxo-7H-pteridin-2-yl]amino]-N-[(2R)-2-hydroxy-3-(4-methylpiperazin-1-yl)propyl]-2,3-dihydrobenzofuran-4-carboxamide

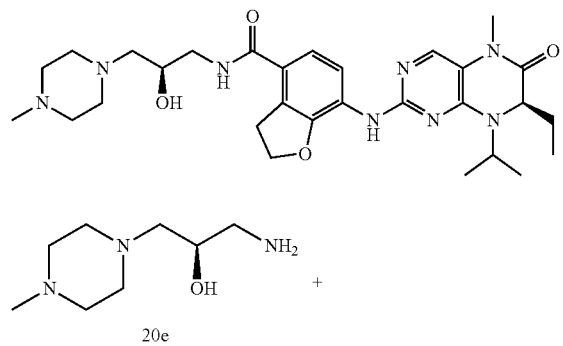

20e

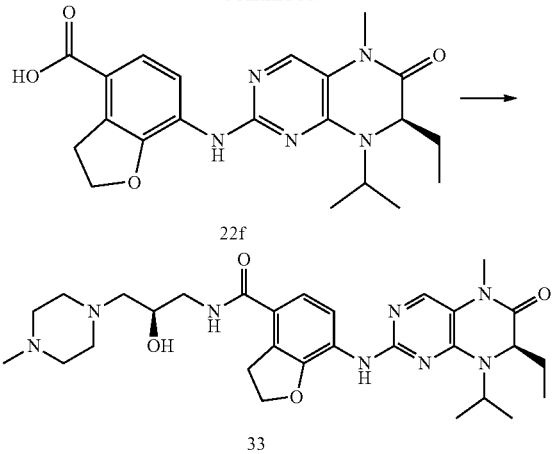

22f

33

7-[[(7R)-7-Ethyl-8-isopropyl-5-methyl-6-oxo-7H-pteridin-2-yl]amino]-2,3-dihydrobenzofuran-4-carboxylic acid 22f (150 mg, 0.36 mmol) and O-(benzotriazol-1-yl)-N,N,N',N'-tetra methyluronium tetrafluoroborate (117 mg, 0.36 mmol) were dissolved in 30 mL of anhydrous dichloromethane followed by the addition of diisopropylethylamine (0.1 mL, 0.80 mmol) and (2R)-1-amino-3-(4-methylpiperazin-1-yl)propan-2-ol 20e (63 mg, 0.36 mmol) successively. The reaction solution was stirred for 2 hours. The resulting solution was added with 30 mL of saturated sodium carbonate solution and extracted with dichloromethane (20 mL×3). The combined organic phase was washed with saturated sodium chloride solution (30 mL), then dried over anhydrous sodium sulfate, filtered and the filtrate was concentrated under reduced pressure. The resulting residue was purified by silica gel column chromatography to obtain the title compound 7-[[(7R)-7-ethyl-8-isopropyl-5-methyl-6-oxo-7H-pteridin-2-yl]amino]-N-[(2R)-2-hydroxy-3-(4-methylpiperazin-1-yl)propyl]-2,3-dihydrobenzofuran-4-carboxamide 33 (78 mg, yield: 40.0%) as a white solid.

MS m/z (ESI): 567.5 [M+1]

$^1$H NMR (400 MHz, CDCl$_3$) δ 8.29 (d, 1H), 7.66 (s, 1H), 7.15 (d, 1H), 7.06 (s, 1H), 6.59 (t, 1H), 4.72 to 4.63 (m, 3H), 4.28 (dd, 1H), 3.94 (d, 1H), 3.75 to 3.65 (m, 1H), 3.59 (t, 2H), 3.37 (d, 1H), 3.31 (s, 3H), 2.79 to 2.56 (m, 6H), 2.53 to 2.38 (m, 3H), 2.34 (s, 3H), 1.90 (dt, 2H), 1.73 (dt, 2H), 1.41 (d, 3H), 1.35 (d, 3H), 0.88 (t, 3H)

Example 34

7-[[(7R)-8-Cyclopentyl-7-ethyl-5-methyl-6-oxo-7H-pteridin-2-yl]amino]-N-[(trans)-4-[4-(cyclopropylmethyl)piperazin-1-yl]cyclohexyl]-2,3-dihydrobenzofuran-4-carboxamide

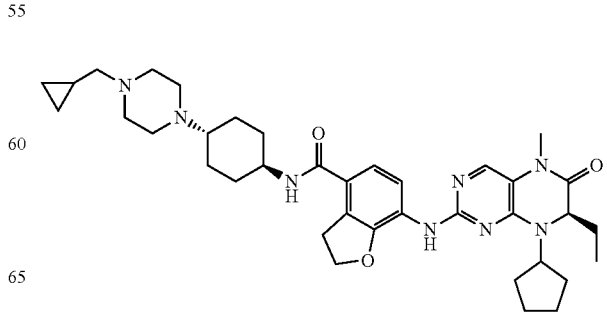

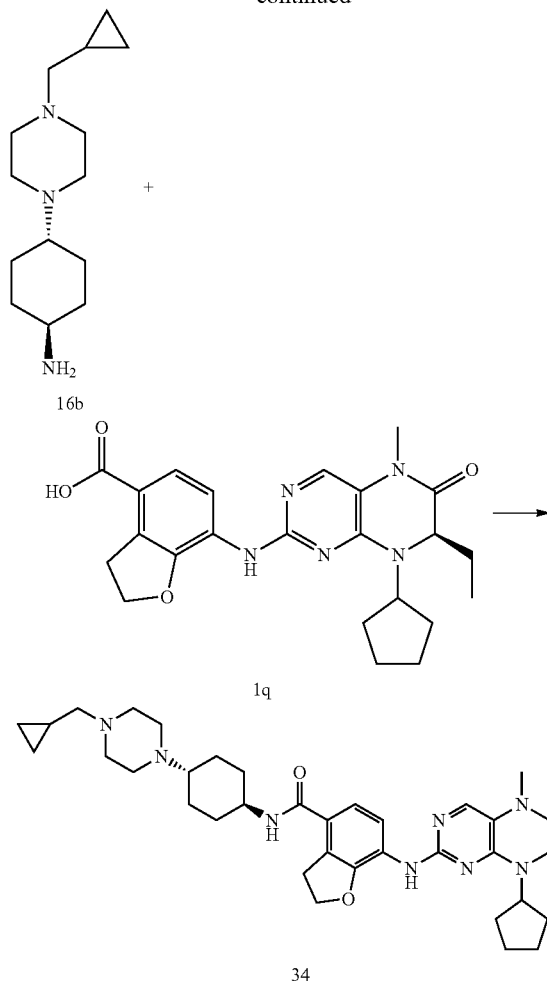

7-[[(7R)-8-Cyclopentyl-7-ethyl-5-methyl-6-oxo-7H-pteridin-2-yl]amino]-2,3-dihydrobenzofuran-4-carboxylic acid 1q (140 mg, 0.346 mmol), (trans)-4-[4-(cyclopropylmethyl)piperazin-1-yl]cyclohexanamine 16b (76 mg, 0.35 mmol), O-(benzotriazol-1-yl)-N,N,N',N'-tetra methyluronium tetrafluoroborate (102 mg, 0.32 mmol) and diisopropylethylamine (103 mg, 0.80 mmol) were dissolved in 25 mL of dichloromethane. The reaction solution was stirred for 2 hours. The resulting solution was added dropwise with saturated sodium bicarbonate solution to adjust pH to 8 to 9 and extracted with dichloromethane (50 mL×3). The combined organic phase was washed with water (20 mL) and saturated sodium chloride solution (20 mL) successively, then dried over anhydrous magnesium sulfate, filtered and the filtrate was concentrated under reduced pressure. The resulting residue was purified by silica gel column chromatography to obtain the title compound 7-[[(7R)-8-cyclopentyl-7-ethyl-5-methyl-6-oxo-7H-pteridin-2-yl]amino]-N-[(trans)-4-[4-(cyclopropylmethyl)piperazin-1-yl]cyclohexyl]-2,3-dihydrobenzofuran-4-carboxamide 34 (50 mg, yield: 40.0%) as a white solid.

MS m/z (ESI): 329.4 [M/2+1]

$^1$H NMR (400 MHz, CDCl$_3$) δ 8.26 (d, 1H), 7.67 (s, 1H), 7.07 to 6.99 (m, 2H), 5.79 (d, 1H), 4.74 to 4.63 (m, 3H), 4.47 (s, 1H), 4.21 (dd, 1H), 3.59 (t, 2H), 3.32 (s, 3H), 2.75 to 2.40 (m, 7H), 2.30 to 2.19 (m, 2H), 2.18 to 2.16 (m, 2H), 2.01 to 1.85 (m, 2H), 1.92 to 1.76 (m, 3H), 1.76 to 1.50 (m, 10H), 1.44 (d, 2H), 1.36 to 1.16 (m, 2H), 0.87 (m, 4H), 0.56 to 0.47 (m, 2H), 0.17 to 0.07 (m, 2H)

Example 35

7-[[(7R)-8-Cyclopentyl-7-ethyl-5-methyl-6-oxo-7H-pteridin-2-yl]amino]-N-[(2S)-3-[4-(cyclopropylmethyl)piperazin-1-yl]-2-methoxy-propyl]-2,3-dihydrobenzofuran-4-carboxamide

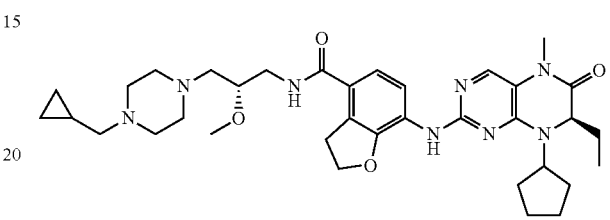

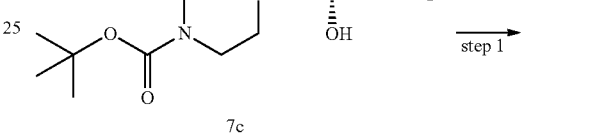

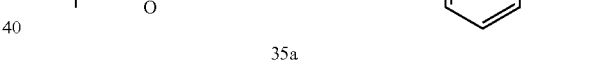

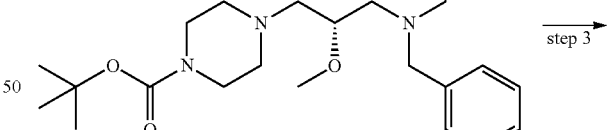

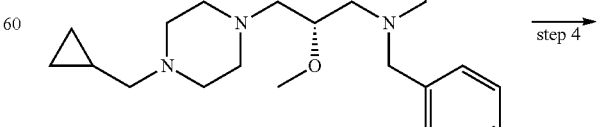

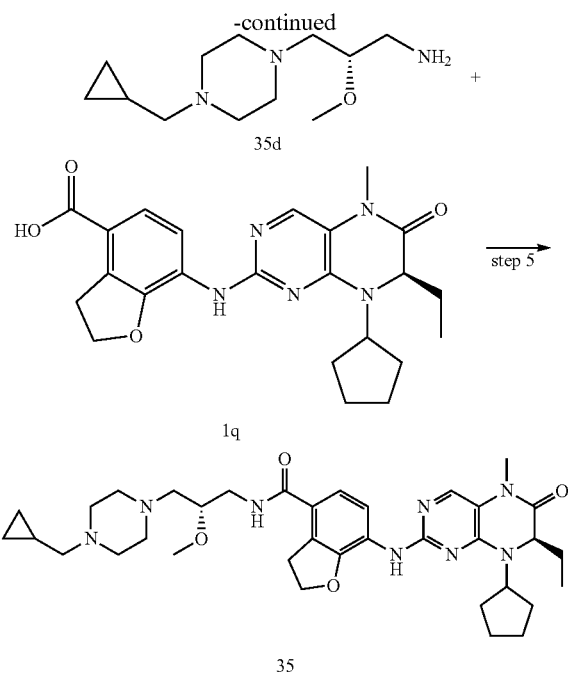

mL×3). The combined organic phase was washed with saturated sodium chloride solution (50 mL), then dried over anhydrous magnesium sulfate, filtered and the filtrate was concentrated under reduced pressure. The resulting residue was purified by silica gel column chromatography to obtain the title compound tert-butyl 4-[(2S)-3-(dibenzylamino)-2-methoxy-propyl]piperazine-1-carboxylate 35b (2.10 g, yield: 56.0%) as a yellow oil.

MS m/z (ESI): 454.5 [M+1]

Step 3

(2S)—N,N-Dibenzyl-3-[4-(cyclopropylmethyl)piperazin-1-yl]-2-methoxy-propan-1-amine Tert-butyl 4-[(2S)-3-(dibenzylamino)-2-methoxy-propyl]piperazine-1-carboxylate 35b (2.10 g, 4.60 mmol) was dissolved in 30 mL of dichloromethane followed by the addition of 20 mL of a 4 M solution of hydrogen chloride in dioxane. The reaction solution was stirred for 0.5 hours. The resulting solution was concentrated under reduced pressure. The residue was added with 40 mL of acetonitrile. In an ice-water bath, the resulting solution was added with triethylamine (2.09 g, 20.70 mmol), stirred for 0.5 hours followed by the addition of bromomethyl-cyclopropane (0.88 g, 6.47 mmol). The reaction solution was stirred for 12 hours. The resulting solution was concentrated under reduced pressure, added with 20 mL of saturated sodium bicarbonate solution and extracted with ethyl acetate (50 mL×3). The combined organic phase was washed with saturated sodium chloride solution (50 mL), then dried over anhydrous magnesium sulfate, filtered and the filtrate was concentrated under reduced pressure. The resulting residue was purified by silica gel column chromatography to obtain the title compound (2S)—N,N-dibenzyl-3-[4-(cyclopropylmethyl)piperazin-1-yl]-2-methoxy-propan-1-amine 35c (1.52 g, yield: 81.3%) as a brown oil.

MS m/z (ESI): 408.4 [M+1]

Step 4

(2S)-3-[4-(Cyclopropylmethyl)piperazin-1-yl]-2-methoxy-propan-1-amine (2S)—N,N-Dibenzyl-3-[4-(cyclopropylmethyl)piperazin-1-yl]-2-methoxy-propan-1-amine 35c (500 mg, 1.23 mmol) was dissolved in 30 mL of methanol followed by the addition of palladium/carbon (100 mg, 10%), filled with hydrogen for three times. The reaction mixture was stirred at room temperature for 12 hours and filtered. The filtrate was concentrated under reduced pressure to obtain the crude title compound (2S)-3-[4-(cyclopropylmethyl)piperazin-1-yl]-2-methoxy-propan-1-amine 35d (299 mg) as a yellow oil liquid, which was used in the next step without further furification.

MS m/z (ESI): 226.2 [M−1]

Step 5

7-[[(7R)-8-Cyclopentyl-7-ethyl-5-methyl-6-oxo-7H-pteridin-2-yl]amino]-N-[(2S)-3-[4-(cyclopropylmethyl)piperazin-1-yl]-2-methoxy-propyl]-2,3-dihydrobenzofuran-4-carboxamide 7-[[(7R)-8-Cyclopentyl-7-ethyl-5-methyl-6-oxo-7H-pteridin-2-yl]amino]-2,3-dihydrobenzofuran-4-carboxylic acid 1q (115 mg, 0.26 mmol) and O-(benzotriazol-1-yl)-N,N,N',N'-tetra methyluronium tetrafluoroborate (85 mg, 0.26 mmol) were dissolved in 30 mL of anhydrous dichloromethane followed by the addition of diisopropylethylamine (0.1 mL, 0.58 mmol) and the crude compound (2S)-3-[4-(cyclopropylmethyl)piperazin-1-yl]-2-methoxy-propan-1-amine 35d (60 mg, 0.26 mmol) successively. The reaction solution was stirred for 2 hours. The resulting solution was added with 30 mL of saturated sodium carbonate solution and extracted with dichloromethane (20 mL×3). The combined organic phase was washed with saturated sodium chloride solution (20 mL), then dried over anhydrous sodium sulfate, filtered and the filtrate was concentrated under reduced pressure. The resulting residue was purified by silica gel column chromatography to obtain the title compound 7-[[(7R)-8-cyclopentyl-7-ethyl-5-methyl-6-oxo-7H-pteridin-2-yl]amino]-N-[(2S)-3-[4-(cyclopropylmethyl)piperazin-1-yl]-2-methoxy-propyl]-2,3-dihydrobenzofuran-4-carboxamide 35 (80 mg, yield: 47.0%) as a white solid.

MS m/z (ESI): 647.6 [M+1]

$^1$H NMR (400 MHz, CDCl$_3$) δ 8.29 (d, 1H), 7.66 (s, 1H), 7.21 to 7.09 (m, 2H), 7.02 (s, 1H), 4.68 (t, 2H), 4.46 (t, 1H), 4.21 (dd, 1H), 3.66 to 3.57 (m, 3H), 3.56 to 3.48 (m, 1H), 3.44 (s, 3H), 3.32 (s, 3H), 2.75 to 2.30 (m, 9H), 2.19 to 2.04 (m, 5H), 2.04 to 1.92 (m, 1H), 1.87 to 1.57 (m, 8H), 0.93 to 0.88 (m, 4H), 0.53 (d, 2H), 0.17 to 0.05 (m, 2H)

Example 36

N-[(2S)-3-[4-(Cyclopropylmethyl)piperazin-1-yl]-2-methoxy-propyl]-7-[[(7R)-7-ethyl-8-isopropyl-5-methyl-6-oxo-7H-pteridin-2-yl]amino]-2,3-dihydrobenzofuran-4-carboxamide

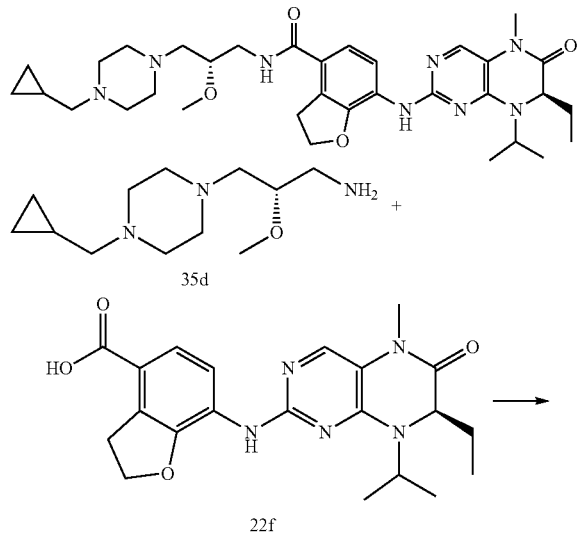

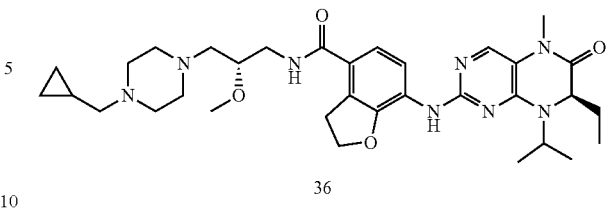

36

7-[[(7R)-7-Ethyl-8-isopropyl-5-methyl-6-oxo-7H-pteridin-2-yl]amino]-2,3-dihydrobenzofuran-4-carboxylic acid 22f (70 mg, 0.17 mmol) and O-(benzotriazol-1-yl)-N,N,N',N'-tetra methyluronium tetrafluoroborate (55 mg, 0.17 mmol) were dissolved in mL of anhydrous dichloromethane followed by the addition of diisopropylethylamine (0.1 mL, 0.58 mmol) and (2S)-3-[4-(cyclopropylmethyl)piperazin-1-yl]-2-methoxy-propan-1-amine 35d (39 mg, 0.17 mmol) successively. The reaction solution was stirred for 2 hours. The resulting solution was added with 30 mL of saturated sodium carbonate solution and extracted with dichloromethane (20 mL×3). The combined organic phase was washed with saturated sodium chloride solution (30 mL), then dried over anhydrous sodium sulfate, filtered and the filtrate was concentrated under reduced pressure. The resulting residue was purified by silica gel column chromatography to obtain the title compound N-[(2S)-3-[4-(cyclopropylmethyl)piperazin-1-yl]-2-methoxy-propyl]-7-[[(7R)-7-ethyl-8-isopropyl-5-methyl-6-oxo-7H-pteridin-2-yl]amino]-2,3-dihydrobenzofuran-4-carboxamide 36 (40 mg, yield: 38.0%) as a white solid.

MS m/z (ESI): 621.6 [M+1]

$^1$H NMR (400 MHz, CDCl$_3$) δ 8.31 (d, 1H), 7.67 (s, 1H), 7.15 (d, 1H), 7.06 (s, 1H), 4.74 to 4.62 (m, 3H), 4.29 (dd, 1H), 3.72 to 3.57 (m, 4H), 3.45 (s, 3H), 3.33 (s, 3H), 2.79 to 2.49 (m, 8H), 2.30 to 2.25 (m, 2H), 2.00 to 1.85 (m, 1H), 1.83 to 1.67 (m, 2H), 1.65 to 1.55 (m, 3H), 1.43 (d, 3H), 1.36 (d, 3H), 0.87 (m, 4H), 0.55 (d, 2H), 0.17 to 0.07 (m, 2H)

Example 37

N-[(trans)-4-[4-(Cyclopropylmethyl)piperazin-1-yl]cyclohexyl]-7-[[(7R)-7-ethyl-8-isopropyl-5-methyl-6-oxo-7H-pteridin-2-yl]amino]-2,3-dihydrobenzofuran-4-carboxamide

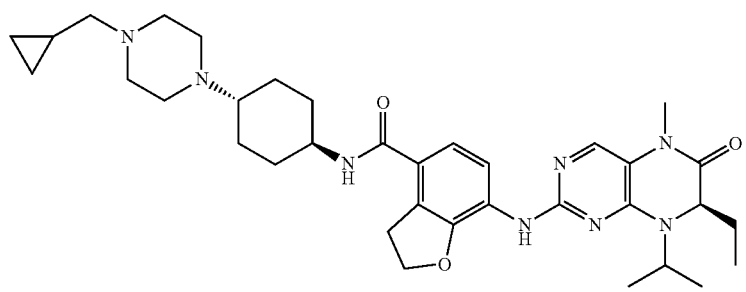

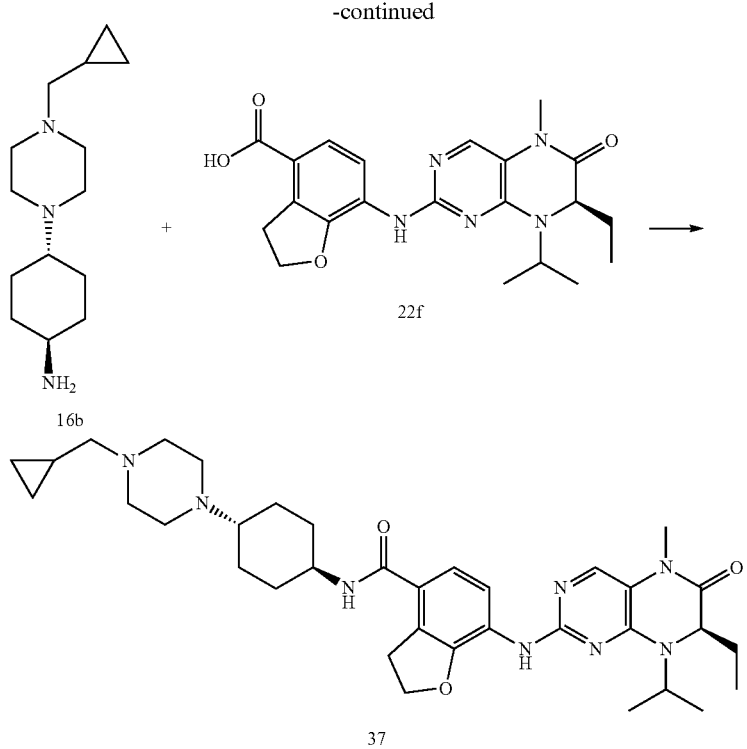

7-[[(7R)-7-Ethyl-8-isopropyl-5-methyl-6-oxo-7H-pteridin-2-yl]amino]-2,3-dihydrobenzofuran-4-carboxylic acid 22f (70 mg, 0.17 mmol) and O-(benzotriazol-1-yl)-N,N,N',N'-tetra methyluronium tetrafluoroborate (55 mg, 0.17 mmol) were dissolved in 15 mL of anhydrous dichloromethane followed by the addition of diisopropylethylamine (0.1 mL, 0.37 mmol) and (trans) 4-[4-(cyclopropylmethyl)piperazin-1-yl]cyclohexanamine 16b (40 mg, 0.17 mmol) successively. The reaction solution was stirred for 2 hours. The resulting solution was added with 30 mL of saturated sodium carbonate solution and extracted with dichloromethane (20 mL×3). The combined organic phase was washed with saturated sodium chloride solution (20 mL), then dried over anhydrous sodium sulfate, filtered and the filtrate was concentrated under reduced pressure. The resulting residue was purified by silica gel column chromatography to obtain the title compound N-[(trans)-4-[4-(cyclopropylmethyl)piperazin-1-yl]cyclohexyl]-7-[[(7R)-7-ethyl-8-isopropyl-5-methyl-6-oxo-7H-pteridin-2-yl]amino]-2,3-dihydrobenzofuran-4-carboxamide 37 (25 mg, yield: 23.0%) as a white solid.

MS m/z (ESI): 631.6 [M+1]

$^1$H NMR (400 MHz, CDCl$_3$) δ 8.28 (d, 1H), 7.66 (s, 1H), 7.10 to 7.02 (m, 2H), 4.73 to 4.63 (m, 3H), 4.28 (d, 1H), 3.59 (t, 2H), 3.32 (s, 3H), 2.75 to 2.55 (m, 6H), 2.40 to 2.24 (m, 3H), 1.78 to 1.66 (m, 3H), 1.65 to 1.55 (m, 6H), 1.47 to 1.37 (m, 4H), 1.35 (d, 3H), 1.31 to 1.20 (m, 4H), 0.86 (m, 4H), 0.54 (d, 2H), 0.14 (d, 2H)

Example 38

7-[[(7R)-8-Cyclopentyl-7-ethyl-5-methyl-6-oxo-7H-pteridin-2-yl]amino]-N-[(2S)-2-methoxy-3-(4-methylpiperazin-1-yl)propyl]-2,3-dihydrobenzofuran-4-carboxamide

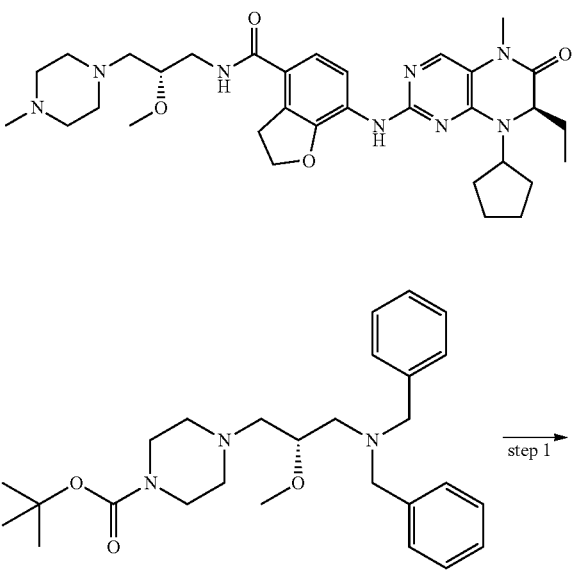

-continued

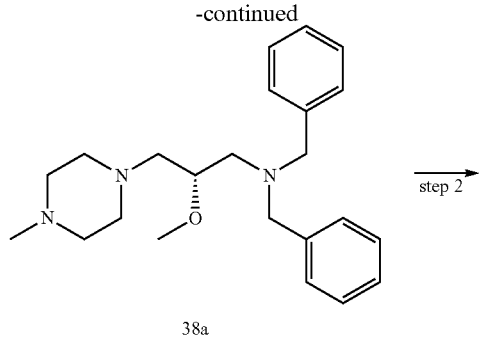

38a

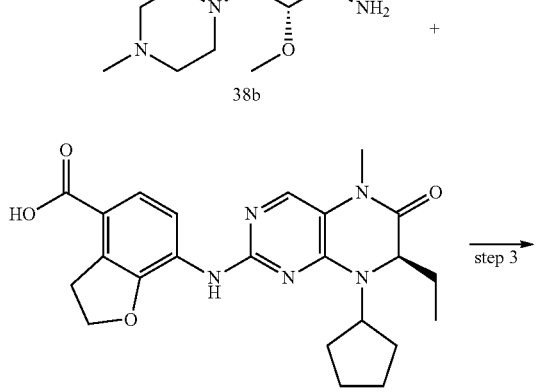

Step 1

(2S)—N,N-Dibenzyl-2-methoxy-3-(4-methylpiperazin-1-yl)propan-1-amine

Tert-butyl 4-[(2S)-3-(dibenzylamino)-2-methoxy-propyl]piperazine-1-carboxylate 35b (4.36 g, 9.60 mmol) was dissolved in 30 mL of dichloromethane followed by the addition of 20 mL of a 4 M solution of hydrogen chloride in dioxane. The reaction solution was stirred for 0.5 hours. The resulting solution was concentrated under reduced pressure. The residue was added with 30 mL of acetonitrile, 30 mL of water and formaldehyde (0.58 g, 19.20 mmol) successively. The reaction solution was stirred for 0.5 hours, added with sodium triacetoxyborohydride (6.10 g, 28.80 mmol). The reaction solution was stirred for 1 hour. The resulting solution was added dropwise with aqueous ammonia to adjust pH to 9 to 10 and extracted with ethyl acetate (50 mL×3). The combined organic phase was washed with saturated sodium chloride solution (20 mL), then dried over anhydrous magnesium sulfate, filtered and the filtrate was concentrated under reduced pressure. The resulting residue was purified by silica gel column chromatography to obtain the title compound (2S)—N,N-dibenzyl-2-methoxy-3-(4-methylpiperazin-1-yl)propan-1-amine 38a (2.90 g, yield: 83.0%) as a brown oil.

MS m/z (ESI): 368.3 [M+1]

Step 2

(2S)-2-Methoxy-3-(4-methylpiperazin-1-yl)propan-1-amine (2S)—N,N-Dibenzyl-2-methoxy-3-(4-methylpiperazin-1-yl)propan-1-amine 38a (500 mg, 1.36 mmol) was dissolved in 20 mL of methanol followed by the addition of palladium/carbon (100 mg, 10%), filled with hydrogen for three times. The reaction mixture was stirred at room temperature for 12 hours and filtered. The filtrate was concentrated under reduced pressure to obtain the crude title compound (2S)-2-methoxy-3-(4-methylpiperazin-1-yl)propan-1-amine 38b (250 mg, as a yellow oil liquid), which was used in the next step without further furification.

MS m/z (ESI): 188.2 [M−1]

Step 3

7-[[(7R)-8-Cyclopentyl-7-ethyl-5-methyl-6-oxo-7H-pteridin-2-yl]amino]-N-[(2S)-2-methoxy-3-(4-methylpiperazin-1-yl)propyl]-2,3-dihydrobenzofuran-4-carboxamide 7-[[(7R)-8-Cyclopentyl-7-ethyl-5-methyl-6-oxo-7H-pteridin-2-yl]amino]-2,3-dihydrobenzofuran-4-carboxylic acid 1q (100 mg, 0.23 mmol) and O-(benzotriazol-1-yl)-N,N,N',N'-tetra methyluronium tetrafluoroborate (74 mg, 0.23 mmol) were dissolved in 20 mL of anhydrous dichloromethane followed by the addition of diisopropylethylamine (0.1 mL, 0.50 mmol) and the crude compound (2S)-2-methoxy-3-(4-methylpiperazin-1-yl)propan-1-amine 38b (43 mg, 0.23 mmol) successively. The reaction solution was stirred for 2 hours, added with 30 mL saturated sodium carbonate solution and extracted with dichloromethane (20 mL×3). The combined organic phase was washed with saturated sodium chloride solution (20 mL), then dried over anhydrous sodium sulfate, filtered and the filtrate was concentrated under reduced pressure. The resulting residue was purified by silica gel column chromatography to obtain the title compound 7-[[(7R)-8-cyclopentyl-7-ethyl-5-methyl-6-oxo-7H-pteridin-2-yl]amino]-N-[(2S)-2-methoxy-3-(4-methylpiperazin-1-yl)propyl]-2,3-dihydrobenzofuran-4-carboxamide 38 (40 mg, yield: 30.0%) as a white solid.

MS m/z (ESI): 607.6 [M+1]

$^1$H NMR (400 MHz, CDCl$_3$) δ 8.29 (d, 1H), 7.71 to 7.63 (m, 1H), 7.13 (d, 1H), 7.03 (s, 1H), 4.74 to 4.63 (m, 2H), 4.47 (s, 1H), 4.21 (dd, 1H), 3.67 to 3.57 (m, 3H), 3.55 to 3.50 (m, 1H), 3.45 (s, 3H), 3.32 (s, 3H), 2.71 to 2.41 (m, 8H), 2.33 (s, 3H), 2.15 to 1.95 (m, 2H), 1.91 to 1.77 (m, 4H), 1.77 to 1.57 (m, 8H), 0.88 (t, 3H)

Example 39

7-[[(7R)-7-Ethyl-8-isopropyl-5-methyl-6-oxo-7H-pteridin-2-yl]amino]-N-[(2S)-2-methoxy-3-(4-methylpiperazin-1-yl)propyl]-2,3-dihydrobenzofuran-4-carboxamide

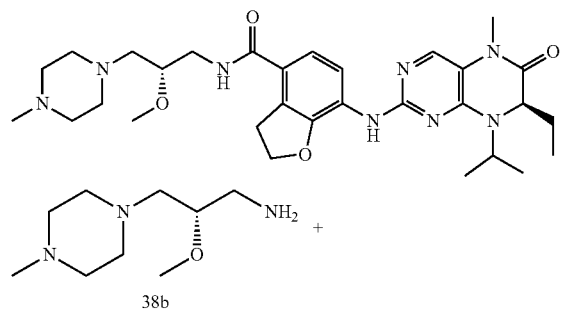

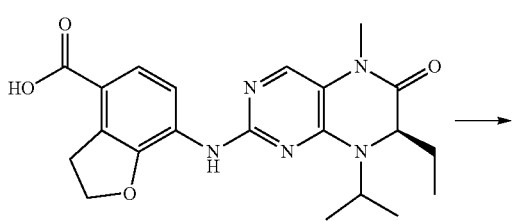

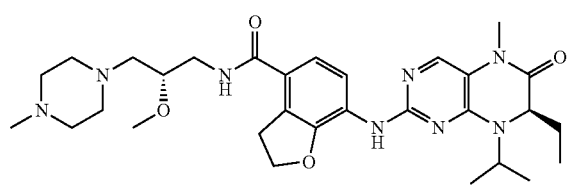

7-[[(7R)-7-Ethyl-8-isopropyl-5-methyl-6-oxo-7H-pteridin-2-yl]amino]-2,3-dihydrobenzofuran-4-carboxylic acid 22f (94 mg, 0.23 mmol) and O-(benzotriazol-1-yl)-N,N,N',N'-tetra methyluronium tetrafluoroborate (74 mg, 0.23 mmol) were dissolved in 20 mL of anhydrous dichloromethane followed by the addition of diisopropylethylamine (0.1 mL, 0.50 mmol) and (2S)-2-methoxy-3-(4-methylpiperazin-1-yl)propan-1-amine 38b (43 mg, 0.23 mmol) successively. The reaction solution was stirred for 2 hours. The resulting solution was added with 30 mL of saturated sodium carbonate solution and extracted with dichloromethane (20 mL×3). The combined organic phase was washed with saturated sodium chloride solution (20 mL), then dried over anhydrous sodium sulfate, filtered and the filtrate was concentrated under reduced pressure. The resulting residue was purified by silica gel column chromatography to obtain the title compound 7-[[(7R)-7-ethyl-8-isopropyl-5-methyl-6-oxo-7H-pteridin-2-yl]amino]-N-[(2S)-2-methoxy-3-(4-methylpiperazin-1-yl)propyl]-2,3-dihydrobenzofuran-4-carboxamide 39 (35 mg, yield: 26.5%) as a white solid.

MS m/z (ESI): 581.5 [M+1]

$^1$H NMR (400 MHz, CDCl$_3$) δ 8.31 (d, 1H), 7.66 (s, 1H), 7.14 (d, 1H), 7.07 (s, 1H), 4.77 to 4.61 (m, 3H), 4.28 (dd, 1H), 3.75 to 3.49 (m, 4H), 3.45 (s, 3H), 3.32 (s, 3H), 2.95 to 2.60 (m, 5H), 2.55 to 2.40 (m, 3H), 1.95 to 1.80 (m, 1H), 1.68 to 1.45 (m, 8H), 1.42 (d, 3H), 1.35 (d, 3H), 0.88 (t, 3H)

Example 40

7-[[(7R)-8-Cyclopentyl-7-ethyl-5-methyl-6-oxo-7H-pteridin-2-yl]amino]-2-(methoxymethyl)-N-(1-methyl-4-piperidyl)-2,3-dihydrobenzofuran-4-carboxamide

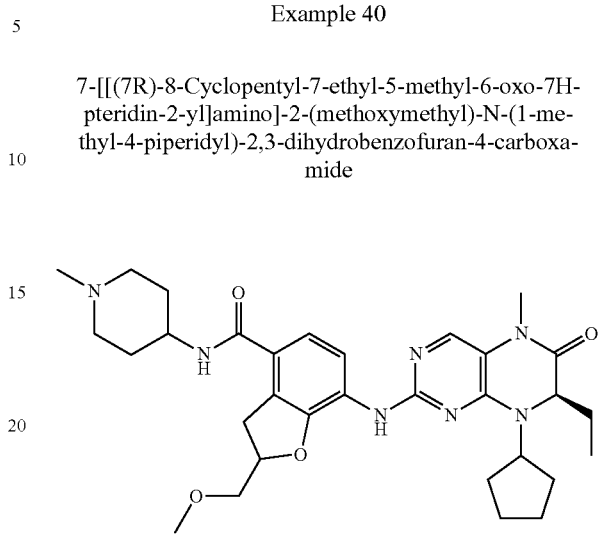

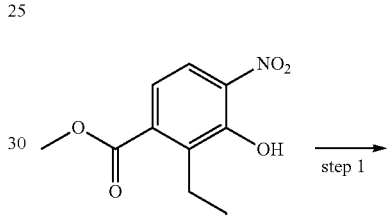

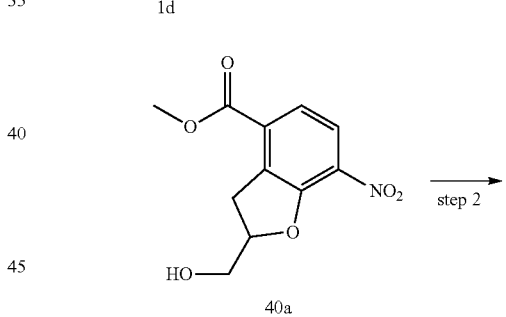

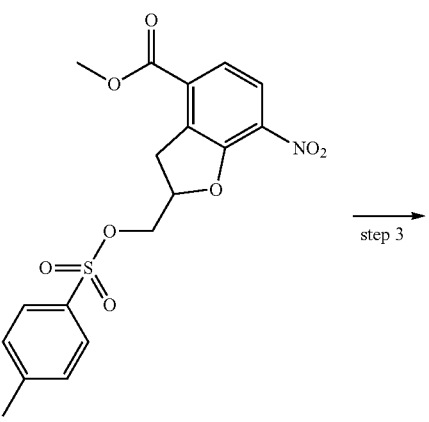

-continued

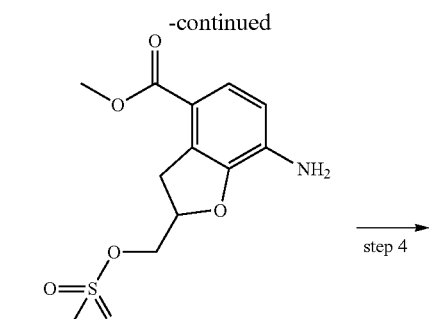

40c

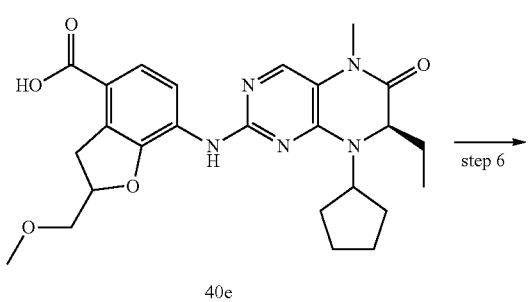

40d

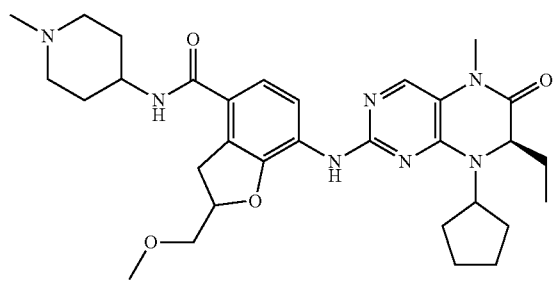

40

Step 1

Methyl 2-(hydroxymethyl)-7-nitro-2,3-dihydrobenzofuran-4-carboxylate

Methyl 2-allyl-3-hydroxy-4-nitro-benzoate 1d (0.47 g, 2 mmol) was dissolved in 80 mL of dichloromethane followed by the addition of m-chloroperbenzoic acid (0.99 g, 4 mmol). The reaction solution was stirred for 24 hours. The resulting solution was added with 20 mL of saturated sodium thiosulfate solution and 20 mL of saturated sodium bicarbonate solution successively, stirred for 5 minutes and extracted with ethyl acetate (20 mL×3). The combined organic phase was washed with water (20 mL) and saturated sodium chloride solution (20 mL) successively, then dried over anhydrous magnesium sulfate, filtered and the filtrate was concentrated under reduced pressure. The resulting residue was purified by silica gel column chromatography to obtain the title compound methyl 2-(hydroxymethyl)-7-nitro-2,3-dihydrobenzofuran-4-carboxylate 40a (440 mg, yield: 87.0%) as a yellow solid.

MS m/z (ESI): 252.1 [M−1]

Step 2

Methyl 7-nitro-2-(tolyl-4-sulfonyloxymethyl)-2,3-dihydrobenzofuran-4-carboxylate Methyl 2-(hydroxymethyl)-7-nitro-2,3-dihydrobenzofuran-4-carboxylate 40a (253 mg, 1 mmol) was dissolved in 40 mL of dichloromethane followed by the addition of diisopropylethylamine (0.3 mL, 2 mmol), 4-dimethylamino pyridine (24 mg, 0.20 mmol) and p-toluene sulfonyl chloride (286 mg, 1.50 mmol). The reaction solution was stirred for 12 hours. The resulting solution was added with 5 mL of saturated sodium bicarbonate solution and extracted with dichloromethane (20 mL×3). The combined organic phase was washed with water (20 mL) and saturated sodium chloride solution (20 mL) successively, then dried over anhydrous magnesium sulfate, filtered and the filtrate was concentrated under reduced pressure. The resulting residue was purified by silica gel column chromatography to obtain the title compound methyl 7-nitro-2-(tolyl-4-sulfonyloxymethyl)-2,3-dihydrobenzofuran-4-carboxylate 40b (160 mg, yield: 39.0%) as a yellow solid.

MS m/z (ESI): 408.2 [M+1]

Step 3

Methyl 7-amino-2-(tolyl-4-sulfonyloxymethyl)-2,3-dihydrobenzofuran-4-carboxylate Methyl 7-nitro-2-(tolyl-4-sulfonyloxymethyl)-2,3-dihydrobenzofuran-4-carboxylate (360 mg, 0.88 mmol) was dissolved in 20 mL of the mixture solvent of methanol and dichloromethane (V:V=1:1). The reaction solution was hydrogenated with H-Cube (column of catalyst: 10% palladium/carbon; temperature: 30° C.; flow rate: 1 mL/min; pressure: 1 atmosphere) for 20 minutes. The resulting solution was concentrated under reduced pressure to obtain the title compound methyl 7-amino-2-(tolyl-4-sulfonyloxymethyl)-2,3-dihydrobenzofuran-4-carboxylate 40c (280 mg, yield: 84.0%) as a light red solid.

MS m/z (ESI): 378.2 [M+1]

Step 4

7-Amino-2-(methoxymethyl)-2,3-dihydrobenzofuran-4-carboxylic acid

Methyl 7-amino-2-(tolyl-4-sulfonyloxymethyl)-2,3-dihydrobenzofuran-4-carboxylate (320 mg, 0.85 mmol) was dissolved in 16 mL of methanol followed by the addition of 4 mL of a 50% solution of sodium methanolate in methanol. The reaction solution was heated to 50° C. and stirred for 5 hours. The resulting solution was added with 100 mL of water, concentrated under reduced pressure and extracted with dichloromethane (50 mL×2). The aqueous phase was added dropwise with dilute hydrochloric acid to adjust pH to 4 and extracted with dichloromethane (50 mL×2). The organic phase was dried over anhydrous magnesium sulfate, filtered and the filtrate was concentrated under reduced pressure to obtain the title compound 7-amino-2-(methoxymethyl)-2,3-dihydrobenzofuran-4-carboxylic acid 40d (160 mg, yield: 84.0%) as a yellow solid.

MS m/z (ESI): 222.1 [M−1]

Step 5

7-[[(7R)-8-Cyclopentyl-7-ethyl-5-methyl-6-oxo-7H-pteridin-2-yl]amino]-2-(methoxymethyl)-2,3-dihydrobenzofuran-4-carboxylic acid 7-Amino-2-(methoxymethyl)-2,3-dihydrobenzofuran-4-carboxylic acid 40d (160 mg, 0.70 mmol) and (7R)-2-chloro-8-cyclopentyl-7-ethyl-5-methyl-7,8-dihydro-5H-pteridin-6-one 1o (232 mg, 0.80 mmol) were dissolved in 34 mL of the mixture solvent of ethanol and water (V:V=1:2.4) followed by the addition of 0.4 mL of concentrated hydrochloric acid. The reaction solution was heated to reflux for 16 hours with stirring, then cooled down resulting in the formation of precipitate. The precipitate was filtered to obtain the title compound 7-[[(7R)-8-cyclopentyl-7-ethyl-5-methyl-6-oxo-7H-pteridin-2-yl]amino]-2-(methoxymethyl)-2,3-dihydrobenzofuran-4-carboxylic acid 40e (0.15 g, yield: 43.0%) as a yellow solid.

MS m/z (ESI): 480.3 [M−1]

Step 6

7-[[(7R)-8-Cyclopentyl-7-ethyl-5-methyl-6-oxo-7H-pteridin-2-yl]amino]-2-(methoxymethyl)-N-(1-methyl-4-piperidyl)-2,3-dihydrobenzofuran-4-carboxamide 7-[[(7R)-8-Cyclopentyl-7-ethyl-5-methyl-6-oxo-7H-pteridin-2-yl]amino]-2-(methoxymethyl)-2,3-dihydrobenzofuran-4-carboxylic acid 40e (50 mg, 0.10 mmol) and O-(benzotriazol-1-yl)-N,N,N',N'-tetra methyluronium tetrafluoroborate (33 mg, 0.10 mmol) were dissolved in 40 mL of dichloromethane followed by the addition of diisopropylethylamine (38 µL, 0.23 mmol) and 1-methyl-piperidyl-4-yl-amine (12 mg, 0.10 mmol) successively. The reaction solution was stirred for 1 hour, added with 20 mL of saturated sodium carbonate solution and extracted with dichloromethane (30 mL×3). The combined organic phase was washed with water (20 mL) and saturated sodium chloride solution (20 mL) successively, then dried over anhydrous magnesium sulfate, filtered and the filtrate was concentrated under reduced pressure. The resulting residue was purified by silica gel column chromatography to obtain the title compound 7-[[(7R)-8-cyclopentyl-7-ethyl-5-methyl-6-oxo-7H-pteridin-2-yl]amino]-2-(methoxymethyl)-N-(1-methyl-4-piperidyl)-2,3-dihydrobenzofuran-4-carboxamide 40 (40 mg, yield: 69.0%) as a light yellow solid.

MS m/z (ESI): 578.5 [M+1]

$^1$H NMR (400 MHz, CDCl$_3$) δ 8.32 (d, 1H), 7.67 (s, 1H), 7.14 (s, 1H), 7.07 (d, 1H), 6.05 (d, 1H), 5.13 to 5.00 (m, 1H), 4.63 to 4.47 (m, 1H), 4.21 (dd, 1H), 4.14 to 3.95 (m, 1H), 3.71 to 3.57 (m, 3H), 3.46 (s, 3H), 3.38 to 3.25 (m, 4H), 3.08 (d, 3H), 2.52 to 2.37 (m, 5H), 2.11 (d, 3H), 2.00 (d, 1H), 1.92 to 1.63 (m, 9H), 0.88 (t, 3H)

Example 41

7-[[(7S)-8-Cyclopentyl-7-ethyl-5-methyl-6-oxo-7H-pteridin-2-yl]amino]-N-(1-methyl-4-piperidyl)-2,3-dihydrobenzofuran-4-carboxamide

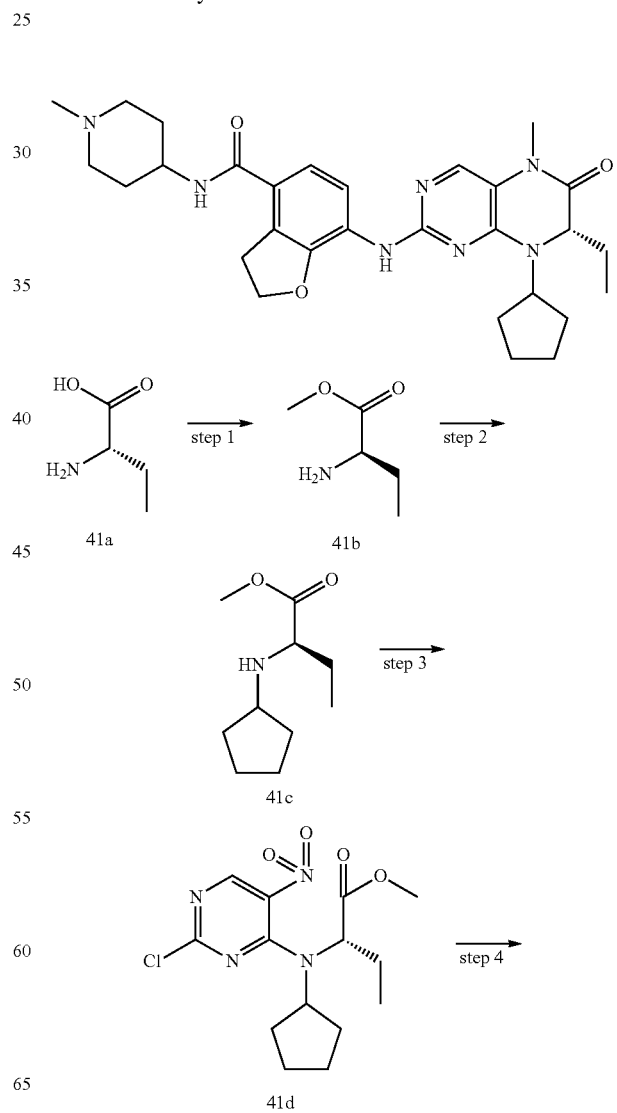

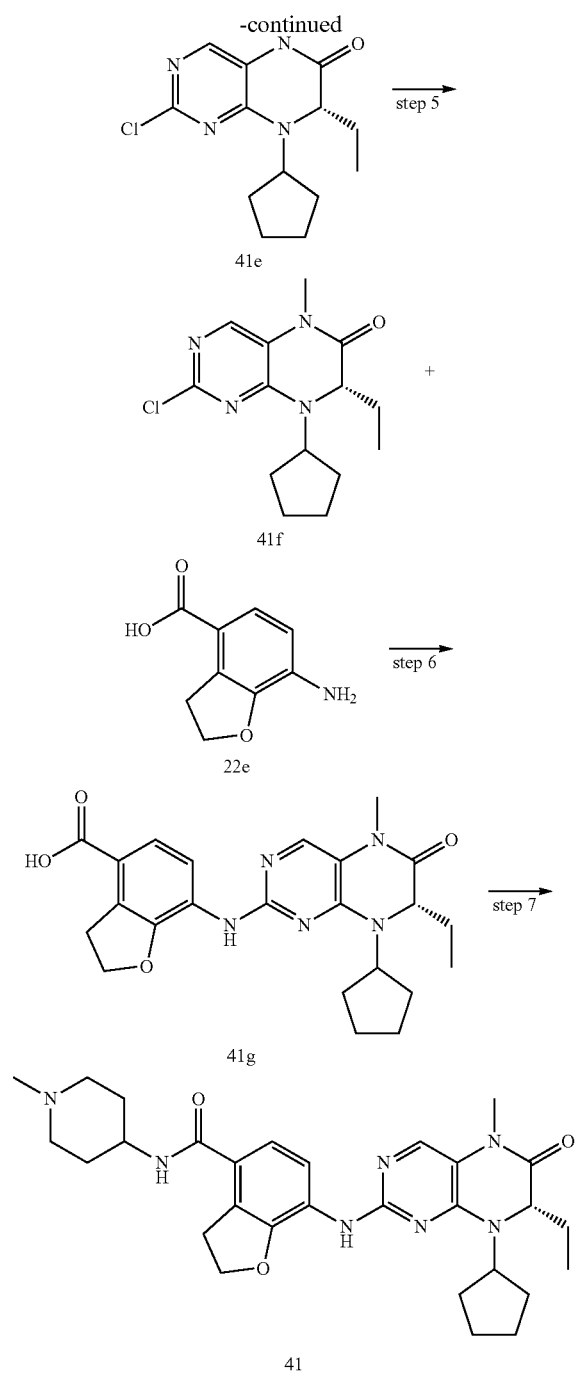

reduced pressure to obtain the title compound methyl (2S)-2-aminobutanoate 41b (31.87 g, yield: 99.3%) as a white solid.

Step 2

Methyl (2S)-2-(cyclopentylamino)butanoate

Methyl (2S)-2-aminobutanoate 41b (18.74 g, 0.12 mol) was dissolved in 280 mL of dichloromethane. The reaction solution was cooled down to 0° C. in an ice-water bath followed by the addition of sodium acetate (5 g, 0.061 mol), cyclopentanone (10.78 g, 0.13 mol) and sodium triacetoxyborohydride (31 g, 0.16 mol) successively. The reaction solution was heated to room temperature and stirred for 4 hours. The reaction solution was poured into 150 mL of water, added dropwise with saturated sodium carbonate solution to adjust pH to 11 to 12 and seperated. The aqueous phase was extracted with dichloromethane (150 mL×2). The combined organic phase was washed with saturated brine (100 mL×2), then dried over anhydrous magnesium sulfate, filtered and the filtrate was concentrated under reduced pressure to obtain the title compound methyl (2S)-2-(cyclopentylamino)butanoate 4k (17.42 g, yield: 77.1%) as a light yellow oil.

MS m/z (ESI): 186.1 [M+1]

Step 3

Methyl (2S)-2-[(2-chloro-5-nitro-pyrimidin-4-yl)-cyclopentyl-amino]butanoate

Methyl (2S)-2-(cyclopentylamino)butanoate 41c (17.36 g, 93.69 mmol) was dissolved in 180 mL of cyclohexane followed by the addition of sodium bicarbonate (31.48 g, 0.37 mol) and 2,4-dichloro-5-nitro-pyrimidine (21.81 g, 0.11 mol) successively. The reaction solution was heated to 85° C. and stirred for 2 hours. The resulting solution was cooled down to room temperature, added with 300 mL of dichloromethane, then dried over anhydrous magnesium sulfate, filtered and the filtrate was concentrated under reduced pressure. The resulting residue was purified by silica gel column chromatography with elution system B to obtain the title compound methyl (2S)-2-[(2-chloro-5-nitro-pyrimidin-4-yl)-cyclopentyl-amino]butanoate 41d (14.24 g, yield: 44.3%) as a yellow solid.

MS m/z (ESI): 343.1 [M+1]

Step 4

(7S)-2-Chloro-8-cyclopentyl-7-ethyl-5,7-dihydropteridin-6-one

Methyl (2S)-2-[(2-chloro-5-nitro-pyrimidin-4-yl)-cyclopentyl-amino]butanoate 41d (14.17 g, 41.33 mmol) was dissolved in 300 mL of acetic acid followed by the addition of iron powder (9 g, 0.17 mol). After exothermic reaction was completed, the reaction solution was heated to 65° C., and stirred for 1.5 hours. The reaction mixture was filtered and the filter cake was washed with dichloromethane (350 mL). The filtrate was concentrated under reduced pressure, added with 150 mL of water and filtered. The filter cake was washed with water (60 mL×3) and the mixture solvent of hexane and acetone (V/V=6:1) (140 mL) successively. The combined organic phase was dried over anhydrous magnesium sulfate, filtered and the filtrate was concentrated under reduced pressure to obtain the title compound (7S)-2-chloro-8-cyclopen- Step 1

Methyl (2S)-2-aminobutanoate (2S)-2-Aminobutanoic acid 41a (21.56 g, 0.21 mol) was dissolved in 120 mL of methanol. The reaction solution was cooled down to 0° C. in an ice-water bath, added dropwise with thionyl chloride (30.5 mL, 0.42 mol) with stirring. Upon the completion of the addition, the reaction mixture was heated to reflux for 2 hours, then cooled down to room temperature. The reaction solution was concentrated under tyl-7-ethyl-5,7-dihydropteridin-6-one 41e (10.67 g, yield: 92.0%) as a light yellow solid.

MS m/z (ESI): 281.1 [M+1]

Step 5

(7S)-2-Chloro-8-cyclopentyl-7-ethyl-5-methyl-7H-pteridin-6-one (7S)-2-Chloro-8-cyclopentyl-7-ethyl-5,7-dihydropteridin-6-one 41e (2.80 g, 10 mmol) was dissolved in 50 mL of acetone followed by the addition of methyl p-toluenesulfonate (2.80 g, 15 mmol) and potassium carbonate (2.76 g, 20 mmol) successively, stirred for 12 hours. The resulting solution was added with 50 mL of water and extracted with ethyl acetate (100 mL×3). The combined organic phase was washed with water (20 mL) and saturated sodium chloride solution (20 mL) successively, then dried over anhydrous magnesium sulfate, filtered and the filtrate was concentrated under reduced pressure, The resulting residue was purified by silica gel column chromatography with elution system B to obtain the title compound (7S)-2-chloro-8-cyclopentyl-7-ethyl-5-methyl-7H-pteridin-6-one 41f (2.50 g, yield: 85.0%) as a white solid.

MS m/z (ESI): 295.1 [M+1]

Step 6

7-[[(7S)-8-Cyclopentyl-7-ethyl-5-methyl-6-oxo-7H-pteridin-2-yl]amino]-2,3-dihydrobenzofuran-4-carboxylic acid (7S)-2-Chloro-8-cyclopentyl-7-ethyl-5-methyl-7H-pteridin-6-one 41f (300 mg, 1.70 mmol) and methyl 7-amino-2,3-dihydrobenzofuran-4-carboxylate 1g (543 mg, 1.80 mmol) were dissolved in 34 mL of the mixture solvent of ethanol and water (V/V=1:2.4) followed by the addition of 0.4 mL of concentrated hydrochloric acid and heated to reflux for 16 hours. The reaction solution was cooled down to room temperature, put into the refrigerator for 1 hour and filtered. The filter cake was washed with water (50 mL) and dissolved in 20 mL of the mixture solvent of water and 1 M lithium hydroxide (V/V=1:1), extracted with ethyl acetate (50 mL×2), the aqueous phase was added dropwise with 1 M hydrochloric acid to adjust pH to 2 resulting in the formation of precipitate. The precipitate was filtered to obtain the title compound 7-[[(7S)-8-cyclopentyl-7-ethyl-5-methyl-6-oxo-7H-pteridin-2-yl]amino]-2,3-dihydrobenzofuran-4-carboxylic acid 41g (0.45 g, yield: 62.0%) as a white solid.

MS m/z (ESI): 438.2 [M+1]

Step 7

7-[[(7S)-8-Cyclopentyl-7-ethyl-5-methyl-6-oxo-7H-pteridin-2-yl]amino]-N-(1-methyl-4-piperidyl)-2,3-dihydrobenzofuran-4-carboxamide 7-[[(7S)-8-Cyclopentyl-7-ethyl-5-methyl-6-oxo-7H-pteridin-2-yl]amino]-2,3-dihydrobenzofuran-4-carboxylic acid 41g (150 mg, 0.34 mmol) and O-(benzotriazol-1-yl)-N,N,N',N'-tetra methyluronium tetrafluoroborate (111 mg, 0.34 mmol) were dissolved in 30 mL of dichloromethane followed by the addition of diisopropylethylamine (0.13 mL, 0.76 mmol), stirred for 10 minute, then added with 1-methyl-piperidyl-4-yl-amine (40 mg, 0.34 mmol), stirred at room temperature for 1 hour. The reaction mixture was added with 20 mL of saturated sodium carbonate solution and extracted with dichloromethane (100 mL×2). The combined organic phase was washed with water (20 mL) and saturated sodium chloride solution (20 mL) successively, then dried over anhydrous magnesium sulfate, filtered and the filtrate was concentrated under reduced pressure. The resulting residue was purified by silica gel column chromatography with elution system A to obtain the title compound 7-[[(7S)-8-cyclopentyl-7-ethyl-5-methyl-6-oxo-7H-pteridin-2-yl]amino]-N-(1-methyl-4-piperidyl)-2,3-dihydrobenzofuran-4-carboxamide 41 (120 mg, yield: 65.0%) as a white solid.

MS m/z (ESI): 267.7 [M/2+1]

$^1$H NMR (400 MHz, CDCl$_3$) δ 8.28 (d, 1H), 7.67 (s, 1H), 7.10 to 7.00 (m, 2H), 5.91 (d, 1H), 4.68 (t, 2H), 4.47 (t, 1H), 4.21 (d, 1H), 4.02 to 3.93 (m, 1H), 3.58 (t, 2H), 3.32 (s, 3H), 2.86 (d, 2H), 2.33 (s, 3H), 2.23 to 1.96 (m, 6H), 1.89 to 1.76 (m, 4H), 1.74 to 1.58 (m, 6H), 0.90 to 0.83 (t, 3H)

Example 42

7-[(8-Cyclopentyl-7,7-diethyl-5-methyl-6-oxo-pteridin-2-yl)amino]-N-(1-methyl-4-piperidyl)-2,3-dihydrobenzofuran-4-carboxamide

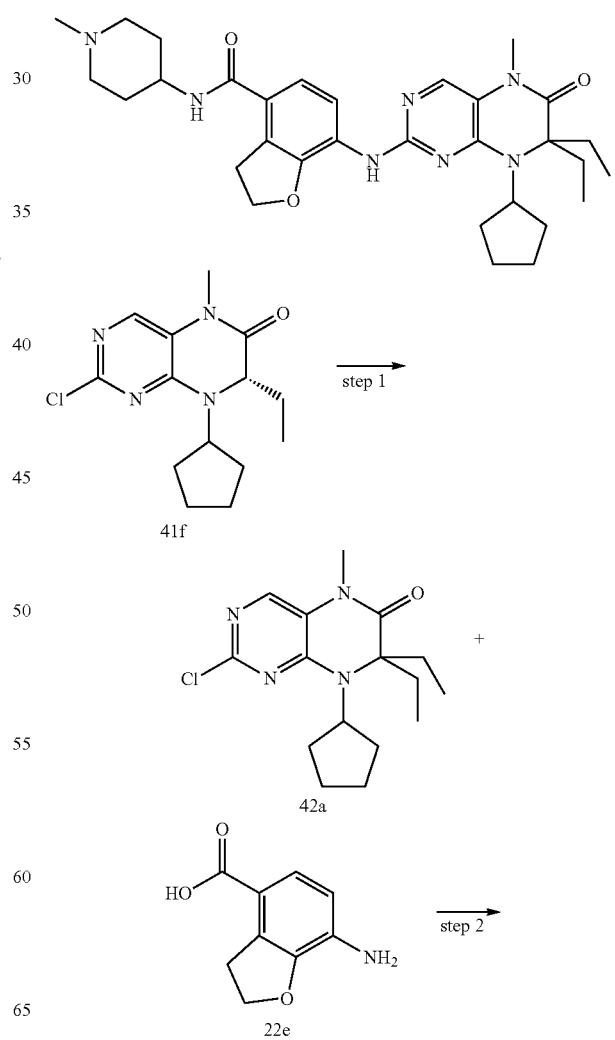

-continued

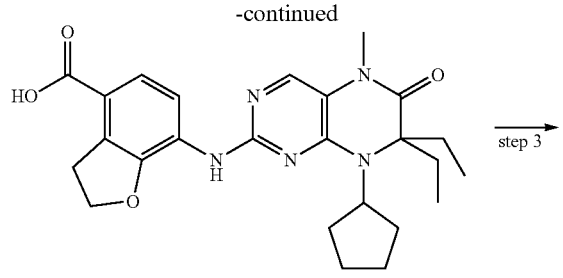

42b

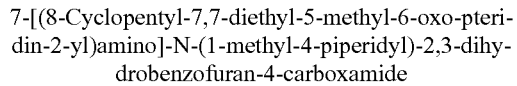

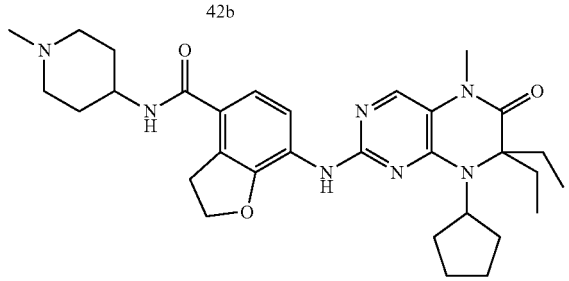

42

Step 1

2-Chloro-8-cyclopentyl-7,7-diethyl-5-methyl-pteridin-6-one (7S)-2-Chloro-8-cyclopentyl-7-ethyl-5-methyl-7H-pteridin-6-one 41f (148 mg, 0.50 mmol) was dissolved in 20 mL of tetrahydrofuran. The reaction solution was cooled down to −78° C. followed by the addition of lithium diisopropylamide (0.5 mL, 1 mmol), stirred for 30 minutes, then added with ethyl iodide (156 mg, 1 mmol) and stirred for another 4 hours. The reaction mixture was added with 50 mL of saturated ammonium chloride solution, concentrated under reduced pressure and and extracted with dichloromethane (100 mL×2). The combined organic phase was washed with water (20 mL) and saturated sodium chloride solution (20 mL) successively, then dried over anhydrous magnesium sulfate, filtered and the filtrate was concentrated under reduced pressure. The resulting residue was purified by silica gel column chromatography with elution system B to obtain the title compound 2-chloro-8-cyclopentyl-7,7-diethyl-5-methyl-pteridin-6-one 42a (100 mg, yield: 62.0%) as a yellow solid.

MS m/z (ESI): 323.2 [M+1]

Step 2

7-[(8-Cyclopentyl-7,7-diethyl-5-methyl-6-oxo-pteridin-2-yl)amino]-2,3-dihydrobenzofuran-4-carboxylic acid 2-Chloro-8-cyclopentyl-7,7-diethyl-5-methyl-pteridin-6-one 42a (100 mg, 0.31 mmol) and methyl 7-amino-2,3-dihydrobenzofuran-4-carboxylic acid 1g (50 mg, 0.28 mmol) were dissolved in 17 mL of the mixture solvent of ethanol and water (V/V=5:12) followed by the addition of 0.2 mL of concentrated hydrochloric acid. The reaction mixture was heated to reflux for 16 hours with stirring. The resulting solution was concentrated under reduced pressure, added dropwise with 1 M lithium hydroxide solution to adjust pH to 12 and extracted with ethyl acetate (50 mL×2), the combined aqueous phase was added dropwise with 1 M hydrochloric acid to adjust pH to 1 and extracted with dichloromethane (50 mL×3). The combined organic phase was dried over anhydrous magnesium sulfate, filtered and the filtrate was concentrated under reduced pressure to obtain 7-[(8-cyclopentyl-7,7-diethyl-5-methyl-6-oxo-pteridin-2-yl)amino]-2,3-dihydrobenzofuran-4-carboxylic acid 42b (50 mg, yield: 38.0%) as a yellow solid.

MS m/z (ESI): 466.3 [M+1]

Step 3

7-[(8-Cyclopentyl-7,7-diethyl-5-methyl-6-oxo-pteridin-2-yl)amino]-N-(1-methyl-4-piperidyl)-2,3-dihydrobenzofuran-4-carboxamide 7-[(8-Cyclopentyl-7,7-diethyl-5-methyl-6-oxo-pteridin-2-yl)amino]-2,3-dihydrobenzofuran-4-carboxylic acid 42b (50 mg, 0.11 mmol) was dissolved in 20 mL of dichloromethane followed by the addition of O-(benzotriazol-1-yl)-N,N,N',N'-tetra methyluronium tetrafluoroborate (35 mg, 0.11 mmol), diisopropylethylamine (31 mg, 0.24 mmol) and 1-methyl-piperidyl-4-yl-amine (13 mg, 0.11 mmol) successively. The reaction solution was stirred at room temperature for 1 hour. The resulting solution was added with 50 mL of saturated sodium carbonate solution and extracted with dichloromethane (100 mL×2). The combined organic phase was washed with water (20 mL) and saturated sodium chloride solution (20 mL) successively, then dried over anhydrous magnesium sulfate, filtered and the filtrate was concentrated under reduced pressure. The resulting residue was purified by silica gel column chromatography with elution system A to obtain the title compound 7-[(8-cyclopentyl-7,7-diethyl-5-methyl-6-oxo-pteridin-2-yl)amino]-N-(1-methyl-4-piperidyl)-2,3-dihydrobenzofuran-4-carboxamide 42 (10 mg, yield: 16.0%) as a white solid.

MS m/z (ESI): 281.7 [M/2+1]

$^1$H NMR (400 MHz, CDCl$_3$) δ 8.25 (d, 1H), 7.56 (s, 1H), 7.06 (d, 1H), 6.78 (s, 1H), 5.89 (d, 1H), 4.68 (t, 2H), 4.06 to 3.92 (m, 1H), 3.83 to 3.71 (m, 1H), 3.58 (t, 2H), 3.32 (s, 3H), 2.89 (d, 2H), 2.58 (d, 2H), 2.35 (s, 3H), 2.28 to 2.14 (m, 4H), 2.10 to 2.00 (m, 4H), 1.80 (d, 2H), 1.74 to 1.56 (m, 6H), 0.84 (t, 6H)

Example 43

N-[(cis)-4-[4-(Cyclopropylmethyl)piperazin-1-yl] cyclohexyl]-7-[[(7S)-7-ethyl-8-isopropyl-5-methyl-6-oxo-7H-pteridin-2-yl]amino]-2,3-dihydrobenzofuran-4-carboxamide

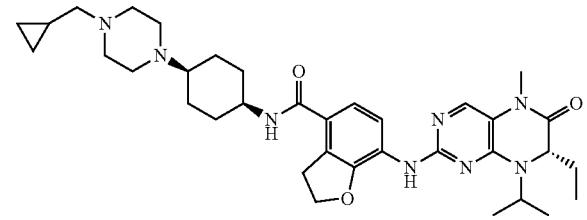

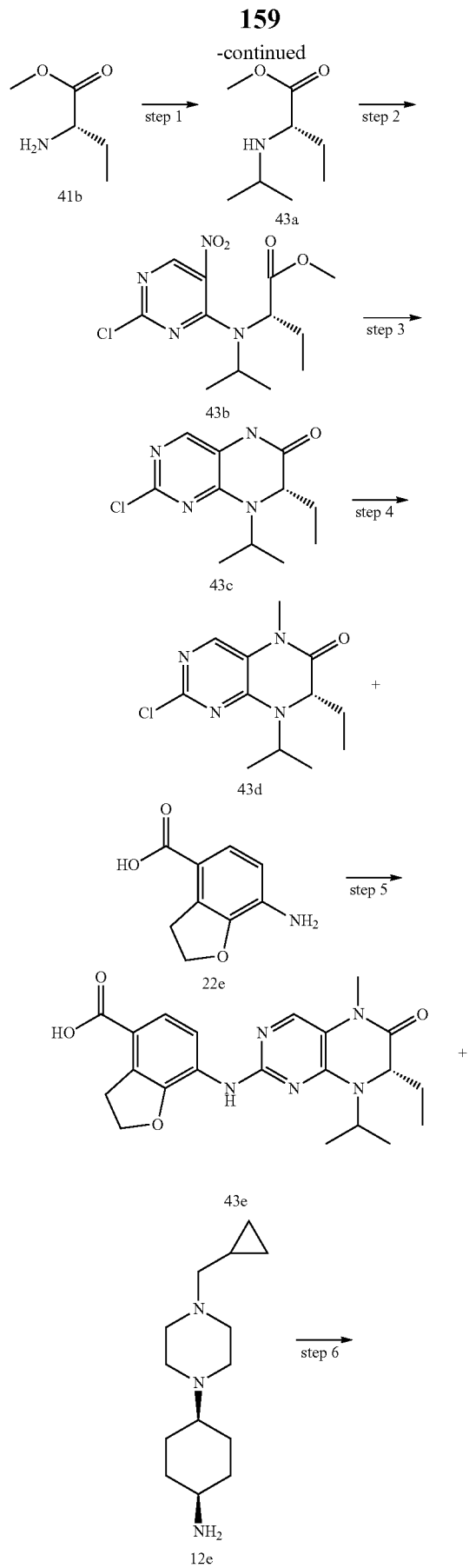

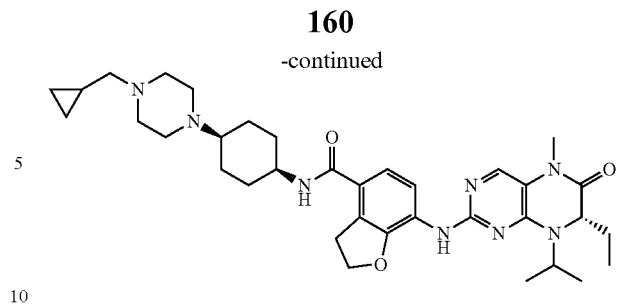

43

Step 1

Methyl (2S)-2-(isopropylamino)butanoate (2S)-2-Aminobutanoate 41b (13.14 g, 85.52 mmol) was dissolved in 200 mL of dichloromethane. The reaction solution was cooled down to 0° C. in an ice-water bath followed by the addition of sodium acetate (3.51 g, 42.76 mmol), acetone (5.96 g, 0.10 mol) and sodium triacetoxyborohydride (21.75 g, 0.10 mol) successively. The reaction solution was heated to room temperature and stirred for 4 hours. The resulting solution was added with 100 mL of water, added dropwise with saturated sodium carbonate solution to adjust pH to 11 to 12 and separated. The aqueous phase was extracted with dichloromethane (150 mL×2). The combined organic phase was washed with saturated brine (100 mL×2), then dried over anhydrous magnesium sulfate, filtered and the filtrate was concentrated under reduced pressure to obtain methyl (2S)-2-(isopropylamino)butanoate 43a (10.85 g, yield: 79.7%) as a light yellow oil.

MS m/z (ESI): 160.2 [M+1]

Step 2

Methyl (2S)-2-[(2-chloro-5-nitro-pyrimidin-4-yl)-isopropyl-amino]butanoate

Methyl (2S)-2-(isopropylamino)butanoate 43a (10.75 g, 67.50 mmol) was dissolved in 180 mL of cyclohexane followed by the addition of sodium bicarbonate (22.68 g, 0.27 mol) and 2,4-dichloro-5-nitro-pyrimidine (15.71 g, 0.081 mol) successively, the reaction mixture was heated to 85° C. and stirred for 2.5 hours. The resulting mixture was cooled down to room temperature, added with 200 mL of dichloromethane, then dried over anhydrous magnesium sulfate, filtered and the filtrate was concentrated under reduced pressure. The resulting residue was purified by silica gel column chromatography with elution system B to obtain methyl (2S)-2-[(2-chloro-5-nitro-pyrimidin-4-yl)-isopropyl-amino]butanoate 43b (8.78 g, yield: 41.1%) as a yellow solid.

MS m/z (ESI): 317.1 [M+1]

Step 3

(7S)-2-Chloro-8-isopropyl-7-ethyl-5,7-dihydropteridin-6-one

Methyl (2S)-2-[(2-chloro-5-nitro-pyrimidin-4-yl)-isopropyl-amino]butanoate 43b (8.74 g, 27.7 mmol) was dissolved in 100 mL of acetic acid followed by the addition of iron powder (6.20 g, 0.11 mol). The reaction mixture was heated to 65° C., stirred for 4 hours and filtered. The filter cake was washed with dichloromethane (100 mL). The filtrate was concentrated under reduced pressure, then added with 100 mL of water and filtered. The filter cake was dried by heating to obtain the crude compound (7S)-2-chloro-8-isopropyl-7-ethyl-5,7-dihydropteridin-6-one 43c (7.17 g) as a gray solid, which was used in the next step without further furification.

MS m/z (ESI): 255.1 [M+1]

Step 4

(7S)-2-Chloro-8-isopropyl-7-ethyl-5-methyl-7H-pteridin-6-one

The crude compound (7S)-2-chloro-8-isopropyl-7-ethyl-5,7-dihydropteridin-6-one 43c (7.17 g, 28.21 mmol), methyl p-toluenesulfonate (5.77 g, 31.03 mmol) and potassium carbonate (11.70 g, 84.60 mmol) were dissolved in 40 mL of acetone. The reaction solution was stirred for 12 hours and the precipitate was filtered. The filter cake was washed with dichloromethane (100 mL). The filtrate was concentrated under reduced pressure. The resulting residue was purified by silica gel column chromatography with elution system B to obtain (7S)-2-chloro-8-isopropyl-7-ethyl-5-methyl-7H-pteridin-6-one 43d (6.14 g, yield: 81.0%) as a white solid.

MS m/z (ESI): 269.1 [M+1]

Step 5

7-[[(7S)-8-Isopropyl-7-ethyl-5-methyl-6-oxo-7H-pteridin-2-yl]amino]-2,3-dihydrobenzofuran-4-carboxylic acid (7S)-2-Chloro-8-isopropyl-7-ethyl-5-methyl-7H-pteridin-6-one 43d (2.50 g, 9.24 mmol) and methyl 7-amino-2,3-dihydrobenzofuran-4-carboxylateic acid 1g (1.50 g, 8.40 mmol) were dissolved in 120 mL of the mixture solvent of ethanol and water (V/V=1:2) followed by the addition of 1.5 mL of concentrated hydrochloric acid. The reaction mixture was heated to reflux for 24 hours with stirring and the precipitate was filtered. The filter cake was washed with dichloromethane (50 mL×3) and dried by heating to obtain the crude compound 7-[[(7S)-8-isopropyl-7-ethyl-5-methyl-6-oxo-7H-pteridin-2-yl]amino]-2,3-dihydrobenzofuran-4-carboxylic acid 43e (2 g) as a gray solid, which was used in the next step without further furification.

MS m/z (ESI): 412.2 [M+1]

Step 6

N-[(cis)-4-[4-(Cyclopropylmethyl)piperazin-1-yl]cyclohexyl]-7-[[(7S)-7-ethyl-8-isopropyl-5-methyl-6-oxo-7H-pteridin-2-yl]amino]-2,3-dihydrobenzofuran-4-carboxamide (cis)-4-[4-(Cyclopropylmethyl)piperazin-1-yl]cyclohexananamine 12e (577 mg, 2.43 mmol), the crude compound 7-[[(7S)-8-isopropyl-7-ethyl-5-methyl-6-oxo-7H-pteridin-2-yl]amino]-2,3-dihydrobenzofuran-4-carboxylic acid 43e (1 g, 2.43 mmol), O-(benzotriazol-1-yl)-N,N,N',N'-tetramethyluronium tetrafluoroborate (780 mg, 2.43 mmol) and diisopropylethylamine (690 mg, 5.35 mmol) were dissolved in 60 mL of dichloromethane. The reaction solution was stirred for 2 hours. The resulting mixture was added with 50 mL of aqueous ammonia and extracted with dichloromethane (50 mL×3). The combined organic phase was washed with saturated brine (50 mL×3), then dried over anhydrous magnesium sulfate, filtered and the filtrate was concentrated under reduced pressure. The resulting residue was purified by silica gel column chromatography with elution system A to obtain the title compound N-[(cis)-4-[4-(cyclopropylmethyl)piperazin-1-yl]cyclohexyl]-7-[[(7S)-7-ethyl-8-isopropyl-5-methyl-6-oxo-7H-pteridin-2-yl]amino]-2,3-dihydrobenzofuran-4-carboxamide 43 (1.12 g, yield: 74.6%) as a white solid.

MS m/z (ESI): 631.4 [M+1]

$^1$H NMR (400 MHz, CDCl$_3$) δ 8.29 (d, 1H), 7.67 (s, 1H), 7.12 to 7.04 (m, 2H), 6.13 (d, 1H), 4.77 to 4.64 (m, 3H), 4.29 (d, 1H), 4.27 to 4.19 (m, 1H), 3.60 (t, 2H), 3.32 (s, 3H), 2.64 (s, 7H), 2.31 to 2.19 (m, 3H), 1.98 to 1.79 (m, 5H), 1.78 to 1.63 (m, 3H), 1.56 (q, 2H), 1.44 (d, 3H), 1.37 (d, 3H), 0.87 (t, 4H), 0.55 to 0.49 (m, 2H), 0.14 to 0.07 (m, 2H)

Example 44

N-[(cis)-4-[4-(Cyclopropylmethyl)piperazin-1-yl]cyclohexyl]-7-[[(7R)-7-ethyl-8-isopropyl-5-methyl-6-oxo-7H-pteridin-2-yl]amino]-2,3-dihydrobenzofuran-4-carboxamide

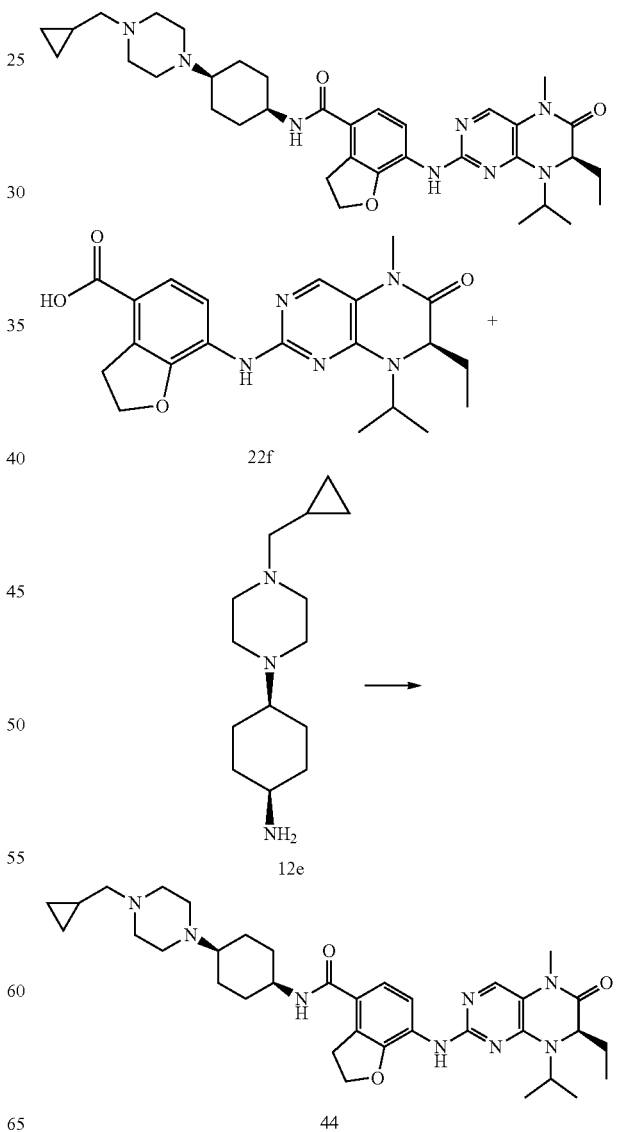

(cis)-4-[4-(Cyclopropylmethyl)piperazin-1-yl]cyclohexanamine 12e (577 mg, 2.43 mmol), 7-[[(7R)-7-ethyl-8-isopropyl-5-methyl-6-oxo-7H-pteridin-2-yl]amino]-2,3-dihydrobenzofuran-4-carboxylic acid 22f (1 g, 2.43 mmol), O-(benzotriazol-1-yl)-N,N,N',N'-tetra methyluronium tetrafluoroborate (780 mg, 2.43 mmol) and diisopropylethylamine (690 mg, 5.35 mmol) were dissolved in 40 mL of dichloromethane. The reaction mixture was stirred for 2 hours. The resulting solution was added with 50 mL of aqueous ammonia and extracted with dichloromethane (50 mL×3). The combined organic phase was washed with saturated brine (50 mL×3), then dried over anhydrous magnesium sulfate, filtered and the filtrate was concentrated under reduced pressure. The resulting residue was purified by silica gel column chromatography with elution system A to obtain the title compound N-[(cis)-4-[4-(cyclopropylmethyl)piperazin-1-yl]cyclohexyl]-7-[[(7R)-7-ethyl-8-isopropyl-5-methyl-6-oxo-7H-pteridin-2-yl]amino]-2,3-dihydrobenzofuran-4-carboxamide 44 (576 mg, yield: 38.0%) as a white solid.

MS m/z (ESI): 631.4 [M+1]

$^1$H NMR (400 MHz, CDCl$_3$) δ 8.28 (d, 1H), 7.66 (s, 1H), 7.15 to 7.08 (m, 2H), 6.17 (d, 1H), 4.75 to 4.64 (m, 3H), 4.31 to 4.20 (m, 2H), 3.60 (t, 2H), 3.32 (s, 3H), 2.69 (s, 7H), 2.36 to 2.22 (m, 3H), 2.01 (s, 1H), 1.95 to 1.80 (m, 5H), 1.77 to 1.56 (m, 5H), 1.44 (d, 3H), 1.37 (d, 3H), 0.92 to 0.84 (m, 4H), 0.58 to 0.50 (m, 2H), 0.13 (q, 2H)

Example 45

N-[(trans)-4-[4-(Cyclopropylmethyl)piperazin-1-yl]cyclohexyl]-7-[[(7S)-7-ethyl-8-isopropyl-5-methyl-6-oxo-7H-pteridin-2-yl]amino]-2,3-dihydrobenzofuran-4-carboxamide

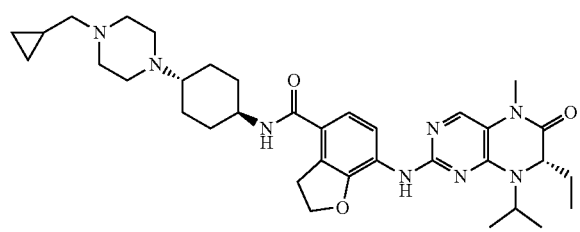

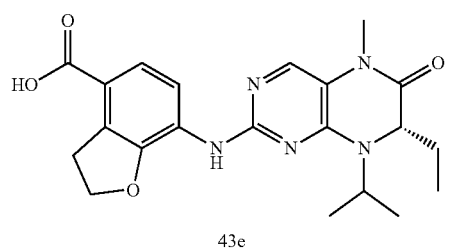

43e

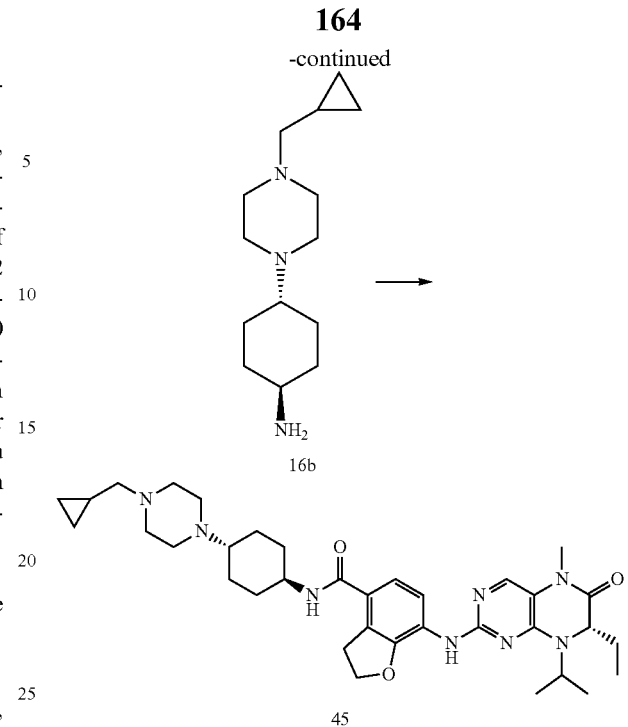

(trans)-4-[4-(Cyclopropylmethyl)piperazin-1-yl]cyclohexanamine 16b (350 mg, 1.48 mmol), 7-[[(7S)-7-ethyl-8-isopropyl-5-methyl-6-oxo-7H-pteridin-2-yl]amino]-2,3-dihydrobenzofuran-4-carboxylic acid 43e (607 mg, 1.48 mmol), O-(benzotriazol-1-yl)-N,N,N',N'-tetra methyluronium tetrafluoroborate (475 mg, 1.48 mmol) and diisopropylethylamine (420 mg, 3.30 mmol) were dissolved in 40 mL of dichloromethane. The reaction solution was stirred for 2 hours. The resulting solution was added with 50 mL of aqueous ammonia and extracted with dichloromethane (50 mL×3). The combined organic phase was washed with saturated brine (50 mL×3), then dried over anhydrous magnesium sulfate, filtered and the filtrate was concentrated under reduced pressure. The resulting residue was purified by silica gel column chromatography with elution system A to obtain the title compound N-[(cis)-4-[4-(cyclopropylmethyl)piperazin-1-yl]cyclohexyl]-7-[[(7S)-7-ethyl-8-isopropyl-5-methyl-6-oxo-7H-pteridin-2-yl]amino]-2,3-dihydrobenzofuran-4-Carboxamide 45 (360 mg, yield: 38.0%) as a white solid.

MS m/z (ESI): 316.2 [M/2+1]

$^1$H NMR (400 MHz, CDCl$_3$) δ 8.27 (d, 1H), 7.66 (s, 1H), 7.09 to 7.02 (m, 2H), 5.82 (d, 1H), 4.73 to 4.63 (m, 3H), 4.28 (d, 1H), 3.96 to 3.82 (m, 1H), 3.59 (t, 2H), 3.32 (s, 3H), 2.66 (s, 8H), 2.35 to 2.25 (m, 3H), 2.17 (d, 2H), 2.04 to 1.86 (m, 5H), 1.76 to 1.68 (m, 1H), 1.50 to 1.39 (m, 5H), 1.35 (d, 3H), 1.26 (d, 2H), 0.86 (t, 4H), 0.55 to 0.48 (m, 2H), 0.11 (q, 2H)

TEST EXAMPLES

Biological Assays

Test Example 1

Plk Cell Proliferation Inhibition Assay

The following in vitro assay is to determine the activity of the compounds of the present invention for inhibiting the proliferation of human cervix cancer cells Hela, which has high expression of Plk.

The in vitro cellular assay described here is to determine the activity of the tested compounds for inhibiting the proliferation of cancer cells, which has high expression of Plk. The activity is represented by the $IC_5$. The general procedures for the assay are given as follows: The Hela cells highly expressing Plk (Institute of biochemistry and cell biology) were seeded to 96-well cell culture plate at a suitable concentration (exp 3000 cells/ml medium). The cells then were cultured in carbon dioxide ($CO_2$) incubator and grew overnight. Then, the cell culture medium was replaced by fresh one with tested compounds added in it at serial concentrations (general 7 to 9 concentrations). Then the cells were put back to the incubator and cultured for continuous 72 hours. 72 hours later, the activity of the tested compounds for inhibiting the cell proliferation was determined by using CCK8 (cell counting kit-8, Dojindo, NO:CK04) method. $IC_{50}$ value on tested cells were calculated by the data of inhibition rates of serial concentrations of the tested compounds.

The Activity of the Compounds of the Invention:

The biological activity of the compounds of the invention was tested by using the assay described above. The $IC_{50}$ values were measured and shown in table below:

| Example No. | $IC_{50}(\mu M)$ |
|---|---|
| 1 | 0.0009 |
| 2 | 0.008 |
| 3 | 0.007 |
| 4 | 0.002 |
| 5 | 0.001 |
| 6 | 0.002 |
| 7 | 0.003 |
| 8 | 0.003 |
| 9 | 0.002 |
| 10 | 0.005 |
| 11 | 0.001 |
| 12 | 0.0008 |
| 13 | 0.001 |
| 14 | 0.001 |
| 15 | 0.003 |
| 16 | 0.03 |
| 17 | 0.01 |
| 19 | 0.003 |
| 20 | 0.008 |
| 21 | 0.007 |
| 22 | 0.002 |
| 24 | 0.002 |
| 25 | 0.003 |
| 26 | 0.003 |
| 27 | 0.001 |
| 28 | 0.003 |
| 29 | 0.03 |
| 30 | 0.004 |
| 32 | 0.009 |
| 33 | 0.007 |
| 34 | 0.0007 |
| 35 | 0.002 |
| 36 | 0.007 |
| 37 | 0.0007 |

-continued

| Example No. | $IC_{50}(\mu M)$ |
|---|---|
| 38 | 0.002 |
| 39 | 0.006 |
| 40 | 0.002 |
| 44 | 0.005 |

Conclusion: the compounds of the present invention had obvious activity for inhibiting the proliferation of Hela cells.

Pharmacokinetics Assay

Test Example 2

The Pharmacokinetics Assay of the Compound of Example 37 of the Present Invention 1. Abstract The compound 37 of the present invention was administrated intravenous injection or intragastrically to rats to determine the drug concentration in plasma at different time points by LC/MS/MS method. The pharmacokinetic behavior of the compounds of the present invention was studied and evaluated in rats.

2. Protocol 2.1 Samples

Compound of Example 37

2.2 Experimental Animals 8 healthy adult SD rats, male and female in half, were purchased from SINO-BRITSH SIPPR/BK LAB. ANIMAL LTD., CO, License number: SCXK (Shanghai) 2003-0016

2.3 Preparation of the Tested Compounds

The right amount of tested compound was dissolved in 0.5 mL of DMSO, added with 1.5 mL of 0.1 M HCl, then diluted with normal saline to 2.5 mg/mL of suspension before use.

2.4 Administration

8 Healthy adult SD rats, male and female in half, were divided into 2 groups. After an overnight fast, the rats were administered intragastrically or administered via tail intravenous injection at a dose of 25.0 mg/kg.

3. Operation

25 µL of rat plasmas taken at various time points after administration were mixed with 20 µL of internal standard solution and 150 µL methanol for 3 minutes by using a vortexer and the mixture was centrifuged for 10 minutes at 13,500 rpm. 5 µL of the supernatant was analyzed by LC-MS/MS.

Plasma concentration was used as the abscissa, the ratio of chromatographic peak area between the sample and internal standard was used as the ordinate, the linear regression was carried out by the weighted least square method ($w=1/x^2$). The main pharmacokinetic parameters were calculated by DAS 2.0 software.

4. Results of Pharmacokinetic Parameters

Pharmacokinetic Parameters of the compounds of the present invention were shown as follows:

| | Pharmacokinetics Assay (25 mg/kg) | | | | | | |
|---|---|---|---|---|---|---|---|
| Number | oral bioavailability F (%) | Plasma Conc. Cmax (µg/mL) | Area Under Curve AUC (µg/mL * h) | Half-Life t½ (h) | Mean Residence Time MRT (h) | Clearance CL/F (l/h/kg) | Apparent Distribution Volume Vz/F (l/kg) |
| Example 37 | 59.4 | 1.86 ± 0.15 (intragastric administration) | 45.56 ± 9.23 | 17.2 ± 4.4 | 26.1 ± 5.0 | 0.57 ± 0.13 | 13.6 ± 1.0 |
| | | intravenous injection | 76.7 ± 6.20 | 17.3 ± 3.3 | 22.8 ± 4.3 | 0.33 ± 0.03 | 8.22 ± 1.74 |

Conclusion: the compound of example 37 had good absorption in pharmacokinetics and high oral bioavailability.

The Therapeutic Effects Against Xenografts of HT-116 Human Colon Cancer in Nude Mice 1. Abstract The therapeutic effect of Example 1 against xenografts of HT-116 human colon cancer in nude mice was estimated. As a Plk-1 inhibitor, the compound of Example 1, with less toxicity, markedly inhibited the growth of HT-116 human colon cancer in nude mice.

2. Purpose

The therapeutic effect of Example 1 against xenografts of HT-116 human colon cancer in nude mice was estimated and compared.

3. Tested Drug

Drug name: the compound of Example 1

Preparation method: the compound of Example 1 was prepared to corresponding concentration by using normal saline.

4. Experimental Animals

BALB/cA-nude mice, 6 to 7 weeks old, ♀, purchased from Slaccas Experimental Animal LTD., CO.

Certificate No.: SCXK 2007 to 0005. Environment: SPF level.

5. Experimental Protocol

Nude mice were hypodermic inoculated HT-116 human colon cancer cell. After tumors grew to 60-150 mm³, mice were randomly divided into teams (d0).

The volume of tumors and the weigh of the mice were measured and recorded for 2-3 times per week.

The calculation formula of the volume of tumor (V) is: V=½×a×b², a: length of tumor, b: width of tumor.

6. Result

The compound of Example 1 markedly inhibited the growth of HT-116 human colon cancer and had less toxicity.

What is claimed is:

1. A compound of formula (I), a tautomer, racemate, enantiomer, diastereoisomer or mixture thereof, or a pharmaceutically acceptable salt thereof:

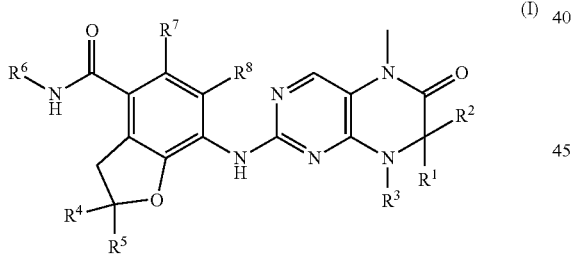

wherein:

$R^1$ and $R^2$ are each independently selected from the group consisting of hydrogen, alkyl, alkenyl, alkynyl, cycloalkyl, heterocyclyl, aryl, heteroaryl, carboxyl and alkyl-C(O)—O-alkyl, wherein the alkyl, alkenyl, alkynyl, cycloalkyl, heterocyclyl, aryl or heteroaryl is each optionally substituted with one or more groups selected from the group consisting of alkyl, halogen, hydroxyl, aryl, sulfuryl, carboxyl and alkyl-C(O)—O-alkyl;

or, $R^1$ and $R^2$ are taken together with the attached atom to form a 3 to 6 membered ring, wherein the 3 to 6 membered ring optionally contains 1 to 2 N, O or S(O)n heteroatoms;

$R^3$ is selected from the group consisting of hydrogen, alkyl, alkenyl, alkynyl, cycloalkyl, heterocyclyl, aryl and heteroaryl, wherein the alkyl, alkenyl, alkynyl, cycloalkyl, heterocyclyl, aryl or heteroaryl is each optionally substituted with one or more groups selected from the group consisting of alkyl, alkoxyl, halogen, hydroxyl, aryl, sulfuryl, carboxyl and alkyl-C(O)—(O)-alkyl;

or, $R^1$ and $R^3$ or $R^2$ and $R^3$ are taken together with the attached atom to form a 3 to 6 membered ring, wherein the 3 to 6 membered ring contains 1 to 2 N, O or S(O)n heteroatoms, and the 3 to 6 membered ring is each optionally substituted with one or more groups selected from the group consisting of alkyl, alkoxyl, halogen, carbonyl, aryl, benzyl, —C(O)R⁹, —C(O)NR⁹R¹⁰, —NR⁹R¹⁰, carboxyl and alkyl-C(O)—O-alkyl;

$R^4$ and $R^5$ are each independently selected from the group consisting of hydrogen, alkyl, alkoxyl, cyano, hydroxyl, halogen, alkenyl, alkynyl, cycloalkyl, heterocyclyl, aryl, heteroaryl, carboxyl and alkyl-C(O)—O-alkyl, wherein the alkyl, alkoxyl, alkenyl, alkynyl, cycloalkyl, heterocyclyl, aryl and heteroaryl is each optionally substituted with one or more groups selected from the group consisting of alkyl, alkoxyl, halogen, hydroxyl, aryl, sulfuryl, —NR⁹R¹⁰, carboxyl and alkyl-C(O)—O-alkyl;

$R^6$ is selected from the group consisting of alkyl, cycloalkyl, heterocyclyl, aryl and heteroaryl, wherein the alkyl, cycloalkyl, heterocyclyl, aryl or heteroaryl is each optionally substituted with one or more groups selected from the group consisting of alkyl, alkoxyl, hydroxyl, sulfuryl, carbonyl, cycloalkyl, cycloalkylalkyl, heterocyclyl, aryl, benzyl, —C(O)R⁹, —C(O)NR⁹R¹⁰, —NR⁹R¹⁰, carboxyl and alkyl-C(O)—O-alkyl;

$R^7$ and $R^8$ are each independently selected from the group consisting of hydrogen, alkyl and halogen;

$R^9$ and $R^{10}$ are each independently selected from the group consisting of hydrogen, alkyl, cycloalkyl, heterocyclyl, aryl, heteroaryl, carboxyl and alkyl-C(O)—O-alkyl, wherein the alkyl, cycloalkyl, heterocyclyl, aryl or heteroaryl is each optionally substituted with one or more groups selected from the group consisting of alkyl, halogen, hydroxyl, cyano, alkoxyl, aryloxyl, cycloalkyl, cycloalkylalkyl, heterocyclyl, aryl, heteroaryl, sulfuryl, carboxyl and alkyl-C(O)—O-alkyl;

or, $R^9$ and $R^{10}$ are taken together with the attached N atom to form a 4 to 8 membered heterocycle, wherein the 4 to 8 membered heterocycle contains one or more N, O or S(O)n heteroatoms, and the 4 to 8 membered heterocycle is each optionally substituted with one or more groups selected from the group consisting of alkyl, halogen, hydroxyl, haloalkyl, cyano, alkoxyl, aryloxyl, hydroxylalkyl, cycloalkyl, cycloalkylalkyl, heterocyclyl, aryl, heteroaryl, sulfuryl, carboxyl and alkyl-C(O)—O-alkyl; and n is 0, 1 or 2.

2. The compound according to claim 1, the tautomer, racemate, enantiomer, diastereoisomer or mixture thereof, or the pharmaceutically acceptable salt thereof, wherein:

$R^1$ and $R^2$ are each independently selected from the group consisting of hydrogen and alkyl; and $R^3$ is selected from the group consisting of hydrogen, alkyl and cycloalkyl.

3. The compound according to claim 1, the tautomer, racemate, enantiomer, diastereoisomer or mixture thereof, or the pharmaceutically acceptable salt thereof, wherein:

$R^1$ and $R^2$ are each independently selected from the group consisting of hydrogen and alkyl;

$R^3$ is selected from the group consisting of alkyl and cycloalkyl;

$R^4$ and $R^5$ are each independently selected from the group consisting of hydrogen and alkyl, wherein the alkyl is optionally substituted with one or more groups selected from the group consisting of alkoxyl and —NR$^9$R$^{10}$;

R$^6$ is selected from the group consisting of alkyl, cycloalkyl and heterocyclyl, wherein the alkyl, cycloalkyl or heterocyclyl is each optionally substituted with one or more groups selected from the group consisting of alkyl, hydroxyl, cycloalkylalkyl, heterocyclyl, —NR$^9$R$^{10}$, carboxyl and alkyl-C(O)—O-alkyl;

R$^7$ and R$^8$ are each independently hydrogen; and

R$^9$ and R$^{10}$ are each independently selected from the group consisting of hydrogen, alkyl, cycloalkyl, heterocyclyl, aryl, heteroaryl, carboxyl and alkyl-C(O)—O-alkyl, wherein the alkyl, cycloalkyl, heterocyclyl, aryl or heteroaryl is each optionally substituted with one or more groups selected from the group consisting of alkyl, halogen, hydroxyl, cyano, alkoxyl, aryloxyl, heterocyclyl, aryl, heteroaryl, sulfuryl, carboxyl and alkyl-C(O)—O-alkyl;

or, R$^9$ and R$^{10}$ are taken together with the attached N atom to form the 4 to 8 membered heterocycle.

4. The compound according to claim 1, the tautomer, racemate, enantiomer, diastereoisomer or mixture thereof, or the pharmaceutically acceptable salt thereof, wherein the compound is selected from the group consisting of:

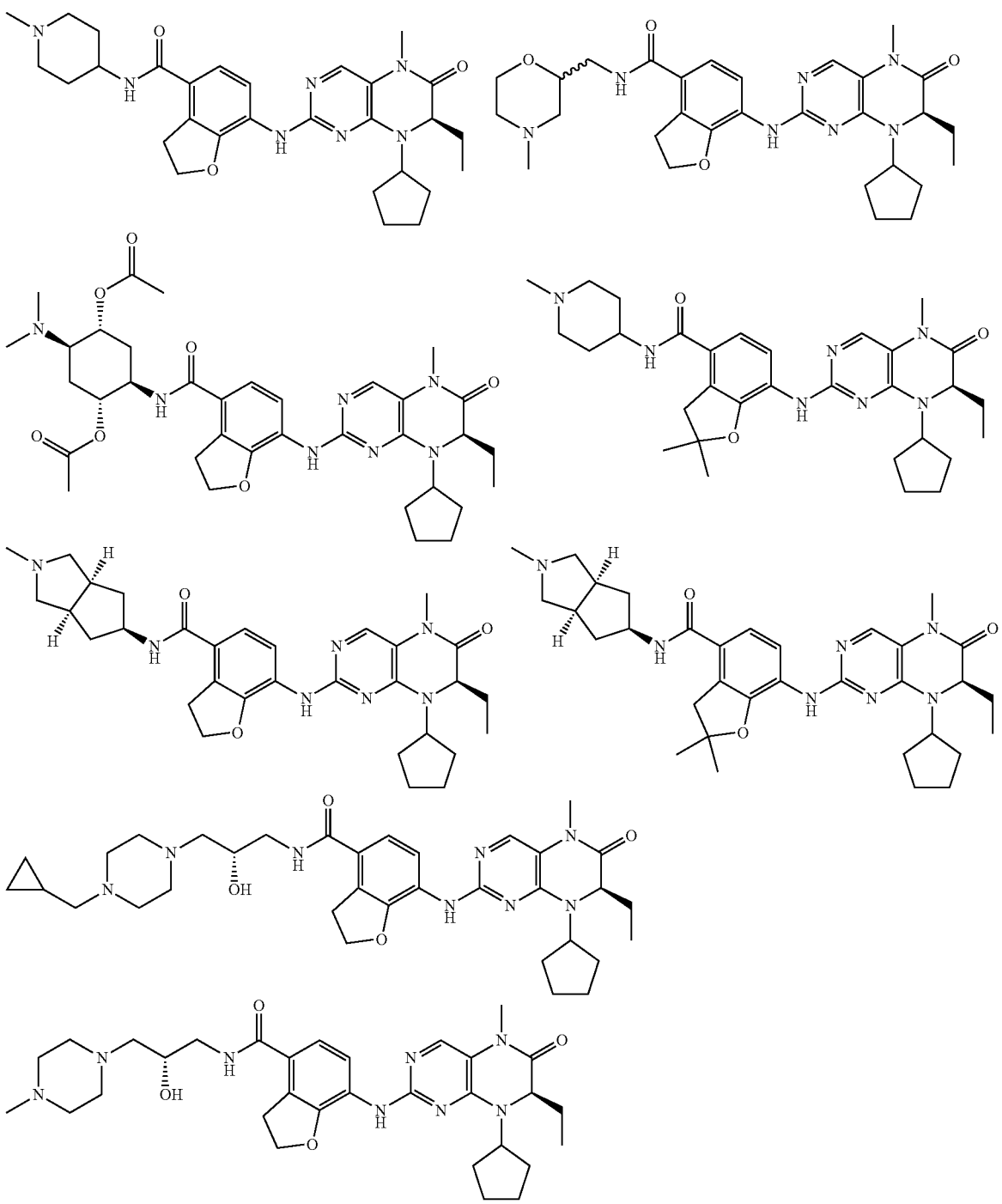

-continued
171
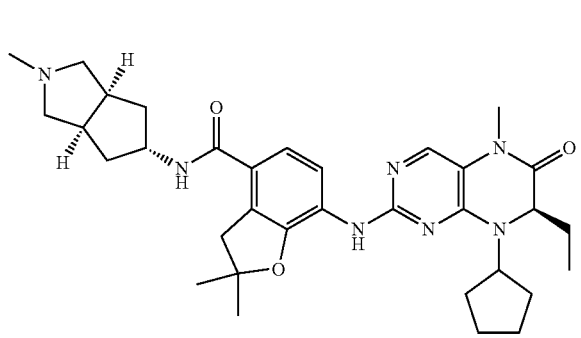
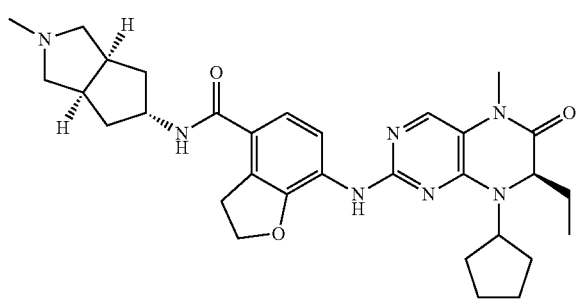
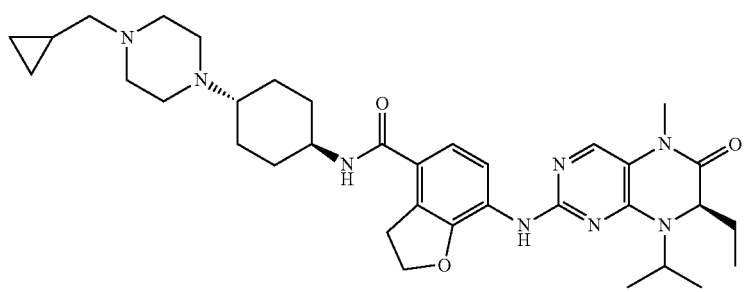
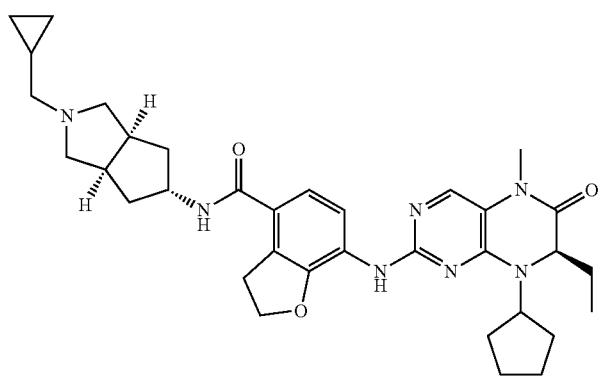
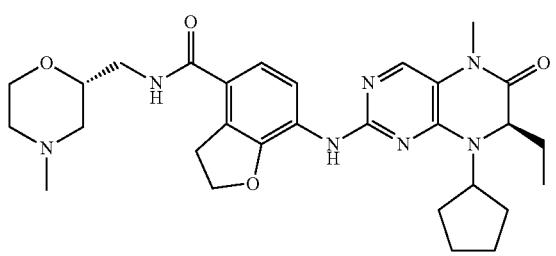
172
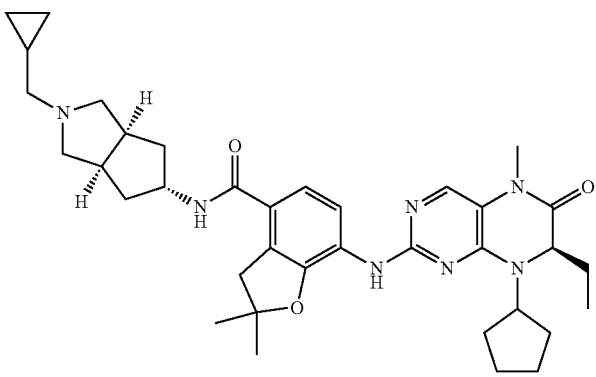
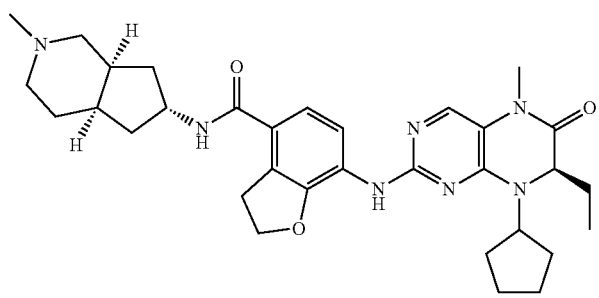

-continued
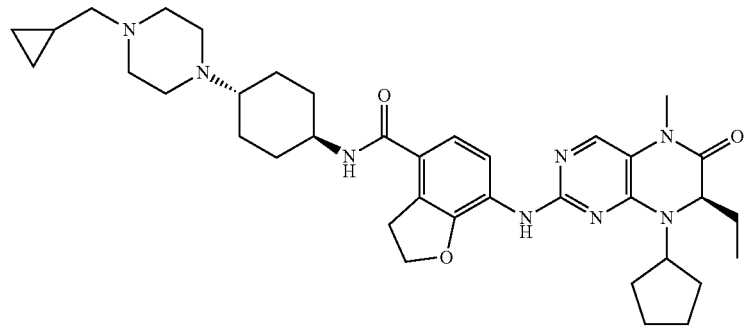
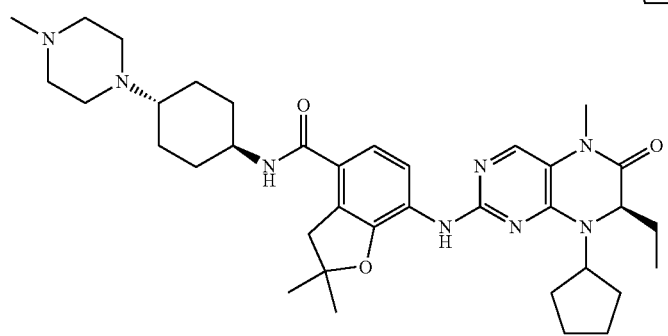
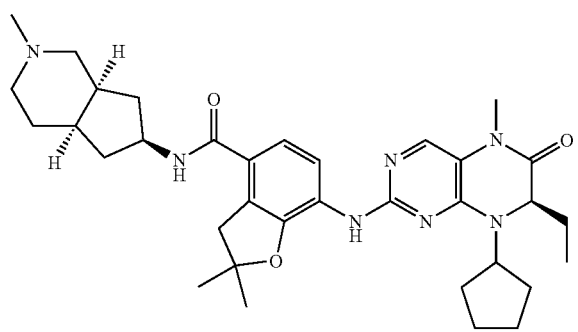
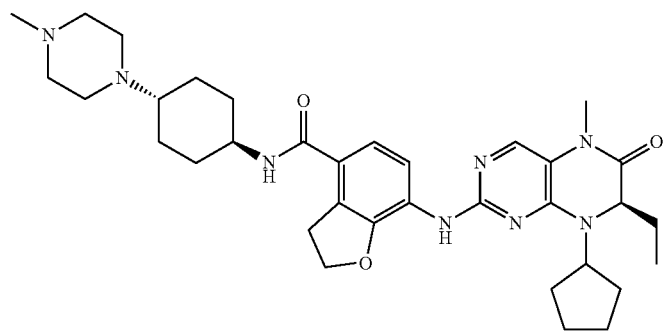
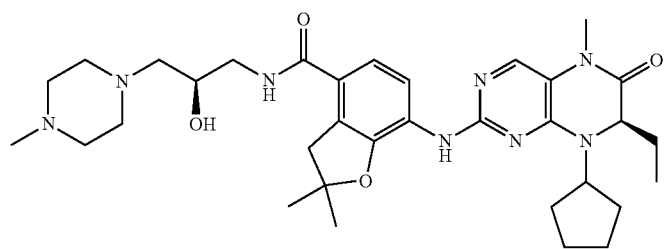

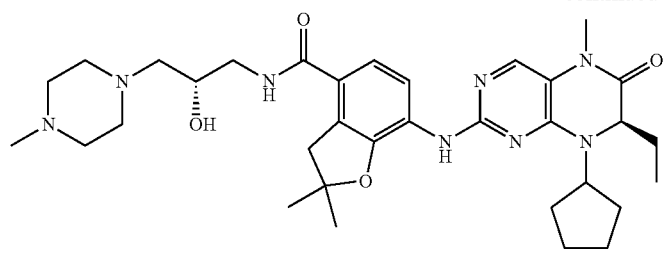
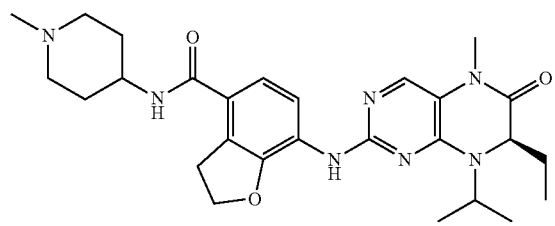
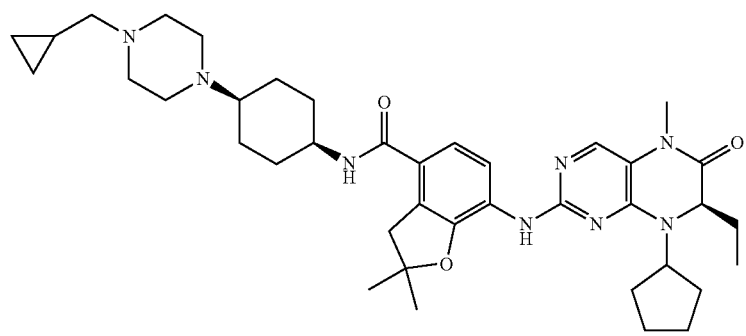
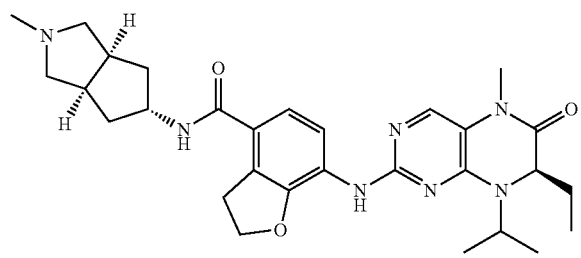
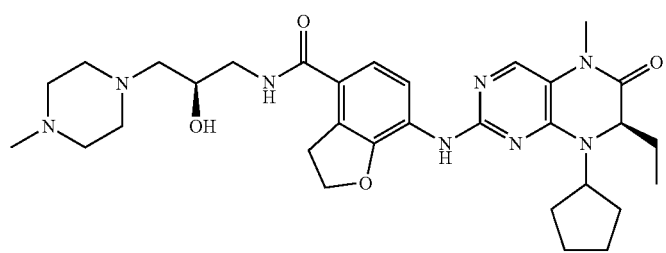
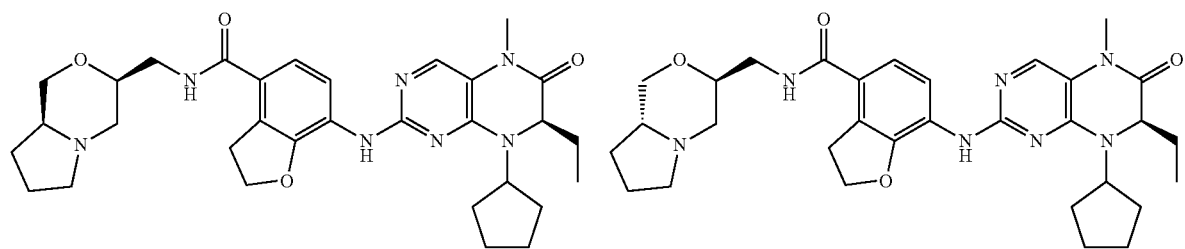

177 178
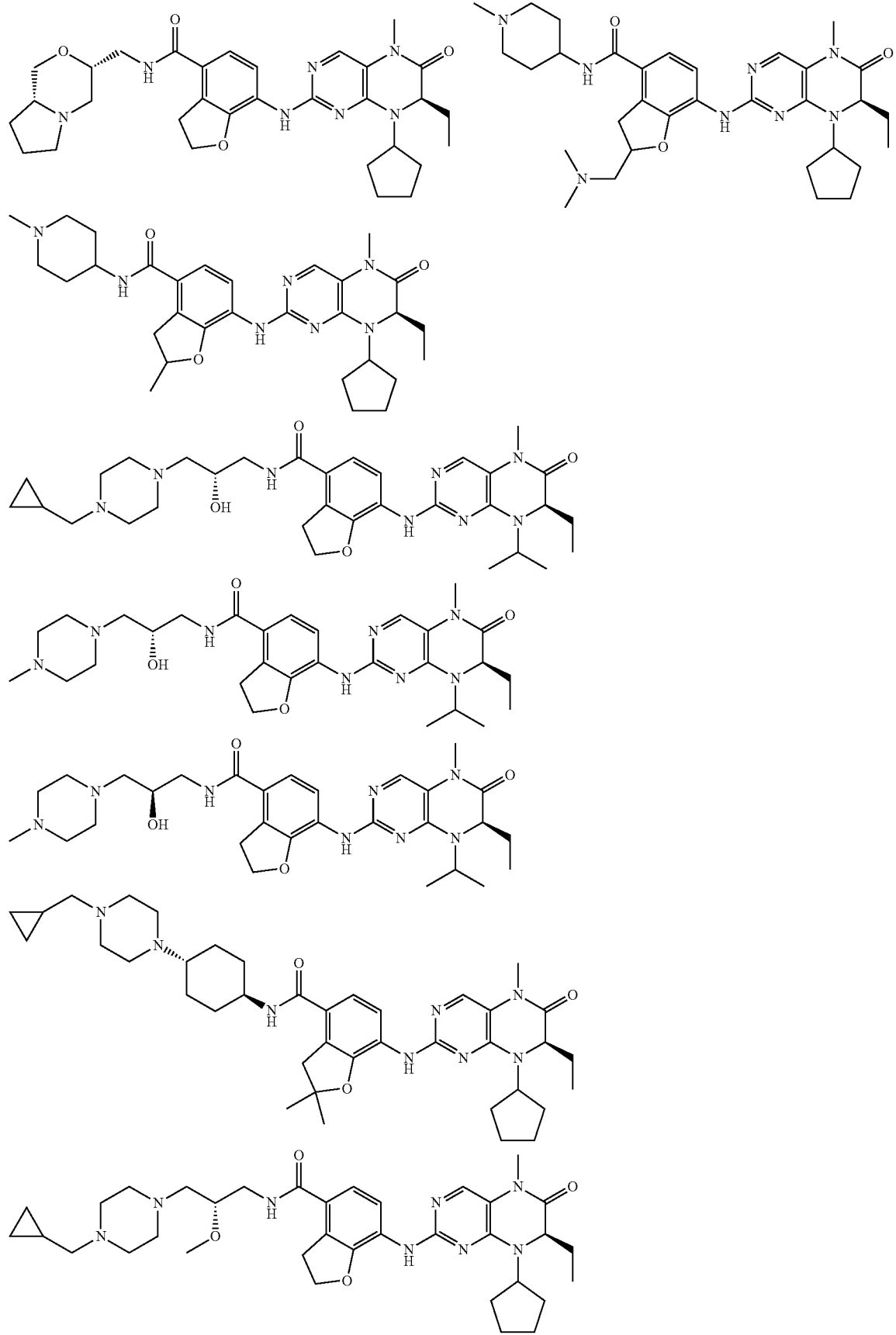
-continued

-continued
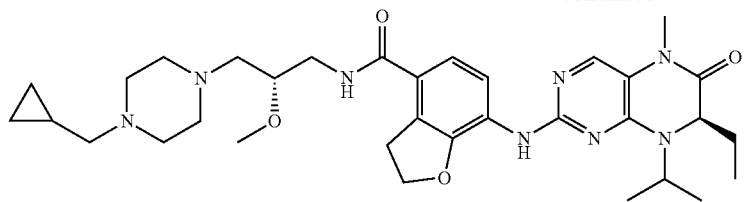
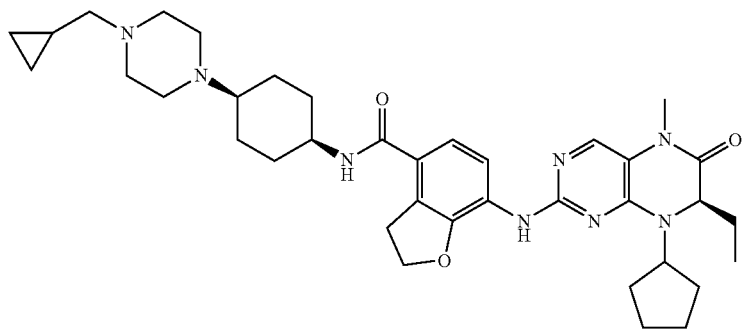
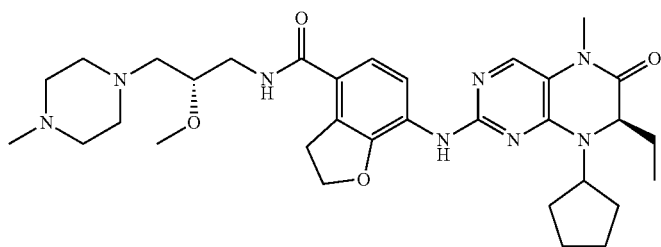
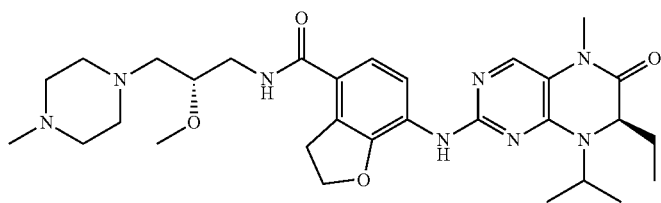
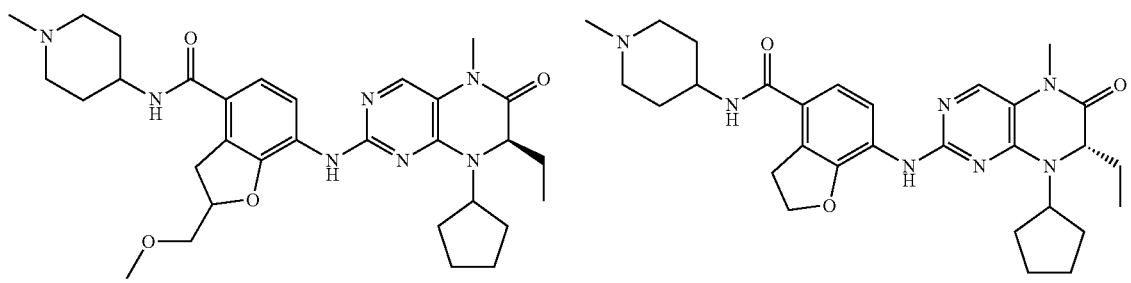
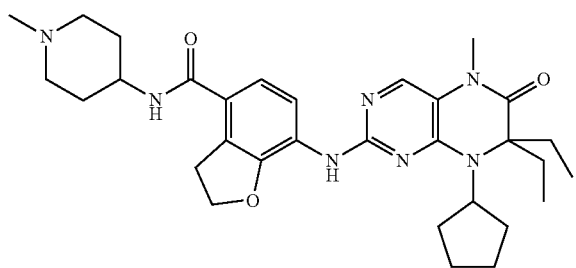

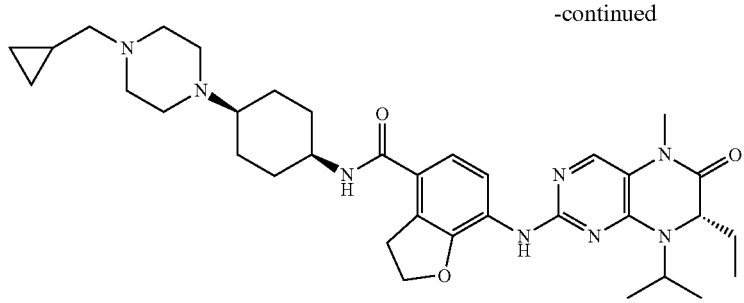

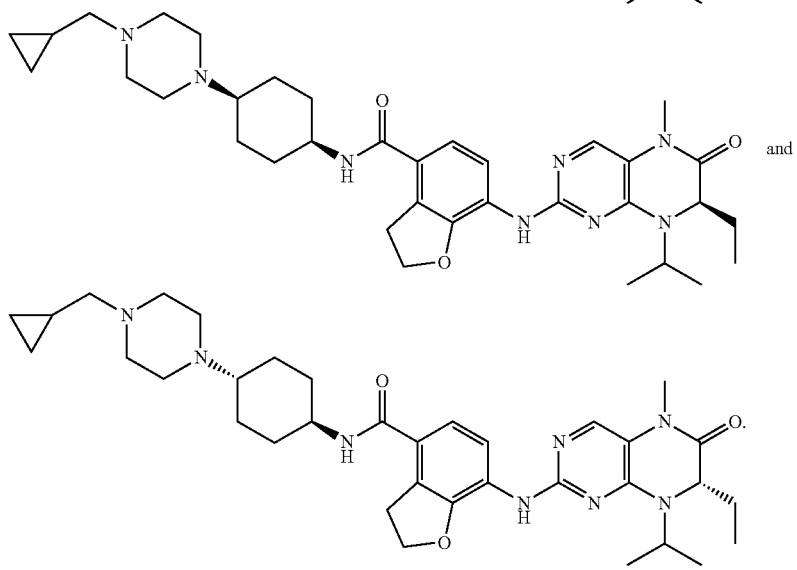

and

5. A compound of formula (IA),

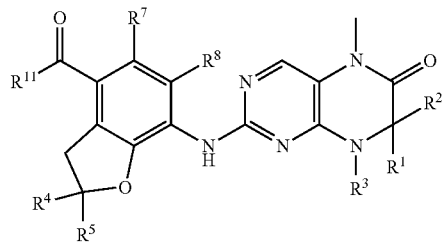

wherein:
R¹ and R² are each independently selected from the group consisting of hydrogen, alkyl, alkenyl, alkynyl, cycloalkyl, heterocyclyl, aryl, heteroaryl, carboxyl and alkyl-C(O)—O-alkyl, wherein the alkyl, alkenyl, alkynyl, cycloalkyl, heterocyclyl, aryl or heteroaryl is each optionally substituted with one or more groups selected from the group consisting of alkyl, halogen, hydroxyl, aryl, sulfuryl, carboxyl and alkyl-C(O)—O-alkyl;

or, R¹ and R² are taken together with the attached atom to form a 3 to 6 membered ring, wherein the 3 to 6 membered ring optionally contains 1 to 2 N, O or S(O)n heteroatoms;

R³ is selected from the group consisting of hydrogen, alkyl, alkenyl, alkynyl, cycloalkyl, heterocyclyl, aryl and heteroaryl, wherein the alkyl, alkenyl, alkynyl, cycloalkyl, heterocyclyl, aryl or heteroaryl is each optionally substituted with one or more groups selected from the group consisting of alkyl, alkoxyl, halogen, hydroxyl, aryl, sulfuryl, carboxyl and alkyl-C(O)—O-alkyl;

or, R¹ and R³ or R² and R³ are taken together with the attached atom to form a 3 to 6 membered ring, wherein the 3 to 6 membered ring contains 1 to 2 N, O or S(O)n heteroatoms, and the 3 to 6 membered ring is each optionally substituted with one or more groups selected from the group consisting of alkyl, alkoxyl, halogen, carbonyl, aryl, benzyl, —C(O)R⁹, —C(O)NR⁹R¹⁰, —NR⁹R¹⁰, carboxyl and alkyl-C(O)—O-alkyl;

R⁴ and R⁵ are each independently selected from the group consisting of hydrogen, alkyl, alkoxyl, cyano, hydroxyl, halogen, alkenyl, alkynyl, cycloalkyl, heterocyclyl, aryl, heteroaryl, carboxyl and alkyl-C(O)—O-alkyl, wherein the alkyl, alkoxyl, alkenyl, alkynyl, cycloalkyl, heterocyclyl, aryl or heteroaryl is each optionally substituted with one or more groups selected from the group consisting of alkyl, alkoxyl, halogen, hydroxyl, aryl, sulfuryl, —NR⁹R¹⁰, carboxyl and alkyl-C(O)—O-alkyl;

R⁷ and R⁸ are each independently selected from the group consisting of hydrogen, alkyl and halogen;

R⁹ and R¹⁰ are each independently selected from the group consisting of hydrogen, alkyl, cycloalkyl, heterocyclyl, aryl, heteroaryl, carboxyl and alkyl-C(O)—O-alkyl, wherein the alkyl, cycloalkyl, heterocyclyl, aryl or heteroaryl is each optionally substituted with one or more groups selected from the group consisting of alkyl, halogen, hydroxyl, cyano, alkoxyl, aryloxyl, cycloalkyl, cycloalkylalkyl, heterocyclyl, aryl, heteroaryl, sulfuryl, carboxyl and alkyl-C(O)—O-alkyl;

or, $R^9$ and $R^{10}$ are taken together with the attached N atom to form a 4 to 8 membered heterocycle, wherein the 4 to 8 membered heterocycle contains one or more N, O or S(O)n heteroatoms, and the 4 to 8 membered heterocycle is each optionally substituted with one or more groups selected from the group consisting of alkyl, halogen, hydroxyl, haloalkyl, cyano, alkoxyl, aryloxyl, hydroxyl alkyl, cycloalkyl, cycloalkylalkyl, heterocyclyl, aryl, heteroaryl, sulfuryl, carboxyl and alkyl-C(O)—O-alkyl;

$R^{11}$ is selected from the group consisting of hydroxyl and alkoxyl; and n is 0, 1 or 2.

6. The compound according to claim 5, wherein:
$R^1$ and $R^2$ are each independently selected from the group consisting of hydrogen and alkyl; and
$R^3$ is selected from the group consisting of hydrogen, alkyl and cycloalkyl.

7. The compound according to claim 5, wherein:
$R^1$ and $R^2$ are each independently selected from the group consisting of hydrogen and alkyl;
$R^3$ is selected from the group consisting of alkyl and cycloalkyl;
$R^4$ and $R^5$ are each independently selected from the group consisting of hydrogen and alkyl, wherein the alkyl is optionally substituted with one or more groups selected from the group consisting of alkoxyl and —$NR^9R^{10}$;
$R^7$ and $R^8$ are each independently hydrogen;
$R^9$ and $R^{10}$ are each independently selected from the group consisting of hydrogen, alkyl, cycloalkyl, heterocyclyl, aryl, heteroaryl, carboxyl and alkyl-C(O)—O-alkyl, wherein the alkyl, cycloalkyl, heterocyclyl, aryl or heteroaryl is each optionally substituted with one or more groups selected from the group consisting of alkyl, halogen, hydroxyl, cyano, alkoxyl, aryloxyl, heterocyclyl, aryl, heteroaryl, sulfuryl, carboxyl and alkyl-C(O)—O-alkyl;
or, $R^9$ and $R^{10}$ are taken together with the attached N atom to form the 4 to 8 membered heterocycle.

8. A process of preparing the compound of formula (I) according to claim 1, comprising:

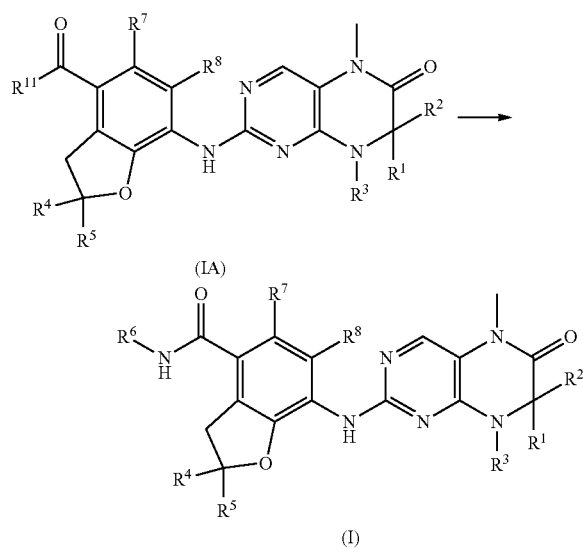

reacting the compound of formula (IA) with $R^6NH_2$ to obtain the compound of formula (I), wherein $R^1$ to $R^8$ are defined as those in claim 1, and $R^{11}$ is selected from the group consisting of hydroxyl and alkoxyl.

9. A process of preparing the compound of formula (IA) according to claim 5, comprising:

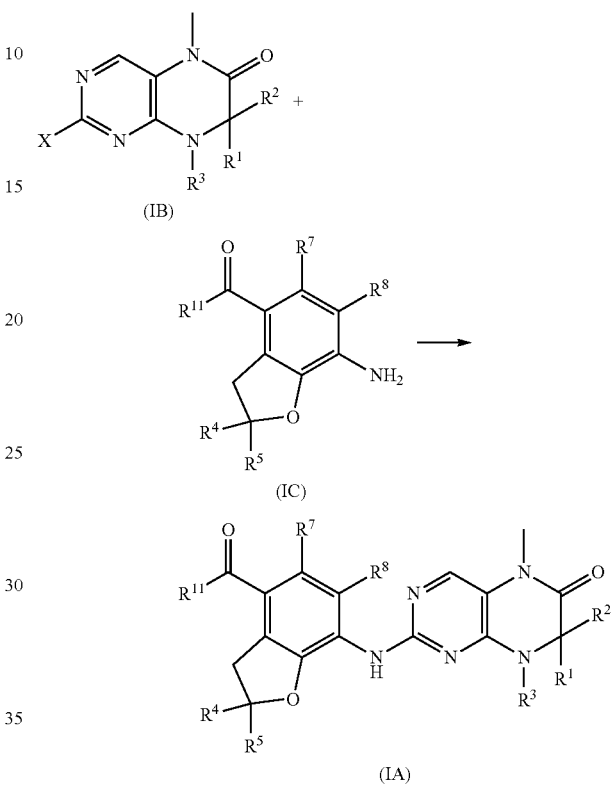

reacting the compound of formula (IB) with the compound of formula (IC) to obtain the compound of formula (IA), wherein $R^1$ to $R^5$, $R^7$, $R^8$ and $R^{11}$ are defined as those in claim 5.

10. A pharmaceutical composition comprising a therapeutically effective amount of the compound according to claim 1, the tautomer, racemate, enantiomer, diastereoisomer or mixture thereof, or the pharmaceutically acceptable salt thereof, and a pharmaceutically acceptable carrier or excipient.

11. A process of preparing a pharmaceutical composition, comprising combining the compound of formula (I) of claim 1, the tautomer, racemate, enantiomer, diastereoisomer or mixture thereof, or the pharmaceutically acceptable salt thereof with a pharmaceutically acceptable carrier or excipient.

12. A method for treating a cell proliferation disorder in a subject in need thereof, comprising administrating to the subject a pharmaceutical composition according to claim 10, wherein the cell proliferation disorder is selected from the group consisting of non small-cell lung cancer, squamous cell carcinoma, breast cancer, ovarian cancer, uterine cervix cancer, papillary carcinoma and colorectal carcinoma.

13. The method of claim 12, wherein the cancer is uterine cervix cancer or colorectal carcinoma.

14. A compound having the following formula:

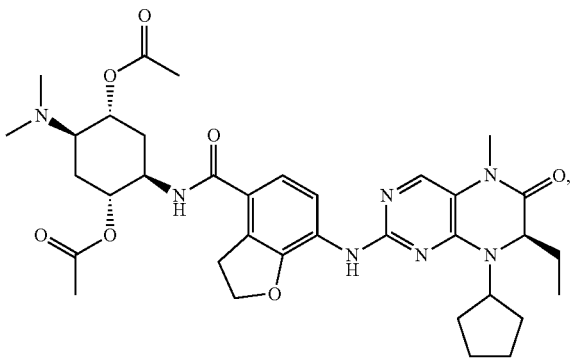 [SMILES: CC[C@@H]1C(=O)N(C)c2cnc(Nc3ccc(C(=O)N[C@@H]4C[C@@H](OC(C)=O)[C@H](N(C)C)C[C@H]4OC(C)=O)c4c3OCC4)nc2N1C1CCCC1]

a tautomer, racemate, enantiomer, diastereoisomer or mixture thereof, or a pharmaceutically acceptable salt thereof.

15. A pharmaceutical composition comprising a therapeutically effective amount of the compound according to claim 14, the tautomer, racemate, enantiomer, diastereoisomer or mixture thereof, or the pharmaceutically acceptable salt thereof, and a pharmaceutically acceptable carrier or excipient.

16. A method for treating a cell proliferation disorder in a subject in need thereof, comprising administrating to the subject a pharmaceutical composition according to claim 15, wherein the cell proliferation disorder is a cancer selected from the group consisting of non small-cell lung cancer, squamous cell carcinoma, breast cancer, ovarian cancer, uterine cervix cancer, papillary carcinoma and colorectal carcinoma.

17. The method of claim 16, wherein the cancer is uterine cervix cancer or colorectal carcinoma.

* * * * *